US009617561B2

(12) United States Patent
Roy et al.

(10) Patent No.: US 9,617,561 B2

(45) Date of Patent: Apr. 11, 2017

(54) SIMIAN ADENOVIRUS 41 AND USES THEREOF

(71) Applicant: The Trustees of the University of Pennsylvania, Philadelphia, PA (US)

(72) Inventors: Soumitra Roy, Noordwijk (NL); James M. Wilson, Glen Mills, PA (US); Luc H. Vandenberghe, Weston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/462,986

(22) Filed: Aug. 19, 2014

(65) Prior Publication Data

US 2015/0071962 A1 Mar. 12, 2015

Related U.S. Application Data

(63) Continuation of application No. 13/321,985, filed as application No. PCT/US2010/036332 on May 27, 2010, now Pat. No. 8,846,031.

(60) Provisional application No. 61/182,290, filed on May 29, 2009, provisional application No. 61/219,917, filed on Jun. 24, 2009.

(51) Int. Cl.

| | |
|---|---|
| ***C12N 15/11*** | (2006.01) |
| ***C12N 15/34*** | (2006.01) |
| ***C12N 15/861*** | (2006.01) |
| ***C12N 15/86*** | (2006.01) |
| ***C07K 14/005*** | (2006.01) |
| ***C12N 7/00*** | (2006.01) |
| ***A61K 39/145*** | (2006.01) |
| *A61K 39/00* | (2006.01) |
| *A61K 48/00* | (2006.01) |

(52) U.S. Cl.

CPC ............ *C12N 15/86* (2013.01); *A61K 39/145* (2013.01); *C07K 14/005* (2013.01); *C12N 7/00* (2013.01); *A61K 48/00* (2013.01); *A61K 2039/5256* (2013.01); *C12N 2710/10043* (2013.01); *C12N 2710/10321* (2013.01); *C12N 2710/10322* (2013.01); *C12N 2710/10343* (2013.01); *C12N 2810/6018* (2013.01)

(58) Field of Classification Search

CPC .............. C12N 15/8613; C12N 15/861; C12N 2710/10321; C12N 2710/10322; C12N 2710/10343; A61K 2039/5256; C07K 14/075

See application file for complete search history.

(56) References Cited

U.S. PATENT DOCUMENTS

| | | | |
|---|---|---|---|
| 6,083,716 A | 7/2000 | Wilson et al. | |
| 7,247,472 B2 | 7/2007 | Wilson et al. | |
| 7,291,498 B2 | 11/2007 | Roy et al. | |
| 7,491,508 B2 | 2/2009 | Roy et al. | |
| 8,105,574 B2 | 1/2012 | Wilson et al. | |
| 2005/0069866 A1 | 3/2005 | Wilson et al. | |
| 2009/0074810 A1 | 3/2009 | Roy et al. | |
| 2009/0215871 A1 | 8/2009 | Wilson et al. | |
| 2010/0247490 A1 | 9/2010 | Roy et al. | |
| 2010/0254947 A1 | 10/2010 | Roy et al. | |
| 2010/0260799 A1 | 10/2010 | Roy et al. | |
| 2011/0217332 A1* | 9/2011 | Colloca et al. | 424/233.1 |

FOREIGN PATENT DOCUMENTS

| | | |
|---|---|---|
| EP | 2012822 | 1/2009 |
| WO | WO 99/29334 | 6/1999 |
| WO | WO 03/000851 | 1/2003 |
| WO | WO 2005/001103 | 1/2005 |
| WO | WO 2005/071093 | 8/2005 |
| WO | WO 2009/073103 | 6/2009 |
| WO | WO 2009/073104 | 8/2009 |
| WO | WO 2009/136977 | 11/2009 |
| WO | WO 2009/105084 | 12/2009 |

OTHER PUBLICATIONS

Richards F.M., Protein stability:still an unsolved problem, Cell. mol. life sci, 1997, pp. 790-802.*

Fumoto et al, Targeted Gene Delivery: Improtance of Administration Routes, 2013, pp. 1-31.*

Farina, Replication-Defective Vector Based on a Chimpanzee Adenovirus, Journal of Virology, 75(23):11603-11613, Dec. 1, 2001.

Roy, Characterization of a Family of Chimpanzee Adenoviruses and Development of Molecular Clones for Gene Transfer Vectors, Human Gene Therapy, 15(5):519-530, May 1, 2004.

Roy, Complete Nucleotide Sequences and Genome Organization of Four Chimpanzee Adenoviruses, Virology, 324(2):361-372, Jul. 1, 2004.

Roy, Generation of an Adenoviral Vaccine Vector Based on Simian Adenovirus 21, Journal of General Virology, 87(9):2477-2485, Sep. 2006.

Roy, Isolation and Characterization of Adenoviruses Persistently Shed from the Gastrointestinal Tract of Non-Human Primates, PLOS, Pathogens, 5(7):1-9, Jul. 1, 2009.

Roy, Partial Protection against H5N1 Influenza in Mice with a Single Dose of a Chimpanzee Adenovirus Vector Expressing Nucleoprotein, Vaccine, 25(39-40):6845-6851, Sep. 15, 2007.

Roy, Rescue of Chimeric Adenoviral Vectors to Expand the Serotype Repertoire, Journal of Virological Methods, 141(1):14-21, Feb. 21, 2007.

(Continued)

*Primary Examiner* — Maria Marvich

(74) *Attorney, Agent, or Firm* — Howson & Howson, LLP

(57) ABSTRACT

Novel simian adenovirus 41 and two isolates thereof are described. Various uses of these isolates, including construction of a recombinant vector which comprises simian adenovirus 41 sequences and a heterologous gene under the control of regulatory sequences are provided. A cell line which expresses simian adenovirus 41 gene(s) is also disclosed. Methods of using the vectors and cell lines are provided.

8 Claims, No Drawings

(56) References Cited

OTHER PUBLICATIONS

Russell, W.C., Update on Adenovirus and its Vectors, Journal of General Virology, 81:2573-2604, (Nov. 2000).

Shenk, T., Adenoviridae: The Viruses and Their Replication, Fields Virology, Third Edition, Chapter 67, pp. 2111-2112, (1996).

Russell, S.J., Replicating vectors for gene therapy of cancer: risks, limitations and prospects, Eur. J. Cancer, 30(A)(8):1165-1171, 1994.

Thomas, C.E., Progress and problems with the use of viral vectors for gene therapy, Nat. Rev. Genet., 4(5):346-358, May 2003.

* cited by examiner

SEQUENCE LISTING

```
<160> NUMBER OF SEQ ID NOS: 69

<210> SEQ ID NO 1
<211> LENGTH: 35100
<212> TYPE: DNA
<213> ORGANISM: Unknown
<220> FEATURE:
<223> OTHER INFORMATION: Simian adenovirus 41.1
<220> FEATURE:
<221> NAME/KEY: repeat_region
<222> LOCATION: (1)..(112)
<223> OTHER INFORMATION: ITR
<220> FEATURE:
<221> NAME/KEY: CDS
<222> LOCATION: (1910)..(3394)
<223> OTHER INFORMATION: Elb[5]5K
<220> FEATURE:
<221> NAME/KEY: CDS
<222> LOCATION: (3491)..(3904)
<223> OTHER INFORMATION: pIX
<220> FEATURE:
<221> NAME/KEY: misc_feature
<222> LOCATION: (3973)..(5594)
<223> OTHER INFORMATION: IVa2    complement (3973..5303,5582..5594)
<220> FEATURE:
<221> NAME/KEY: misc_feature
<222> LOCATION: (5076)..(13879)
<223> OTHER INFORMATION: pol    complement (5076..8645,13871..13879)
<220> FEATURE:
<221> NAME/KEY: misc_feature
<222> LOCATION: (8447)..(13879)
<223> OTHER INFORMATION: pTP    complement (8447..10402,13871..13879)
<220> FEATURE:
<221> NAME/KEY: CDS
<222> LOCATION: (10883)..(12049)
<223> OTHER INFORMATION: 52K
<220> FEATURE:
<221> NAME/KEY: CDS
<222> LOCATION: (12077)..(13837)
<223> OTHER INFORMATION: pIIIa
<220> FEATURE:
<221> NAME/KEY: CDS
<222> LOCATION: (13924)..(15675)
<223> OTHER INFORMATION: penton
<220> FEATURE:
```

<221> NAME/KEY: CDS
<222> LOCATION: (15683)..(16258)
<223> OTHER INFORMATION: pVII
<220> FEATURE:
<221> NAME/KEY: CDS
<222> LOCATION: (16304)..(17353)
<223> OTHER INFORMATION: V
<220> FEATURE:
<221> NAME/KEY: CDS
<222> LOCATION: (17385)..(17609)
<223> OTHER INFORMATION: pX
<220> FEATURE:
<221> NAME/KEY: CDS
<222> LOCATION: (17686)..(18435)
<223> OTHER INFORMATION: pVI
<220> FEATURE:
<221> NAME/KEY: CDS
<222> LOCATION: (18550)..(21378)
<223> OTHER INFORMATION: hexon
<220> FEATURE:
<221> NAME/KEY: CDS
<222> LOCATION: (21412)..(22038)
<223> OTHER INFORMATION: protease
<220> FEATURE:
<221> NAME/KEY: misc_feature
<222> LOCATION: (22133)..(23689)
<223> OTHER INFORMATION: DBP complement (22133..23689)
<220> FEATURE:
<221> NAME/KEY: CDS
<222> LOCATION: (23720)..(26212)
<223> OTHER INFORMATION: 100K
<220> FEATURE:
<221> NAME/KEY: CDS
<222> LOCATION: (26866)..(27546)
<223> OTHER INFORMATION: pVIII
<220> FEATURE:
<221> NAME/KEY: CDS
<222> LOCATION: (27549)..(27863)
<223> OTHER INFORMATION: E3[1]2.5K
<220> FEATURE:
<221> NAME/KEY: CDS
<222> LOCATION: (28251)..(28787)
<223> OTHER INFORMATION: E3>p19K
<220> FEATURE:
<221> NAME/KEY: CDS
<222> LOCATION: (28820)..(29428)
<223> OTHER INFORMATION: E3©R1-beta
<220> FEATURE:
<221> NAME/KEY: CDS
<222> LOCATION: (29442)..(29780)
<223> OTHER INFORMATION: E3©R1-gamma
<220> FEATURE:
<221> NAME/KEY: CDS
<222> LOCATION: (29822)..(30094)
<223> OTHER INFORMATION: E3®IDålpha
<220> FEATURE:
<221> NAME/KEY: CDS
<222> LOCATION: (30487)..(30891)
<223> OTHER INFORMATION: E3[1]4.7K
<220> FEATURE:
<221> NAME/KEY: misc_feature
<222> LOCATION: (30948)..(31105)
<223> OTHER INFORMATION: U[e]xon complement (30948..31105)
<220> FEATURE:
<221> NAME/KEY: CDS
<222> LOCATION: (31118)..(32080)
<223> OTHER INFORMATION: fiber
<220> FEATURE:
<221> NAME/KEY: misc_feature
<222> LOCATION: (32126)..(33300)
<223> OTHER INFORMATION: E4ørf[6]/7 complement (32126..32374,33097..
33300)
<220> FEATURE:
<221> NAME/KEY: misc_feature
<222> LOCATION: (32374)..(33300)
<223> OTHER INFORMATION: E4ørf6 complement (32374..33300)
<220> FEATURE:
<221> NAME/KEY: misc_feature
<222> LOCATION: (33176)..(33556)

<223> OTHER INFORMATION: E4ørf4 complement (33176..33556)
<220> FEATURE:
<221> NAME/KEY: misc_feature
<222> LOCATION: (33569)..(33919)
<223> OTHER INFORMATION: E4ørf3 complement (33569..33919)
<220> FEATURE:
<221> NAME/KEY: misc_feature
<222> LOCATION: (33919)..(34305)
<223> OTHER INFORMATION: E4ørf2 complement (33919..34305)
<220> FEATURE:
<221> NAME/KEY: misc_feature
<222> LOCATION: (34350)..(34721)
<223> OTHER INFORMATION: E4ørf1 complement (34350..34721)
<220> FEATURE:
<221> NAME/KEY: repeat_region
<222> LOCATION: (34989)..(35100)
<223> OTHER INFORMATION: ITR[\]m(1bp ismatch complement (34989..35100)

<400> SEQUENCE: 1
catcatcaat aatatacctt ataaatggaa cggtgccaac atgcaaatga gcttttgaaa 60
atggagggcg gaaggggatt ggccagcggg ttcaacggtc aaaaggggcg gggaggtgac 120
gtgtttactg tgggaggagt tatgttgcaa gttctcgcgg taaatgtgac gtaaaacgag 180
gtgtggtttg aacacggaag tagacagttt tcccgcgctg actgacagga tatgaggtag 240
ttttgggcgg atgcaagtga aaattctcca ttttcgcgcg aaaactgaat gaggaagtga 300
atttctgagt aatttcgagt ttatgacagg gcggagtatt taccgagggc cgagtagact 360
ttgaccgatt acgtggaggt ttcgattacc gtgtttttca cctaaatttc cgcgtacggt 420
gtcaaagtcc tgtgttttta cgtaggcgtc agctgatcgc tagggtattt aaacctgacg 480
agttccgtca agaggccact cttgagtgcc agcgagaaga gatttctcct ccgcgccgcg 540
agtcagatct ccactttgaa aaaatgagac acctgcgatt cctgcctcag gaaatctcca 600
ttgcgaccgg gaatgaaata ctgcagtttg tggtagatgc cctgatggga gacgatccgg 660
agccgcctgc gcagcctttc gatcctccta cgcttcatga actgtatgat ttagaggtag 720
acgggccgga ggatcctaac gaggaagctg tgaatgggtt tttcagcgat tctatgctat 780
tagctgctag tgaaggagtg gacttagacc caccttctga gacccttgat accccagggg 840
tggtggtgga aagcggcaga ggtgggaaaa aattgcctga acttggtgct gctgaaatgg 900
atttgcactg ttatgaagag ggctttcctc cgagtgatga tgacgatgag gaaaatgtgc 960
agtcgatcca gaccgcagcg ggtgagggaa tgaaagctgc caatgatggt tttaagttgg 1020
actgcccgga gctgcctgga catggctgta agtcttgtga atttcacagg aatagtactg 1080
gactaaaaga actgttgtgc tcgctttgct atatgagaac gcactgccat tttatttaca 1140
gtaagtgtgt ctaacttaaa tttaaaggga cagtgtagca gtttaatgtc tgttgaatgt 1200
gggatttatg tctttgtgat ttttataggt cctgtgtctg atgctgatga atcgccttct 1260
cctgattcaa ctacctcacc tcctgaaatt caggcgccag tccctgcaaa cgtatgcaag 1320
cccattcctg tgaaggctaa gcctgggaaa cgccctgctg tggataaact ggaggacttg 1380
cttgagggtg gggatggacc tttggacttg agtacccgga aactgccaag gcaatgagtg 1440
ccctgcacct gtgtttattt aatgtgacgt cagtatttat gtgagagtgc catgtaataa 1500
aattatgtca gctgctgagt attttattgc ttcttgggtg gggacttgga tatataagta 1560
ggagcagacc tgtgtggtta gctcacagca gcttgctgcc atccatggag gtttgggcta 1620
tcttggaaga tctcaggcag actagacaac tgctagaaaa cgcctcggac ggagtctcta 1680
gtctttggag attctggttc ggtggtgatc tagctaggct agtctttagg gtaaaacggg 1740
agtatagtga agaatttgaa aagttattgg aagacagtcc aggacttttt gaagccctta 1800

```
actttgggcca ccaggctcat tttaaggaga aggttttatc agttttagat ttttctaccc   1860

ctggtagaac tgctgctgct gtagctttcc ttacttttat attggataa atg gat ccc   1918
                                                       Met Asp Pro
                                                       1

aca aac cca ctt cag caa ggg ata cgt ctt gga ttt cat agc agc agc      1966
Thr Asn Pro Leu Gln Gln Gly Ile Arg Leu Gly Phe His Ser Ser Ser
    5                   10                  15

ttt gtg gag aac atg gaa ggc ccg cag gct gag gat aat ctt aga tta      2014
Phe Val Glu Asn Met Glu Gly Pro Gln Ala Glu Asp Asn Leu Arg Leu
20                  25                  30                  35

ctg gcc agt gca gcc tct ggg cgt agc agc aat cct gag aca ccc acc      2062
Leu Ala Ser Ala Ala Ser Gly Arg Ser Ser Asn Pro Glu Thr Pro Thr
                40                  45                  50

ggc cat gcc agc ggt ttt gga gga gga gca gca gga gga caa ccc gag      2110
Gly His Ala Ser Gly Phe Gly Gly Gly Ala Ala Gly Gly Gln Pro Glu
            55                  60                  65

agc cgg cct gga ccc tcc ggt gga gga ggc gga gga gta gct gac ctg      2158
Ser Arg Pro Gly Pro Ser Gly Gly Gly Gly Gly Gly Val Ala Asp Leu
        70                  75                  80

ttt cct gaa ctg cga cgg gtg ctt act agg tct acg tcc agt gga cag      2206
Phe Pro Glu Leu Arg Arg Val Leu Thr Arg Ser Thr Ser Ser Gly Gln
    85                  90                  95

gac agg ggc att aag agg gag agg aat gct agt ggg cat aat tca aga      2254
Asp Arg Gly Ile Lys Arg Glu Arg Asn Ala Ser Gly His Asn Ser Arg
100                 105                 110                 115

act gag ttg gct tta agt tta atg agt cgc agc cgc cct gaa act atc      2302
Thr Glu Leu Ala Leu Ser Leu Met Ser Arg Ser Arg Pro Glu Thr Ile
                120                 125                 130

tgg tgg cat gag gtt cag agc gag ggc agg gat gaa gtt tca ata ttg      2350
Trp Trp His Glu Val Gln Ser Glu Gly Arg Asp Glu Val Ser Ile Leu
            135                 140                 145

cag gaa aaa tat tct cta gaa caa att aaa acc tgt tgg ttg gaa cct      2398
Gln Glu Lys Tyr Ser Leu Glu Gln Ile Lys Thr Cys Trp Leu Glu Pro
        150                 155                 160

gag gat gat tgg gag gtg gcc att agg aat tat gct aag ata tct ctg      2446
Glu Asp Asp Trp Glu Val Ala Ile Arg Asn Tyr Ala Lys Ile Ser Leu
    165                 170                 175

agg cct gat aaa cag tat aaa att acc aaa aag att aat atc aga aat      2494
Arg Pro Asp Lys Gln Tyr Lys Ile Thr Lys Lys Ile Asn Ile Arg Asn
180                 185                 190                 195

gca tgc tac ata gca ggg aat ggg gcc gag gtt ata ata gat aca cca      2542
Ala Cys Tyr Ile Ala Gly Asn Gly Ala Glu Val Ile Ile Asp Thr Pro
                200                 205                 210

gat aaa aca gct ttt agg tgt tgc atg atg ggt atg tgg cca ggg gtg      2590
Asp Lys Thr Ala Phe Arg Cys Cys Met Met Gly Met Trp Pro Gly Val
            215                 220                 225

gct ggc atg gag gca gtg acc ctt atg aat ata agg ttt agg gga gat      2638
Ala Gly Met Glu Ala Val Thr Leu Met Asn Ile Arg Phe Arg Gly Asp
        230                 235                 240

ggg tat aat ggg att gtc ttt atg gct aac act aag ctg att ctg cat      2686
Gly Tyr Asn Gly Ile Val Phe Met Ala Asn Thr Lys Leu Ile Leu His
    245                 250                 255

ggt tgt agc ttt ttt ggg ttt aat aat act tgt gtg gaa tct tgg gga      2734
Gly Cys Ser Phe Phe Gly Phe Asn Asn Thr Cys Val Glu Ser Trp Gly
260                 265                 270                 275

caa gtc agt atc agg ggt tgt agt ttc tat gca tgc tgg att gca cta      2782
Gln Val Ser Ile Arg Gly Cys Ser Phe Tyr Ala Cys Trp Ile Ala Leu
                280                 285                 290
```

```
tca ggc aga acc aag agt cag ttg tct gtg aag aaa tgc atg ttc gag     2830
Ser Gly Arg Thr Lys Ser Gln Leu Ser Val Lys Lys Cys Met Phe Glu
            295                 300                 305

aga tgt aac ctg ggc ata ctg aat gaa ggt gaa gca agg gtc cgc cac     2878
Arg Cys Asn Leu Gly Ile Leu Asn Glu Gly Glu Ala Arg Val Arg His
        310                 315                 320

tgt gct gct aca gaa act ggc tgc ttc att cta ata aag gga aat gcc     2926
Cys Ala Ala Thr Glu Thr Gly Cys Phe Ile Leu Ile Lys Gly Asn Ala
    325                 330                 335

agt gtg aag cat aac atg atc tgt gga ccc ttg gat gag agg cct tat     2974
Ser Val Lys His Asn Met Ile Cys Gly Pro Leu Asp Glu Arg Pro Tyr
340                 345                 350                 355

cag atg ctg acc tgt gct gga gga cat tgc aat atg ctg gct act gtg     3022
Gln Met Leu Thr Cys Ala Gly Gly His Cys Asn Met Leu Ala Thr Val
                360                 365                 370

cat att gtt tct cat gca cgc aag aaa tgg cct gtt ttt gaa cat aat     3070
His Ile Val Ser His Ala Arg Lys Lys Trp Pro Val Phe Glu His Asn
            375                 380                 385

gtg atg acc aag tgc acc atg cac gca ggt ggt cgc agg gga atg ttt     3118
Val Met Thr Lys Cys Thr Met His Ala Gly Gly Arg Arg Gly Met Phe
        390                 395                 400

atg cct tac cag tgt aac atg aat cat gtg aag gtg atg ttg gaa cca     3166
Met Pro Tyr Gln Cys Asn Met Asn His Val Lys Val Met Leu Glu Pro
    405                 410                 415

gat gcc ttt tcc aga atg agc tta aca gga atc ttt gat atg aat gtg     3214
Asp Ala Phe Ser Arg Met Ser Leu Thr Gly Ile Phe Asp Met Asn Val
420                 425                 430                 435

caa cta tgg aag atc ctg aga tat gat gag acc aaa tcg agg gtg cgc     3262
Gln Leu Trp Lys Ile Leu Arg Tyr Asp Glu Thr Lys Ser Arg Val Arg
                440                 445                 450

gca tgc gag tgc ggg ggc aag cat gcc agg ttc cag ccg gtg tgt gtg     3310
Ala Cys Glu Cys Gly Gly Lys His Ala Arg Phe Gln Pro Val Cys Val
            455                 460                 465

gat gtg acg gaa gac ctg aga ccc gat cat ttg gtg ctt gcc tgc act     3358
Asp Val Thr Glu Asp Leu Arg Pro Asp His Leu Val Leu Ala Cys Thr
        470                 475                 480

gga gcg gag ttc ggt tct agt ggg gaa gaa act gac taaagtgagt          3404
Gly Ala Glu Phe Gly Ser Ser Gly Glu Glu Thr Asp
    485                 490                 495

agtggggaat gctgtggagg ggggcttcca ggcgggtaag gtgggcagat tgggtaaatt   3464

ctgtttcttt ctgtcttgca gctgcc atg agt gga agc gct tct ttt gag ggg    3517
                             Met Ser Gly Ser Ala Ser Phe Glu Gly
                                             500

gga gtc ttt agc cct tat ctg acg ggg cga ctc cca ccc tgg gca gga     3565
Gly Val Phe Ser Pro Tyr Leu Thr Gly Arg Leu Pro Pro Trp Ala Gly
505                 510                 515                 520

gtt cgt cag aat gtc atg gga tcc act gtg gat ggg agg ccc gtc cag     3613
Val Arg Gln Asn Val Met Gly Ser Thr Val Asp Gly Arg Pro Val Gln
                525                 530                 535

ccc gcc aat tcc tca acg ctg acc tat gcc act ttg agc tct tca ccc     3661
Pro Ala Asn Ser Ser Thr Leu Thr Tyr Ala Thr Leu Ser Ser Ser Pro
            540                 545                 550

ttg gat gca gct gca gcc gct gcc gcc tct gct gcc gcc aac act gtc     3709
Leu Asp Ala Ala Ala Ala Ala Ala Ala Ser Ala Ala Ala Asn Thr Val
        555                 560                 565

ctt gga atg ggc tat tat gga agc atc gtt gcc aat tcc agt tcc tca     3757
Leu Gly Met Gly Tyr Tyr Gly Ser Ile Val Ala Asn Ser Ser Ser Ser
    570                 575                 580

aat aac cct tcg acc ctg gct gag gac aag cta ctt gtc ctc ttg gct     3805
```

```
Asn Asn Pro Ser Thr Leu Ala Glu Asp Lys Leu Leu Val Leu Leu Ala
585                 590                 595                 600

cag ctc gag gcc ttg acc cag cgc cta ggc gaa ctg tct cag cag gtg      3853
Gln Leu Glu Ala Leu Thr Gln Arg Leu Gly Glu Leu Ser Gln Gln Val
                605                 610                 615

gcc cag ttg cgc gag caa act gag tct gct gtt gcc aca gca aag tct      3901
Ala Gln Leu Arg Glu Gln Thr Glu Ser Ala Val Ala Thr Ala Lys Ser
            620                 625                 630

aaa taaagattcc caaatcaata aataaaggag atccttgttg attgtaaaac          3954
Lys

aagtgtaatg aatctttatt tgatttttcg cgcgcggtat gccctggacc accggtctcg   4014

atcattgaga actcggtgga tcttttccag gaccctgtag aggtgggatt gaatgtttag   4074

atacatgggc attaggccgt ctcgggggtg gagatagctc cattgaagag cctcatgctc   4134

tggggtagtg ttataaatca cccagtcata acaaggtcgg agtgcatggt gttgcacaat   4194

atcttttagg agcaggctaa ttgcaacggg gaggccctta gtgtaggtgt ttacaaatct   4254

gttgagctgg gacgggtgca ttcggggtga aattatatgc attttggact ggatcttgag   4314

gttggcaatg ttgccgccta gatcccgtct cgggttcata ttgtgcagga ccaccaagac   4374

agtgtatccg gtgcacttgg gaaatttatc atgcagctta gagggaaaag catgaaaaaa   4434

tttcgagacg cctttgtgtc cgcccagatt ctccatgcac tcatccataa tgatagcgat   4494

ggggccgtgg gcggcggcgc gggcaaacac gttccggggg tctgacacat catagttatg   4554

ctcctgagtc aggtcatcat aagccatttt aataaacttg ggcggagggg tgccagattg   4614

ggggatgaaa gttccctcgg gccccggagc atagtttccc tcacatattt gcatttccca   4674

ggctttcagt tcagaggggg ggatcatgtc cacctgcggg gctataaaaa ataccgtttc   4734

tggagcgggg gtgattaact gggatgagag caaattcctg agcagctgag acttgccgca   4794

cccagtggga ccgtaaatga ccccgattac gggttgcaga tggtagttta gggagcggca   4854

gctgccgtcc tcccggagca ggggggccac ttcgttcatc atttccctta catggatatt   4914

ttcccgcacc aagtccgtta ggaggcgctc tcccccccagg gatagaagct cctggagcga   4974

ggagaagttt ttcagcggct tcagcccgtc agccatgggc attttggaga gagtctgttg   5034

caagagctcg agccggtccc agagctcggt gatgtgttct atggcatctc gatccagcag   5094

acctcctcgt ttcgcgggtt ggggcggctc ctggagtatg gtatcagacg atgggcgtcc   5154

agcgctgcca gggtccgatc tttccagggt cgcagcgttc gagtcagggt tgtttccgtc   5214

acggtgaagg ggtgcgcgcc tggttgggcg cttgcgaggg tgcgtttcag gctcatcctg   5274

ctggtcgaga accgctgccg atcggcgccc tgcatgtcgg ccaggtagca gtttaccatg   5334

agttcgtagt tgagtgcctc ggccgcgtgg cctttggcgc ggagcttacc tttggaagtt   5394

ttctggcagg cggggcagta cagacacttg agggcataca gtttgggagc gaggaagatg   5454

gattcggggg agtatgcgtc cgcaccgcag gaggcgcaga cggtttcgca ttccacgagc   5514

caggtcagat ccggctcatc ggggtcaaaa acaagttttc ccccatgttt tttgatgcgt   5574

ttcttacctt tggtctccat gagttcgtgt ccccgctggg tgacaaagag gctgtccgtg   5634

tccccgtaga ccgattttat gggcctgtcc tcgagcggag tgcctcggtc ctcttcgtag   5694

aggaactcgg accactctga tacaaaggcg cgcgtccagg ccagcacaaa agaggccacg   5754

tgggaggggt agcggtcgtt gtcaaccagg gggtccacct tctccacggt atgtaaacac   5814

atgtccccct cctccacatc caagaatgtg attggcttgt aagtgtatgc cacgtgacca   5874

ggggtccccg ccgggggggt ataaaagggg gcgggtctct gctcgtcctc actgtcttcc   5934
```

```
ggatcgctgt ccaggagcgc cagctgttgg ggtaggtatt ccctctcgaa ggcgggcata   5994
acctctgcac tcaggttgtc agtttctagg aacgaggagg atttgatatt gacagtgcca   6054
gccgagatgc ctttcataag actctcgtcc atttggtcag aaaatacaat ctttttgttg   6114
tccagcttgg tggcaaagga tccatagagg gcattggata agagcttggc tatggagcgc   6174
atggtttggt tcttttcctt gtcagcgcgc tccttggcag caatgttgag ctggacatac   6234
tcgcgcgcca gacacttcca ttcagggaag atggttgtca gttcatctgg cacgattctg   6294
actcgccagc ccctgttatg cagggtgatc agatccacac tggtggtcac ttcgcctctg   6354
aggggctcgt tggtccagca gagtcgaccc ccttttctcg aacagaaagg tgggaggggg   6414
tctagcatga gttcatcagg ggggtctgca tccatagtga agattcctgg gagcagatcc   6474
ttgtcaaaat agctgatggg tgtggggtca tccaaagcca tctgccattc tcgagccgcc   6534
agcgcgcgct catagggggtt gagaggggtg ccccatggca tggggtgggt gagtgcagag   6594
gcatacatgc cacagatgtc atagacatag aggggctctt caagaatgcc aatgtaggtg   6654
ggataacagc gcccccctct gatgcttgct cgcacatagt catagagttc atgcgagggg   6714
gcgagcagac ccgagcccaa attagtgcga ttgggttttt cagccctgta gacgatctgg   6774
cgaaagatgg catgtgaatt tgaagagatg gtgggtctct gaaagatgtt aaaatgggca   6834
tgaggtagac ctacagagtc cctgatgaag tgggcatatg actcttgcag cttggccacc   6894
agctctgcag tgacaaggac atccaaggcg cagtagtcaa gggtctcttg gatgatgtca   6954
taacctggtt ggtttttctt ttcccacagc tcgcggttga gaaggtattc ttcgcgatcc   7014
ttccagtact cttcgagggg aaacccgtct ttgtctgcac ggtaagagcc cagcatgtag   7074
aactgattaa ctgctttgta gggacagcat cccttctcca cggggagaga gtatgcttgg   7134
gctgccttgc gcagtgaggt atgagtgagg gcgaaggtgt ccctgaccat gactttgagg   7194
aactggtgct tgaaatcgat gtcatcacag gccccctgtt cccagagttg gaagtccacc   7254
cgcttcttgt aggcggggtt gggcaaagcg aaagtaacat cattgaagag aatcttgccg   7314
gccctgggca tgaaattgcg ggtgatgcgg aaaggctggg gcacctctgc ccggttattg   7374
atcacctgag cggctaggac gatctcgtca aagccattga tgttgtgtcc cacaatgtaa   7434
agttctatga atcgcggggt gcccctgaca tgaggcagct tcttgagttc ttcaaaagtg   7494
aggtctgtag ggtcagagag agcatagtgt tcgagggccc attcgtgcag gtgagggttt   7554
gcattgagga aggaggacca gagatccact gccagtgctg tttgtaactg gtctcggtac   7614
tggcgaaaat gctggccgac tgccatcttt tctggggtga tacagtagaa ggtttttgggg   7674
tcttgctgcc agcgatccca cttgagtttg atggcgaggt cgtaggcgat gttgacgagc   7734
cgctcgtccc ccgaaagttt catgaccagc atgaatggga tcagctgctt gccaaaggac   7794
cccatccagg tgtaggtttc cacatcgtag gtgaggaaga gcctttctgt gcgaggatga   7854
gagccgatcg ggaagaactg gatctcctgc caccagttgg aggaatggct gttgatgtga   7914
tggaagtaga actccctgcg gcgcgccgag cattcatgct tgtgcttata cagacggccg   7974
cagtactcgc agcgcttcac gggatgcacc tcatgaatga gttgtacctg gcttcctttg   8034
acgagaaatt tcagtgggaa gttgaggcct ggcgcttgta cctcgcgctc tactatgtta   8094
tctgcatcgg cctggccatc ttctgtctcg atggtggtca tgctgacgag cccccgcggg   8154
aggcaagtcc agacctcggc gcgggagggg cggagctcga ggacgagagc gcgcaggccg   8214
gagctgtcca gggtcctgag tcgctgcgga gtcaggttag taggtagtgt caggagatta   8274
```

```
acttgcatga tcttttcgag ggcatgcggg aggttcagat ggtacttgat ttccacgggt   8334
ccgttggtgg agatgtcgat ggcttgcagg gtcccatgcc ccttgggcgc caccaccgtg   8394
cccttgtttt tccttttggg cggcggtggc tctgttgctt cttgcatgtt cagaagcggt   8454
ggcgagggcg cgcgccgggc ggtaggggcg gctctggccc cggcggcatg gctggtagag   8514
gcacgtcggc gccgcgcgcg ggtaggttct ggtactgcgc cctgagaaga cttgcgtgcg   8574
cgacgacgcg gcggttgacg tcctggatct gacgcctctg ggtgaaagct accggacccg   8634
tgagcttgaa cctgaaagag agttcaacag aatcaatttc ggtatcgttg acggcggctt   8694
gcctcaggat ctcttgcacg tcgcccgagt tgtcctggta ggcgatctcg gccatgaact   8754
gctcgatttc ttcctcctga agatctccgc ggcccgctct ctcgacggtg gccgcgaggt   8814
cgttggagat gcgacccatg agttgagaga atgcattcat gcccgcctcg ttccagacgc   8874
ggctgtagac cacggccccc tcgggatctc tcgcgcgcat gaccacctgg gcgaggttga   8934
gctccacgtg gcgggtgaag accgcatagt tgcataggcg ctggaagagg tagttgagtg   8994
tggtggcgat gtgctcggtg acgaagaaat acatgatcca tcgtctcagc ggcatctcgc   9054
tgacatcgcc cagggcttcc aagcgctcca tggcctcgta gaagtccaca gcgaagttga   9114
aaaactggga gttgcgcgcg gacacggtca actcctcctc cagaagacgg atgagatcgg   9174
cgatggtggc gcgcacctcg cgctcgaagg cccccgggat ttcttcctcc tcctcttcta   9234
tctcttcttc cactaacatc tcttcttcct cttcaggcgg gggcggagga ggagggggcg   9294
cgcggcgacg ccggcggcgc acgggcagac ggtcgatgaa tctttcaatg acctctccgc   9354
ggcggcggcg catggtctcg gtgacggcgc ggccgttctc cctgggtctc aaagtgaaga   9414
cgcctccgcg catctccttg aagtggtgac tgggggggctc tccgttgggc agggacaggg   9474
cgctgatgat gcattttatc aattgccccg tagggactcc gcgcaaggac ctgatcgtct   9534
gaagatccac gggatctgaa aacctttcga cgaaagcgtc taaccagtcg caatcgcaag   9594
gtaggctgag caccgtttct tgcgggcggg ggttctctct tccttctcct tcctcatcat   9654
ctcgggaggg taagacgatg ctgctggtga tgaaattaaa ataggcagtt ctgagacggc   9714
ggatggtggc gaggagcacc aggtctttgg gtccggcttg ctggatgcgc aggcgatcgg   9774
ccattcccca agcattgtcc tggcatctgg ccagatcttt atagtagtct tgcatgagtc   9834
gctccacggg cacttcttct tcgcccgctc taccatgcat gcgcgtgagc ccgaacccgc   9894
gcatgggctg gacaagtgcc aagtccgcta cgaccctttc ggcgaggatg gcttgctgca   9954
cctgggtgag ggtggcttgg aagtcgtcaa agtccacgaa gcgatggtag gccccggtgt  10014
taatggtgta ggagcagttg gccatgactg accagttgac tgtctggtgc cccgggcgca  10074
cgatctcggt gtacttgagt cgcgagtagg cgcgggtgtc aaagatgtaa tcgttgcagg  10134
tgcgcaccag gtactggtag ccgatgagaa agtgcggcgg tggctggcgg tagaggggcc  10194
atcgctctgt agccggggct ccgggggcga ggtcttccag catgaggcgg tggtatccgt  10254
agatgtacct ggacatccag gtgatcccgg aggcggtggt ggacgctcgc gggaactcgc  10314
gcactcggtt ccagatgttg cgcagcggca tgaagtagtt catggtaggc acggtctggc  10374
cagtgaggcg ggcgcagtca ttgatgctct atagacacgg agaaaacgaa agcgatgagc  10434
ggctcgcctc cgtggcctgg aggaacgtga acgggttggg tcgcggtgta ccccggttcg  10494
agaccaaagc caagcgagca caactcgggc cggccggagc cgtggctaac gtggtattgg  10554
cgatcccgtc tcgacccagc cgacgaatat ccaggatacg gagtcgagtc gttttgctgc  10614
ttgttgcttt ttctggacgg gagccagcac cgcgtcaagc tttagaacgc tcagttcacg  10674
```

```
gggtcgggag tggctcgcgc ccgtagtctg gagaatcaat cgccagggtt gcgttgcggt  10734

gtgccccggt tcgagcctta gcgcggcccg gatcggccgg tttccgcggc aagcgagggt  10794

ttggcagccc cgtcatttct aagaccccgc cagccgactt ctccagttta cgggagcgag  10854

ccctcttttt tttgtttttg tcgcccag atg cat ccc gtg ctg cga cag atg     10906
                              Met His Pro Val Leu Arg Gln Met
                                  635                 640

cgc ccc cag caa cag gcc cct tct cag caa cag cag cag cca caa aag    10954
Arg Pro Gln Gln Gln Ala Pro Ser Gln Gln Gln Gln Gln Pro Gln Lys
            645                 650                 655

gct ctt cct gct cct gct ccc gca act act gca gtc gca gcc gtg tgc    11002
Ala Leu Pro Ala Pro Ala Pro Ala Thr Thr Ala Val Ala Ala Val Cys
        660                 665                 670

ggc gcg ggt cag ccc gcc tat gat ctg gac ttg gaa gag ggc gag gga    11050
Gly Ala Gly Gln Pro Ala Tyr Asp Leu Asp Leu Glu Glu Gly Glu Gly
    675                 680                 685

ctg gca cgc ctg ggt gca cca tcg ccc gag cgg cac ccg cgg gtg caa    11098
Leu Ala Arg Leu Gly Ala Pro Ser Pro Glu Arg His Pro Arg Val Gln
690                 695                 700                 705

ctg aaa aag gac tct cgc gag gcg tac gtg ccc cag cag aac ctg ttc    11146
Leu Lys Lys Asp Ser Arg Glu Ala Tyr Val Pro Gln Gln Asn Leu Phe
                710                 715                 720

agg gac agg agc ggc gag gag ccc gag gag atg cga gcc tcc cgc ttt    11194
Arg Asp Arg Ser Gly Glu Glu Pro Glu Glu Met Arg Ala Ser Arg Phe
            725                 730                 735

aac gcg ggt cgc gag ctg cgc cac ggt ctg gac cga aga cgg gtg ctg    11242
Asn Ala Gly Arg Glu Leu Arg His Gly Leu Asp Arg Arg Arg Val Leu
        740                 745                 750

cgg gac gag gat ttc gag gtc gat gaa atg aca ggg atc agc ccc gct    11290
Arg Asp Glu Asp Phe Glu Val Asp Glu Met Thr Gly Ile Ser Pro Ala
    755                 760                 765

agg gca cat gtg gcc gcg gcc aac ctc gtc tcg gcc tac gag cag acc    11338
Arg Ala His Val Ala Ala Ala Asn Leu Val Ser Ala Tyr Glu Gln Thr
770                 775                 780                 785

gtg aag gag gag cgc aat ttc caa aaa tca ttc aac aac cat gtg cgc    11386
Val Lys Glu Glu Arg Asn Phe Gln Lys Ser Phe Asn Asn His Val Arg
                790                 795                 800

acc ctg atc gcc cgt gag gaa gtg acc ctg ggt ctg atg cac ctg tgg    11434
Thr Leu Ile Ala Arg Glu Glu Val Thr Leu Gly Leu Met His Leu Trp
            805                 810                 815

gac ctg atg gaa gct atc acc cag aac cca act agc aaa ccc ctg acc    11482
Asp Leu Met Glu Ala Ile Thr Gln Asn Pro Thr Ser Lys Pro Leu Thr
        820                 825                 830

gct cag ctg ttt ctg gtg gtg caa cac agc agg gac aat gag gca ttc    11530
Ala Gln Leu Phe Leu Val Val Gln His Ser Arg Asp Asn Glu Ala Phe
    835                 840                 845

agg gag gcg ctg cta aac atc acc gag ccc gaa ggg aga tgg ttg tat    11578
Arg Glu Ala Leu Leu Asn Ile Thr Glu Pro Glu Gly Arg Trp Leu Tyr
850                 855                 860                 865

gac ctg atc aat atc ctg cag agt att ata gtg cag gaa cgt agc ttg    11626
Asp Leu Ile Asn Ile Leu Gln Ser Ile Ile Val Gln Glu Arg Ser Leu
                870                 875                 880

ggt ctg gct gag aaa gtg gca gcc atc aac tac tcg gtc ttg agc ctg    11674
Gly Leu Ala Glu Lys Val Ala Ala Ile Asn Tyr Ser Val Leu Ser Leu
            885                 890                 895

ggc aag tac tac gct cgc aag atc tac aag acc ccc tac gtg ccc ata    11722
Gly Lys Tyr Tyr Ala Arg Lys Ile Tyr Lys Thr Pro Tyr Val Pro Ile
        900                 905                 910
```

```
gac aag gag gtg aag ata gat ggg ttt tac atg cgc atg act ctc aag    11770
Asp Lys Glu Val Lys Ile Asp Gly Phe Tyr Met Arg Met Thr Leu Lys
    915                 920                 925

gtt ctg act ctc agt gac gat ctg gga gtg tac cgc aat gac agg atg    11818
Val Leu Thr Leu Ser Asp Asp Leu Gly Val Tyr Arg Asn Asp Arg Met
930                 935                 940                 945

cac cgc gcg gtg agc gcc agc agg agg cgc gag ctg agc gac agg gaa    11866
His Arg Ala Val Ser Ala Ser Arg Arg Arg Glu Leu Ser Asp Arg Glu
                950                 955                 960

ctt atg cac agc ttg caa aga gct ctg acg ggg gca ggg aca gat ggg    11914
Leu Met His Ser Leu Gln Arg Ala Leu Thr Gly Ala Gly Thr Asp Gly
            965                 970                 975

gag aac tac ttt gac atg ggg gca gac ttg caa tgg caa cct agc cgc    11962
Glu Asn Tyr Phe Asp Met Gly Ala Asp Leu Gln Trp Gln Pro Ser Arg
        980                 985                 990

cgg gcc ctg gac gcg gca ggg  tgt gag ctt cct tac  gta gaa gag gtg  12010
Arg Ala Leu Asp Ala Ala Gly  Cys Glu Leu Pro Tyr  Val Glu Glu Val
    995                 1000                1005

gat  gaa ggc gag gag gag  gag ggc gag tac ctg  gaa gac tgatggcgcg  12059
Asp  Glu Gly Glu Glu Glu  Glu Gly Glu Tyr Leu  Glu Asp
1010                 1015                 1020

acccgtattt ttgctag atg gaa cag  cag gca ccg gac ccc  gca atg cgg   12109
                   Met Glu Gln  Gln Ala Pro Asp Pro  Ala Met Arg
                                1025                 1030

gcg gcg  ctg cag agc cag ccg  tcc ggc att aac tcc  tcg gac gat     12154
Ala Ala  Leu Gln Ser Gln Pro  Ser Gly Ile Asn Ser  Ser Asp Asp
    1035                 1040                 1045

tgg acc  cag gcc atg caa cgc  atc atg gcg ctg acg  acc cgc aac     12199
Trp Thr  Gln Ala Met Gln Arg  Ile Met Ala Leu Thr  Thr Arg Asn
    1050                 1055                 1060

ccc gaa  gcc ttt aga cag caa  ccc cag gcc aac cgc  ctt tcg gcc     12244
Pro Glu  Ala Phe Arg Gln Gln  Pro Gln Ala Asn Arg  Leu Ser Ala
    1065                 1070                 1075

atc ctg  gag gcc gta gtt cct  tcc cgc tcc aac ccc  acc cac gag     12289
Ile Leu  Glu Ala Val Val Pro  Ser Arg Ser Asn Pro  Thr His Glu
    1080                 1085                 1090

aag gtc  ctg gcc atc gtg aac  gcg ctg gtg gag aac  aag gcc atc     12334
Lys Val  Leu Ala Ile Val Asn  Ala Leu Val Glu Asn  Lys Ala Ile
    1095                 1100                 1105

cgt ccc  gat gag gcc ggg ctg  gta tac aat gcc ctc  ttg gag cgc     12379
Arg Pro  Asp Glu Ala Gly Leu  Val Tyr Asn Ala Leu  Leu Glu Arg
    1110                 1115                 1120

gtg gcc  cgc tac aac agc agc  aac gtg cag acc aac  ctg gac cgg     12424
Val Ala  Arg Tyr Asn Ser Ser  Asn Val Gln Thr Asn  Leu Asp Arg
    1125                 1130                 1135

atg gtg  aca gat gtg cgc gag  gcc gtg tct cag cgc  gag cgg ttc     12469
Met Val  Thr Asp Val Arg Glu  Ala Val Ser Gln Arg  Glu Arg Phe
    1140                 1145                 1150

cag cgc  gat gcc aac ttg ggg  tcg ctg gtg gcg ctg  aac gcc ttc     12514
Gln Arg  Asp Ala Asn Leu Gly  Ser Leu Val Ala Leu  Asn Ala Phe
    1155                 1160                 1165

ctc agc  acc cag cct gcc aac  gtg ccc cgc ggc cag  caa gac tat     12559
Leu Ser  Thr Gln Pro Ala Asn  Val Pro Arg Gly Gln  Gln Asp Tyr
    1170                 1175                 1180

aca aac  ttt cta agt gca ctg  aga ctc atg gta acc  gaa gtc cct     12604
Thr Asn  Phe Leu Ser Ala Leu  Arg Leu Met Val Thr  Glu Val Pro
    1185                 1190                 1195

cag agc  gag gtg tac cag tcc  gga cca gac tac ttt  ttc cag acc     12649
Gln Ser  Glu Val Tyr Gln Ser  Gly Pro Asp Tyr Phe  Phe Gln Thr
    1200                 1205                 1210
```

-continued

```
agc aga  cag ggc ttg cag aca  gtg aac ctg agc cag  gct ttc aaa     12694
Ser Arg  Gln Gly Leu Gln Thr  Val Asn Leu Ser Gln  Ala Phe Lys
    1215                 1220                 1225

aac ctc  aga ggc ctg tgg gga  gtg cac gcc cca gta  gga gat cgc     12739
Asn Leu  Arg Gly Leu Trp Gly  Val His Ala Pro Val  Gly Asp Arg
    1230                 1235                 1240

gcg acc  gtg tct agc ttg ctg  act ccc aac tcc cgc  cta ctg ctg     12784
Ala Thr  Val Ser Ser Leu Leu  Thr Pro Asn Ser Arg  Leu Leu Leu
    1245                 1250                 1255

ctg ctg  gta tcc ccc ttc act  gac agc ggt agc atc  gac cgc aac     12829
Leu Leu  Val Ser Pro Phe Thr  Asp Ser Gly Ser Ile  Asp Arg Asn
    1260                 1265                 1270

tcc tac  ttg ggc tac ctg ctg  aac ttg tat cgc gag  gcc ata ggg     12874
Ser Tyr  Leu Gly Tyr Leu Leu  Asn Leu Tyr Arg Glu  Ala Ile Gly
    1275                 1280                 1285

cag agt  cag gtg gac gag cag  acc tac caa gaa atc  acc caa gtg     12919
Gln Ser  Gln Val Asp Glu Gln  Thr Tyr Gln Glu Ile  Thr Gln Val
    1290                 1295                 1300

agc cgc  gcc ctg ggt cag gaa  gac acg ggc agc ttg  gaa gcc acc     12964
Ser Arg  Ala Leu Gly Gln Glu  Asp Thr Gly Ser Leu  Glu Ala Thr
    1305                 1310                 1315

ctg aac  ttc ttg ctg acc aac  cgg tcg cag aag atc  cct cct cag     13009
Leu Asn  Phe Leu Leu Thr Asn  Arg Ser Gln Lys Ile  Pro Pro Gln
    1320                 1325                 1330

tat gcg  ctt acc gcg gag gag  gag cgg atc ctc aga  tat gtg cag     13054
Tyr Ala  Leu Thr Ala Glu Glu  Glu Arg Ile Leu Arg  Tyr Val Gln
    1335                 1340                 1345

cag agc  gtg gga ctg ttc ctg  atg caa gag ggg gcg  acc cct agt     13099
Gln Ser  Val Gly Leu Phe Leu  Met Gln Glu Gly Ala  Thr Pro Ser
    1350                 1355                 1360

gcc gcg  ctg gac atg aca gcc  cga aac atg gag ccc  agc atg tat     13144
Ala Ala  Leu Asp Met Thr Ala  Arg Asn Met Glu Pro  Ser Met Tyr
    1365                 1370                 1375

gcc agt  aac cgg cct ttc atc  aac aaa ctg ctg gac  tac ctg cac     13189
Ala Ser  Asn Arg Pro Phe Ile  Asn Lys Leu Leu Asp  Tyr Leu His
    1380                 1385                 1390

agg gcg  gcc gcc atg aac tct  gat tat ttc acc aat  gct att ctc     13234
Arg Ala  Ala Ala Met Asn Ser  Asp Tyr Phe Thr Asn  Ala Ile Leu
    1395                 1400                 1405

aac ccc  cac tgg ctg ccc ccg  cct gga ttt tac acg  ggc gag tac     13279
Asn Pro  His Trp Leu Pro Pro  Pro Gly Phe Tyr Thr  Gly Glu Tyr
    1410                 1415                 1420

gac atg  ccc gac ccc aat gac  ggg ttc ctg tgg gac  gat gtg gac     13324
Asp Met  Pro Asp Pro Asn Asp  Gly Phe Leu Trp Asp  Asp Val Asp
    1425                 1430                 1435

agc agc  ata ttc tcc ccg ccc  cct ggt tat aac act  tgg aag aag     13369
Ser Ser  Ile Phe Ser Pro Pro  Pro Gly Tyr Asn Thr  Trp Lys Lys
    1440                 1445                 1450

gaa ggg  ggc gat aga aga cac  tct tcc gtg tcg ctg  tcc ggg tcg     13414
Glu Gly  Gly Asp Arg Arg His  Ser Ser Val Ser Leu  Ser Gly Ser
    1455                 1460                 1465

agg ggt  gct gcc gcc gcg gtg  ccc gag gct gca agt  cct ttc cct     13459
Arg Gly  Ala Ala Ala Ala Val  Pro Glu Ala Ala Ser  Pro Phe Pro
    1470                 1475                 1480

agc ctg  ccc ttt tct ctg aac  agc gtg cgc agc agt  gaa ctg ggg     13504
Ser Leu  Pro Phe Ser Leu Asn  Ser Val Arg Ser Ser  Glu Leu Gly
    1485                 1490                 1495

aga ata  acc cgc ccg cgc ttg  atg ggc gag gat gag  tac ttg aac     13549
Arg Ile  Thr Arg Pro Arg Leu  Met Gly Glu Asp Glu  Tyr Leu Asn
```

```
    1500                1505                1510

gac tcc  ttg ctt aga ccc gag  agg gaa aag aac ttc  ccc aac aat     13594
Asp Ser  Leu Leu Arg Pro Glu  Arg Glu Lys Asn Phe  Pro Asn Asn
    1515                1520                1525

ggt ata  gag agc ctg gtg gac  aag atg agt aga tgg  aag aca tat     13639
Gly Ile  Glu Ser Leu Val Asp  Lys Met Ser Arg Trp  Lys Thr Tyr
    1530                1535                1540

gca cag  gat cac aaa gac gag  cct agg atc ttg ggg  gct gcg agc     13684
Ala Gln  Asp His Lys Asp Glu  Pro Arg Ile Leu Gly  Ala Ala Ser
    1545                1550                1555

ggg acg  acc cgt aga cgc cag  cgc cat gac aga cag  agg ggt ctt     13729
Gly Thr  Thr Arg Arg Arg Gln  Arg His Asp Arg Gln  Arg Gly Leu
    1560                1565                1570

gtg tgg  gac gat gag gac tcg  gcc gat gac agc agc  gtg ttg gac     13774
Val Trp  Asp Asp Glu Asp Ser  Ala Asp Asp Ser Ser  Val Leu Asp
    1575                1580                1585

ttg ggt  ggg aga gga ggg ggc  aac ccg ttc gct cat  ctg cgc ccg     13819
Leu Gly  Gly Arg Gly Gly Gly  Asn Pro Phe Ala His  Leu Arg Pro
    1590                1595                1600

cac ttt  ggg cgc atg ttg taaaagtgaa agtaaaataa aaaggcaact          13867
His Phe  Gly Arg Met Leu
    1605

caccaaggcc atggcgacga gcgtgcgttc gttcttttct gttatctgtg tctagt      13923

atg  atg agg cga gcc gtg  cta ggc gga gcg gtg  gtg tat ccg gag     13968
Met  Met Arg Arg Ala Val  Leu Gly Gly Ala Val  Val Tyr Pro Glu
1610                1615                1620

ggt  cct cct cct tcg tac  gag agc gtg atg cag  cag cag gcg gcg     14013
Gly  Pro Pro Pro Ser Tyr  Glu Ser Val Met Gln  Gln Gln Ala Ala
1625                1630                1635

gcg  gtg atg cag ccc tcg  ctg gag gct ccc ttt  gta ccc ccg cgg     14058
Ala  Val Met Gln Pro Ser  Leu Glu Ala Pro Phe  Val Pro Pro Arg
1640                1645                1650

tac  ctg gcg cct aca gag  ggg aga aac agc att  cgt tac tcg gag     14103
Tyr  Leu Ala Pro Thr Glu  Gly Arg Asn Ser Ile  Arg Tyr Ser Glu
1655                1660                1665

ctg  gca ccc cag tac gat  acc acc agg ttg tat  ctg gtg gac aac     14148
Leu  Ala Pro Gln Tyr Asp  Thr Thr Arg Leu Tyr  Leu Val Asp Asn
1670                1675                1680

aag  tcg gcg gac atc gcc  tca ttg aac tat cag  aac gac cac agc     14193
Lys  Ser Ala Asp Ile Ala  Ser Leu Asn Tyr Gln  Asn Asp His Ser
1685                1690                1695

aac  ttc ctg acc acg gtg  gtg cag aac aat gac  ttt acc ccc acg     14238
Asn  Phe Leu Thr Thr Val  Val Gln Asn Asn Asp  Phe Thr Pro Thr
1700                1705                1710

gag  gcc agc acc cag acc  atc aac ttt gac gag  cgg tcg cgg tgg     14283
Glu  Ala Ser Thr Gln Thr  Ile Asn Phe Asp Glu  Arg Ser Arg Trp
1715                1720                1725

ggc  ggt cag ctg aag acc  atc atg cac acc aac  atg ccc aac gtg     14328
Gly  Gly Gln Leu Lys Thr  Ile Met His Thr Asn  Met Pro Asn Val
1730                1735                1740

aac  gag tac atg ttc agc  aac aag ttc aag gcg  cgg gtg atg gtg     14373
Asn  Glu Tyr Met Phe Ser  Asn Lys Phe Lys Ala  Arg Val Met Val
1745                1750                1755

tca  cgc aag aaa cct gaa  ggc tat aca ggg gat  aaa aat gat aca     14418
Ser  Arg Lys Lys Pro Glu  Gly Tyr Thr Gly Asp  Lys Asn Asp Thr
1760                1765                1770

agt  cag gat att ctg gag  tat gag tgg ttt gag  ttc act tta cca     14463
Ser  Gln Asp Ile Leu Glu  Tyr Glu Trp Phe Glu  Phe Thr Leu Pro
1775                1780                1785
```

```
gaa  ggc aac ttc tca gcc  acc atg acc atc gac  ctg atg aac aat     14508
Glu  Gly Asn Phe Ser Ala  Thr Met Thr Ile Asp  Leu Met Asn Asn
1790                1795                1800

gcc  atc att gac aac tac  ctg gca gtg ggc aga  cag aat gga gtg     14553
Ala  Ile Ile Asp Asn Tyr  Leu Ala Val Gly Arg  Gln Asn Gly Val
1805                1810                1815

ttg  gaa agc gac atc ggt  gtc aag ttt gat acc  agg aac ttc agg     14598
Leu  Glu Ser Asp Ile Gly  Val Lys Phe Asp Thr  Arg Asn Phe Arg
1820                1825                1830

ctg  ggc tgg gac ccc ata  act aaa ctt gtt atg  cca gga gtc tac     14643
Leu  Gly Trp Asp Pro Ile  Thr Lys Leu Val Met  Pro Gly Val Tyr
1835                1840                1845

act  tat gaa gcc ttc cat  cct gat att gtg cta  cta cct ggc tgt     14688
Thr  Tyr Glu Ala Phe His  Pro Asp Ile Val Leu  Leu Pro Gly Cys
1850                1855                1860

ggg  gtg gac ttt act gag  agc cgc ctt agc aac  ttg ctt ggt att     14733
Gly  Val Asp Phe Thr Glu  Ser Arg Leu Ser Asn  Leu Leu Gly Ile
1865                1870                1875

agg  aag aga cac cca ttc  cag gaa ggt ttt aaa  att atg tat gag     14778
Arg  Lys Arg His Pro Phe  Gln Glu Gly Phe Lys  Ile Met Tyr Glu
1880                1885                1890

gat  ctt gag ggg ggt aat  atc ccc gcc ctt ttg  gat gta gat gcc     14823
Asp  Leu Glu Gly Gly Asn  Ile Pro Ala Leu Leu  Asp Val Asp Ala
1895                1900                1905

tat  gaa aaa agc aaa aag  gaa aac aca gac acc  acc acc act acc     14868
Tyr  Glu Lys Ser Lys Lys  Glu Asn Thr Asp Thr  Thr Thr Thr Thr
1910                1915                1920

act  gtt act act act gaa  gta gca act gtt gca  aga cac gtt tct     14913
Thr  Val Thr Thr Thr Glu  Val Ala Thr Val Ala  Arg His Val Ser
1925                1930                1935

gaa  gta act act gaa gca  gca acg gtt gtt gca  gtg gat cct att     14958
Glu  Val Thr Thr Glu Ala  Ala Thr Val Val Ala  Val Asp Pro Ile
1940                1945                1950

gtt  gaa gag aac aat aat  act gtt aga gga gat  aat atc cat act     15003
Val  Glu Glu Asn Asn Asn  Thr Val Arg Gly Asp  Asn Ile His Thr
1955                1960                1965

gcc  aat gag atg aaa gca  gca gct gat gat aca  aca gtt gta gtt     15048
Ala  Asn Glu Met Lys Ala  Ala Ala Asp Asp Thr  Thr Val Val Val
1970                1975                1980

gtg  cct ggc gct gta gtg  act gaa act gaa acc  aaa acc aag aca     15093
Val  Pro Gly Ala Val Val  Thr Glu Thr Glu Thr  Lys Thr Lys Thr
1985                1990                1995

ctc  acc att caa cct cta  gaa aag gat acc aag  gag cgc agt tac     15138
Leu  Thr Ile Gln Pro Leu  Glu Lys Asp Thr Lys  Glu Arg Ser Tyr
2000                2005                2010

aat  gtc atc tct ggc acc  aat gat act gcc tat  cgt agt tgg tac     15183
Asn  Val Ile Ser Gly Thr  Asn Asp Thr Ala Tyr  Arg Ser Trp Tyr
2015                2020                2025

cta  gca tac aac tat ggc  gac cct gaa aaa gga  gtc cgc tcc tgg     15228
Leu  Ala Tyr Asn Tyr Gly  Asp Pro Glu Lys Gly  Val Arg Ser Trp
2030                2035                2040

acg  ctg ctc acc act tca  gat gtc acc tgc gga  gcg gag caa gta     15273
Thr  Leu Leu Thr Thr Ser  Asp Val Thr Cys Gly  Ala Glu Gln Val
2045                2050                2055

tat  tgg tcg ctc cct gac  atg atg cag gac ccc  gtc acc ttt cga     15318
Tyr  Trp Ser Leu Pro Asp  Met Met Gln Asp Pro  Val Thr Phe Arg
2060                2065                2070

tcc  acg aga caa gtc agc  aac tac ccc gtg gtg  ggt gca gag ctc     15363
Ser  Thr Arg Gln Val Ser  Asn Tyr Pro Val Val  Gly Ala Glu Leu
```

```
2075                2080                2085

atg  ccc gtc ttc tca aag  agt ttc tac aac gag  caa gcc gtg tac     15408
Met  Pro Val Phe Ser Lys  Ser Phe Tyr Asn Glu  Gln Ala Val Tyr
2090                2095                2100

tcc  cag cag ctc cgc cag  acc acc tcg ctt acg  cac atc ttc gat     15453
Ser  Gln Gln Leu Arg Gln  Thr Thr Ser Leu Thr  His Ile Phe Asp
2105                2110                2115

cgc  ttc cct gag aat cag  atc ctc atc cgc ccg  ccg gcg ccc acc     15498
Arg  Phe Pro Glu Asn Gln  Ile Leu Ile Arg Pro  Pro Ala Pro Thr
2120                2125                2130

att  acc acc gtt agt gaa  aac gtt cct gct ctc  aca gat cac ggg     15543
Ile  Thr Thr Val Ser Glu  Asn Val Pro Ala Leu  Thr Asp His Gly
2135                2140                2145

acc  ctg ccg ttg cgc agc  agt atc cgg gga gtc  cag cgc gtg acc     15588
Thr  Leu Pro Leu Arg Ser  Ser Ile Arg Gly Val  Gln Arg Val Thr
2150                2155                2160

gtt  act gac gcc aga cgc  cgc acc tgc ccc tac  gtc tac aag gcc     15633
Val  Thr Asp Ala Arg Arg  Arg Thr Cys Pro Tyr  Val Tyr Lys Ala
2165                2170                2175

ctg  ggc ata gtc gcg ccg  cgc gtc ctt tca agc  cgc act ttc         15675
Leu  Gly Ile Val Ala Pro  Arg Val Leu Ser Ser  Arg Thr Phe
2180                2185                2190

taaaaaa atg tcc  att ctc atc tca ccc  agt aat aac acc ggt  tgg     15721
        Met Ser  Ile Leu Ile Ser Pro  Ser Asn Asn Thr Gly  Trp
            2195                 2200                 2205

ggg ctg cgc aca  ccc acc agg atg tac  gga ggc gct cgc aaa  cgg     15766
Gly Leu Arg Thr  Pro Thr Arg Met Tyr  Gly Gly Ala Arg Lys  Arg
            2210                 2215                 2220

tct acc cag cac  cct gtg cgt gtg cgc  ggg cat ttc cgc gct  ccc     15811
Ser Thr Gln His  Pro Val Arg Val Arg  Gly His Phe Arg Ala  Pro
            2225                 2230                 2235

tgg ggc gcc ctc  aag ggc cgt act cgc  act cgg acc acc gtc  gat     15856
Trp Gly Ala Leu  Lys Gly Arg Thr Arg  Thr Arg Thr Thr Val  Asp
            2240                 2245                 2250

gat gtg atc gac  cag gtg gtt gca gat  gct cgt aat tat act  cct     15901
Asp Val Ile Asp  Gln Val Val Ala Asp  Ala Arg Asn Tyr Thr  Pro
            2255                 2260                 2265

gct gca cct gca  tct act gtg gat gca  gtt att gac agc gtg  gtg     15946
Ala Ala Pro Ala  Ser Thr Val Asp Ala  Val Ile Asp Ser Val  Val
            2270                 2275                 2280

gct gac gct cgc  gag tat gct cgc cgg  aag agc agg cga aga  cgc     15991
Ala Asp Ala Arg  Glu Tyr Ala Arg Arg  Lys Ser Arg Arg Arg  Arg
            2285                 2290                 2295

att gcc agg cgc  cac cgg gct acc ccc  gct atg cga gct gca  aga     16036
Ile Ala Arg Arg  His Arg Ala Thr Pro  Ala Met Arg Ala Ala  Arg
            2300                 2305                 2310

gct ctg ctg cgg  aga gcc aaa cgc gtg  ggg cga aga gcc atg  ctt     16081
Ala Leu Leu Arg  Arg Ala Lys Arg Val  Gly Arg Arg Ala Met  Leu
            2315                 2320                 2325

aga gcg gcc agg  cgc gcg gct tca ggt  gcc agc gca ggc aga  tcc     16126
Arg Ala Ala Arg  Arg Ala Ala Ser Gly  Ala Ser Ala Gly Arg  Ser
            2330                 2335                 2340

cgc agg cgc gcg  gcc acg gcg gca gca  gcg gcc att gcc aac  atg     16171
Arg Arg Arg Ala  Ala Thr Ala Ala Ala  Ala Ala Ile Ala Asn  Met
            2345                 2350                 2355

gcc caa ccg cga  aga ggc aat gtg tac  tgg gtg cgc gat gcc  act     16216
Ala Gln Pro Arg  Arg Gly Asn Val Tyr  Trp Val Arg Asp Ala  Thr
            2360                 2365                 2370

acc ggc cag cgc  gtg ccc gtg cgc acc  cgt ccc cct cgc act          16258
```

-continued

```
Thr Gly Gln Arg  Val Pro Val Arg Thr  Arg Pro Pro Arg Thr
            2375                 2380                 2385

tagaagatac tgagcagtct ccgatgttgt gtcccagcgg cgagg atg tcc aag cgc  16315
                                                  Met Ser Lys Arg

aaa  tac aag gaa gag atg  ctc cag gtc atc gcg  cct gaa atc tac     16360
Lys  Tyr Lys Glu Glu Met  Leu Gln Val Ile Ala  Pro Glu Ile Tyr
2390                 2395                 2400

ggt  cca ccg gtg aag gat  gaa aaa aag ccc cgc  aaa atc aag cgg     16405
Gly  Pro Pro Val Lys Asp  Glu Lys Lys Pro Arg  Lys Ile Lys Arg
2405                 2410                 2415

gtc  aaa aag gac aaa aag  gaa gaa gat ggc gat  gat ggg ctg gtg     16450
Val  Lys Lys Asp Lys Lys  Glu Glu Asp Gly Asp  Asp Gly Leu Val
2420                 2425                 2430

gag  ttt gtg cgc gag ttc  gct cca agg cgg cgc  gta cag tgg cgc     16495
Glu  Phe Val Arg Glu Phe  Ala Pro Arg Arg Arg  Val Gln Trp Arg
2435                 2440                 2445

ggg  cgc aaa gtg cgg ccg  gtg ctg aga cca gga  acc acg gtg gtc     16540
Gly  Arg Lys Val Arg Pro  Val Leu Arg Pro Gly  Thr Thr Val Val
2450                 2455                 2460

ttc  acg ccc ggc gag cgc  tcc agc act act ttt  aaa cgc tcc tat     16585
Phe  Thr Pro Gly Glu Arg  Ser Ser Thr Thr Phe  Lys Arg Ser Tyr
2465                 2470                 2475

gat  gag gtg tac ggg gat  gat gat att ctg gag  cag gcg gcc gac     16630
Asp  Glu Val Tyr Gly Asp  Asp Asp Ile Leu Glu  Gln Ala Ala Asp
2480                 2485                 2490

cgc  ctg ggc gag ttt gct  tat ggc aag cgc agc  cgc tcc agt ccc     16675
Arg  Leu Gly Glu Phe Ala  Tyr Gly Lys Arg Ser  Arg Ser Ser Pro
2495                 2500                 2505

aag  gat gag gcg gtg tcc  ata ccc ttg gat cat  gga aat ccc acc     16720
Lys  Asp Glu Ala Val Ser  Ile Pro Leu Asp His  Gly Asn Pro Thr
2510                 2515                 2520

cca  agt cta aaa cca gtc  acc ctg cag caa gtg  cta ccc gtg cct     16765
Pro  Ser Leu Lys Pro Val  Thr Leu Gln Gln Val  Leu Pro Val Pro
2525                 2530                 2535

cca  cgg aga ggt gtc aag  cga gag ggc gag gat  ctg tat ccc acc     16810
Pro  Arg Arg Gly Val Lys  Arg Glu Gly Glu Asp  Leu Tyr Pro Thr
2540                 2545                 2550

atg  caa ctg atg gtg ccc  aag cgc cag aag ctg  gag gac gtg ctg     16855
Met  Gln Leu Met Val Pro  Lys Arg Gln Lys Leu  Glu Asp Val Leu
2555                 2560                 2565

gag  aaa atg aaa gtg gat  ccc gat atc cag cct  gaa gtt aaa gtc     16900
Glu  Lys Met Lys Val Asp  Pro Asp Ile Gln Pro  Glu Val Lys Val
2570                 2575                 2580

aga  ccc atc aag cag gtg  gcg ccc ggt ctg gga  gtg caa acc gtg     16945
Arg  Pro Ile Lys Gln Val  Ala Pro Gly Leu Gly  Val Gln Thr Val
2585                 2590                 2595

gac  atc aag att ccc acc  gag tcc atg gaa gtc  cag act gaa cct     16990
Asp  Ile Lys Ile Pro Thr  Glu Ser Met Glu Val  Gln Thr Glu Pro
2600                 2605                 2610

gca  aag ccc gca gcc acc  tct att gag gtg cag  acg gat cct tgg     17035
Ala  Lys Pro Ala Ala Thr  Ser Ile Glu Val Gln  Thr Asp Pro Trp
2615                 2620                 2625

ata  ccc gcg ccc gtt gca  acc acc gcc agt acc  gcc cga aga ccc     17080
Ile  Pro Ala Pro Val Ala  Thr Thr Ala Ser Thr  Ala Arg Arg Pro
2630                 2635                 2640

cgg  cga aag tat ggt cct  gcg agt ctg ctg ttg  ccc aac tat gct     17125
Arg  Arg Lys Tyr Gly Pro  Ala Ser Leu Leu Leu  Pro Asn Tyr Ala
2645                 2650                 2655

ctg  cac cca tcc att att  cca act ccg ggt tac  cga ggc act cgc     17170
```

```
Leu  His Pro Ser Ile Ile  Pro Thr Pro Gly Tyr  Arg Gly Thr Arg
2660                2665                 2670

tac  tac cgc agc cgg agc  acc act tcc cgc cgt  cgc aaa aca cct     17215
Tyr  Tyr Arg Ser Arg Ser  Thr Thr Ser Arg Arg  Arg Lys Thr Pro
2675                2680                 2685

gca  agc cgc agt cgc cgt  cgc cgc cgc cgc gcc  gcc agc aaa ctg     17260
Ala  Ser Arg Ser Arg Arg  Arg Arg Arg Arg Ala  Ala Ser Lys Leu
2690                2695                 2700

act  ccc gcc gct ttg gtg  cgg agg gtg tat cgc  gat ggc cgc gca     17305
Thr  Pro Ala Ala Leu Val  Arg Arg Val Tyr Arg  Asp Gly Arg Ala
2705                2710                 2715

gag  ccc ctg atg ctg ccg  cgc gca cgc tac cat  cca agc atc acc     17350
Glu  Pro Leu Met Leu Pro  Arg Ala Arg Tyr His  Pro Ser Ile Thr
2720                2725                 2730

act  taatgactgt tgccgctgcc tccttgcaga t atg gcc ctc act tgc  cgc    17402
Thr                                     Met Ala Leu Thr Cys  Arg
2735                                                    2740

ctt cgc gtc ccc  att act ggc tac cga  gga aga aac tcg cgc  cgt     17447
Leu Arg Val Pro  Ile Thr Gly Tyr Arg  Gly Arg Asn Ser Arg  Arg
            2745                 2750                 2755

aga agg atg ttg  ggt agc ggg atg cgt  cgc cac agg cgg cgg  cgc     17492
Arg Arg Met Leu  Gly Ser Gly Met Arg  Arg His Arg Arg Arg  Arg
            2760                 2765                 2770

gct atc agc aag  agg ctg ggg ggt ggc  ttt ctg acc gct ttg  att     17537
Ala Ile Ser Lys  Arg Leu Gly Gly Gly  Phe Leu Thr Ala Leu  Ile
            2775                 2780                 2785

ccc att atc gcc  gcg gcg atc ggg gcg  gta cca ggc ata gct  tcc     17582
Pro Ile Ile Ala  Ala Ala Ile Gly Ala  Val Pro Gly Ile Ala  Ser
            2790                 2795                 2800

gtg gcg gtt cag  gcc tcg cag cgc cac  tgacattgga aaacacttat        17629
Val Ala Val Gln  Ala Ser Gln Arg His
            2805                 2810

aaataaaaata gaatggactc tgacgctcct ggtcctgtga ctatgttttt gtagag atg  17688
                                                             Met

gaa gac atc aat  ttt tca tcc ctg gct  ccg cga cac ggc acg  agg     17733
Glu Asp Ile Asn  Phe Ser Ser Leu Ala  Pro Arg His Gly Thr  Arg
            2815                 2820                 2825

ccg tac atg ggc  acc tgg agc gac atc  ggc acc agc caa ctg  aac     17778
Pro Tyr Met Gly  Thr Trp Ser Asp Ile  Gly Thr Ser Gln Leu  Asn
            2830                 2835                 2840

ggg ggc gcc ttc  aat tgg agc agt atc  tgg agc ggg ctt aaa  aat     17823
Gly Gly Ala Phe  Asn Trp Ser Ser Ile  Trp Ser Gly Leu Lys  Asn
            2845                 2850                 2855

ttt ggc tct gcc  ata aaa acc tat ggg  aac aaa gct tgg aac  agc     17868
Phe Gly Ser Ala  Ile Lys Thr Tyr Gly  Asn Lys Ala Trp Asn  Ser
            2860                 2865                 2870

agc aca ggg cag  gca cta agg aat aag  ctt aaa gag cag aac  ttc     17913
Ser Thr Gly Gln  Ala Leu Arg Asn Lys  Leu Lys Glu Gln Asn  Phe
            2875                 2880                 2885

cag cag aag gtg  gtc gat ggg atc gcc  tct ggc atc aat ggg  gta     17958
Gln Gln Lys Val  Val Asp Gly Ile Ala  Ser Gly Ile Asn Gly  Val
            2890                 2895                 2900

gtg gat ctg gcc  aac cag gcc gtg cag  aaa cag ata aac agc  cgc     18003
Val Asp Leu Ala  Asn Gln Ala Val Gln  Lys Gln Ile Asn Ser  Arg
            2905                 2910                 2915

ctg gac ccg ccg  ccc gca gcc cct ggc  gaa atg gaa gtg gag  gaa     18048
Leu Asp Pro Pro  Pro Ala Ala Pro Gly  Glu Met Glu Val Glu  Glu
            2920                 2925                 2930

gag ctc cct ccc  ctg gaa aag cgg gga  gac aag cgc ccg cgt  ccc     18093
```

```
Glu Leu Pro Pro  Leu Glu Lys Arg Gly  Asp Lys Arg Pro Arg  Pro
            2935                 2940                 2945

gat atg gag gag  acg ctg gtg acg cgg  gga gac gaa ccg cct  cca     18138
Asp Met Glu Glu  Thr Leu Val Thr Arg  Gly Asp Glu Pro Pro  Pro
            2950                 2955                 2960

tat gag gag gcg  ata aag ctt gga atg  ccc act acc agg cct  ata     18183
Tyr Glu Glu Ala  Ile Lys Leu Gly Met  Pro Thr Thr Arg Pro  Ile
            2965                 2970                 2975

gct ccc atg gcc  acc ggg gta atg aaa  cct tct cag tcg cat  cga     18228
Ala Pro Met Ala  Thr Gly Val Met Lys  Pro Ser Gln Ser His  Arg
            2980                 2985                 2990

ccc gcc acc ttg  gac ttg cct cct gcc  cct gct gct gca gcg  ccc     18273
Pro Ala Thr Leu  Asp Leu Pro Pro Ala  Pro Ala Ala Ala Ala  Pro
            2995                 3000                 3005

gct cca aag cct  gtc gct acc ccg aag  ccc acc tcc gta cag  ccc     18318
Ala Pro Lys Pro  Val Ala Thr Pro Lys  Pro Thr Ser Val Gln  Pro
            3010                 3015                 3020

gtc gcc gta gcc  aga ccg cgt cct ggg  ggc act ccg cgc ccg  aat     18363
Val Ala Val Ala  Arg Pro Arg Pro Gly  Gly Thr Pro Arg Pro  Asn
            3025                 3030                 3035

gca aac tgg cag  agt act ctg aac agc  atc gtg ggt ttg ggc  gtg     18408
Ala Asn Trp Gln  Ser Thr Leu Asn Ser  Ile Val Gly Leu Gly  Val
            3040                 3045                 3050

cag agt gta aag  cgc cgt cgc tgc tat  taaatatgga gtagcgctta       18455
Gln Ser Val Lys  Arg Arg Arg Cys Tyr
            3055                 3060

acttgcttgt ctgtgtgtat gtgtcatcac cacgccgccg cagcagcaga ggagaaagga  18515

agaggtcgcg cgccgaggct gagttgcttt caag atg gcc acc cca tcg  atg     18567
                                      Met Ala Thr Pro Ser  Met
                                                      3065

ctg ccc cag tgg  gca tac atg cac atc  gcc gga cag gat gct  tcg     18612
Leu Pro Gln Trp  Ala Tyr Met His Ile  Ala Gly Gln Asp Ala  Ser
            3070                 3075                 3080

gag tac ctg agt  ccg ggt ctg gtg cag  ttc gcc cgt gcc aca  gat     18657
Glu Tyr Leu Ser  Pro Gly Leu Val Gln  Phe Ala Arg Ala Thr  Asp
            3085                 3090                 3095

acc tac ttc aat  ctg gga aac aag ttt  agg aac ccc acc gtg  gct     18702
Thr Tyr Phe Asn  Leu Gly Asn Lys Phe  Arg Asn Pro Thr Val  Ala
            3100                 3105                 3110

ccc acc cac gat  gtg acc acc gac cga  agc cag cgg ctg atg  ctg     18747
Pro Thr His Asp  Val Thr Thr Asp Arg  Ser Gln Arg Leu Met  Leu
            3115                 3120                 3125

cgc ttt gtg ccc  gtt gat cgg gag gac  aat act tac tct tac  aaa     18792
Arg Phe Val Pro  Val Asp Arg Glu Asp  Asn Thr Tyr Ser Tyr  Lys
            3130                 3135                 3140

gtt cgc tac aca  ctg gct gtg gga gac  aac aga gtg ctg gat  atg     18837
Val Arg Tyr Thr  Leu Ala Val Gly Asp  Asn Arg Val Leu Asp  Met
            3145                 3150                 3155

gcc agc acc ttc  ttt gac atc agg ggg  gtg ctt gac aga ggt  ccc     18882
Ala Ser Thr Phe  Phe Asp Ile Arg Gly  Val Leu Asp Arg Gly  Pro
            3160                 3165                 3170

agt ttc aaa ccc  tac tct ggg aca gca  tac aat tcc ctg gcc  cct     18927
Ser Phe Lys Pro  Tyr Ser Gly Thr Ala  Tyr Asn Ser Leu Ala  Pro
            3175                 3180                 3185

aag gga gct cct  aat act agt cag tgg  ata gtt aca act aat  ggg     18972
Lys Gly Ala Pro  Asn Thr Ser Gln Trp  Ile Val Thr Thr Asn  Gly
            3190                 3195                 3200

caa gat aat gca  gta act acc act aca  aac aca ttt ggc att  gct     19017
Gln Asp Asn Ala  Val Thr Thr Thr Thr  Asn Thr Phe Gly Ile  Ala
```

```
            3205                3210                3215

tcc atg aaa gga  gac aat att act aaa  gaa ggt tta gaa att  gga     19062
Ser Met Lys Gly  Asp Asn Ile Thr Lys  Glu Gly Leu Glu Ile  Gly
            3220                3225                3230

aaa gat att act  gaa gaa gat aaa ccc  atc tat gcc gat aaa  aca     19107
Lys Asp Ile Thr  Glu Glu Asp Lys Pro  Ile Tyr Ala Asp Lys  Thr
            3235                3240                3245

tat cag cca gaa  cct caa gtt gga gaa  gaa tca tgg act gat  acc     19152
Tyr Gln Pro Glu  Pro Gln Val Gly Glu  Glu Ser Trp Thr Asp  Thr
            3250                3255                3260

gat gga aca aat  gaa aag ttt ggc ggt  aga gcg ctt aaa ccc  gct     19197
Asp Gly Thr Asn  Glu Lys Phe Gly Gly  Arg Ala Leu Lys Pro  Ala
            3265                3270                3275

acc aac atg aaa  cca tgc tat ggg tca  ttt gca aga cct aca  aac     19242
Thr Asn Met Lys  Pro Cys Tyr Gly Ser  Phe Ala Arg Pro Thr  Asn
            3280                3285                3290

ata aaa ggt ggt  caa gct aaa aat aga  aaa gta aag ccg aca  acc     19287
Ile Lys Gly Gly  Gln Ala Lys Asn Arg  Lys Val Lys Pro Thr  Thr
            3295                3300                3305

gag gga ggg gtt  gaa act gag gaa ccg  gat att gat atg gaa  ttt     19332
Glu Gly Gly Val  Glu Thr Glu Glu Pro  Asp Ile Asp Met Glu  Phe
            3310                3315                3320

ttc gat ggt aga  gat gct gct gaa gga  gct tta tcg cct gaa  att     19377
Phe Asp Gly Arg  Asp Ala Ala Glu Gly  Ala Leu Ser Pro Glu  Ile
            3325                3330                3335

gtg ctt tac aca  gaa aat gta aat ttg  gaa act cca gac acc  cat     19422
Val Leu Tyr Thr  Glu Asn Val Asn Leu  Glu Thr Pro Asp Thr  His
            3340                3345                3350

gtg gta tac aaa  cca gga act tca gat  gat aac tct cat gca  aat     19467
Val Val Tyr Lys  Pro Gly Thr Ser Asp  Asp Asn Ser His Ala  Asn
            3355                3360                3365

ttg ggt caa caa  gct atg ccc aac aga  ccc aat tac att ggc  ttc     19512
Leu Gly Gln Gln  Ala Met Pro Asn Arg  Pro Asn Tyr Ile Gly  Phe
            3370                3375                3380

aga gac aac ttt  gtt gga ctc ttg tac  tac aac agc act ggc  aac     19557
Arg Asp Asn Phe  Val Gly Leu Leu Tyr  Tyr Asn Ser Thr Gly  Asn
            3385                3390                3395

atg gga gtg ttg  gca ggt caa gca tca  caa cta aat gca gta  gtt     19602
Met Gly Val Leu  Ala Gly Gln Ala Ser  Gln Leu Asn Ala Val  Val
            3400                3405                3410

gac ttg cag gac  aga aac act gaa ctg  tcc tat cag ctt ttg  ctt     19647
Asp Leu Gln Asp  Arg Asn Thr Glu Leu  Ser Tyr Gln Leu Leu  Leu
            3415                3420                3425

gat tct ctt ggg  gac aga acc aga tac  ttc agc atg tgg aat  cag     19692
Asp Ser Leu Gly  Asp Arg Thr Arg Tyr  Phe Ser Met Trp Asn  Gln
            3430                3435                3440

gcc gtg gat agt  tat gat cct gat gtt  cgc att att gaa aat  cat     19737
Ala Val Asp Ser  Tyr Asp Pro Asp Val  Arg Ile Ile Glu Asn  His
            3445                3450                3455

ggt atc gag gat  gaa cta ccc aac tac  tgt ttt cct ctg gat  ggc     19782
Gly Ile Glu Asp  Glu Leu Pro Asn Tyr  Cys Phe Pro Leu Asp  Gly
            3460                3465                3470

ata gga cca ggg  aac tca tat caa ggc  atc aag gct aaa aac  ggt     19827
Ile Gly Pro Gly  Asn Ser Tyr Gln Gly  Ile Lys Ala Lys Asn  Gly
            3475                3480                3485

gat aat aat gga  tgg gaa aaa gat act  aat gct tct act gct  aat     19872
Asp Asn Asn Gly  Trp Glu Lys Asp Thr  Asn Ala Ser Thr Ala  Asn
            3490                3495                3500

gaa ata gcc ata  gga aac aac ctg gct  atg gaa att aat atc  cag     19917
```

```
Glu Ile Ala Ile  Gly Asn Asn Leu Ala  Met Glu Ile Asn Ile  Gln
            3505                3510                3515

gct aac ctt tgg  aga agt ttt ctg tac  tcc aac gtg gct ttg  tac     19962
Ala Asn Leu Trp  Arg Ser Phe Leu Tyr  Ser Asn Val Ala Leu  Tyr
            3520                3525                3530

ctt cca gac gct  tac aag tac acg cca  gcc aac att act ttg  cct     20007
Leu Pro Asp Ala  Tyr Lys Tyr Thr Pro  Ala Asn Ile Thr Leu  Pro
            3535                3540                3545

gcc aat acc aac  acc tat gaa tac atg  aac ggg cga gtg gtg  gca     20052
Ala Asn Thr Asn  Thr Tyr Glu Tyr Met  Asn Gly Arg Val Val  Ala
            3550                3555                3560

cca tct ttg gtt  gat tcg tac atc aac  att gga gcc agg tgg  tct     20097
Pro Ser Leu Val  Asp Ser Tyr Ile Asn  Ile Gly Ala Arg Trp  Ser
            3565                3570                3575

ctt gac cca atg  gac aat gtg aac ccc  ttc aat cac cac cga  aac     20142
Leu Asp Pro Met  Asp Asn Val Asn Pro  Phe Asn His His Arg  Asn
            3580                3585                3590

gct ggg ctg cgt  tac aga tcc atg ctt  ctg ggc aat ggt cgc  tat     20187
Ala Gly Leu Arg  Tyr Arg Ser Met Leu  Leu Gly Asn Gly Arg  Tyr
            3595                3600                3605

gtg cct ttc cac  atc caa gtg cct cag  aaa ttc ttt gct atc  aag     20232
Val Pro Phe His  Ile Gln Val Pro Gln  Lys Phe Phe Ala Ile  Lys
            3610                3615                3620

aac ctg ctt ctc  ctc cca ggc tcc tat  acc tat gag tgg aac  ttc     20277
Asn Leu Leu Leu  Leu Pro Gly Ser Tyr  Thr Tyr Glu Trp Asn  Phe
            3625                3630                3635

aga aag gat gtg  aac atg gtc ctg cag  agt tcc ctt ggc aat  gat     20322
Arg Lys Asp Val  Asn Met Val Leu Gln  Ser Ser Leu Gly Asn  Asp
            3640                3645                3650

ctc aga act gat  gga gcc agc atc agt  ttt act agc atc aac  ctc     20367
Leu Arg Thr Asp  Gly Ala Ser Ile Ser  Phe Thr Ser Ile Asn  Leu
            3655                3660                3665

tat gcc acc ttc  ttc ccc atg gct cac  aat act gct tcc acc  ctt     20412
Tyr Ala Thr Phe  Phe Pro Met Ala His  Asn Thr Ala Ser Thr  Leu
            3670                3675                3680

gaa gcc atg ctg  cgc aat gac aca aat  gac cag tca ttc aat  gac     20457
Glu Ala Met Leu  Arg Asn Asp Thr Asn  Asp Gln Ser Phe Asn  Asp
            3685                3690                3695

tac ctt tct gca  gct aac atg ctc tac  cct att cca gcc aat  gca     20502
Tyr Leu Ser Ala  Ala Asn Met Leu Tyr  Pro Ile Pro Ala Asn  Ala
            3700                3705                3710

acc aac att ccc  att tcc att ccc tct  cgc aac tgg gct gcc  ttt     20547
Thr Asn Ile Pro  Ile Ser Ile Pro Ser  Arg Asn Trp Ala Ala  Phe
            3715                3720                3725

agg ggt tgg tcc  ttc acc aga ctc aaa  aca aag gaa aca ccc  tct     20592
Arg Gly Trp Ser  Phe Thr Arg Leu Lys  Thr Lys Glu Thr Pro  Ser
            3730                3735                3740

ttg gga tca ggc  ttt gat ccc tac ttt  gtt tac tct ggc tcc  att     20637
Leu Gly Ser Gly  Phe Asp Pro Tyr Phe  Val Tyr Ser Gly Ser  Ile
            3745                3750                3755

ccc tac ctg gat  ggc acc ttc tac ctc  aac cac act ttc aag  aag     20682
Pro Tyr Leu Asp  Gly Thr Phe Tyr Leu  Asn His Thr Phe Lys  Lys
            3760                3765                3770

gtg tcc atc atg  ttt gac tcc tca gtc  agc tgg cca ggc aat  gac     20727
Val Ser Ile Met  Phe Asp Ser Ser Val  Ser Trp Pro Gly Asn  Asp
            3775                3780                3785

aga ttg cta act  cca aat gag ttt gaa  atc aag cgc act gtg  gat     20772
Arg Leu Leu Thr  Pro Asn Glu Phe Glu  Ile Lys Arg Thr Val  Asp
            3790                3795                3800
```

```
gga gaa ggg tac  aat gtg gct caa tgc  aac atg acc aag gat  tgg     20817
Gly Glu Gly Tyr  Asn Val Ala Gln Cys  Asn Met Thr Lys Asp  Trp
            3805                 3810                 3815

ttc ctg gtt cag  atg ctt gcc aac tat  aac att ggc tac cag  ggc     20862
Phe Leu Val Gln  Met Leu Ala Asn Tyr  Asn Ile Gly Tyr Gln  Gly
            3820                 3825                 3830

ttc tac atc cca  gag ggg tac aag gat  cgc atg tac tcc ttc  ttc     20907
Phe Tyr Ile Pro  Glu Gly Tyr Lys Asp  Arg Met Tyr Ser Phe  Phe
            3835                 3840                 3845

aga aac ttc cag  ccc atg agc aga cag  gtg gtt gat gag gtg  aac     20952
Arg Asn Phe Gln  Pro Met Ser Arg Gln  Val Val Asp Glu Val  Asn
            3850                 3855                 3860

tac acc gat tac  aaa gcc gtc act cta  gca tac caa cac aac  aac     20997
Tyr Thr Asp Tyr  Lys Ala Val Thr Leu  Ala Tyr Gln His Asn  Asn
            3865                 3870                 3875

tct ggc ttt gtg  ggt tac ctt gcg ccc  act atg agg cag gga  gaa     21042
Ser Gly Phe Val  Gly Tyr Leu Ala Pro  Thr Met Arg Gln Gly  Glu
            3880                 3885                 3890

cct tac ccc gct  aac tac cca tac ccc  cta atc gga acc act  gct     21087
Pro Tyr Pro Ala  Asn Tyr Pro Tyr Pro  Leu Ile Gly Thr Thr  Ala
            3895                 3900                 3905

gtt aag agt gtt  acc cag aaa aag ttc  ctg tgc gac agg acc  atg     21132
Val Lys Ser Val  Thr Gln Lys Lys Phe  Leu Cys Asp Arg Thr  Met
            3910                 3915                 3920

tgg cgc atc ccc  ttc tcc agc aac ttc  atg tcc atg ggt gcc  ctt     21177
Trp Arg Ile Pro  Phe Ser Ser Asn Phe  Met Ser Met Gly Ala  Leu
            3925                 3930                 3935

acc gac ctg gga  cag aac atg ctt tat  gcc aac tca gcc cat  gcg     21222
Thr Asp Leu Gly  Gln Asn Met Leu Tyr  Ala Asn Ser Ala His  Ala
            3940                 3945                 3950

ctg gac atg act  ttt gag gtg gat ccc  atg gat gag ccc acc  ctg     21267
Leu Asp Met Thr  Phe Glu Val Asp Pro  Met Asp Glu Pro Thr  Leu
            3955                 3960                 3965

ctt tat gtt ctt  ttc gaa gtc ttc gac  gtg gtc aga gtg cac  cag     21312
Leu Tyr Val Leu  Phe Glu Val Phe Asp  Val Val Arg Val His  Gln
            3970                 3975                 3980

cca cac cgc ggc  gtc atc gag gct gtc  tac ctg cgt acc cca  ttc     21357
Pro His Arg Gly  Val Ile Glu Ala Val  Tyr Leu Arg Thr Pro  Phe
            3985                 3990                 3995

tca gct ggt aac  gcc acc aca taagaagctt cttgcttctt gcaagcagct gcc  21411
Ser Ala Gly Asn  Ala Thr Thr
            4000

atg gcc  tgt ggg tcc ggc aac  gga tcc agc gag caa  gag ctc agg     21456
Met Ala  Cys Gly Ser Gly Asn  Gly Ser Ser Glu Gln  Glu Leu Arg
    4005                 4010                 4015

gcc att  gct aga gac ctg ggc  tgc gga ccc tat ttc  ctt gga acc     21501
Ala Ile  Ala Arg Asp Leu Gly  Cys Gly Pro Tyr Phe  Leu Gly Thr
    4020                 4025                 4030

ttt gat  aaa cgc ttc ccg ggg  ttc atg gcc ccc aac  aag ctc gcc     21546
Phe Asp  Lys Arg Phe Pro Gly  Phe Met Ala Pro Asn  Lys Leu Ala
    4035                 4040                 4045

tgc gcc  att gtc aac acg gcc  ggt cgc gag acg ggg  gga gag cac     21591
Cys Ala  Ile Val Asn Thr Ala  Gly Arg Glu Thr Gly  Gly Glu His
    4050                 4055                 4060

tgg ctg  gct ttt ggt tgg aac  ccg cgc tcc aac acc  tgc tac ctt     21636
Trp Leu  Ala Phe Gly Trp Asn  Pro Arg Ser Asn Thr  Cys Tyr Leu
    4065                 4070                 4075

ttt gat  cct ttt ggc ttc tcg  gac gag cgc ctc aag  caa atc tac     21681
Phe Asp  Pro Phe Gly Phe Ser  Asp Glu Arg Leu Lys  Gln Ile Tyr
    4080                 4085                 4090
```

```
cag ttt  gag tat gag ggg ctt  ctg cgc cgc agt gcc  cta gct acc     21726
Gln Phe  Glu Tyr Glu Gly Leu  Leu Arg Arg Ser Ala  Leu Ala Thr
    4095                 4100                 4105

aag gac  cgc tgt atc acc ctg  gaa aag tca acc cag  acc gtg cag     21771
Lys Asp  Arg Cys Ile Thr Leu  Glu Lys Ser Thr Gln  Thr Val Gln
    4110                 4115                 4120

ggc ccg  cgc tcc gca gcc tgt  gga ctg ttt tgc tgc  atg ttc ctc     21816
Gly Pro  Arg Ser Ala Ala Cys  Gly Leu Phe Cys Cys  Met Phe Leu
    4125                 4130                 4135

cac gct  ttt gtg cac tgg cca  gac cgc ccc atg gac  gga aac ccc     21861
His Ala  Phe Val His Trp Pro  Asp Arg Pro Met Asp  Gly Asn Pro
    4140                 4145                 4150

acc atg  aag ttg ctg act ggg  gtg ccc aac agc atg  ctc caa tcg     21906
Thr Met  Lys Leu Leu Thr Gly  Val Pro Asn Ser Met  Leu Gln Ser
    4155                 4160                 4165

ccc caa  gtc cag ccc acc ctg  cgc cac aac cag gag  gcg ctc tac     21951
Pro Gln  Val Gln Pro Thr Leu  Arg His Asn Gln Glu  Ala Leu Tyr
    4170                 4175                 4180

cgc ttc  cta aac tcc cac tca  tct tac ttt cgt tct  cac cgc gcg     21996
Arg Phe  Leu Asn Ser His Ser  Ser Tyr Phe Arg Ser  His Arg Ala
    4185                 4190                 4195

cgc atc  gaa aag gcc acc gcg  ttt gac cgt atg gat  atg caa         22038
Arg Ile  Glu Lys Ala Thr Ala  Phe Asp Arg Met Asp  Met Gln
    4200                 4205                 4210

taataagtca tgtaaaaccg tgttcaaata aacagcactt tattttttac atgcactgtg  22098

gctctgggtt gctcattcat tcatcattca ctcagaagtc gaaggggttc tggcgggaat  22158

cagcgtgacc cgctggcagg gatacgttgc ggaactggaa cctgttctgc cacttgaact  22218

cggggatcac cagcttggga actgggatct cggggaaggt gtcttgccac agctttctgg  22278

ttagttgcag agcaccaagc aggtcaggag cagagatctt gaaatcacag ttggggccag  22338

cattttgggc acgggagttg cggtacactg ggttgcagca ctggaacacc atcagggcgg  22398

ggtgtctcac gctcgccagc acggtcgggt cgctgatggt agtcacatcc aagtcttcag  22458

cattggccat tccaaagggg gtcatcttac aggtctgcct gcccatcacg ggagcgcagc  22518

cgggcttgtg gttgcaatcg cagcgaatgg ggatcagcat catcctggcc tggtcggggg  22578

ttatccctgg atacaccgcc ttcataaagg cttcgtactg cttgaaagct tcctgcgcct  22638

tgcttccctc ggtgtagaac atcccacagg acttgctgga aaattgatta gtagcacagt  22698

tggcatcatt cacacagcag cgggcatcgt tgttggccag ctggaccaca ttcctgcccc  22758

agcggttctg ggtgatcttg gctcggtctg ggttctcctt catcgcgcgc tgcccgttct  22818

cgctcgccac atccatctcg atgatgtgat ccttctggat catgatagtg ccatgcaggc  22878

atttcacctt gccttcataa tcggtgcagc catgagccca cagagcgcac ccggtgcact  22938

cccaattgtt gtgggcgatc tcagaataag aatgcaccaa tccctgcatg aatcttccca  22998

tcatgctggt gagggtcttt atgctggtaa atgtcagcgg gatgccacgg tgctcctcgt  23058

tcacatactg gtggcagata cgcctgtact gctcgtgctg ctcgggcatc agcttgaaag  23118

aggttctcag gtcattatcc agcctgtacc tctccattag cacggccatt acttccatgc  23178

ccttctccca ggcagagacc aagggcaggc tcatgggatt cctaacagca atagcagcag  23238

acgcagctcc tttagccaga gggtcattct tgtcaatctt ctcaacactt ctcttgccat  23298

ccttctcagt gatgcgcact ggggggtagc tgaagcccac ggccaccagc tccgcctgtt  23358

ctctttcttc ttcgctgtcc tggctgatgt cttgcaaagg gacatgcttg gtcttcctgg  23418
```

```
gcttcttctt gggagggatc gggggagggc tgttgctccg ctccggagac agggaggacc  23478

gcgaagtttc gctcaccagt accacctggc tctcggtaga agaaccggac cccacgcggc  23538

ggtaggtgtt cctcttcggg ggcagaggtg gaggcgactg cgatggactg cggtccggcc  23598

tgggaggcgg atggctggca gagcctcttc cgcgttcggg ggtgtgctcc cggtggcggt  23658

cgcttgactg atttcctccg cggctggcca ttgtgttctc ctaggcagag aaacaacaga  23718

c atg gag act  cag cca tcg ctg cca  aca ccg ctg caa gcg  cca tca   23764
  Met Glu Thr  Gln Pro Ser Leu Pro  Thr Pro Leu Gln Ala  Pro Ser
          4215                 4220                 4225

cac ctc gcc  ccc agc agc gac gag  gag gag agc tta acc  acc cca     23809
His Leu Ala  Pro Ser Ser Asp Glu  Glu Glu Ser Leu Thr  Thr Pro
        4230                 4235                 4240

cca ccc agt  ccc gcc acc acc acc  tct acc cta gag gat  gag gag     23854
Pro Pro Ser  Pro Ala Thr Thr Thr  Ser Thr Leu Glu Asp  Glu Glu
        4245                 4250                 4255

gag gtc gac  gca ccc cag gag atg  cag gat atg gag gat  gag aaa     23899
Glu Val Asp  Ala Pro Gln Glu Met  Gln Asp Met Glu Asp  Glu Lys
        4260                 4265                 4270

gcg gaa gag  att gag gca gat gtc  gag cag gac ccg ggc  tat gtg     23944
Ala Glu Glu  Ile Glu Ala Asp Val  Glu Gln Asp Pro Gly  Tyr Val
        4275                 4280                 4285

aca ccg gcg  gag cac gag gag gag  ctg aga cgc ttt cta  gac aga     23989
Thr Pro Ala  Glu His Glu Glu Glu  Leu Arg Arg Phe Leu  Asp Arg
        4290                 4295                 4300

gag gat gac  aac cgc cca gag cag  aaa gca gat ggc gat  cac cag     24034
Glu Asp Asp  Asn Arg Pro Glu Gln  Lys Ala Asp Gly Asp  His Gln
        4305                 4310                 4315

gag gct ggg  ctc ggg gat cat gtc  gcc gaa tac ctc acc  ggg ctt     24079
Glu Ala Gly  Leu Gly Asp His Val  Ala Glu Tyr Leu Thr  Gly Leu
        4320                 4325                 4330

ggc ggg gag  gac gtg ctc ctc aaa  cat cta gca agg cag  tcg atc     24124
Gly Gly Glu  Asp Val Leu Leu Lys  His Leu Ala Arg Gln  Ser Ile
        4335                 4340                 4345

ata gtt aaa  gac gca ctg ctc gac  cgc acc gaa gtg ccc  atc agt     24169
Ile Val Lys  Asp Ala Leu Leu Asp  Arg Thr Glu Val Pro  Ile Ser
        4350                 4355                 4360

gtg gaa gag  ctc agc cgc gcc tac  gag ctc aac ctg ttc  tca cct     24214
Val Glu Glu  Leu Ser Arg Ala Tyr  Glu Leu Asn Leu Phe  Ser Pro
        4365                 4370                 4375

agg gtg ccc  ccc aaa cgt cag cca  aac ggc acc tgc gag  ccc aac     24259
Arg Val Pro  Pro Lys Arg Gln Pro  Asn Gly Thr Cys Glu  Pro Asn
        4380                 4385                 4390

cct cgc ctc  aac ttc tat ccg gcc  ttt gct gtc cca gaa  gtg ctt     24304
Pro Arg Leu  Asn Phe Tyr Pro Ala  Phe Ala Val Pro Glu  Val Leu
        4395                 4400                 4405

gct acc tac  cac atc ttt ttc aag  aac caa aag att cca  gtt tcc     24349
Ala Thr Tyr  His Ile Phe Phe Lys  Asn Gln Lys Ile Pro  Val Ser
        4410                 4415                 4420

tgc cgt gcc  aac cgc acc cgc gcc  gat gcc ctg ctc aac  ttg gga     24394
Cys Arg Ala  Asn Arg Thr Arg Ala  Asp Ala Leu Leu Asn  Leu Gly
        4425                 4430                 4435

ccg ggt gct  cgc tta cct gat ata  gct tcc ttg gaa gag  gtt cca     24439
Pro Gly Ala  Arg Leu Pro Asp Ile  Ala Ser Leu Glu Glu  Val Pro
        4440                 4445                 4450

aag atc ttc  gag ggt ctg ggc agt  gat gag act cgg gcc  gca aat     24484
Lys Ile Phe  Glu Gly Leu Gly Ser  Asp Glu Thr Arg Ala  Ala Asn
        4455                 4460                 4465

gct ctg caa  cag gga gag aat ggc  atg gat gaa cat cac  agc gcg     24529
```

```
Ala Leu Gln  Gln Gly Glu Asn Gly  Met Asp Glu His His  Ser Ala
        4470                 4475                 4480

ctg gtg gag  ttg gag ggc gac aat  gcc cgg ctt gca gta  ctg aag     24574
Leu Val Glu  Leu Glu Gly Asp Asn  Ala Arg Leu Ala Val  Leu Lys
        4485                 4490                 4495

cgc agt atc  gag gtc acc cat ttt  gcc tac ccc gct gtt  aac ctg     24619
Arg Ser Ile  Glu Val Thr His Phe  Ala Tyr Pro Ala Val  Asn Leu
        4500                 4505                 4510

ccc ccc aaa  gtc atg agc gct gtc  atg gac cag ctg ctc  atc aag     24664
Pro Pro Lys  Val Met Ser Ala Val  Met Asp Gln Leu Leu  Ile Lys
        4515                 4520                 4525

cga gca agc  ccc ctt tcc gaa gac  cag aac atg cag gat  cca gac     24709
Arg Ala Ser  Pro Leu Ser Glu Asp  Gln Asn Met Gln Asp  Pro Asp
        4530                 4535                 4540

gcc tct gac  gag ggc aag ccg gtg  gtc agt gac gag cag  ctg tct     24754
Ala Ser Asp  Glu Gly Lys Pro Val  Val Ser Asp Glu Gln  Leu Ser
        4545                 4550                 4555

cgc tgg ctg  gcc acc aac tcc ccg  cga gac ttg gaa gag  aga cgc     24799
Arg Trp Leu  Ala Thr Asn Ser Pro  Arg Asp Leu Glu Glu  Arg Arg
        4560                 4565                 4570

aag ctt atg  atg gct gta gtg cta  gtc act gtg gag ctg  gag tgt     24844
Lys Leu Met  Met Ala Val Val Leu  Val Thr Val Glu Leu  Glu Cys
        4575                 4580                 4585

ctc cgc cgc  ttt ttc acc gac cct  gag acc ctg cgc aag  ctt gag     24889
Leu Arg Arg  Phe Phe Thr Asp Pro  Glu Thr Leu Arg Lys  Leu Glu
        4590                 4595                 4600

gag aac ctg  cac tat act ttc aga  cat ggc ttc gtg cgc  cag gca     24934
Glu Asn Leu  His Tyr Thr Phe Arg  His Gly Phe Val Arg  Gln Ala
        4605                 4610                 4615

tgc aag atc  tcc aac gtg gag ctc  acc aac ctg gtc tcc  tac atg     24979
Cys Lys Ile  Ser Asn Val Glu Leu  Thr Asn Leu Val Ser  Tyr Met
        4620                 4625                 4630

ggc att ttg  cat gag aac cgc ctg  ggg caa agt gtg ctg  cac acc     25024
Gly Ile Leu  His Glu Asn Arg Leu  Gly Gln Ser Val Leu  His Thr
        4635                 4640                 4645

acc ctg aag  ggg gag gcc cgt cgc  gac tac atc cgc gac  tgt gtc     25069
Thr Leu Lys  Gly Glu Ala Arg Arg  Asp Tyr Ile Arg Asp  Cys Val
        4650                 4655                 4660

tac ctc tac  ctc tgc cat acc tgg  cag act ggc atg ggt  gta tgg     25114
Tyr Leu Tyr  Leu Cys His Thr Trp  Gln Thr Gly Met Gly  Val Trp
        4665                 4670                 4675

cag cag tgt  ttg gaa gag cag aac  ctg aaa gag ctg gac  aag ctc     25159
Gln Gln Cys  Leu Glu Glu Gln Asn  Leu Lys Glu Leu Asp  Lys Leu
        4680                 4685                 4690

ttg cag aga  tcc ctc aaa gcc ctg  tgg aca ggt ttt gac  gag cgc     25204
Leu Gln Arg  Ser Leu Lys Ala Leu  Trp Thr Gly Phe Asp  Glu Arg
        4695                 4700                 4705

acc gtc gcc  tca gac ctg gca gac  atc atc ttt ccc gag  cgt ctc     25249
Thr Val Ala  Ser Asp Leu Ala Asp  Ile Ile Phe Pro Glu  Arg Leu
        4710                 4715                 4720

agg gtt act  ctg cgc aac ggc ctg  cct gac ttc atg agc  cag agc     25294
Arg Val Thr  Leu Arg Asn Gly Leu  Pro Asp Phe Met Ser  Gln Ser
        4725                 4730                 4735

atg ctt aac  aac ttt cgc tct ttc  atc ctg gaa cgc tcc  ggt atc     25339
Met Leu Asn  Asn Phe Arg Ser Phe  Ile Leu Glu Arg Ser  Gly Ile
        4740                 4745                 4750

ctg ccc gcc  acc tgc tgc gcg ctg  ccc tcc gac ttt gtg  cct ctc     25384
Leu Pro Ala  Thr Cys Cys Ala Leu  Pro Ser Asp Phe Val  Pro Leu
        4755                 4760                 4765
```

```
acc tac cgc  gag tgc ccc ccg ccg  cta tgg agc cac tgc  tac ctg     25429
Thr Tyr Arg  Glu Cys Pro Pro Pro  Leu Trp Ser His Cys  Tyr Leu
        4770                 4775                 4780

ttc cgc ctg  gcc aac tac ctc tcc  tac cac tcg gat gtg  atc gag     25474
Phe Arg Leu  Ala Asn Tyr Leu Ser  Tyr His Ser Asp Val  Ile Glu
        4785                 4790                 4795

gat gtg agc  gga gac ggc ctg ctg  gat tgc cac tgc cgc  tgc aat     25519
Asp Val Ser  Gly Asp Gly Leu Leu  Asp Cys His Cys Arg  Cys Asn
        4800                 4805                 4810

ctt tgc aca  ccc cac cgt tcc ctt  gcc tgc aac ccc cag  ttg ctg     25564
Leu Cys Thr  Pro His Arg Ser Leu  Ala Cys Asn Pro Gln  Leu Leu
        4815                 4820                 4825

agc gag acc  cag atc atc ggc acc  ttc gag ttg cag ggt  ccc agc     25609
Ser Glu Thr  Gln Ile Ile Gly Thr  Phe Glu Leu Gln Gly  Pro Ser
        4830                 4835                 4840

agt gaa ggc  gag ggg tct tct ccg  ggg cag agt ctg aaa  ctg acc     25654
Ser Glu Gly  Glu Gly Ser Ser Pro  Gly Gln Ser Leu Lys  Leu Thr
        4845                 4850                 4855

ccg ggg ctg  tgg acc tcc gcc tac  ctg cgc aag ttc gcc  cct gaa     25699
Pro Gly Leu  Trp Thr Ser Ala Tyr  Leu Arg Lys Phe Ala  Pro Glu
        4860                 4865                 4870

gac tac cac  ccc tat gag atc agg  ttc tat gag gac caa  tca cag     25744
Asp Tyr His  Pro Tyr Glu Ile Arg  Phe Tyr Glu Asp Gln  Ser Gln
        4875                 4880                 4885

ccg ccc aaa  gcc gag ctc tca gcc  tgc gtc atc act cag  ggg gca     25789
Pro Pro Lys  Ala Glu Leu Ser Ala  Cys Val Ile Thr Gln  Gly Ala
        4890                 4895                 4900

att ctc gcc  caa ttg caa gcc atc  caa aaa tcc cgc caa  gaa ttt     25834
Ile Leu Ala  Gln Leu Gln Ala Ile  Gln Lys Ser Arg Gln  Glu Phe
        4905                 4910                 4915

ctg ctg aaa  aag ggg aac ggg gtc  tac ctc gac ccc cag  acc ggt     25879
Leu Leu Lys  Lys Gly Asn Gly Val  Tyr Leu Asp Pro Gln  Thr Gly
        4920                 4925                 4930

gag gag ctc  aac aca agg ttc cct  cag gat gtc cca gcg  ccg agg     25924
Glu Glu Leu  Asn Thr Arg Phe Pro  Gln Asp Val Pro Ala  Pro Arg
        4935                 4940                 4945

aag caa gaa  gtt gaa agt gca gct  gcc gcc ccc aga gga  cat gga     25969
Lys Gln Glu  Val Glu Ser Ala Ala  Ala Ala Pro Arg Gly  His Gly
        4950                 4955                 4960

gga aga ctg  gga cag tca ggc aga  gga gga gga gat gga  aga ttg     26014
Gly Arg Leu  Gly Gln Ser Gly Arg  Gly Gly Gly Asp Gly  Arg Leu
        4965                 4970                 4975

gga cag cca  ggc aga gga ggc gga  cag cct gga gga aga  cag ttt     26059
Gly Gln Pro  Gly Arg Gly Gly Gly  Gln Pro Gly Gly Arg  Gln Phe
        4980                 4985                 4990

gga gga gga  aga cga gga ggc aga  gga ggt gga aga agc  aac cgc     26104
Gly Gly Gly  Arg Arg Gly Gly Arg  Gly Gly Gly Arg Ser  Asn Arg
        4995                 5000                 5005

cgc caa aca  att gtc ctc ggc agc  gga gac aag caa ggt  ccc aga     26149
Arg Gln Thr  Ile Val Leu Gly Ser  Gly Asp Lys Gln Gly  Pro Arg
        5010                 5015                 5020

cag cag cag  cag cac ggc tac aat  ctc cgc tcc ggg tcg  ggg ggc     26194
Gln Gln Gln  Gln His Gly Tyr Asn  Leu Arg Ser Gly Ser  Gly Gly
        5025                 5030                 5035

cca gca gcg  tcc caa cag tagatgggac gagaccgggc gattcccgaa          26242
Pro Ala Ala  Ser Gln Gln
        5040

cccgaccacc gcttccaaga ccggtaagaa ggagcggcag ggatacaagt cctggcgggg  26302

gcataagaat gccatcatct cctgcttgca tgaatgcggg ggcaacatat ccttcacccg  26362
```

```
acgctacctg ctcttccacc acggggtgaa cttccccgc aatgtcttgc attactaccg  26422

tcacctccac agcccttact acagccagca agtcccgaca gcctcgacaa agaaagacag  26482

cagcagcagc ggggacctcc agcagaaaac cagcagcagc agttagaaaa tccagtgcag  26542

caggaggagg actgaggatc acagcgaacg agccagcgca gacccgagag ctgagaaaca  26602

ggatctttcc aaccctctat gccatcttcc agcagagtcg gggcaagag caggaactga  26662

aagtaaaaaa ccgatctctg cgctcgctca cccgaagttg tttgtatcac aagagcgaag  26722

accaacttca gcgcactctc gaggacgccg aggctctctt caacaagtac tgcgcgctga  26782

ctcttaaaga gtagcccgcg cccgcgctcg ctcgaaaaag gcgggaatta cgtcaccctt  26842

ggcacctgtc ctttgccctc gtc atg agt  aaa gaa att ccc acg  cct tac    26892
                      Met Ser  Lys Glu Ile Pro Thr  Pro Tyr
                          5045                 5050

atg tgg agc  tat cag ccc caa atg  gga ctg gca gca ggc  gcc tcc     26937
Met Trp Ser  Tyr Gln Pro Gln Met  Gly Leu Ala Ala Gly  Ala Ser
        5055                 5060                 5065

cag gac tac  tcc acc cgc atg aat  tgg ctc agc gcc ggc  ccc tcg     26982
Gln Asp Tyr  Ser Thr Arg Met Asn  Trp Leu Ser Ala Gly  Pro Ser
        5070                 5075                 5080

atg atc tca  cgg gtt aat gat ata  cga gct tac cga aac  cag tta     27027
Met Ile Ser  Arg Val Asn Asp Ile  Arg Ala Tyr Arg Asn  Gln Leu
        5085                 5090                 5095

ctc cta gaa  cag tca gct ctc acc  acc aca ccc cgc caa  cac ctt     27072
Leu Leu Glu  Gln Ser Ala Leu Thr  Thr Thr Pro Arg Gln  His Leu
        5100                 5105                 5110

aat ccc cgg  aat tgg ccc gcc gcc  ctg gtg tac cag gaa  act ccc     27117
Asn Pro Arg  Asn Trp Pro Ala Ala  Leu Val Tyr Gln Glu  Thr Pro
        5115                 5120                 5125

gct ccc acc  acc gta cta ctt cct  cga gac gcc cag gcc  gaa gtt     27162
Ala Pro Thr  Thr Val Leu Leu Pro  Arg Asp Ala Gln Ala  Glu Val
        5130                 5135                 5140

cag atg act  aac gca ggt gta cag  ctg gcg ggc ggt tcc  gcc ctg     27207
Gln Met Thr  Asn Ala Gly Val Gln  Leu Ala Gly Gly Ser  Ala Leu
        5145                 5150                 5155

tgt cgt cac  cgg cct cag cag agt  ata aaa cgc ctg gtg  atc aga     27252
Cys Arg His  Arg Pro Gln Gln Ser  Ile Lys Arg Leu Val  Ile Arg
        5160                 5165                 5170

ggc cga ggt  atc cag ctc aac gac  gag tcg gtg agc tct  tcg ctt     27297
Gly Arg Gly  Ile Gln Leu Asn Asp  Glu Ser Val Ser Ser  Ser Leu
        5175                 5180                 5185

ggt ctg cga  cca gac gga gtc ttc  cag atc gcc ggc tgt  ggg aga     27342
Gly Leu Arg  Pro Asp Gly Val Phe  Gln Ile Ala Gly Cys  Gly Arg
        5190                 5195                 5200

tct tcc ttc  act cct cgt cag gct  gtc ctg act ttg gag  agt tcg     27387
Ser Ser Phe  Thr Pro Arg Gln Ala  Val Leu Thr Leu Glu  Ser Ser
        5205                 5210                 5215

tcc tcg cag  ccc cgc tcg ggc ggc  atc ggg act ctc cag  ttt gtg     27432
Ser Ser Gln  Pro Arg Ser Gly Gly  Ile Gly Thr Leu Gln  Phe Val
        5220                 5225                 5230

gag gag ttt  act ccc tct gtc tac  ttc aac ccc ttc tcc  ggc tct     27477
Glu Glu Phe  Thr Pro Ser Val Tyr  Phe Asn Pro Phe Ser  Gly Ser
        5235                 5240                 5245

ccc ggc cag  tac ccg gac gag ttc  ata ccg aac ttc gac  gca atc     27522
Pro Gly Gln  Tyr Pro Asp Glu Phe  Ile Pro Asn Phe Asp  Ala Ile
        5250                 5255                 5260

agc gag tca  gtg gat ggc tat gat  tg atg tct ggt ggc gcg  gct gag  27569
Ser Glu Ser  Val Asp Gly Tyr Asp     Met Ser Gly Gly Ala  Ala Glu
```

-continued

```
        5265                5270                5275

tta gct cga  ctg cga cat cta gac  cac tgc cgc cgc ttt  cgc tgt      27614
Leu Ala Arg  Leu Arg His Leu Asp  His Cys Arg Arg Phe  Arg Cys
        5280                5285                5290

ttc gcc cgg  gaa ctc acc gag ttc  atc tac ttc gaa ctc  ccc gag      27659
Phe Ala Arg  Glu Leu Thr Glu Phe  Ile Tyr Phe Glu Leu  Pro Glu
        5295                5300                5305

gag cac cct  cag gga ccg gcc cac  gga gtg cgg att acc  atc gaa      27704
Glu His Pro  Gln Gly Pro Ala His  Gly Val Arg Ile Thr  Ile Glu
        5310                5315                5320

ggg gga ata  gac tct cgc ctg cat  cgg atc ttc tgc cag  cga ccc      27749
Gly Gly Ile  Asp Ser Arg Leu His  Arg Ile Phe Cys Gln  Arg Pro
        5325                5330                5335

gtg ctg atc  gag cgc gac cag gga  act aca aca gtc tcc  atc tac      27794
Val Leu Ile  Glu Arg Asp Gln Gly  Thr Thr Thr Val Ser  Ile Tyr
        5340                5345                5350

tgc atc tgt  aac cac ccc gga ttg  cat gaa agc ctt tgc  tgt ctt      27839
Cys Ile Cys  Asn His Pro Gly Leu  His Glu Ser Leu Cys  Cys Leu
        5355                5360                5365

att tgt gct  gag ttt aat aaa aac  tgagttaaga ctcacctttg             27883
Ile Cys Ala  Glu Phe Asn Lys Asn
        5370                5375

gactaccgct tcttcaaccc ggactttaca acaccagcca gactctccgt tccagccaga  27943

agacccaggc ccttcctctg atccaggact ctaattctac ctccccagca ccatccccta  28003

ctaaccttcc cgaaactaac aacctcggag ctcagctgca accccgcttc tccagaagcc  28063

tcctttctgc caatactact actcccagaa ccggaggtga gctccgtggt ctccctactg  28123

acaaccccctg ggtggtagcg ggttttgtag cgctaggagt agttgcgggt gggctggtgc  28183

ttatcctctg ctacctatac acaccttgct gtgcttattt agtagtattg tgctgctggt  28243

ttaagaa atg ggg gtc gta cta  gta tcg ttt gct tta  ctt tcg ctt ttg  28292
        Met Gly Val Val Leu  Val Ser Phe Ala Leu  Leu Ser Leu Leu
                        5380                5385

ggt  ctg ggc tct gct acg  cta aga aat cag cct  ttg cta tta gat      28337
Gly  Leu Gly Ser Ala Thr  Leu Arg Asn Gln Pro  Leu Leu Leu Asp
5390                5395                5400

ccc  gat gat gtt gat cca  tgt ctg gac ttt gat  cca gag aac tgc      28382
Pro  Asp Asp Val Asp Pro  Cys Leu Asp Phe Asp  Pro Glu Asn Cys
5405                5410                5415

aca  ctc act ttt gca cct  gaa aca agt cgc ttc  tgt gga gtt gtt      28427
Thr  Leu Thr Phe Ala Pro  Glu Thr Ser Arg Phe  Cys Gly Val Val
5420                5425                5430

att  agg tgc gga ttt gaa  tgc agg tcc att gag  att aca cac aat      28472
Ile  Arg Cys Gly Phe Glu  Cys Arg Ser Ile Glu  Ile Thr His Asn
5435                5440                5445

aac  aaa act tgg aac aat  acc tta ttc aca ata  tgg caa cca gga      28517
Asn  Lys Thr Trp Asn Asn  Thr Leu Phe Thr Ile  Trp Gln Pro Gly
5450                5455                5460

gat  cct cag tgg tat act  gtc tct gtc cgg ggt  cct gac ggt tcc      28562
Asp  Pro Gln Trp Tyr Thr  Val Ser Val Arg Gly  Pro Asp Gly Ser
5465                5470                5475

gcc  cgc atg gct aat aac  act ttc att ttt gct  gaa atg tgc gat      28607
Ala  Arg Met Ala Asn Asn  Thr Phe Ile Phe Ala  Glu Met Cys Asp
5480                5485                5490

atg  gcc atg ttc atg agc  aga cag tat gac cta  tgg cct ccc agc      28652
Met  Ala Met Phe Met Ser  Arg Gln Tyr Asp Leu  Trp Pro Pro Ser
5495                5500                5505

aaa  gag aac att gtg gca  ttc tcc att gct tat  tgc tta tgt act      28697
```

```
Lys  Glu Asn Ile Val Ala  Phe Ser Ile Ala Tyr  Cys Leu Cys Thr
5510                5515                5520

tgc  att acc act gct atc  ata tgt gtg tgc ata  cac ttg ctc ata     28742
Cys  Ile Thr Thr Ala Ile  Ile Cys Val Cys Ile  His Leu Leu Ile
5525                5530                5535

gca  act cgc tcc aaa aac  agc aat gag gaa aaa  gag aaa atg cct     28787
Ala  Thr Arg Ser Lys Asn  Ser Asn Glu Glu Lys  Glu Lys Met Pro
5540                5545                5550

tgaccttttt tcctcgtttt ctgttcacag ct atg  att ttt att aca tcc  atc  28840
                                    Met  Ile Phe Ile Thr Ser  Ile
                                    5555                 5560

ttt att gtc agc  att tca act att gca  cat gga caa caa ata  aat     28885
Phe Ile Val Ser  Ile Ser Thr Ile Ala  His Gly Gln Gln Ile  Asn
            5565                 5570                 5575

gca ggc gac aat  ttc aca tta gtt ggg  cct aaa aaa cca gtt  gtc     28930
Ala Gly Asp Asn  Phe Thr Leu Val Gly  Pro Lys Lys Pro Val  Val
            5580                 5585                 5590

tcc tgg ttc tgg  act aaa cct gat cca  tgg gct aaa act gat  tac     28975
Ser Trp Phe Trp  Thr Lys Pro Asp Pro  Trp Ala Lys Thr Asp  Tyr
            5595                 5600                 5605

tgg gtt tca ctt  tgt gat ggt gta ttt  ctg tat aaa tct aac  ctt     29020
Trp Val Ser Leu  Cys Asp Gly Val Phe  Leu Tyr Lys Ser Asn  Leu
            5610                 5615                 5620

aca ttc aat tgc  aat aat caa aac cta  aca cta atc aat gtt  act     29065
Thr Phe Asn Cys  Asn Asn Gln Asn Leu  Thr Leu Ile Asn Val  Thr
            5625                 5630                 5635

aaa gat tat gaa  gga aca tac tat gga  gat gga atc tta tat  aga     29110
Lys Asp Tyr Glu  Gly Thr Tyr Tyr Gly  Asp Gly Ile Leu Tyr  Arg
            5640                 5645                 5650

att aga gta ata  gac act cct aag aga  ttc aaa aga gct aca  act     29155
Ile Arg Val Ile  Asp Thr Pro Lys Arg  Phe Lys Arg Ala Thr  Thr
            5655                 5660                 5665

aaa gtt aca gat  cca caa cca aaa atc  tct agc atc act act  atc     29200
Lys Val Thr Asp  Pro Gln Pro Lys Ile  Ser Ser Ile Thr Thr  Ile
            5670                 5675                 5680

ttt act aac agt  aca tat acc aat tta  caa ttg gct tat gtt  aac     29245
Phe Thr Asn Ser  Thr Tyr Thr Asn Leu  Gln Leu Ala Tyr Val  Asn
            5685                 5690                 5695

tca tca aat att  aca atc ctg cct aca  cca atc aat gaa gaa  att     29290
Ser Ser Asn Ile  Thr Ile Leu Pro Thr  Pro Ile Asn Glu Glu  Ile
            5700                 5705                 5710

cct aaa tca atg  att ggg atc att gtg  gcg gtg gca gtg gga  atg     29335
Pro Lys Ser Met  Ile Gly Ile Ile Val  Ala Val Ala Val Gly  Met
            5715                 5720                 5725

atc ata atc ata  ata tgt atg atc acc  tat gct tgc tgc tac  aga     29380
Ile Ile Ile Ile  Ile Cys Met Ile Thr  Tyr Ala Cys Cys Tyr  Arg
            5730                 5735                 5740

aag ttt tat tat  gaa gaa aaa gga gac  ccc cta cta aat ttt  gac     29425
Lys Phe Tyr Tyr  Glu Glu Lys Gly Asp  Pro Leu Leu Asn Phe  Asp
            5745                 5750                 5755

att taattttta tag atg aaa caa  cta ggt atc ttg att  att tac tgc   29474
Ile               Met Lys Gln  Leu Gly Ile Leu Ile  Ile Tyr Cys
                          5760                 5765

agc att  aat ctt tct caa tta  aca cca aca cca act  agt aac aat     29519
Ser Ile  Asn Leu Ser Gln Leu  Thr Pro Thr Pro Thr  Ser Asn Asn
    5770                 5775                 5780

gtg cag  act act tta cca gtc  acc ata aac aaa act  acc tca gtt     29564
Val Gln  Thr Thr Leu Pro Val  Thr Ile Asn Lys Thr  Thr Ser Val
    5785                 5790                 5795
```

-continued

```
ttt cta  aat aat aca gac ttt  aat act aac tcc aac  tct aaa gat     29609
Phe Leu  Asn Asn Thr Asp Phe  Asn Thr Asn Ser Asn  Ser Lys Asp
    5800                5805                5810

ttt ctt  caa ctt caa atc act  gct ctt att ata att  gga tta ata     29654
Phe Leu  Gln Leu Gln Ile Thr  Ala Leu Ile Ile Ile  Gly Leu Ile
    5815                5820                5825

att cta  gca atc ctt cta tac  ttt gtc ttt tgc cgc  aac atc ccc     29699
Ile Leu  Ala Ile Leu Leu Tyr  Phe Val Phe Cys Arg  Asn Ile Pro
    5830                5835                5840

aat gtt  cac aaa ccc att aaa  aag cgt cct att tac  aac ccc atc     29744
Asn Val  His Lys Pro Ile Lys  Lys Arg Pro Ile Tyr  Asn Pro Ile
    5845                5850                5855

tta agc  gag cca caa ctt aga  cgg tgg agg gaa atc  taatacatct      29790
Leu Ser  Glu Pro Gln Leu Arg  Arg Trp Arg Glu Ile
    5860                5865                5870

ctcttttctt tcagtatggt gatcatcaaa c atg atc cct aga aat  ttt ttc    29842
                                   Met Ile Pro Arg Asn  Phe Phe
                                                   5875

ttc acc ata  ctc atc tgc ctt ctc  aat atc tgc gct acc  ctt gct     29887
Phe Thr Ile  Leu Ile Cys Leu Leu  Asn Ile Cys Ala Thr  Leu Ala
        5880                5885                5890

gcg gtc act  agc gtc tca cca gac  tgc ata gga cca ttt  gcc acc     29932
Ala Val Thr  Ser Val Ser Pro Asp  Cys Ile Gly Pro Phe  Ala Thr
        5895                5900                5905

tac ttg ctt  ttt gca ttg atc acc  tgt atc tgt gtg agt  agc aca     29977
Tyr Leu Leu  Phe Ala Leu Ile Thr  Cys Ile Cys Val Ser  Ser Thr
        5910                5915                5920

gtc tgt ctg  gtt att aat ttt ttc  caa ctt ata gac tgg  att ttt     30022
Val Cys Leu  Val Ile Asn Phe Phe  Gln Leu Ile Asp Trp  Ile Phe
        5925                5930                5935

gtg cgc att  gcc tac ctg aga cac  cat cca gaa tac cgc  aac cat     30067
Val Arg Ile  Ala Tyr Leu Arg His  His Pro Glu Tyr Arg  Asn His
        5940                5945                5950

gat att gcg  gca cta ctc aga ctt  ctt taaaaccata caggctttgc        30114
Asp Ile Ala  Ala Leu Leu Arg Leu  Leu
        5955                5960

taccactgct attgctgcta ctgccctgtg acactatagc caccacacct accctaaacc  30174

caaatcttag aaaatgtaaa ttccaagagc catggaattt cctcaaatgt tataatgaaa  30234

caattgattt tccaccctat tggataacaa tcattggaat ccttaatgtg gtatgctgca  30294

ccatatttgc attccttgta tatcccatgt ttgattttgg gtggaatgtc cccaatgcac  30354

tcactcaccc acaagaacca caggaacata tcccactaca aaacatgcaa ccactagcac  30414

taatagaata tgaaaatgag ccacagcctc cactactccc tgccattagc tacttcaacc  30474

taaccggtag ag atg act gac cca  ctc gcc gca tcc gcc  gct gcc gag    30522
              Met Thr Asp Pro  Leu Ala Ala Ser Ala  Ala Ala Glu
                          5965                5970

gaa cta  ctt gat atg gac ggc  cgt gcc tcc gaa cag  cga ctc gcc     30567
Glu Leu  Leu Asp Met Asp Gly  Arg Ala Ser Glu Gln  Arg Leu Ala
    5975                5980                5985

caa cta  cgc att cgc cag cag  cag gaa cgt gcc gcc  aag gag ctc     30612
Gln Leu  Arg Ile Arg Gln Gln  Gln Glu Arg Ala Ala  Lys Glu Leu
    5990                5995                6000

agg gat  gct att gag att cac  cag tgc aaa aaa ggc  ata ttc tgc     30657
Arg Asp  Ala Ile Glu Ile His  Gln Cys Lys Lys Gly  Ile Phe Cys
    6005                6010                6015

tta gta  aaa caa gct aag atc  tcc tac gag att acc  gct aac gac     30702
Leu Val  Lys Gln Ala Lys Ile  Ser Tyr Glu Ile Thr  Ala Asn Asp
    6020                6025                6030
```

```
cac cgc ctc tca tat gag ctt ggg ccg cag cgt cag aaa ttc act     30747
His Arg Leu Ser Tyr Glu Leu Gly Pro Gln Arg Gln Lys Phe Thr
    6035                6040                6045

tgc atg gtg gga att aac ccc ata gtc atc acc cag caa gct gga     30792
Cys Met Val Gly Ile Asn Pro Ile Val Ile Thr Gln Gln Ala Gly
    6050                6055                6060

gat acc aag ggt tgc atc cat tgt tcc tgt gaa tcc acc gag tgc     30837
Asp Thr Lys Gly Cys Ile His Cys Ser Cys Glu Ser Thr Glu Cys
    6065                6070                6075

atc tac acc ctg ctg aag acc ctc tgc ggc ctt cga gac atc cta     30882
Ile Tyr Thr Leu Leu Lys Thr Leu Cys Gly Leu Arg Asp Ile Leu
    6080                6085                6090

ccc atg aac taatcaacaa accataccct cttcccatta aaatccaatt         30931
Pro Met Asn
    6095

aataaaattc acttacttaa aatcagaaac aaagtttttg tccaagttgt tttcaatcag  30991

cacctcactt ccctcttccc aactctggta ctctaagcct cggcgggcgg catacttcct  31051

ccacactttg aaagggatgt caaatttcag ttcttctttt cccacaatct tcatttctct  31111

tcccag atg gcc aaa cga gct cgt cta agc agc tcc ttc aac ccg gtc  31159
       Met Ala Lys Arg Ala Arg Leu Ser Ser Ser Phe Asn Pro Val
                   6100                6105                6110

tac ccc tat gaa gat gaa aac agc tca caa cac ccc ttt ata aac     31204
Tyr Pro Tyr Glu Asp Glu Asn Ser Ser Gln His Pro Phe Ile Asn
                6115                6120                6125

ccc ggt ttc att tcc ccc aat ggg ttt aca caa aat tca gat gga     31249
Pro Gly Phe Ile Ser Pro Asn Gly Phe Thr Gln Asn Ser Asp Gly
                6130                6135                6140

gtt cta gct ctt aaa tgc gca gct cca ctt acc acc aca ggt ggt     31294
Val Leu Ala Leu Lys Cys Ala Ala Pro Leu Thr Thr Thr Gly Gly
                6145                6150                6155

tct ctt cag ctt aaa gtg ggt agg ggg ctt aca att gac act act     31339
Ser Leu Gln Leu Lys Val Gly Arg Gly Leu Thr Ile Asp Thr Thr
                6160                6165                6170

gac ggg aca tta gaa gag gac ata aac atc tta gca cca ctt aca     31384
Asp Gly Thr Leu Glu Glu Asp Ile Asn Ile Leu Ala Pro Leu Thr
                6175                6180                6185

aaa act gcc cac tcc ata ggt tta tca ttg gga aat ggg tta gaa     31429
Lys Thr Ala His Ser Ile Gly Leu Ser Leu Gly Asn Gly Leu Glu
                6190                6195                6200

tta aaa gac agc aaa cta tat gtt aaa cta gga gat ggt cta aaa     31474
Leu Lys Asp Ser Lys Leu Tyr Val Lys Leu Gly Asp Gly Leu Lys
                6205                6210                6215

ttt aac tca aac agc ata tgt tta gac cat gac att aac act tta     31519
Phe Asn Ser Asn Ser Ile Cys Leu Asp His Asp Ile Asn Thr Leu
                6220                6225                6230

tgg acc gga atg aat ccg tcc att aac tgt aac att atg caa caa     31564
Trp Thr Gly Met Asn Pro Ser Ile Asn Cys Asn Ile Met Gln Gln
                6235                6240                6245

gat gac aat gac agc aag cta act cta gtc tta act aaa aat gga     31609
Asp Asp Asn Asp Ser Lys Leu Thr Leu Val Leu Thr Lys Asn Gly
                6250                6255                6260

gga atg gta aat gca tat gta tca ttg gta ggg gca tct gat att     31654
Gly Met Val Asn Ala Tyr Val Ser Leu Val Gly Ala Ser Asp Ile
                6265                6270                6275

gta aac tca cta ttt aaa cgg gcc act gca aat atc aca ata agg     31699
Val Asn Ser Leu Phe Lys Arg Ala Thr Ala Asn Ile Thr Ile Arg
                6280                6285                6290
```

```
cta agc ttt gat gcc  tct ggc aat tta cta  aca agc cta tca gac      31744
Leu Ser Phe Asp Ala  Ser Gly Asn Leu Leu  Thr Ser Leu Ser Asp
                6295                 6300                 6305

cta aaa acc cca ctg  aat cac aga tat ggc  aat gac atg gac act      31789
Leu Lys Thr Pro Leu  Asn His Arg Tyr Gly  Asn Asp Met Asp Thr
                6310                 6315                 6320

gac aca tta act aat  ggc aag agt ttt atg  ccc agc act aca gcc      31834
Asp Thr Leu Thr Asn  Gly Lys Ser Phe Met  Pro Ser Thr Thr Ala
                6325                 6330                 6335

tat ccc ttt aat gac  act aca agg gat aaa  gaa aac tac ata tat      31879
Tyr Pro Phe Asn Asp  Thr Thr Arg Asp Lys  Glu Asn Tyr Ile Tyr
                6340                 6345                 6350

ggc acc tgt tat tat  aaa tca act gaa gac  gca ttg tac ccg cta      31924
Gly Thr Cys Tyr Tyr  Lys Ser Thr Glu Asp  Ala Leu Tyr Pro Leu
                6355                 6360                 6365

gaa gtt gcc gtc aca  ctt aac aga cgg atg  agc agt gct gcc gtt      31969
Glu Val Ala Val Thr  Leu Asn Arg Arg Met  Ser Ser Ala Ala Val
                6370                 6375                 6380

tct tat gct atg act  att gct tgg act tta  agt gca aac aca ccc      32014
Ser Tyr Ala Met Thr  Ile Ala Trp Thr Leu  Ser Ala Asn Thr Pro
                6385                 6390                 6395

cct gaa act acc ata  gca acc ctt gtt acc  tcc ccc ttc act ttt      32059
Pro Glu Thr Thr Ile  Ala Thr Leu Val Thr  Ser Pro Phe Thr Phe
                6400                 6405                 6410

tcc tat att aga gaa  aat gac tgacaacaaa aataaatttt aactttttat      32110
Ser Tyr Ile Arg Glu  Asn Asp
                6415

tgaaaaatca gtttacagga ttcgagtagt tattttgcct ccccttccc atttcatacg  32170

atacaccaat ctctccccac gcacagcttt aaacatttgg attccatttg agatagtcat  32230

ggatttagat tccacattcc acacagtttc agagctagat aatcttggat cagtgataga  32290

tataaatcca tcggggcagt ccttcaaggt gatttcacag tccagttgct gtggctgcgg  32350

ctccggagtc tggatcagag tcatctggaa caagaacgat gggagtcata atccgagaac  32410

gggatcgggc ggttgtgtct catcaaaccc cgaagcagtc gctgtctgcg ccgctccgtg  32470

cgactgctgc tgatgggatc ggggtccaca gtctctcgaa gcatgattct aatagccctc  32530

aacattaaca tcctggtgcg atgcgcacag cagcgcatcc tgatctcact tagctcacag  32590

caataggtac aacacaacac cacaatattg tttaacaggc cataattaaa ggcactccag  32650

ccaaaactca tttcaggaat aatttgccca gcgtgaccat cgtaccaaat cctgatgtaa  32710

atcagatggc gccccctcca gaacacactg cccacataca tgatctcctt aggcatatgc  32770

atattcacaa tctctcggta ccatggacag cgctggttaa tcatgcagcc ccgaataacc  32830

ttccggaacc aaatggccag cactgcgccc ccagcaatac attgaagaga accctgtcga  32890

ttacagtgac aatggagaac ccacttctct cgcccatgga tcacttggga ataaaatata  32950

tctattgtgg cacaacacag acataaatgc atacatcttc tcatcaccct taactcttca  33010

ggggttaaaa acatatccca gggaatagga agctcttgca aaacagtaaa ggtggcagaa  33070

caaggcagac cgcgaacata acttacactg tgcatggtca aggtattgca atctggtaac  33130

agcggatgct cttcagtcat agaagctctg gtttcacttt cctcacagcg tggtaaaggg  33190

gccctcagtt gaggttccct ggtgtaagga tggtgtctgg cgcacgatgt cgagcgtgca  33250

cgcgacctcg ttgtaatgga gctgcttcct gacattctcg tattttgcat agcagaacct  33310

agtcttggca cagcacacgt cccgtcgcct cctgtcccgc cgcctagcac gttcagtgtg  33370

gtaattatag tacagccatt cccgtagatt ggtcaaaaga tcttcagcct cagttgtcat  33430
```

```
aaaaactcca tcatatctta ctgctctgat aaaatcattc actgtagaaa gtgcaatgcc  33490

cagccaggca atgcaattag cttgtgtttc gaccaaagga gggggaggaa gacatggaag  33550

aaccataatt aatttttatg ccagacgatc ccgcagtatt tctatatgga gatcacgaag  33610

atggcacctc tcgcccccac tgtgttgatg aaaaatgaca gctaggtcaa acataatgcg  33670

attttccagg tgctcaacgg tggcttcaag caaagcctcc aaacgtacat ccaaaaacaa  33730

aagaacagca aaagcaggag cattttctaa ttcctcaatc atcatattac attcctgtac  33790

cattcccaaa taattttcat ctttccatcc ttgaattatt cgtgttattt catctggtaa  33850

atccaatcca cacatgagaa atagctcccg gagggcgccc tccaccggca atctcaagca  33910

taccctcata gtgacaaaat atcgtgctcc tctgtcacct gcagcaaatt gagaatggca  33970

atatcaaacg gaatgccact ggctctaagt tcttctctaa gttccagttg taaaaactct  34030

tgcatatcat cgccaaactg cttagccata ggtcctccag gaataagagc gggggacgct  34090

acagtgcaga acaagcgcat gccgccccaa ttgcctccag caaaagtgag gttgcaatat  34150

gcatactgag aacctccagt gatatcatcc agtgtactgg aaagataatc aggcagagct  34210

tctcgtatgc aattaataat agaaaagtct gccagatgaa catttaaagc ctgtgggatg  34270

cagatgcaat aagttatcgc gctgcgctcc aacattgtta gtatggttag tctgtaaaaa  34330

caaaaaacaa aaaaaattac atcacgctag actggcgaac gggtggaaaa atcactctct  34390

ccaacaccag gcaggctaca gggtctccag cgcgaccctc gtaaaacctg tcagtatgat  34450

tgaaaagcat caccgaaagg ggttgttgat ggccagcata tattatttgc gatgaagcat  34510

acaatccaga agtgttagta tcagttaaag aaaaaaatcg gccaagatag catctcggaa  34570

cgattatgct caatctcaaa tgcagcaaag cgacacctcg cggatgcaaa gtaaaatcca  34630

caggagcata aaaaaagtaa ttattcccct cttgcacagg cagcctagct cccggcccct  34690

ccaaaatcac atataatgct tcagcagcca tagcttaccg cgcaaatcag gcacagcagt  34750

cagatagaga aaaagctgtg aactgactgc ccagcctgtg cgcaatatat agagaaccct  34810

tacactgacg taattgggca aagtctaaaa aatcccgcca aaaaaacagc acacgcccaa  34870

aagtgtgaca ctcgctaaaa aaatattttt cacttcctcg ttccgtatat gacgtcaatt  34930

ccgctttccc acgaatcgtc acttccggcc atcttgcaac gtcacctccc cgcgccggcc  34990

cgccccttttt gaccgttgaa cccgctagcc aatccccttc cgccctccat tttcaaaagc  35050

tcatttgcat gttggcaccg ttccatttat aaggtatatt attgatgatg             35100
```

```
<210> SEQ ID NO 2
<211> LENGTH: 495
<212> TYPE: PRT
<213> ORGANISM: Unknown
<220> FEATURE:
<223> OTHER INFORMATION: Synthetic Construct

<400> SEQUENCE: 2

Met Asp Pro Thr Asn Pro Leu Gln Gln Gly Ile Arg Leu Gly Phe His
1               5                   10                  15

Ser Ser Ser Phe Val Glu Asn Met Glu Gly Pro Gln Ala Glu Asp Asn
            20                  25                  30

Leu Arg Leu Leu Ala Ser Ala Ala Ser Gly Arg Ser Ser Asn Pro Glu
        35                  40                  45

Thr Pro Thr Gly His Ala Ser Gly Phe Gly Gly Gly Ala Ala Gly Gly
    50                  55                  60
```

```
Gln Pro Glu Ser Arg Pro Gly Pro Ser Gly Gly Gly Gly Gly Gly Val
65                  70                  75                  80

Ala Asp Leu Phe Pro Glu Leu Arg Arg Val Leu Thr Arg Ser Thr Ser
                85                  90                  95

Ser Gly Gln Asp Arg Gly Ile Lys Arg Glu Arg Asn Ala Ser Gly His
            100                 105                 110

Asn Ser Arg Thr Glu Leu Ala Leu Ser Leu Met Ser Arg Ser Arg Pro
        115                 120                 125

Glu Thr Ile Trp Trp His Glu Val Gln Ser Glu Gly Arg Asp Glu Val
    130                 135                 140

Ser Ile Leu Gln Glu Lys Tyr Ser Leu Glu Gln Ile Lys Thr Cys Trp
145                 150                 155                 160

Leu Glu Pro Glu Asp Asp Trp Glu Val Ala Ile Arg Asn Tyr Ala Lys
                165                 170                 175

Ile Ser Leu Arg Pro Asp Lys Gln Tyr Lys Ile Thr Lys Lys Ile Asn
            180                 185                 190

Ile Arg Asn Ala Cys Tyr Ile Ala Gly Asn Gly Ala Glu Val Ile Ile
        195                 200                 205

Asp Thr Pro Asp Lys Thr Ala Phe Arg Cys Cys Met Met Gly Met Trp
    210                 215                 220

Pro Gly Val Ala Gly Met Glu Ala Val Thr Leu Met Asn Ile Arg Phe
225                 230                 235                 240

Arg Gly Asp Gly Tyr Asn Gly Ile Val Phe Met Ala Asn Thr Lys Leu
                245                 250                 255

Ile Leu His Gly Cys Ser Phe Phe Gly Phe Asn Asn Thr Cys Val Glu
            260                 265                 270

Ser Trp Gly Gln Val Ser Ile Arg Gly Cys Ser Phe Tyr Ala Cys Trp
        275                 280                 285

Ile Ala Leu Ser Gly Arg Thr Lys Ser Gln Leu Ser Val Lys Lys Cys
    290                 295                 300

Met Phe Glu Arg Cys Asn Leu Gly Ile Leu Asn Glu Gly Glu Ala Arg
305                 310                 315                 320

Val Arg His Cys Ala Ala Thr Glu Thr Gly Cys Phe Ile Leu Ile Lys
                325                 330                 335

Gly Asn Ala Ser Val Lys His Asn Met Ile Cys Gly Pro Leu Asp Glu
            340                 345                 350

Arg Pro Tyr Gln Met Leu Thr Cys Ala Gly Gly His Cys Asn Met Leu
        355                 360                 365

Ala Thr Val His Ile Val Ser His Ala Arg Lys Lys Trp Pro Val Phe
    370                 375                 380

Glu His Asn Val Met Thr Lys Cys Thr Met His Ala Gly Gly Arg Arg
385                 390                 395                 400

Gly Met Phe Met Pro Tyr Gln Cys Asn Met Asn His Val Lys Val Met
                405                 410                 415

Leu Glu Pro Asp Ala Phe Ser Arg Met Ser Leu Thr Gly Ile Phe Asp
            420                 425                 430

Met Asn Val Gln Leu Trp Lys Ile Leu Arg Tyr Asp Glu Thr Lys Ser
        435                 440                 445

Arg Val Arg Ala Cys Glu Cys Gly Gly Lys His Ala Arg Phe Gln Pro
    450                 455                 460

Val Cys Val Asp Val Thr Glu Asp Leu Arg Pro Asp His Leu Val Leu
465                 470                 475                 480

Ala Cys Thr Gly Ala Glu Phe Gly Ser Ser Gly Glu Glu Thr Asp
```

```
                485                 490                 495

<210> SEQ ID NO 3
<211> LENGTH: 138
<212> TYPE: PRT
<213> ORGANISM: Unknown
<220> FEATURE:
<223> OTHER INFORMATION: Synthetic Construct

<400> SEQUENCE: 3

Met Ser Gly Ser Ala Ser Phe Glu Gly Gly Val Phe Ser Pro Tyr Leu
1               5                   10                  15

Thr Gly Arg Leu Pro Pro Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45

Thr Tyr Ala Thr Leu Ser Ser Ser Pro Leu Asp Ala Ala Ala Ala Ala
    50                  55                  60

Ala Ala Ser Ala Ala Ala Asn Thr Val Leu Gly Met Gly Tyr Tyr Gly
65                  70                  75                  80

Ser Ile Val Ala Asn Ser Ser Ser Ser Asn Asn Pro Ser Thr Leu Ala
                85                  90                  95

Glu Asp Lys Leu Leu Val Leu Leu Ala Gln Leu Glu Ala Leu Thr Gln
            100                 105                 110

Arg Leu Gly Glu Leu Ser Gln Gln Val Ala Gln Leu Arg Glu Gln Thr
        115                 120                 125

Glu Ser Ala Val Ala Thr Ala Lys Ser Lys
    130                 135


<210> SEQ ID NO 4
<211> LENGTH: 389
<212> TYPE: PRT
<213> ORGANISM: Unknown
<220> FEATURE:
<223> OTHER INFORMATION: Synthetic Construct

<400> SEQUENCE: 4

Met His Pro Val Leu Arg Gln Met Arg Pro Gln Gln Gln Ala Pro Ser
1               5                   10                  15

Gln Gln Gln Gln Gln Pro Gln Lys Ala Leu Pro Ala Pro Ala Pro Ala
            20                  25                  30

Thr Thr Ala Val Ala Ala Val Cys Gly Ala Gly Gln Pro Ala Tyr Asp
        35                  40                  45

Leu Asp Leu Glu Glu Gly Glu Gly Leu Ala Arg Leu Gly Ala Pro Ser
    50                  55                  60

Pro Glu Arg His Pro Arg Val Gln Leu Lys Lys Asp Ser Arg Glu Ala
65                  70                  75                  80

Tyr Val Pro Gln Gln Asn Leu Phe Arg Asp Arg Ser Gly Glu Glu Pro
                85                  90                  95

Glu Glu Met Arg Ala Ser Arg Phe Asn Ala Gly Arg Glu Leu Arg His
            100                 105                 110

Gly Leu Asp Arg Arg Arg Val Leu Arg Asp Glu Asp Phe Glu Val Asp
        115                 120                 125

Glu Met Thr Gly Ile Ser Pro Ala Arg Ala His Val Ala Ala Ala Asn
    130                 135                 140

Leu Val Ser Ala Tyr Glu Gln Thr Val Lys Glu Glu Arg Asn Phe Gln
145                 150                 155                 160
```

```
Lys Ser Phe Asn Asn His Val Arg Thr Leu Ile Ala Arg Glu Glu Val
                165                 170                 175

Thr Leu Gly Leu Met His Leu Trp Asp Leu Met Glu Ala Ile Thr Gln
            180                 185                 190

Asn Pro Thr Ser Lys Pro Leu Thr Ala Gln Leu Phe Leu Val Val Gln
        195                 200                 205

His Ser Arg Asp Asn Glu Ala Phe Arg Glu Ala Leu Leu Asn Ile Thr
    210                 215                 220

Glu Pro Glu Gly Arg Trp Leu Tyr Asp Leu Ile Asn Ile Leu Gln Ser
225                 230                 235                 240

Ile Ile Val Gln Glu Arg Ser Leu Gly Leu Ala Glu Lys Val Ala Ala
                245                 250                 255

Ile Asn Tyr Ser Val Leu Ser Leu Gly Lys Tyr Tyr Ala Arg Lys Ile
            260                 265                 270

Tyr Lys Thr Pro Tyr Val Pro Ile Asp Lys Glu Val Lys Ile Asp Gly
        275                 280                 285

Phe Tyr Met Arg Met Thr Leu Lys Val Leu Thr Leu Ser Asp Asp Leu
    290                 295                 300

Gly Val Tyr Arg Asn Asp Arg Met His Arg Ala Val Ser Ala Ser Arg
305                 310                 315                 320

Arg Arg Glu Leu Ser Asp Arg Glu Leu Met His Ser Leu Gln Arg Ala
                325                 330                 335

Leu Thr Gly Ala Gly Thr Asp Gly Glu Asn Tyr Phe Asp Met Gly Ala
            340                 345                 350

Asp Leu Gln Trp Gln Pro Ser Arg Arg Ala Leu Asp Ala Ala Gly Cys
        355                 360                 365

Glu Leu Pro Tyr Val Glu Glu Val Asp Glu Gly Glu Glu Glu Glu Gly
    370                 375                 380

Glu Tyr Leu Glu Asp
385


<210> SEQ ID NO 5
<211> LENGTH: 587
<212> TYPE: PRT
<213> ORGANISM: Unknown
<220> FEATURE:
<223> OTHER INFORMATION: Synthetic Construct

<400> SEQUENCE: 5

Met Glu Gln Gln Ala Pro Asp Pro Ala Met Arg Ala Ala Leu Gln Ser
1               5                   10                  15

Gln Pro Ser Gly Ile Asn Ser Ser Asp Asp Trp Thr Gln Ala Met Gln
            20                  25                  30

Arg Ile Met Ala Leu Thr Thr Arg Asn Pro Glu Ala Phe Arg Gln Gln
        35                  40                  45

Pro Gln Ala Asn Arg Leu Ser Ala Ile Leu Glu Ala Val Val Pro Ser
    50                  55                  60

Arg Ser Asn Pro Thr His Glu Lys Val Leu Ala Ile Val Asn Ala Leu
65                  70                  75                  80

Val Glu Asn Lys Ala Ile Arg Pro Asp Glu Ala Gly Leu Val Tyr Asn
                85                  90                  95

Ala Leu Leu Glu Arg Val Ala Arg Tyr Asn Ser Ser Asn Val Gln Thr
            100                 105                 110

Asn Leu Asp Arg Met Val Thr Asp Val Arg Glu Ala Val Ser Gln Arg
        115                 120                 125
```

```
Glu Arg Phe Gln Arg Asp Ala Asn Leu Gly Ser Leu Val Ala Leu Asn
    130                 135                 140

Ala Phe Leu Ser Thr Gln Pro Ala Asn Val Pro Arg Gly Gln Gln Asp
145                 150                 155                 160

Tyr Thr Asn Phe Leu Ser Ala Leu Arg Leu Met Val Thr Glu Val Pro
                165                 170                 175

Gln Ser Glu Val Tyr Gln Ser Gly Pro Asp Tyr Phe Phe Gln Thr Ser
            180                 185                 190

Arg Gln Gly Leu Gln Thr Val Asn Leu Ser Gln Ala Phe Lys Asn Leu
        195                 200                 205

Arg Gly Leu Trp Gly Val His Ala Pro Val Gly Asp Arg Ala Thr Val
    210                 215                 220

Ser Ser Leu Leu Thr Pro Asn Ser Arg Leu Leu Leu Leu Leu Val Ser
225                 230                 235                 240

Pro Phe Thr Asp Ser Gly Ser Ile Asp Arg Asn Ser Tyr Leu Gly Tyr
                245                 250                 255

Leu Leu Asn Leu Tyr Arg Glu Ala Ile Gly Gln Ser Gln Val Asp Glu
            260                 265                 270

Gln Thr Tyr Gln Glu Ile Thr Gln Val Ser Arg Ala Leu Gly Gln Glu
        275                 280                 285

Asp Thr Gly Ser Leu Glu Ala Thr Leu Asn Phe Leu Leu Thr Asn Arg
    290                 295                 300

Ser Gln Lys Ile Pro Pro Gln Tyr Ala Leu Thr Ala Glu Glu Glu Arg
305                 310                 315                 320

Ile Leu Arg Tyr Val Gln Gln Ser Val Gly Leu Phe Leu Met Gln Glu
                325                 330                 335

Gly Ala Thr Pro Ser Ala Ala Leu Asp Met Thr Ala Arg Asn Met Glu
            340                 345                 350

Pro Ser Met Tyr Ala Ser Asn Arg Pro Phe Ile Asn Lys Leu Leu Asp
        355                 360                 365

Tyr Leu His Arg Ala Ala Ala Met Asn Ser Asp Tyr Phe Thr Asn Ala
    370                 375                 380

Ile Leu Asn Pro His Trp Leu Pro Pro Pro Gly Phe Tyr Thr Gly Glu
385                 390                 395                 400

Tyr Asp Met Pro Asp Pro Asn Asp Gly Phe Leu Trp Asp Asp Val Asp
                405                 410                 415

Ser Ser Ile Phe Ser Pro Pro Pro Gly Tyr Asn Thr Trp Lys Lys Glu
            420                 425                 430

Gly Gly Asp Arg Arg His Ser Ser Val Ser Leu Ser Gly Ser Arg Gly
        435                 440                 445

Ala Ala Ala Ala Val Pro Glu Ala Ala Ser Pro Phe Pro Ser Leu Pro
    450                 455                 460

Phe Ser Leu Asn Ser Val Arg Ser Ser Glu Leu Gly Arg Ile Thr Arg
465                 470                 475                 480

Pro Arg Leu Met Gly Glu Asp Glu Tyr Leu Asn Asp Ser Leu Leu Arg
                485                 490                 495

Pro Glu Arg Glu Lys Asn Phe Pro Asn Asn Gly Ile Glu Ser Leu Val
            500                 505                 510

Asp Lys Met Ser Arg Trp Lys Thr Tyr Ala Gln Asp His Lys Asp Glu
        515                 520                 525

Pro Arg Ile Leu Gly Ala Ala Ser Gly Thr Thr Arg Arg Arg Gln Arg
    530                 535                 540

His Asp Arg Gln Arg Gly Leu Val Trp Asp Asp Glu Asp Ser Ala Asp
```

```
545                 550                 555                 560

Asp Ser Ser Val Leu Asp Leu Gly Gly Arg Gly Gly Gly Asn Pro Phe
                565                 570                 575

Ala His Leu Arg Pro His Phe Gly Arg Met Leu
            580                 585


<210> SEQ ID NO 6
<211> LENGTH: 584
<212> TYPE: PRT
<213> ORGANISM: Unknown
<220> FEATURE:
<223> OTHER INFORMATION: Synthetic Construct

<400> SEQUENCE: 6

Met Met Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Ala Val
            20                  25                  30

Met Gln Pro Ser Leu Glu Ala Pro Phe Val Pro Pro Arg Tyr Leu Ala
        35                  40                  45

Pro Thr Glu Gly Arg Asn Ser Ile Arg Tyr Ser Glu Leu Ala Pro Gln
    50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Thr Val
                85                  90                  95

Val Gln Asn Asn Asp Phe Thr Pro Thr Glu Ala Ser Thr Gln Thr Ile
            100                 105                 110

Asn Phe Asp Glu Arg Ser Arg Trp Gly Gly Gln Leu Lys Thr Ile Met
        115                 120                 125

His Thr Asn Met Pro Asn Val Asn Glu Tyr Met Phe Ser Asn Lys Phe
    130                 135                 140

Lys Ala Arg Val Met Val Ser Arg Lys Lys Pro Glu Gly Tyr Thr Gly
145                 150                 155                 160

Asp Lys Asn Asp Thr Ser Gln Asp Ile Leu Glu Tyr Glu Trp Phe Glu
                165                 170                 175

Phe Thr Leu Pro Glu Gly Asn Phe Ser Ala Thr Met Thr Ile Asp Leu
            180                 185                 190

Met Asn Asn Ala Ile Ile Asp Asn Tyr Leu Ala Val Gly Arg Gln Asn
        195                 200                 205

Gly Val Leu Glu Ser Asp Ile Gly Val Lys Phe Asp Thr Arg Asn Phe
    210                 215                 220

Arg Leu Gly Trp Asp Pro Ile Thr Lys Leu Val Met Pro Gly Val Tyr
225                 230                 235                 240

Thr Tyr Glu Ala Phe His Pro Asp Ile Val Leu Leu Pro Gly Cys Gly
                245                 250                 255

Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
        275                 280                 285

Gly Gly Asn Ile Pro Ala Leu Leu Asp Val Asp Ala Tyr Glu Lys Ser
    290                 295                 300

Lys Lys Glu Asn Thr Asp Thr Thr Thr Thr Thr Thr Val Thr Thr Thr
305                 310                 315                 320

Glu Val Ala Thr Val Ala Arg His Val Ser Glu Val Thr Thr Glu Ala
```

```
                325                 330                 335

Ala Thr Val Val Ala Val Asp Pro Ile Val Glu Glu Asn Asn Asn Thr
            340                 345                 350

Val Arg Gly Asp Asn Ile His Thr Ala Asn Glu Met Lys Ala Ala Ala
        355                 360                 365

Asp Asp Thr Thr Val Val Val Val Pro Gly Ala Val Val Thr Glu Thr
    370                 375                 380

Glu Thr Lys Thr Lys Thr Leu Thr Ile Gln Pro Leu Glu Lys Asp Thr
385                 390                 395                 400

Lys Glu Arg Ser Tyr Asn Val Ile Ser Gly Thr Asn Asp Thr Ala Tyr
                405                 410                 415

Arg Ser Trp Tyr Leu Ala Tyr Asn Tyr Gly Asp Pro Glu Lys Gly Val
            420                 425                 430

Arg Ser Trp Thr Leu Leu Thr Thr Ser Asp Val Thr Cys Gly Ala Glu
        435                 440                 445

Gln Val Tyr Trp Ser Leu Pro Asp Met Met Gln Asp Pro Val Thr Phe
    450                 455                 460

Arg Ser Thr Arg Gln Val Ser Asn Tyr Pro Val Val Gly Ala Glu Leu
465                 470                 475                 480

Met Pro Val Phe Ser Lys Ser Phe Tyr Asn Glu Gln Ala Val Tyr Ser
                485                 490                 495

Gln Gln Leu Arg Gln Thr Thr Ser Leu Thr His Ile Phe Asp Arg Phe
            500                 505                 510

Pro Glu Asn Gln Ile Leu Ile Arg Pro Pro Ala Pro Thr Ile Thr Thr
        515                 520                 525

Val Ser Glu Asn Val Pro Ala Leu Thr Asp His Gly Thr Leu Pro Leu
    530                 535                 540

Arg Ser Ser Ile Arg Gly Val Gln Arg Val Thr Val Thr Asp Ala Arg
545                 550                 555                 560

Arg Arg Thr Cys Pro Tyr Val Tyr Lys Ala Leu Gly Ile Val Ala Pro
                565                 570                 575

Arg Val Leu Ser Ser Arg Thr Phe
            580


<210> SEQ ID NO 7
<211> LENGTH: 192
<212> TYPE: PRT
<213> ORGANISM: Unknown
<220> FEATURE:
<223> OTHER INFORMATION: Synthetic Construct

<400> SEQUENCE: 7

Met Ser Ile Leu Ile Ser Pro Ser Asn Asn Thr Gly Trp Gly Leu Arg
1               5                   10                  15

Thr Pro Thr Arg Met Tyr Gly Gly Ala Arg Lys Arg Ser Thr Gln His
            20                  25                  30

Pro Val Arg Val Arg Gly His Phe Arg Ala Pro Trp Gly Ala Leu Lys
        35                  40                  45

Gly Arg Thr Arg Thr Arg Thr Thr Val Asp Asp Val Ile Asp Gln Val
    50                  55                  60

Val Ala Asp Ala Arg Asn Tyr Thr Pro Ala Ala Pro Ala Ser Thr Val
65                  70                  75                  80

Asp Ala Val Ile Asp Ser Val Val Ala Asp Ala Arg Glu Tyr Ala Arg
                85                  90                  95

Arg Lys Ser Arg Arg Arg Arg Ile Ala Arg Arg His Arg Ala Thr Pro
```

```
            100                 105                 110

Ala Met Arg Ala Ala Arg Ala Leu Leu Arg Arg Ala Lys Arg Val Gly
        115                 120                 125

Arg Arg Ala Met Leu Arg Ala Ala Arg Arg Ala Ala Ser Gly Ala Ser
    130                 135                 140

Ala Gly Arg Ser Arg Arg Arg Ala Ala Thr Ala Ala Ala Ala Ala Ile
145                 150                 155                 160

Ala Asn Met Ala Gln Pro Arg Arg Gly Asn Val Tyr Trp Val Arg Asp
                165                 170                 175

Ala Thr Thr Gly Gln Arg Val Pro Val Arg Thr Arg Pro Pro Arg Thr
            180                 185                 190


<210> SEQ ID NO 8
<211> LENGTH: 350
<212> TYPE: PRT
<213> ORGANISM: Unknown
<220> FEATURE:
<223> OTHER INFORMATION: Synthetic Construct

<400> SEQUENCE: 8

Met Ser Lys Arg Lys Tyr Lys Glu Glu Met Leu Gln Val Ile Ala Pro
1               5                   10                  15

Glu Ile Tyr Gly Pro Pro Val Lys Asp Glu Lys Lys Pro Arg Lys Ile
            20                  25                  30

Lys Arg Val Lys Lys Asp Lys Lys Glu Glu Asp Gly Asp Asp Gly Leu
        35                  40                  45

Val Glu Phe Val Arg Glu Phe Ala Pro Arg Arg Arg Val Gln Trp Arg
    50                  55                  60

Gly Arg Lys Val Arg Pro Val Leu Arg Pro Gly Thr Thr Val Val Phe
65                  70                  75                  80

Thr Pro Gly Glu Arg Ser Ser Thr Thr Phe Lys Arg Ser Tyr Asp Glu
                85                  90                  95

Val Tyr Gly Asp Asp Asp Ile Leu Glu Gln Ala Ala Asp Arg Leu Gly
            100                 105                 110

Glu Phe Ala Tyr Gly Lys Arg Ser Arg Ser Ser Pro Lys Asp Glu Ala
        115                 120                 125

Val Ser Ile Pro Leu Asp His Gly Asn Pro Thr Pro Ser Leu Lys Pro
    130                 135                 140

Val Thr Leu Gln Gln Val Leu Pro Val Pro Pro Arg Arg Gly Val Lys
145                 150                 155                 160

Arg Glu Gly Glu Asp Leu Tyr Pro Thr Met Gln Leu Met Val Pro Lys
                165                 170                 175

Arg Gln Lys Leu Glu Asp Val Leu Glu Lys Met Lys Val Asp Pro Asp
            180                 185                 190

Ile Gln Pro Glu Val Lys Val Arg Pro Ile Lys Gln Val Ala Pro Gly
        195                 200                 205

Leu Gly Val Gln Thr Val Asp Ile Lys Ile Pro Thr Glu Ser Met Glu
    210                 215                 220

Val Gln Thr Glu Pro Ala Lys Pro Ala Ala Thr Ser Ile Glu Val Gln
225                 230                 235                 240

Thr Asp Pro Trp Ile Pro Ala Pro Val Ala Thr Thr Ala Ser Thr Ala
                245                 250                 255

Arg Arg Pro Arg Arg Lys Tyr Gly Pro Ala Ser Leu Leu Leu Pro Asn
            260                 265                 270

Tyr Ala Leu His Pro Ser Ile Ile Pro Thr Pro Gly Tyr Arg Gly Thr
```

```
        275                 280                 285

Arg Tyr Tyr Arg Ser Arg Ser Thr Thr Ser Arg Arg Arg Lys Thr Pro
    290                 295                 300

Ala Ser Arg Ser Arg Arg Arg Arg Arg Arg Ala Ala Ser Lys Leu Thr
305                 310                 315                 320

Pro Ala Ala Leu Val Arg Arg Val Tyr Arg Asp Gly Arg Ala Glu Pro
                325                 330                 335

Leu Met Leu Pro Arg Ala Arg Tyr His Pro Ser Ile Thr Thr
            340                 345                 350


<210> SEQ ID NO 9
<211> LENGTH: 75
<212> TYPE: PRT
<213> ORGANISM: Unknown
<220> FEATURE:
<223> OTHER INFORMATION: Synthetic Construct

<400> SEQUENCE: 9

Met Ala Leu Thr Cys Arg Leu Arg Val Pro Ile Thr Gly Tyr Arg Gly
1               5                   10                  15

Arg Asn Ser Arg Arg Arg Arg Met Leu Gly Ser Gly Met Arg Arg His
            20                  25                  30

Arg Arg Arg Arg Ala Ile Ser Lys Arg Leu Gly Gly Gly Phe Leu Thr
        35                  40                  45

Ala Leu Ile Pro Ile Ile Ala Ala Ala Ile Gly Ala Val Pro Gly Ile
    50                  55                  60

Ala Ser Val Ala Val Gln Ala Ser Gln Arg His
65                  70                  75


<210> SEQ ID NO 10
<211> LENGTH: 250
<212> TYPE: PRT
<213> ORGANISM: Unknown
<220> FEATURE:
<223> OTHER INFORMATION: Synthetic Construct

<400> SEQUENCE: 10

Met Glu Asp Ile Asn Phe Ser Ser Leu Ala Pro Arg His Gly Thr Arg
1               5                   10                  15

Pro Tyr Met Gly Thr Trp Ser Asp Ile Gly Thr Ser Gln Leu Asn Gly
            20                  25                  30

Gly Ala Phe Asn Trp Ser Ser Ile Trp Ser Gly Leu Lys Asn Phe Gly
        35                  40                  45

Ser Ala Ile Lys Thr Tyr Gly Asn Lys Ala Trp Asn Ser Ser Thr Gly
    50                  55                  60

Gln Ala Leu Arg Asn Lys Leu Lys Glu Gln Asn Phe Gln Gln Lys Val
65                  70                  75                  80

Val Asp Gly Ile Ala Ser Gly Ile Asn Gly Val Val Asp Leu Ala Asn
                85                  90                  95

Gln Ala Val Gln Lys Gln Ile Asn Ser Arg Leu Asp Pro Pro Pro Ala
            100                 105                 110

Ala Pro Gly Glu Met Glu Val Glu Glu Glu Leu Pro Pro Leu Glu Lys
        115                 120                 125

Arg Gly Asp Lys Arg Pro Arg Pro Asp Met Glu Glu Thr Leu Val Thr
    130                 135                 140

Arg Gly Asp Glu Pro Pro Pro Tyr Glu Glu Ala Ile Lys Leu Gly Met
145                 150                 155                 160
```

```
Pro Thr Thr Arg Pro Ile Ala Pro Met Ala Thr Gly Val Met Lys Pro
                165                 170                 175

Ser Gln Ser His Arg Pro Ala Thr Leu Asp Leu Pro Pro Ala Pro Ala
            180                 185                 190

Ala Ala Ala Pro Ala Pro Lys Pro Val Ala Thr Pro Lys Pro Thr Ser
        195                 200                 205

Val Gln Pro Val Ala Val Ala Arg Pro Arg Pro Gly Gly Thr Pro Arg
    210                 215                 220

Pro Asn Ala Asn Trp Gln Ser Thr Leu Asn Ser Ile Val Gly Leu Gly
225                 230                 235                 240

Val Gln Ser Val Lys Arg Arg Arg Cys Tyr
                245                 250


<210> SEQ ID NO 11
<211> LENGTH: 943
<212> TYPE: PRT
<213> ORGANISM: Unknown
<220> FEATURE:
<223> OTHER INFORMATION: Synthetic Construct

<400> SEQUENCE: 11

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Gln Asp Asn
    130                 135                 140

Ala Val Thr Thr Thr Thr Asn Thr Phe Gly Ile Ala Ser Met Lys Gly
145                 150                 155                 160

Asp Asn Ile Thr Lys Glu Gly Leu Glu Ile Gly Lys Asp Ile Thr Glu
                165                 170                 175

Glu Asp Lys Pro Ile Tyr Ala Asp Lys Thr Tyr Gln Pro Glu Pro Gln
            180                 185                 190

Val Gly Glu Glu Ser Trp Thr Asp Thr Asp Gly Thr Asn Glu Lys Phe
        195                 200                 205

Gly Gly Arg Ala Leu Lys Pro Ala Thr Asn Met Lys Pro Cys Tyr Gly
    210                 215                 220

Ser Phe Ala Arg Pro Thr Asn Ile Lys Gly Gly Gln Ala Lys Asn Arg
225                 230                 235                 240

Lys Val Lys Pro Thr Thr Glu Gly Gly Val Glu Thr Glu Glu Pro Asp
                245                 250                 255

Ile Asp Met Glu Phe Phe Asp Gly Arg Asp Ala Ala Glu Gly Ala Leu
            260                 265                 270
```

```
Ser Pro Glu Ile Val Leu Tyr Thr Glu Asn Val Asn Leu Glu Thr Pro
        275                 280                 285

Asp Thr His Val Val Tyr Lys Pro Gly Thr Ser Asp Asp Asn Ser His
    290                 295                 300

Ala Asn Leu Gly Gln Gln Ala Met Pro Asn Arg Pro Asn Tyr Ile Gly
305                 310                 315                 320

Phe Arg Asp Asn Phe Val Gly Leu Leu Tyr Tyr Asn Ser Thr Gly Asn
                325                 330                 335

Met Gly Val Leu Ala Gly Gln Ala Ser Gln Leu Asn Ala Val Val Asp
            340                 345                 350

Leu Gln Asp Arg Asn Thr Glu Leu Ser Tyr Gln Leu Leu Leu Asp Ser
        355                 360                 365

Leu Gly Asp Arg Thr Arg Tyr Phe Ser Met Trp Asn Gln Ala Val Asp
    370                 375                 380

Ser Tyr Asp Pro Asp Val Arg Ile Ile Glu Asn His Gly Ile Glu Asp
385                 390                 395                 400

Glu Leu Pro Asn Tyr Cys Phe Pro Leu Asp Gly Ile Gly Pro Gly Asn
                405                 410                 415

Ser Tyr Gln Gly Ile Lys Ala Lys Asn Gly Asp Asn Asn Gly Trp Glu
            420                 425                 430

Lys Asp Thr Asn Ala Ser Thr Ala Asn Glu Ile Ala Ile Gly Asn Asn
        435                 440                 445

Leu Ala Met Glu Ile Asn Ile Gln Ala Asn Leu Trp Arg Ser Phe Leu
    450                 455                 460

Tyr Ser Asn Val Ala Leu Tyr Leu Pro Asp Ala Tyr Lys Tyr Thr Pro
465                 470                 475                 480

Ala Asn Ile Thr Leu Pro Ala Asn Thr Asn Thr Tyr Glu Tyr Met Asn
                485                 490                 495

Gly Arg Val Val Ala Pro Ser Leu Val Asp Ser Tyr Ile Asn Ile Gly
            500                 505                 510

Ala Arg Trp Ser Leu Asp Pro Met Asp Asn Val Asn Pro Phe Asn His
        515                 520                 525

His Arg Asn Ala Gly Leu Arg Tyr Arg Ser Met Leu Leu Gly Asn Gly
    530                 535                 540

Arg Tyr Val Pro Phe His Ile Gln Val Pro Gln Lys Phe Phe Ala Ile
545                 550                 555                 560

Lys Asn Leu Leu Leu Leu Pro Gly Ser Tyr Thr Tyr Glu Trp Asn Phe
                565                 570                 575

Arg Lys Asp Val Asn Met Val Leu Gln Ser Ser Leu Gly Asn Asp Leu
            580                 585                 590

Arg Thr Asp Gly Ala Ser Ile Ser Phe Thr Ser Ile Asn Leu Tyr Ala
        595                 600                 605

Thr Phe Phe Pro Met Ala His Asn Thr Ala Ser Thr Leu Glu Ala Met
    610                 615                 620

Leu Arg Asn Asp Thr Asn Asp Gln Ser Phe Asn Asp Tyr Leu Ser Ala
625                 630                 635                 640

Ala Asn Met Leu Tyr Pro Ile Pro Ala Asn Ala Thr Asn Ile Pro Ile
                645                 650                 655

Ser Ile Pro Ser Arg Asn Trp Ala Ala Phe Arg Gly Trp Ser Phe Thr
            660                 665                 670

Arg Leu Lys Thr Lys Glu Thr Pro Ser Leu Gly Ser Gly Phe Asp Pro
        675                 680                 685

Tyr Phe Val Tyr Ser Gly Ser Ile Pro Tyr Leu Asp Gly Thr Phe Tyr
```

```
    690                 695                 700

Leu Asn His Thr Phe Lys Lys Val Ser Ile Met Phe Asp Ser Ser Val
705                 710                 715                 720

Ser Trp Pro Gly Asn Asp Arg Leu Leu Thr Pro Asn Glu Phe Glu Ile
                725                 730                 735

Lys Arg Thr Val Asp Gly Glu Gly Tyr Asn Val Ala Gln Cys Asn Met
            740                 745                 750

Thr Lys Asp Trp Phe Leu Val Gln Met Leu Ala Asn Tyr Asn Ile Gly
        755                 760                 765

Tyr Gln Gly Phe Tyr Ile Pro Glu Gly Tyr Lys Asp Arg Met Tyr Ser
    770                 775                 780

Phe Phe Arg Asn Phe Gln Pro Met Ser Arg Gln Val Val Asp Glu Val
785                 790                 795                 800

Asn Tyr Thr Asp Tyr Lys Ala Val Thr Leu Ala Tyr Gln His Asn Asn
                805                 810                 815

Ser Gly Phe Val Gly Tyr Leu Ala Pro Thr Met Arg Gln Gly Glu Pro
            820                 825                 830

Tyr Pro Ala Asn Tyr Pro Tyr Pro Leu Ile Gly Thr Thr Ala Val Lys
        835                 840                 845

Ser Val Thr Gln Lys Lys Phe Leu Cys Asp Arg Thr Met Trp Arg Ile
    850                 855                 860

Pro Phe Ser Ser Asn Phe Met Ser Met Gly Ala Leu Thr Asp Leu Gly
865                 870                 875                 880

Gln Asn Met Leu Tyr Ala Asn Ser Ala His Ala Leu Asp Met Thr Phe
                885                 890                 895

Glu Val Asp Pro Met Asp Glu Pro Thr Leu Leu Tyr Val Leu Phe Glu
            900                 905                 910

Val Phe Asp Val Val Arg Val His Gln Pro His Arg Gly Val Ile Glu
        915                 920                 925

Ala Val Tyr Leu Arg Thr Pro Phe Ser Ala Gly Asn Ala Thr Thr
    930                 935                 940


<210> SEQ ID NO 12
<211> LENGTH: 209
<212> TYPE: PRT
<213> ORGANISM: Unknown
<220> FEATURE:
<223> OTHER INFORMATION: Synthetic Construct

<400> SEQUENCE: 12

Met Ala Cys Gly Ser Gly Asn Gly Ser Ser Glu Gln Glu Leu Arg Ala
1               5                   10                  15

Ile Ala Arg Asp Leu Gly Cys Gly Pro Tyr Phe Leu Gly Thr Phe Asp
            20                  25                  30

Lys Arg Phe Pro Gly Phe Met Ala Pro Asn Lys Leu Ala Cys Ala Ile
        35                  40                  45

Val Asn Thr Ala Gly Arg Glu Thr Gly Gly Glu His Trp Leu Ala Phe
    50                  55                  60

Gly Trp Asn Pro Arg Ser Asn Thr Cys Tyr Leu Phe Asp Pro Phe Gly
65                  70                  75                  80

Phe Ser Asp Glu Arg Leu Lys Gln Ile Tyr Gln Phe Glu Tyr Glu Gly
                85                  90                  95

Leu Leu Arg Arg Ser Ala Leu Ala Thr Lys Asp Arg Cys Ile Thr Leu
            100                 105                 110

Glu Lys Ser Thr Gln Thr Val Gln Gly Pro Arg Ser Ala Ala Cys Gly
```

```
        115                 120                 125

Leu Phe Cys Cys Met Phe Leu His Ala Phe Val His Trp Pro Asp Arg
    130                 135                 140

Pro Met Asp Gly Asn Pro Thr Met Lys Leu Leu Thr Gly Val Pro Asn
145                 150                 155                 160

Ser Met Leu Gln Ser Pro Gln Val Gln Pro Thr Leu Arg His Asn Gln
                165                 170                 175

Glu Ala Leu Tyr Arg Phe Leu Asn Ser His Ser Ser Tyr Phe Arg Ser
            180                 185                 190

His Arg Ala Arg Ile Glu Lys Ala Thr Ala Phe Asp Arg Met Asp Met
        195                 200                 205

Gln


<210> SEQ ID NO 13
<211> LENGTH: 831
<212> TYPE: PRT
<213> ORGANISM: Unknown
<220> FEATURE:
<223> OTHER INFORMATION: Synthetic Construct

<400> SEQUENCE: 13

Met Glu Thr Gln Pro Ser Leu Pro Thr Pro Leu Gln Ala Pro Ser His
1               5                   10                  15

Leu Ala Pro Ser Ser Asp Glu Glu Glu Ser Leu Thr Thr Pro Pro Pro
            20                  25                  30

Ser Pro Ala Thr Thr Thr Ser Thr Leu Glu Asp Glu Glu Glu Val Asp
        35                  40                  45

Ala Pro Gln Glu Met Gln Asp Met Glu Asp Glu Lys Ala Glu Glu Ile
    50                  55                  60

Glu Ala Asp Val Glu Gln Asp Pro Gly Tyr Val Thr Pro Ala Glu His
65                  70                  75                  80

Glu Glu Glu Leu Arg Arg Phe Leu Asp Arg Glu Asp Asp Asn Arg Pro
                85                  90                  95

Glu Gln Lys Ala Asp Gly Asp His Gln Glu Ala Gly Leu Gly Asp His
            100                 105                 110

Val Ala Glu Tyr Leu Thr Gly Leu Gly Gly Glu Asp Val Leu Leu Lys
        115                 120                 125

His Leu Ala Arg Gln Ser Ile Ile Val Lys Asp Ala Leu Leu Asp Arg
    130                 135                 140

Thr Glu Val Pro Ile Ser Val Glu Glu Leu Ser Arg Ala Tyr Glu Leu
145                 150                 155                 160

Asn Leu Phe Ser Pro Arg Val Pro Pro Lys Arg Gln Pro Asn Gly Thr
                165                 170                 175

Cys Glu Pro Asn Pro Arg Leu Asn Phe Tyr Pro Ala Phe Ala Val Pro
            180                 185                 190

Glu Val Leu Ala Thr Tyr His Ile Phe Phe Lys Asn Gln Lys Ile Pro
        195                 200                 205

Val Ser Cys Arg Ala Asn Arg Thr Arg Ala Asp Ala Leu Leu Asn Leu
    210                 215                 220

Gly Pro Gly Ala Arg Leu Pro Asp Ile Ala Ser Leu Glu Glu Val Pro
225                 230                 235                 240

Lys Ile Phe Glu Gly Leu Gly Ser Asp Glu Thr Arg Ala Ala Asn Ala
                245                 250                 255

Leu Gln Gln Gly Glu Asn Gly Met Asp Glu His His Ser Ala Leu Val
            260                 265                 270
```

```
Glu Leu Glu Gly Asp Asn Ala Arg Leu Ala Val Leu Lys Arg Ser Ile
        275                 280                 285

Glu Val Thr His Phe Ala Tyr Pro Ala Val Asn Leu Pro Pro Lys Val
    290                 295                 300

Met Ser Ala Val Met Asp Gln Leu Leu Ile Lys Arg Ala Ser Pro Leu
305                 310                 315                 320

Ser Glu Asp Gln Asn Met Gln Asp Pro Asp Ala Ser Asp Glu Gly Lys
                325                 330                 335

Pro Val Val Ser Asp Glu Gln Leu Ser Arg Trp Leu Ala Thr Asn Ser
            340                 345                 350

Pro Arg Asp Leu Glu Glu Arg Arg Lys Leu Met Met Ala Val Val Leu
        355                 360                 365

Val Thr Val Glu Leu Glu Cys Leu Arg Arg Phe Phe Thr Asp Pro Glu
    370                 375                 380

Thr Leu Arg Lys Leu Glu Glu Asn Leu His Tyr Thr Phe Arg His Gly
385                 390                 395                 400

Phe Val Arg Gln Ala Cys Lys Ile Ser Asn Val Glu Leu Thr Asn Leu
                405                 410                 415

Val Ser Tyr Met Gly Ile Leu His Glu Asn Arg Leu Gly Gln Ser Val
            420                 425                 430

Leu His Thr Thr Leu Lys Gly Glu Ala Arg Arg Asp Tyr Ile Arg Asp
        435                 440                 445

Cys Val Tyr Leu Tyr Leu Cys His Thr Trp Gln Thr Gly Met Gly Val
    450                 455                 460

Trp Gln Gln Cys Leu Glu Glu Gln Asn Leu Lys Glu Leu Asp Lys Leu
465                 470                 475                 480

Leu Gln Arg Ser Leu Lys Ala Leu Trp Thr Gly Phe Asp Glu Arg Thr
                485                 490                 495

Val Ala Ser Asp Leu Ala Asp Ile Ile Phe Pro Glu Arg Leu Arg Val
            500                 505                 510

Thr Leu Arg Asn Gly Leu Pro Asp Phe Met Ser Gln Ser Met Leu Asn
        515                 520                 525

Asn Phe Arg Ser Phe Ile Leu Glu Arg Ser Gly Ile Leu Pro Ala Thr
    530                 535                 540

Cys Cys Ala Leu Pro Ser Asp Phe Val Pro Leu Thr Tyr Arg Glu Cys
545                 550                 555                 560

Pro Pro Pro Leu Trp Ser His Cys Tyr Leu Phe Arg Leu Ala Asn Tyr
                565                 570                 575

Leu Ser Tyr His Ser Asp Val Ile Glu Asp Val Ser Gly Asp Gly Leu
            580                 585                 590

Leu Asp Cys His Cys Arg Cys Asn Leu Cys Thr Pro His Arg Ser Leu
        595                 600                 605

Ala Cys Asn Pro Gln Leu Leu Ser Glu Thr Gln Ile Ile Gly Thr Phe
    610                 615                 620

Glu Leu Gln Gly Pro Ser Ser Glu Gly Glu Gly Ser Ser Pro Gly Gln
625                 630                 635                 640

Ser Leu Lys Leu Thr Pro Gly Leu Trp Thr Ser Ala Tyr Leu Arg Lys
                645                 650                 655

Phe Ala Pro Glu Asp Tyr His Pro Tyr Glu Ile Arg Phe Tyr Glu Asp
            660                 665                 670

Gln Ser Gln Pro Pro Lys Ala Glu Leu Ser Ala Cys Val Ile Thr Gln
        675                 680                 685
```

```
Gly Ala Ile Leu Ala Gln Leu Gln Ala Ile Gln Lys Ser Arg Gln Glu
    690                 695                 700

Phe Leu Leu Lys Lys Gly Asn Gly Val Tyr Leu Asp Pro Gln Thr Gly
705                 710                 715                 720

Glu Glu Leu Asn Thr Arg Phe Pro Gln Asp Val Pro Ala Pro Arg Lys
                725                 730                 735

Gln Glu Val Glu Ser Ala Ala Ala Ala Pro Arg Gly His Gly Gly Arg
            740                 745                 750

Leu Gly Gln Ser Gly Arg Gly Gly Gly Asp Gly Arg Leu Gly Gln Pro
        755                 760                 765

Gly Arg Gly Gly Gly Gln Pro Gly Gly Arg Gln Phe Gly Gly Gly Arg
    770                 775                 780

Arg Gly Gly Arg Gly Gly Gly Arg Ser Asn Arg Arg Gln Thr Ile Val
785                 790                 795                 800

Leu Gly Ser Gly Asp Lys Gln Gly Pro Arg Gln Gln Gln Gln His Gly
                805                 810                 815

Tyr Asn Leu Arg Ser Gly Ser Gly Gly Pro Ala Ala Ser Gln Gln
            820                 825                 830


<210> SEQ ID NO 14
<211> LENGTH: 227
<212> TYPE: PRT
<213> ORGANISM: Unknown
<220> FEATURE:
<223> OTHER INFORMATION: Synthetic Construct

<400> SEQUENCE: 14

Met Ser Lys Glu Ile Pro Thr Pro Tyr Met Trp Ser Tyr Gln Pro Gln
1               5                   10                  15

Met Gly Leu Ala Ala Gly Ala Ser Gln Asp Tyr Ser Thr Arg Met Asn
            20                  25                  30

Trp Leu Ser Ala Gly Pro Ser Met Ile Ser Arg Val Asn Asp Ile Arg
        35                  40                  45

Ala Tyr Arg Asn Gln Leu Leu Leu Glu Gln Ser Ala Leu Thr Thr Thr
    50                  55                  60

Pro Arg Gln His Leu Asn Pro Arg Asn Trp Pro Ala Ala Leu Val Tyr
65                  70                  75                  80

Gln Glu Thr Pro Ala Pro Thr Thr Val Leu Leu Pro Arg Asp Ala Gln
                85                  90                  95

Ala Glu Val Gln Met Thr Asn Ala Gly Val Gln Leu Ala Gly Gly Ser
            100                 105                 110

Ala Leu Cys Arg His Arg Pro Gln Gln Ser Ile Lys Arg Leu Val Ile
        115                 120                 125

Arg Gly Arg Gly Ile Gln Leu Asn Asp Glu Ser Val Ser Ser Ser Leu
    130                 135                 140

Gly Leu Arg Pro Asp Gly Val Phe Gln Ile Ala Gly Cys Gly Arg Ser
145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
            180                 185                 190

Thr Pro Ser Val Tyr Phe Asn Pro Phe Ser Gly Ser Pro Gly Gln Tyr
        195                 200                 205

Pro Asp Glu Phe Ile Pro Asn Phe Asp Ala Ile Ser Glu Ser Val Asp
    210                 215                 220
```

```
Gly Tyr Asp
225


<210> SEQ ID NO 15
<211> LENGTH: 105
<212> TYPE: PRT
<213> ORGANISM: Unknown
<220> FEATURE:
<223> OTHER INFORMATION: Synthetic Construct

<400> SEQUENCE: 15

Met Ser Gly Gly Ala Ala Glu Leu Ala Arg Leu Arg His Leu Asp His
1               5                   10                  15

Cys Arg Arg Phe Arg Cys Phe Ala Arg Glu Leu Thr Glu Phe Ile Tyr
            20                  25                  30

Phe Glu Leu Pro Glu Glu His Pro Gln Gly Pro Ala His Gly Val Arg
        35                  40                  45

Ile Thr Ile Glu Gly Gly Ile Asp Ser Arg Leu His Arg Ile Phe Cys
    50                  55                  60

Gln Arg Pro Val Leu Ile Glu Arg Asp Gln Gly Thr Thr Thr Val Ser
65                  70                  75                  80

Ile Tyr Cys Ile Cys Asn His Pro Gly Leu His Glu Ser Leu Cys Cys
                85                  90                  95

Leu Ile Cys Ala Glu Phe Asn Lys Asn
            100                 105


<210> SEQ ID NO 16
<211> LENGTH: 179
<212> TYPE: PRT
<213> ORGANISM: Unknown
<220> FEATURE:
<223> OTHER INFORMATION: Synthetic Construct

<400> SEQUENCE: 16

Met Gly Val Val Leu Val Ser Phe Ala Leu Leu Ser Leu Leu Gly Leu
1               5                   10                  15

Gly Ser Ala Thr Leu Arg Asn Gln Pro Leu Leu Leu Asp Pro Asp Asp
            20                  25                  30

Val Asp Pro Cys Leu Asp Phe Asp Pro Glu Asn Cys Thr Leu Thr Phe
        35                  40                  45

Ala Pro Glu Thr Ser Arg Phe Cys Gly Val Val Ile Arg Cys Gly Phe
    50                  55                  60

Glu Cys Arg Ser Ile Glu Ile Thr His Asn Asn Lys Thr Trp Asn Asn
65                  70                  75                  80

Thr Leu Phe Thr Ile Trp Gln Pro Gly Asp Pro Gln Trp Tyr Thr Val
                85                  90                  95

Ser Val Arg Gly Pro Asp Gly Ser Ala Arg Met Ala Asn Asn Thr Phe
            100                 105                 110

Ile Phe Ala Glu Met Cys Asp Met Ala Met Phe Met Ser Arg Gln Tyr
        115                 120                 125

Asp Leu Trp Pro Pro Ser Lys Glu Asn Ile Val Ala Phe Ser Ile Ala
    130                 135                 140

Tyr Cys Leu Cys Thr Cys Ile Thr Thr Ala Ile Ile Cys Val Cys Ile
145                 150                 155                 160

His Leu Leu Ile Ala Thr Arg Ser Lys Asn Ser Asn Glu Glu Lys Glu
                165                 170                 175

Lys Met Pro
```

<210> SEQ ID NO 17
<211> LENGTH: 203
<212> TYPE: PRT
<213> ORGANISM: Unknown
<220> FEATURE:
<223> OTHER INFORMATION: Synthetic Construct

<400> SEQUENCE: 17

```
Met Ile Phe Ile Thr Ser Ile Phe Ile Val Ser Ile Ser Thr Ile Ala
1               5                   10                  15

His Gly Gln Gln Ile Asn Ala Gly Asp Asn Phe Thr Leu Val Gly Pro
            20                  25                  30

Lys Lys Pro Val Val Ser Trp Phe Trp Thr Lys Pro Asp Pro Trp Ala
        35                  40                  45

Lys Thr Asp Tyr Trp Val Ser Leu Cys Asp Gly Val Phe Leu Tyr Lys
    50                  55                  60

Ser Asn Leu Thr Phe Asn Cys Asn Asn Gln Asn Leu Thr Leu Ile Asn
65                  70                  75                  80

Val Thr Lys Asp Tyr Glu Gly Thr Tyr Tyr Gly Asp Gly Ile Leu Tyr
                85                  90                  95

Arg Ile Arg Val Ile Asp Thr Pro Lys Arg Phe Lys Arg Ala Thr Thr
            100                 105                 110

Lys Val Thr Asp Pro Gln Pro Lys Ile Ser Ser Ile Thr Thr Ile Phe
        115                 120                 125

Thr Asn Ser Thr Tyr Thr Asn Leu Gln Leu Ala Tyr Val Asn Ser Ser
    130                 135                 140

Asn Ile Thr Ile Leu Pro Thr Pro Ile Asn Glu Glu Ile Pro Lys Ser
145                 150                 155                 160

Met Ile Gly Ile Ile Val Ala Val Ala Val Gly Met Ile Ile Ile Ile
                165                 170                 175

Ile Cys Met Ile Thr Tyr Ala Cys Cys Tyr Arg Lys Phe Tyr Tyr Glu
            180                 185                 190

Glu Lys Gly Asp Pro Leu Leu Asn Phe Asp Ile
        195                 200
```

<210> SEQ ID NO 18
<211> LENGTH: 113
<212> TYPE: PRT
<213> ORGANISM: Unknown
<220> FEATURE:
<223> OTHER INFORMATION: Synthetic Construct

<400> SEQUENCE: 18

```
Met Lys Gln Leu Gly Ile Leu Ile Ile Tyr Cys Ser Ile Asn Leu Ser
1               5                   10                  15

Gln Leu Thr Pro Thr Pro Thr Ser Asn Asn Val Gln Thr Thr Leu Pro
            20                  25                  30

Val Thr Ile Asn Lys Thr Thr Ser Val Phe Leu Asn Asn Thr Asp Phe
        35                  40                  45

Asn Thr Asn Ser Asn Ser Lys Asp Phe Leu Gln Leu Gln Ile Thr Ala
    50                  55                  60

Leu Ile Ile Ile Gly Leu Ile Ile Leu Ala Ile Leu Leu Tyr Phe Val
65                  70                  75                  80

Phe Cys Arg Asn Ile Pro Asn Val His Lys Pro Ile Lys Lys Arg Pro
                85                  90                  95

Ile Tyr Asn Pro Ile Leu Ser Glu Pro Gln Leu Arg Arg Trp Arg Glu
            100                 105                 110
```

Ile

<210> SEQ ID NO 19
<211> LENGTH: 91
<212> TYPE: PRT
<213> ORGANISM: Unknown
<220> FEATURE:
<223> OTHER INFORMATION: Synthetic Construct

<400> SEQUENCE: 19

```
Met Ile Pro Arg Asn Phe Phe Phe Thr Ile Leu Ile Cys Leu Leu Asn
1               5                   10                  15

Ile Cys Ala Thr Leu Ala Ala Val Thr Ser Val Ser Pro Asp Cys Ile
            20                  25                  30

Gly Pro Phe Ala Thr Tyr Leu Leu Phe Ala Leu Ile Thr Cys Ile Cys
        35                  40                  45

Val Ser Ser Thr Val Cys Leu Val Ile Asn Phe Phe Gln Leu Ile Asp
    50                  55                  60

Trp Ile Phe Val Arg Ile Ala Tyr Leu Arg His His Pro Glu Tyr Arg
65                  70                  75                  80

Asn His Asp Ile Ala Ala Leu Leu Arg Leu Leu
                85                  90
```

<210> SEQ ID NO 20
<211> LENGTH: 135
<212> TYPE: PRT
<213> ORGANISM: Unknown
<220> FEATURE:
<223> OTHER INFORMATION: Synthetic Construct

<400> SEQUENCE: 20

```
Met Thr Asp Pro Leu Ala Ala Ser Ala Ala Ala Glu Glu Leu Leu Asp
1               5                   10                  15

Met Asp Gly Arg Ala Ser Glu Gln Arg Leu Ala Gln Leu Arg Ile Arg
            20                  25                  30

Gln Gln Gln Glu Arg Ala Ala Lys Glu Leu Arg Asp Ala Ile Glu Ile
        35                  40                  45

His Gln Cys Lys Lys Gly Ile Phe Cys Leu Val Lys Gln Ala Lys Ile
    50                  55                  60

Ser Tyr Glu Ile Thr Ala Asn Asp His Arg Leu Ser Tyr Glu Leu Gly
65                  70                  75                  80

Pro Gln Arg Gln Lys Phe Thr Cys Met Val Gly Ile Asn Pro Ile Val
                85                  90                  95

Ile Thr Gln Gln Ala Gly Asp Thr Lys Gly Cys Ile His Cys Ser Cys
            100                 105                 110

Glu Ser Thr Glu Cys Ile Tyr Thr Leu Leu Lys Thr Leu Cys Gly Leu
        115                 120                 125

Arg Asp Ile Leu Pro Met Asn
    130                 135
```

<210> SEQ ID NO 21
<211> LENGTH: 321
<212> TYPE: PRT
<213> ORGANISM: Unknown
<220> FEATURE:
<223> OTHER INFORMATION: Synthetic Construct

<400> SEQUENCE: 21

```
Met Ala Lys Arg Ala Arg Leu Ser Ser Ser Phe Asn Pro Val Tyr Pro
```

```
1               5                   10                  15

Tyr Glu Asp Glu Asn Ser Ser Gln His Pro Phe Ile Asn Pro Gly Phe
            20                  25                  30

Ile Ser Pro Asn Gly Phe Thr Gln Asn Ser Asp Gly Val Leu Ala Leu
        35                  40                  45

Lys Cys Ala Ala Pro Leu Thr Thr Thr Gly Gly Ser Leu Gln Leu Lys
    50                  55                  60

Val Gly Arg Gly Leu Thr Ile Asp Thr Thr Asp Gly Thr Leu Glu Glu
65                  70                  75                  80

Asp Ile Asn Ile Leu Ala Pro Leu Thr Lys Thr Ala His Ser Ile Gly
                85                  90                  95

Leu Ser Leu Gly Asn Gly Leu Glu Leu Lys Asp Ser Lys Leu Tyr Val
            100                 105                 110

Lys Leu Gly Asp Gly Leu Lys Phe Asn Ser Asn Ser Ile Cys Leu Asp
        115                 120                 125

His Asp Ile Asn Thr Leu Trp Thr Gly Met Asn Pro Ser Ile Asn Cys
    130                 135                 140

Asn Ile Met Gln Gln Asp Asp Asn Asp Ser Lys Leu Thr Leu Val Leu
145                 150                 155                 160

Thr Lys Asn Gly Gly Met Val Asn Ala Tyr Val Ser Leu Val Gly Ala
                165                 170                 175

Ser Asp Ile Val Asn Ser Leu Phe Lys Arg Ala Thr Ala Asn Ile Thr
            180                 185                 190

Ile Arg Leu Ser Phe Asp Ala Ser Gly Asn Leu Leu Thr Ser Leu Ser
        195                 200                 205

Asp Leu Lys Thr Pro Leu Asn His Arg Tyr Gly Asn Asp Met Asp Thr
    210                 215                 220

Asp Thr Leu Thr Asn Gly Lys Ser Phe Met Pro Ser Thr Thr Ala Tyr
225                 230                 235                 240

Pro Phe Asn Asp Thr Thr Arg Asp Lys Glu Asn Tyr Ile Tyr Gly Thr
                245                 250                 255

Cys Tyr Tyr Lys Ser Thr Glu Asp Ala Leu Tyr Pro Leu Glu Val Ala
            260                 265                 270

Val Thr Leu Asn Arg Arg Met Ser Ser Ala Ala Val Ser Tyr Ala Met
        275                 280                 285

Thr Ile Ala Trp Thr Leu Ser Ala Asn Thr Pro Pro Glu Thr Thr Ile
    290                 295                 300

Ala Thr Leu Val Thr Ser Pro Phe Thr Phe Ser Tyr Ile Arg Glu Asn
305                 310                 315                 320

Asp


<210> SEQ ID NO 22
<211> LENGTH: 560
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (5)..(547)
<223> OTHER INFORMATION: Elb[1]9K

<400> SEQUENCE: 22

atcc atg gag gtt tgg gct atc ttg gaa gat ctc agg cag act aga caa      49
     Met Glu Val Trp Ala Ile Leu Glu Asp Leu Arg Gln Thr Arg Gln
     1               5                   10                  15
```

```
ctg cta gaa aac gcc tcg gac gga gtc tct agt ctt tgg aga ttc tgg       97
Leu Leu Glu Asn Ala Ser Asp Gly Val Ser Ser Leu Trp Arg Phe Trp
                20                  25                  30

ttc ggt ggt gat cta gct agg cta gtc ttt agg gta aaa cgg gag tat      145
Phe Gly Gly Asp Leu Ala Arg Leu Val Phe Arg Val Lys Arg Glu Tyr
            35                  40                  45

agt gaa gaa ttt gaa aag tta ttg gaa gac agt cca gga ctt ttt gaa      193
Ser Glu Glu Phe Glu Lys Leu Leu Glu Asp Ser Pro Gly Leu Phe Glu
        50                  55                  60

gcc ctt aac ttg ggc cac cag gct cat ttt aag gag aag gtt tta tca      241
Ala Leu Asn Leu Gly His Gln Ala His Phe Lys Glu Lys Val Leu Ser
    65                  70                  75

gtt tta gat ttt tct acc cct ggt aga act gct gct gct gta gct ttc      289
Val Leu Asp Phe Ser Thr Pro Gly Arg Thr Ala Ala Ala Val Ala Phe
80                  85                  90                  95

ctt act ttt ata ttg gat aaa tgg atc cca caa acc cac ttc agc aag      337
Leu Thr Phe Ile Leu Asp Lys Trp Ile Pro Gln Thr His Phe Ser Lys
                100                 105                 110

gga tac gtc ttg gat ttc ata gca gca gct ttg tgg aga aca tgg aag      385
Gly Tyr Val Leu Asp Phe Ile Ala Ala Ala Leu Trp Arg Thr Trp Lys
            115                 120                 125

gcc cgc agg ctg agg ata atc tta gat tac tgg cca gtg cag cct ctg      433
Ala Arg Arg Leu Arg Ile Ile Leu Asp Tyr Trp Pro Val Gln Pro Leu
        130                 135                 140

ggc gta gca gca atc ctg aga cac cca ccg gcc atg cca gcg gtt ttg      481
Gly Val Ala Ala Ile Leu Arg His Pro Pro Ala Met Pro Ala Val Leu
    145                 150                 155

gag gag gag cag cag gag gac aac ccg aga gcc ggc ctg gac cct ccg      529
Glu Glu Glu Gln Gln Glu Asp Asn Pro Arg Ala Gly Leu Asp Pro Pro
160                 165                 170                 175

gtg gag gag gcg gag gag tagctgacct gtt                               560
Val Glu Glu Ala Glu Glu
                180
```

<210> SEQ ID NO 23
<211> LENGTH: 181
<212> TYPE: PRT
<213> ORGANISM: Unknown
<220> FEATURE:
<223> OTHER INFORMATION: Synthetic Construct

<400> SEQUENCE: 23

```
Met Glu Val Trp Ala Ile Leu Glu Asp Leu Arg Gln Thr Arg Gln Leu
1               5                   10                  15

Leu Glu Asn Ala Ser Asp Gly Val Ser Ser Leu Trp Arg Phe Trp Phe
            20                  25                  30

Gly Gly Asp Leu Ala Arg Leu Val Phe Arg Val Lys Arg Glu Tyr Ser
        35                  40                  45

Glu Glu Phe Glu Lys Leu Leu Glu Asp Ser Pro Gly Leu Phe Glu Ala
    50                  55                  60

Leu Asn Leu Gly His Gln Ala His Phe Lys Glu Lys Val Leu Ser Val
65                  70                  75                  80

Leu Asp Phe Ser Thr Pro Gly Arg Thr Ala Ala Ala Val Ala Phe Leu
                85                  90                  95

Thr Phe Ile Leu Asp Lys Trp Ile Pro Gln Thr His Phe Ser Lys Gly
            100                 105                 110

Tyr Val Leu Asp Phe Ile Ala Ala Ala Leu Trp Arg Thr Trp Lys Ala
        115                 120                 125

Arg Arg Leu Arg Ile Ile Leu Asp Tyr Trp Pro Val Gln Pro Leu Gly
```

```
    130                 135                 140

Val Ala Ala Ile Leu Arg His Pro Pro Ala Met Pro Ala Val Leu Glu
145                 150                 155                 160

Glu Glu Gln Gln Glu Asp Asn Pro Arg Ala Gly Leu Asp Pro Pro Val
                165                 170                 175

Glu Glu Ala Glu Glu
            180


<210> SEQ ID NO 24
<211> LENGTH: 4600
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (8)..(625)
<223> OTHER INFORMATION: 22K
<220> FEATURE:
<221> NAME/KEY: CDS
<222> LOCATION: (1920)..(2363)
<223> OTHER INFORMATION: E3©R1-alpha
<220> FEATURE:
<221> NAME/KEY: CDS
<222> LOCATION: (4166)..(4591)
<223> OTHER INFORMATION: E3®IDeta

<400> SEQUENCE: 24

cctcagg atg tcc cag cgc cga gga agc aag aag ttg aaa gtg cag ctg       49
        Met Ser Gln Arg Arg Gly Ser Lys Lys Leu Lys Val Gln Leu
        1               5                   10

ccg ccc cca gag gac atg gag gaa gac tgg gac agt cag gca gag gag       97
Pro Pro Pro Glu Asp Met Glu Glu Asp Trp Asp Ser Gln Ala Glu Glu
15                  20                  25                  30

gag gag atg gaa gat tgg gac agc cag gca gag gag gcg gac agc ctg      145
Glu Glu Met Glu Asp Trp Asp Ser Gln Ala Glu Glu Ala Asp Ser Leu
                35                  40                  45

gag gaa gac agt ttg gag gag gaa gac gag gag gca gag gag gtg gaa      193
Glu Glu Asp Ser Leu Glu Glu Glu Asp Glu Glu Ala Glu Glu Val Glu
            50                  55                  60

gaa gca acc gcc gcc aaa caa ttg tcc tcg gca gcg gag aca agc aag      241
Glu Ala Thr Ala Ala Lys Gln Leu Ser Ser Ala Ala Glu Thr Ser Lys
        65                  70                  75

gtc cca gac agc agc agc agc acg gct aca atc tcc gct ccg ggt cgg      289
Val Pro Asp Ser Ser Ser Ser Thr Ala Thr Ile Ser Ala Pro Gly Arg
    80                  85                  90

ggg gcc cag cag cgt ccc aac agt aga tgg gac gag acc ggg cga ttc      337
Gly Ala Gln Gln Arg Pro Asn Ser Arg Trp Asp Glu Thr Gly Arg Phe
95                  100                 105                 110

ccg aac ccg acc acc gct tcc aag acc ggt aag aag gag cgg cag gga      385
Pro Asn Pro Thr Thr Ala Ser Lys Thr Gly Lys Lys Glu Arg Gln Gly
                115                 120                 125

tac aag tcc tgg cgg ggg cat aag aat gcc atc atc tcc tgc ttg cat      433
Tyr Lys Ser Trp Arg Gly His Lys Asn Ala Ile Ile Ser Cys Leu His
            130                 135                 140

gaa tgc ggg ggc aac ata tcc ttc acc cga cgc tac ctg ctc ttc cac      481
Glu Cys Gly Gly Asn Ile Ser Phe Thr Arg Arg Tyr Leu Leu Phe His
        145                 150                 155

cac ggg gtg aac ttc ccc cgc aat gtc ttg cat tac tac cgt cac ctc      529
His Gly Val Asn Phe Pro Arg Asn Val Leu His Tyr Tyr Arg His Leu
    160                 165                 170

cac agc cct tac tac agc cag caa gtc ccg aca gcc tcg aca aag aaa      577
His Ser Pro Tyr Tyr Ser Gln Gln Val Pro Thr Ala Ser Thr Lys Lys
```

```
175                 180                 185                 190

gac agc agc agc agc ggg gac ctc cag cag aaa acc agc agc agc agt      625
Asp Ser Ser Ser Ser Gly Asp Leu Gln Gln Lys Thr Ser Ser Ser Ser
                195                 200                 205

tagaaaatcc agtgcagcag gaggaggact gaggatcaca gcgaacgagc cagcgcagac    685

ccgagagctg agaaacagga tctttccaac cctctatgcc atcttccagc agagtcgggg    745

gcaagagcag gaactgaaag taaaaaaccg atctctgcgc tcgctcaccc gaagttgttt    805

gtatcacaag agcgaagacc aacttcagcg cactctcgag gacgccgagg ctctcttcaa    865

caagtactgc gcgctgactc ttaaagagta gcccgcgccc gcgctcgctc gaaaaaggcg    925

ggaattacgt caccettggc acctgtcctt tgccctcgtc atgagtaaag aaattcccac    985

gccttacatg tggagctatc agccccaaat gggactggca gcaggcgcct cccaggacta   1045

ctccacccgc atgaattggc tcagcgccgg cccctcgatg atctcacggg ttaatgatat   1105

acgagcttac cgaaaccagt tactcctaga acagtcagct ctcaccacca caccccgcca   1165

acaccttaat ccccggaatt ggcccgccgc cctggtgtac caggaaactc ccgctcccac   1225

caccgtacta cttcctcgag acgcccaggc cgaagttcag atgactaacg caggtgtaca   1285

gctggcgggc ggttccgccc tgtgtcgtca ccggcctcag cagagtataa aacgcctggt   1345

gatcagaggc cgaggtatcc agctcaacga cgagtcggtg agctcttcgc ttggtctgcg   1405

accagacgga gtcttccaga tcgccggctg tgggagatct tccttcactc ctcgtcaggc   1465

tgtcctgact ttggagagtt cgtcctcgca gccccgctcg ggcggcatcg ggactctcca   1525

gtttgtggag gagtttactc cctctgtcta cttcaacccc ttctccggct ctcccggcca   1585

gtacccggac gagttcatac cgaacttcga cgcaatcagc gagtcagtgg atggctatga   1645

ttgatgtctg gtggcgcggc tgagttagct cgactgcgac atctagacca ctgccgccgc   1705

tttcgctgtt tcgcccggga actcaccgag ttcatctact tcgaactccc cgaggagcac   1765

cctcagggac cggcccacgg agtgcggatt accatcgaag gggaatagat ctctcgcctg   1825

catcggatct tctgccagcg acccgtgctg atcgagcgcg accagggaac tacaacagtc   1885

tccatctact gcatctgtaa ccaccccgga ttgc atg aaa gcc ttt gct gtc tta   1940
                                      Met Lys Ala Phe Ala Val Leu
                                                      210

ttt gtg ctg agt tta ata aaa act gag tta aga ctc acc ttt gga cta      1988
Phe Val Leu Ser Leu Ile Lys Thr Glu Leu Arg Leu Thr Phe Gly Leu
    215                 220                 225

ccg ctt ctt caa ccc gga ctt tac aac acc agc cag act ctc cgt tcc      2036
Pro Leu Leu Gln Pro Gly Leu Tyr Asn Thr Ser Gln Thr Leu Arg Ser
230                 235                 240                 245

agc cag aag acc cag gcc ctt cct ctg atc cag gac tct aat tct acc      2084
Ser Gln Lys Thr Gln Ala Leu Pro Leu Ile Gln Asp Ser Asn Ser Thr
                250                 255                 260

tcc cca gca cca tcc cct act aac ctt ccc gaa act aac aac ctc gga      2132
Ser Pro Ala Pro Ser Pro Thr Asn Leu Pro Glu Thr Asn Asn Leu Gly
            265                 270                 275

gct cag ctg caa ccc cgc ttc tcc aga agc ctc ctt tct gcc aat act      2180
Ala Gln Leu Gln Pro Arg Phe Ser Arg Ser Leu Leu Ser Ala Asn Thr
        280                 285                 290

act act ccc aga acc gga ggt gag ctc cgt ggt ctc cct act gac aac      2228
Thr Thr Pro Arg Thr Gly Gly Glu Leu Arg Gly Leu Pro Thr Asp Asn
    295                 300                 305

ccc tgg gtg gta gcg ggt ttt gta gcg cta gga gta gtt gcg ggt ggg      2276
Pro Trp Val Val Ala Gly Phe Val Ala Leu Gly Val Val Ala Gly Gly
310                 315                 320                 325
```

```
ctg gtg ctt atc ctc tgc tac cta tac aca cct tgc tgt gct tat tta      2324
Leu Val Leu Ile Leu Cys Tyr Leu Tyr Thr Pro Cys Cys Ala Tyr Leu
                330                 335                 340

gta gta ttg tgc tgc tgg ttt aag aaa tgg ggg tcg tac tagtatcgtt      2373
Val Val Leu Cys Cys Trp Phe Lys Lys Trp Gly Ser Tyr
            345                 350

tgctttactt tcgcttttgg gtctgggctc tgctacgcta agaaatcagc ctttgctatt   2433

agatcccgat gatgttgatc catgtctgga ctttgatcca gagaactgca cactcacttt   2493

tgcacctgaa acaagtcgct tctgtggagt tgttattagg tgcggatttg aatgcaggtc   2553

cattgagatt acacacaata acaaaacttg gaacaatacc ttattcacaa tatggcaacc   2613

aggagatcct cagtggtata ctgtctctgt ccggggtcct gacggttccg cccgcatggc   2673

taataacact ttcatttttg ctgaaatgtg cgatatggcc atgttcatga gcagacagta   2733

tgacctatgg cctcccagca aagagaacat tgtggcattc tccattgctt attgcttatg   2793

tacttgcatt accactgcta tcatatgtgt gtgcatacac ttgctcatag caactcgctc   2853

caaaaacagc aatgaggaaa aagagaaaat gccttgacct tttttcctcg ttttctgttc   2913

acagctatga tttttattac atccatcttt attgtcagca tttcaactat tgcacatgga   2973

caacaaataa atgcaggcga caatttcaca ttagttgggc ctaaaaaacc agttgtctcc   3033

tggttctgga ctaaacctga tccatgggct aaaactgatt actgggtttc actttgtgat   3093

ggtgtatttc tgtataaatc taaccttaca ttcaattgca ataatcaaaa cctaacacta   3153

atcaatgtta ctaaagatta tgaaggaaca tactatggag atggaatctt atatagaatt   3213

agagtaatag acactcctaa gagattcaaa agagctacaa ctaaagttac agatccacaa   3273

ccaaaaatct ctagcatcac tactatcttt actaacagta catataccaa tttacaattg   3333

gcttatgtta actcatcaaa tattacaatc ctgcctacac caatcaatga agaaattcct   3393

aaatcaatga ttgggatcat tgtggcggtg gcagtgggaa tgatcataat cataaatatgt  3453

atgatcacct atgcttgctg ctacagaaag ttttattatg aagaaaaagg agacccccta   3513

ctaaattttg acatttaatt ttttatagat gaaacaacta ggtatcttga ttatttactg   3573

cagcattaat ctttctcaat taacaccaac accaactagt aacaatgtgc agactacttt   3633

accagtcacc ataaacaaaa ctacctcagt tttctaaat aatacagact ttaatactaa    3693

ctccaactct aaagatttc ttcaacttca aatcactgct cttattataa ttggattaat    3753

aattctagca atccttctat actttgtctt ttgccgcaac atccccaatg ttcacaaacc   3813

cattaaaaag cgtcctattt acaaccccat cttaagcgag ccacaactta gacggtggag   3873

ggaaatctaa tacatctctc ttttctttca gtatggtgat catcaaacat gatccctaga   3933

aatttttct tcaccatact catctgcctt ctcaatatct gcgctaccct tgctgcggtc    3993

actagcgtct caccagactg cataggacca tttgccacct acttgctttt tgcattgatc   4053

acctgtatct gtgtgagtag cacagtctgt ctggttatta attttttcca acttatagac   4113

tggatttttg tgcgcattgc ctacctgaga caccatccag aataccgcaa cc atg ata   4171
                                                          Met Ile
                                                          355

ttg cgg cac tac tca gac ttc ttt aaa acc ata cag gct ttg cta cca      4219
Leu Arg His Tyr Ser Asp Phe Phe Lys Thr Ile Gln Ala Leu Leu Pro
            360                 365                 370

ctg cta ttg ctg cta ctg ccc tgt gac act ata gcc acc aca cct acc      4267
Leu Leu Leu Leu Leu Leu Pro Cys Asp Thr Ile Ala Thr Thr Pro Thr
        375                 380                 385
```

```
cta aac cca aat ctt aga aaa tgt aaa ttc caa gag cca tgg aat ttc      4315
Leu Asn Pro Asn Leu Arg Lys Cys Lys Phe Gln Glu Pro Trp Asn Phe
    390                 395                 400

ctc aaa tgt tat aat gaa aca att gat ttt cca ccc tat tgg ata aca      4363
Leu Lys Cys Tyr Asn Glu Thr Ile Asp Phe Pro Pro Tyr Trp Ile Thr
405                 410                 415                 420

atc att gga atc ctt aat gtg gta tgc tgc acc ata ttt gca ttc ctt      4411
Ile Ile Gly Ile Leu Asn Val Val Cys Cys Thr Ile Phe Ala Phe Leu
                425                 430                 435

gta tat ccc atg ttt gat ttt ggg tgg aat gtc ccc aat gca ctc act      4459
Val Tyr Pro Met Phe Asp Phe Gly Trp Asn Val Pro Asn Ala Leu Thr
            440                 445                 450

cac cca caa gaa cca cag gaa cat atc cca cta caa aac atg caa cca      4507
His Pro Gln Glu Pro Gln Glu His Ile Pro Leu Gln Asn Met Gln Pro
        455                 460                 465

cta gca cta ata gaa tat gaa aat gag cca cag cct cca cta ctc cct      4555
Leu Ala Leu Ile Glu Tyr Glu Asn Glu Pro Gln Pro Pro Leu Leu Pro
    470                 475                 480

gcc att agc tac ttc aac cta acc ggt aga gat gac tgacccact           4600
Ala Ile Ser Tyr Phe Asn Leu Thr Gly Arg Asp Asp
485                 490                 495


<210> SEQ ID NO 25
<211> LENGTH: 206
<212> TYPE: PRT
<213> ORGANISM: Unknown
<220> FEATURE:
<223> OTHER INFORMATION: Synthetic Construct

<400> SEQUENCE: 25

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
            20                  25                  30

Met Glu Asp Trp Asp Ser Gln Ala Glu Glu Ala Asp Ser Leu Glu Glu
        35                  40                  45

Asp Ser Leu Glu Glu Glu Asp Glu Glu Ala Glu Glu Val Glu Glu Ala
    50                  55                  60

Thr Ala Ala Lys Gln Leu Ser Ser Ala Ala Glu Thr Ser Lys Val Pro
65                  70                  75                  80

Asp Ser Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
            100                 105                 110

Pro Thr Thr Ala Ser Lys Thr Gly Lys Lys Glu Arg Gln Gly Tyr Lys
        115                 120                 125

Ser Trp Arg Gly His Lys Asn Ala Ile Ile Ser Cys Leu His Glu Cys
    130                 135                 140

Gly Gly Asn Ile Ser Phe Thr Arg Arg Tyr Leu Leu Phe His His Gly
145                 150                 155                 160

Val Asn Phe Pro Arg Asn Val Leu His Tyr Tyr Arg His Leu His Ser
                165                 170                 175

Pro Tyr Tyr Ser Gln Gln Val Pro Thr Ala Ser Thr Lys Lys Asp Ser
            180                 185                 190

Ser Ser Ser Gly Asp Leu Gln Gln Lys Thr Ser Ser Ser Ser
        195                 200                 205


<210> SEQ ID NO 26
```

<211> LENGTH: 148
<212> TYPE: PRT
<213> ORGANISM: Unknown
<220> FEATURE:
<223> OTHER INFORMATION: Synthetic Construct

<400> SEQUENCE: 26

```
Met Lys Ala Phe Ala Val Leu Phe Val Leu Ser Leu Ile Lys Thr Glu
1               5                   10                  15

Leu Arg Leu Thr Phe Gly Leu Pro Leu Leu Gln Pro Gly Leu Tyr Asn
            20                  25                  30

Thr Ser Gln Thr Leu Arg Ser Ser Gln Lys Thr Gln Ala Leu Pro Leu
        35                  40                  45

Ile Gln Asp Ser Asn Ser Thr Ser Pro Ala Pro Ser Pro Thr Asn Leu
    50                  55                  60

Pro Glu Thr Asn Asn Leu Gly Ala Gln Leu Gln Pro Arg Phe Ser Arg
65                  70                  75                  80

Ser Leu Leu Ser Ala Asn Thr Thr Thr Pro Arg Thr Gly Gly Glu Leu
                85                  90                  95

Arg Gly Leu Pro Thr Asp Asn Pro Trp Val Val Ala Gly Phe Val Ala
            100                 105                 110

Leu Gly Val Val Ala Gly Gly Leu Val Leu Ile Leu Cys Tyr Leu Tyr
        115                 120                 125

Thr Pro Cys Cys Ala Tyr Leu Val Val Leu Cys Cys Trp Phe Lys Lys
    130                 135                 140

Trp Gly Ser Tyr
145
```

<210> SEQ ID NO 27
<211> LENGTH: 142
<212> TYPE: PRT
<213> ORGANISM: Unknown
<220> FEATURE:
<223> OTHER INFORMATION: Synthetic Construct

<400> SEQUENCE: 27

```
Met Ile Leu Arg His Tyr Ser Asp Phe Phe Lys Thr Ile Gln Ala Leu
1               5                   10                  15

Leu Pro Leu Leu Leu Leu Leu Leu Pro Cys Asp Thr Ile Ala Thr Thr
            20                  25                  30

Pro Thr Leu Asn Pro Asn Leu Arg Lys Cys Lys Phe Gln Glu Pro Trp
        35                  40                  45

Asn Phe Leu Lys Cys Tyr Asn Glu Thr Ile Asp Phe Pro Pro Tyr Trp
    50                  55                  60

Ile Thr Ile Ile Gly Ile Leu Asn Val Val Cys Cys Thr Ile Phe Ala
65                  70                  75                  80

Phe Leu Val Tyr Pro Met Phe Asp Phe Gly Trp Asn Val Pro Asn Ala
                85                  90                  95

Leu Thr His Pro Gln Glu Pro Gln Glu His Ile Pro Leu Gln Asn Met
            100                 105                 110

Gln Pro Leu Ala Leu Ile Glu Tyr Glu Asn Glu Pro Gln Pro Pro Leu
        115                 120                 125

Leu Pro Ala Ile Ser Tyr Phe Asn Leu Thr Gly Arg Asp Asp
    130                 135                 140
```

<210> SEQ ID NO 28
<211> LENGTH: 880
<212> TYPE: DNA

```
<213> ORGANISM: Unknown
<220> FEATURE:
<223> OTHER INFORMATION: Simian adenovirus 41.1
<220> FEATURE:
<221> NAME/KEY: CDS
<222> LOCATION: (4)..(580)
<223> OTHER INFORMATION: Ela
<220> FEATURE:
<221> NAME/KEY: CDS
<222> LOCATION: (669)..(874)
<223> OTHER INFORMATION: Ela

<400> SEQUENCE: 28

aaa atg aga cac ctg cga ttc ctg cct cag gaa atc tcc att gcg acc       48
    Met Arg His Leu Arg Phe Leu Pro Gln Glu Ile Ser Ile Ala Thr
    1               5                   10                  15

ggg aat gaa ata ctg cag ttt gtg gta gat gcc ctg atg gga gac gat       96
Gly Asn Glu Ile Leu Gln Phe Val Val Asp Ala Leu Met Gly Asp Asp
                20                  25                  30

ccg gag ccg cct gcg cag cct ttc gat cct cct acg ctt cat gaa ctg      144
Pro Glu Pro Pro Ala Gln Pro Phe Asp Pro Pro Thr Leu His Glu Leu
            35                  40                  45

tat gat tta gag gta gac ggg ccg gag gat cct aac gag gaa gct gtg      192
Tyr Asp Leu Glu Val Asp Gly Pro Glu Asp Pro Asn Glu Glu Ala Val
        50                  55                  60

aat ggg ttt ttc agc gat tct atg cta tta gct gct agt gaa gga gtg      240
Asn Gly Phe Phe Ser Asp Ser Met Leu Leu Ala Ala Ser Glu Gly Val
    65                  70                  75

gac tta gac cca cct tct gag acc ctt gat acc cca ggg gtg gtg gtg      288
Asp Leu Asp Pro Pro Ser Glu Thr Leu Asp Thr Pro Gly Val Val Val
80                  85                  90                  95

gaa agc ggc aga ggt ggg aaa aaa ttg cct gaa ctt ggt gct gct gaa      336
Glu Ser Gly Arg Gly Gly Lys Lys Leu Pro Glu Leu Gly Ala Ala Glu
                100                 105                 110

atg gat ttg cac tgt tat gaa gag ggc ttt cct ccg agt gat gat gac      384
Met Asp Leu His Cys Tyr Glu Glu Gly Phe Pro Pro Ser Asp Asp Asp
            115                 120                 125

gat gag gaa aat gtg cag tcg atc cag acc gca gcg ggt gag gga atg      432
Asp Glu Glu Asn Val Gln Ser Ile Gln Thr Ala Ala Gly Glu Gly Met
        130                 135                 140

aaa gct gcc aat gat ggt ttt aag ttg gac tgc ccg gag ctg cct gga      480
Lys Ala Ala Asn Asp Gly Phe Lys Leu Asp Cys Pro Glu Leu Pro Gly
    145                 150                 155

cat ggc tgt aag tct tgt gaa ttt cac agg aat agt act gga cta aaa      528
His Gly Cys Lys Ser Cys Glu Phe His Arg Asn Ser Thr Gly Leu Lys
160                 165                 170                 175

gaa ctg ttg tgc tcg ctt tgc tat atg aga acg cac tgc cat ttt att      576
Glu Leu Leu Cys Ser Leu Cys Tyr Met Arg Thr His Cys His Phe Ile
                180                 185                 190

tac a gtaagtgtgt ctaacttaaa tttaaaggga cagtgtagca gtttaatgtc         630
Tyr

tgttgaatgt gggatttatg tctttgtgat ttttatag gt  cct gtg tct gat gct    685
                                          Ser Pro Val Ser Asp Ala
                                              195

gat gaa tcg cct tct cct gat tca act acc tca cct cct gaa att cag      733
Asp Glu Ser Pro Ser Pro Asp Ser Thr Thr Ser Pro Pro Glu Ile Gln
    200                 205                 210

gcg cca gtc cct gca aac gta tgc aag ccc att cct gtg aag gct aag      781
Ala Pro Val Pro Ala Asn Val Cys Lys Pro Ile Pro Val Lys Ala Lys
215                 220                 225                 230

cct ggg aaa cgc cct gct gtg gat aaa ctg gag gac ttg ctt gag ggt      829
Pro Gly Lys Arg Pro Ala Val Asp Lys Leu Glu Asp Leu Leu Glu Gly
```

```
            235                 240                 245

ggg gat gga cct ttg gac ttg agt acc cgg aaa ctg cca agg caa          874
Gly Asp Gly Pro Leu Asp Leu Ser Thr Arg Lys Leu Pro Arg Gln
        250                 255                 260

tgagtg                                                               880


<210> SEQ ID NO 29
<211> LENGTH: 261
<212> TYPE: PRT
<213> ORGANISM: Unknown
<220> FEATURE:
<223> OTHER INFORMATION: Synthetic Construct

<400> SEQUENCE: 29

Met Arg His Leu Arg Phe Leu Pro Gln Glu Ile Ser Ile Ala Thr Gly
1               5                   10                  15

Asn Glu Ile Leu Gln Phe Val Val Asp Ala Leu Met Gly Asp Asp Pro
            20                  25                  30

Glu Pro Pro Ala Gln Pro Phe Asp Pro Pro Thr Leu His Glu Leu Tyr
        35                  40                  45

Asp Leu Glu Val Asp Gly Pro Glu Asp Pro Asn Glu Glu Ala Val Asn
    50                  55                  60

Gly Phe Phe Ser Asp Ser Met Leu Leu Ala Ala Ser Glu Gly Val Asp
65                  70                  75                  80

Leu Asp Pro Pro Ser Glu Thr Leu Asp Thr Pro Gly Val Val Val Glu
                85                  90                  95

Ser Gly Arg Gly Gly Lys Lys Leu Pro Glu Leu Gly Ala Ala Glu Met
            100                 105                 110

Asp Leu His Cys Tyr Glu Glu Gly Phe Pro Pro Ser Asp Asp Asp Asp
        115                 120                 125

Glu Glu Asn Val Gln Ser Ile Gln Thr Ala Ala Gly Glu Gly Met Lys
    130                 135                 140

Ala Ala Asn Asp Gly Phe Lys Leu Asp Cys Pro Glu Leu Pro Gly His
145                 150                 155                 160

Gly Cys Lys Ser Cys Glu Phe His Arg Asn Ser Thr Gly Leu Lys Glu
                165                 170                 175

Leu Leu Cys Ser Leu Cys Tyr Met Arg Thr His Cys His Phe Ile Tyr
            180                 185                 190

Ser Pro Val Ser Asp Ala Asp Glu Ser Pro Ser Pro Asp Ser Thr Thr
        195                 200                 205

Ser Pro Pro Glu Ile Gln Ala Pro Val Pro Ala Asn Val Cys Lys Pro
    210                 215                 220

Ile Pro Val Lys Ala Lys Pro Gly Lys Arg Pro Ala Val Asp Lys Leu
225                 230                 235                 240

Glu Asp Leu Leu Glu Gly Gly Asp Gly Pro Leu Asp Leu Ser Thr Arg
                245                 250                 255

Lys Leu Pro Arg Gln
            260


<210> SEQ ID NO 30
<211> LENGTH: 900
<212> TYPE: DNA
<213> ORGANISM: Unknown
<220> FEATURE:
<223> OTHER INFORMATION: Simian adenovirus 41.1
<220> FEATURE:
<221> NAME/KEY: CDS
<222> LOCATION: (8)..(365)
```

```
<223> OTHER INFORMATION: 33K
<220> FEATURE:
<221> NAME/KEY: CDS
<222> LOCATION: (535)..(893)
<223> OTHER INFORMATION: 33K

<400> SEQUENCE: 30

cctcagg atg tcc cag cgc cga gga agc aag aag ttg aaa gtg cag ctg       49
        Met Ser Gln Arg Arg Gly Ser Lys Lys Leu Lys Val Gln Leu
        1               5                   10

ccg ccc cca gag gac atg gag gaa gac tgg gac agt cag gca gag gag       97
Pro Pro Pro Glu Asp Met Glu Glu Asp Trp Asp Ser Gln Ala Glu Glu
15                  20                  25                  30

gag gag atg gaa gat tgg gac agc cag gca gag gag gcg gac agc ctg      145
Glu Glu Met Glu Asp Trp Asp Ser Gln Ala Glu Glu Ala Asp Ser Leu
                35                  40                  45

gag gaa gac agt ttg gag gag gaa gac gag gag gca gag gag gtg gaa      193
Glu Glu Asp Ser Leu Glu Glu Glu Asp Glu Glu Ala Glu Glu Val Glu
            50                  55                  60

gaa gca acc gcc gcc aaa caa ttg tcc tcg gca gcg gag aca agc aag      241
Glu Ala Thr Ala Ala Lys Gln Leu Ser Ser Ala Ala Glu Thr Ser Lys
        65                  70                  75

gtc cca gac agc agc agc agc acg gct aca atc tcc gct ccg ggt cgg      289
Val Pro Asp Ser Ser Ser Ser Thr Ala Thr Ile Ser Ala Pro Gly Arg
    80                  85                  90

ggg gcc cag cag cgt ccc aac agt aga tgg gac gag acc ggg cga ttc      337
Gly Ala Gln Gln Arg Pro Asn Ser Arg Trp Asp Glu Thr Gly Arg Phe
95                  100                 105                 110

ccg aac ccg acc acc gct tcc aag acc g gtaagaagga gcggcaggga          385
Pro Asn Pro Thr Thr Ala Ser Lys Thr
                115

tacaagtcct ggcgggggca taagaatgcc atcatctcct gcttgcatga atgcgggggc    445

aacatatcct tcacccgacg ctacctgctc ttccaccacg ggtgaactt cccccgcaat     505

gtcttgcatt actaccgtca cctccacag cc  ctt act aca gcc agc aag tcc      557
                                Ala Leu Thr Thr Ala Ser Lys Ser
                                120                 125

cga cag cct cga caa aga aag aca gca gca gca gcg ggg acc tcc agc      605
Arg Gln Pro Arg Gln Arg Lys Thr Ala Ala Ala Ala Gly Thr Ser Ser
        130                 135                 140

aga aaa cca gca gca gca gtt aga aaa tcc agt gca gca gga gga gga      653
Arg Lys Pro Ala Ala Ala Val Arg Lys Ser Ser Ala Ala Gly Gly Gly
    145                 150                 155

ctg agg atc aca gcg aac gag cca gcg cag acc cga gag ctg aga aac      701
Leu Arg Ile Thr Ala Asn Glu Pro Ala Gln Thr Arg Glu Leu Arg Asn
160                 165                 170                 175

agg atc ttt cca acc ctc tat gcc atc ttc cag cag agt cgg ggg caa      749
Arg Ile Phe Pro Thr Leu Tyr Ala Ile Phe Gln Gln Ser Arg Gly Gln
                180                 185                 190

gag cag gaa ctg aaa gta aaa aac cga tct ctg cgc tcg ctc acc cga      797
Glu Gln Glu Leu Lys Val Lys Asn Arg Ser Leu Arg Ser Leu Thr Arg
            195                 200                 205

agt tgt ttg tat cac aag agc gaa gac caa ctt cag cgc act ctc gag      845
Ser Cys Leu Tyr His Lys Ser Glu Asp Gln Leu Gln Arg Thr Leu Glu
        210                 215                 220

gac gcc gag gct ctc ttc aac aag tac tgc gcg ctg act ctt aaa gag      893
Asp Ala Glu Ala Leu Phe Asn Lys Tyr Cys Ala Leu Thr Leu Lys Glu
    225                 230                 235

tagcccg                                                              900
```

<210> SEQ ID NO 31
<211> LENGTH: 239
<212> TYPE: PRT
<213> ORGANISM: Unknown
<220> FEATURE:
<223> OTHER INFORMATION: Synthetic Construct

<400> SEQUENCE: 31

```
Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
            20                  25                  30

Met Glu Asp Trp Asp Ser Gln Ala Glu Glu Ala Asp Ser Leu Glu Glu
        35                  40                  45

Asp Ser Leu Glu Glu Glu Asp Glu Glu Ala Glu Glu Val Glu Glu Ala
    50                  55                  60

Thr Ala Ala Lys Gln Leu Ser Ser Ala Ala Glu Thr Ser Lys Val Pro
65                  70                  75                  80

Asp Ser Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
            100                 105                 110

Pro Thr Thr Ala Ser Lys Thr Ala Leu Thr Thr Ala Ser Lys Ser Arg
        115                 120                 125

Gln Pro Arg Gln Arg Lys Thr Ala Ala Ala Ala Gly Thr Ser Ser Arg
    130                 135                 140

Lys Pro Ala Ala Ala Val Arg Lys Ser Ser Ala Ala Gly Gly Gly Leu
145                 150                 155                 160

Arg Ile Thr Ala Asn Glu Pro Ala Gln Thr Arg Glu Leu Arg Asn Arg
                165                 170                 175

Ile Phe Pro Thr Leu Tyr Ala Ile Phe Gln Gln Ser Arg Gly Gln Glu
            180                 185                 190

Gln Glu Leu Lys Val Lys Asn Arg Ser Leu Arg Ser Leu Thr Arg Ser
        195                 200                 205

Cys Leu Tyr His Lys Ser Glu Asp Gln Leu Gln Arg Thr Leu Glu Asp
    210                 215                 220

Ala Glu Ala Leu Phe Asn Lys Tyr Cys Ala Leu Thr Leu Lys Glu
225                 230                 235
```

<210> SEQ ID NO 32
<211> LENGTH: 23
<212> TYPE: DNA
<213> ORGANISM: Artificial
<220> FEATURE:
<223> OTHER INFORMATION: based on Simian adenovirus 41.1

<400> SEQUENCE: 32

```
caggatgctt cggagtacct gag                                              23
```

<210> SEQ ID NO 33
<211> LENGTH: 26
<212> TYPE: DNA
<213> ORGANISM: Artificial
<220> FEATURE:
<223> OTHER INFORMATION: based on Simian adenovirus 41.1
<220> FEATURE:
<221> NAME/KEY: misc_feature
<222> LOCATION: (6)..(6)
<223> OTHER INFORMATION: n is a, c, g, or t

<400> SEQUENCE: 33
ttggcnggda tdgggtavag catgtt 26

<210> SEQ ID NO 34
<211> LENGTH: 35767
<212> TYPE: DNA
<213> ORGANISM: Unknown
<220> FEATURE:
<223> OTHER INFORMATION: Simian adenovirus 41.2
<220> FEATURE:
<221> NAME/KEY: repeat_region
<222> LOCATION: (1)..(132)
<223> OTHER INFORMATION: ITR
<220> FEATURE:
<221> NAME/KEY: CDS
<222> LOCATION: (1924)..(3408)
<223> OTHER INFORMATION: E1b/55K
<220> FEATURE:
<221> NAME/KEY: CDS
<222> LOCATION: (3503)..(3916)
<223> OTHER INFORMATION: pIX
<220> FEATURE:
<221> NAME/KEY: misc_feature
<222> LOCATION: (3985)..(5606)
<223> OTHER INFORMATION: IVa2 complement (3985..5315,5594..5606)
<220> FEATURE:
<221> NAME/KEY: misc_feature
<222> LOCATION: (5088)..(13917)
<223> OTHER INFORMATION: pol complement (5088..8657,13909..13917)
<220> FEATURE:
<221> NAME/KEY: misc_feature
<222> LOCATION: (8459)..(13917)
<223> OTHER INFORMATION: pTP complement (8459..10435,13909..13917)
<220> FEATURE:
<221> NAME/KEY: CDS
<222> LOCATION: (10921)..(12087)
<223> OTHER INFORMATION: 52K
<220> FEATURE:
<221> NAME/KEY: CDS
<222> LOCATION: (12115)..(13875)
<223> OTHER INFORMATION: pIIIa
<220> FEATURE:
<221> NAME/KEY: CDS
<222> LOCATION: (13962)..(15713)
<223> OTHER INFORMATION: penton
<220> FEATURE:
<221> NAME/KEY: CDS
<222> LOCATION: (15720)..(16295)
<223> OTHER INFORMATION: pVII
<220> FEATURE:
<221> NAME/KEY: CDS
<222> LOCATION: (16341)..(17390)
<223> OTHER INFORMATION: V
<220> FEATURE:
<221> NAME/KEY: CDS
<222> LOCATION: (17422)..(17646)
<223> OTHER INFORMATION: pX
<220> FEATURE:
<221> NAME/KEY: CDS
<222> LOCATION: (17724)..(18473)
<223> OTHER INFORMATION: pVI
<220> FEATURE:
<221> NAME/KEY: CDS
<222> LOCATION: (18592)..(21420)
<223> OTHER INFORMATION: hexon
<220> FEATURE:
<221> NAME/KEY: misc_feature
<222> LOCATION: (22175)..(23731)
<223> OTHER INFORMATION: DBP complement (22175..23731)
<220> FEATURE:
<221> NAME/KEY: CDS
<222> LOCATION: (25950)..(26564)
<223> OTHER INFORMATION: 22K
<220> FEATURE:
<221> NAME/KEY: CDS
<222> LOCATION: (26905)..(27585)
<223> OTHER INFORMATION: pVIII
<220> FEATURE:

```
<221> NAME/KEY: CDS
<222> LOCATION: (27588)..(27902)
<223> OTHER INFORMATION: E3[1]2.5K
<220> FEATURE:
<221> NAME/KEY: CDS
<222> LOCATION: (28272)..(28787)
<223> OTHER INFORMATION: E3>p19K
<220> FEATURE:
<221> NAME/KEY: CDS
<222> LOCATION: (28819)..(29421)
<223> OTHER INFORMATION: E3©R1eta
<220> FEATURE:
<221> NAME/KEY: CDS
<222> LOCATION: (29474)..(30118)
<223> OTHER INFORMATION: E3©R1>amma
<220> FEATURE:
<221> NAME/KEY: CDS
<222> LOCATION: (30138)..(30443)
<223> OTHER INFORMATION: E3©R1÷elta
<220> FEATURE:
<221> NAME/KEY: CDS
<222> LOCATION: (30476)..(30748)
<223> OTHER INFORMATION: E3®IDålpha
<220> FEATURE:
<221> NAME/KEY: CDS
<222> LOCATION: (31138)..(31533)
<223> OTHER INFORMATION: E3[1]4.7K
<220> FEATURE:
<221> NAME/KEY: misc_feature
<222> LOCATION: (31594)..(31751)
<223> OTHER INFORMATION: U[e]xon  complement (31594..31751)
<220> FEATURE:
<221> NAME/KEY: CDS
<222> LOCATION: (31766)..(32740)
<223> OTHER INFORMATION: fiber
<220> FEATURE:
<221> NAME/KEY: misc_feature
<222> LOCATION: (32789)..(33963)
<223> OTHER INFORMATION: E4ørf6/7  complement (32789..33037,33760..
      33963)
<220> FEATURE:
<221> NAME/KEY: misc_feature
<222> LOCATION: (33037)..(33963)
<223> OTHER INFORMATION: E4ørf6  complement (33037..33963)
<220> FEATURE:
<221> NAME/KEY: misc_feature
<222> LOCATION: (33839)..(34219)
<223> OTHER INFORMATION: E4ørf4  complement (33839..34219)
<220> FEATURE:
<221> NAME/KEY: misc_feature
<222> LOCATION: (34232)..(34582)
<223> OTHER INFORMATION: E4ørf3  complement (34232..34582)
<220> FEATURE:
<221> NAME/KEY: misc_feature
<222> LOCATION: (34582)..(34968)
<223> OTHER INFORMATION: E4ørf2  complement (34582..34968)
<220> FEATURE:
<221> NAME/KEY: misc_feature
<222> LOCATION: (35018)..(35389)
<223> OTHER INFORMATION: E4ørf1  complement (35018..35389)
<220> FEATURE:
<221> NAME/KEY: repeat_region
<222> LOCATION: (35636)..(35767)
<223> OTHER INFORMATION: ITR   complement  (35636..35767)

<400> SEQUENCE: 34

catcatcaat aatatacctt ataaatggaa cggtgccaac atgcaaatga gcttttgaaa     60

atggagggcg gaaggggatt ggccagcggg ttcaacggtc aaaaggggcg ggccggcgcg    120

gggaggtgac gtggttagtg tgggaggagt tatgttgcaa gttctcgcgg taaatgtgac    180

gtaaaacgag gtgtggtttg aacacggaag tacacagttt tcccgcgctg actgacagga    240

tatgaggtag ttttgggcgg atgcaagtga aaattctcca ttttcgcgcg aaaactgaat    300

gaggaagtga atttctgagt aatttcgagt ttatgacagg gcggagtatt taccgagggc    360
```

-continued

```
cgagtagact ttgaccgatt acgtggaggt ttcgattacc gtgtttttca cctaaatttc    420

cgcgtacggt gtcaaagtcc tgtgttttta cgtaggcgtc agctgatcgc tagggtattt    480

aaacctgacg agttccgtca agaggccact cttgagtgcc agcgagaaga gatttctcct    540

ccgcgccgcg agtcagatct ccactttgaa aaatgagaca cctgcgattc ctgcctcagg    600

aaatctccat tgcgaccggg aatgaaatac tgcagtttgt ggtagatgcc ctgatgggag    660

acgatccgga gccgcctgcg cagcctttcg atcctcctac gcttcatgaa ctgtatgatt    720

tagaggtaga cgggccggag gatcctaacg aggaagctgt gaatggtttt ttcagcgatt    780

ctatgctatt agctgctagt gaaggagtgg acttagaccc accttctgag acccttgata    840

ccccaggggt ggtggtggaa agcggcagag gtgggaaaaa attgcctgaa cttggtgctg    900

ctgaaatgga tttgcactgt tatgaagagg gctttcctcc gagtgatgat gaagatgagg    960

aaaatgtgca gtcgatccag accgcagctg gtgagggaat gaaagctgcc aatgatggtt   1020

ttaagttgga ctacccggag ctgcctggac atggctgtaa gtcttgtgaa tttcacagga   1080

atagtactgg actaaaagaa ctgttgtgct cgctttgcta tatgagaacg cactgccatt   1140

ttatttacag taagtgtgtt taagttaaat ttaaagggac agtgtagcag tgttaataac   1200

tgtgaatgtg ggatttatgt tttttgcttg tgatttttat aggtcctgtg tctgatgctg   1260

atgaatcgcc ttctcctgat tcaactacct cacctcctga aattcaggcg ccagtccctg   1320

caaacgtatg caagcccatt cctgtgaagg ctaagcctgg gaaacgccct gctgtggata   1380

agctggagga cttgcttgag ggtggggatg gacctttgga cttgagtacc cggaaactgc   1440

caaggcaatg agtaccctgc acctgtgttt atttaatgtg acgtcagtat ttatgtgaga   1500

gtgccatgta ataaaattat gtcagctgct gagtatttta ttgcttcttg ggtggggact   1560

tgggtatata agtaggagca gacctgtgtg gttagctcac agcagcttgc tgccatccat   1620

ggaggtttgg gctatcttgg aagatctcag acagactagg caactgctag aaaacgcctc   1680

ggacggagtc tctagtcttt ggagattctg gttcggtggt gatctagcta ggctagtctt   1740

tagggtaaaa cgggagtata gtgaagaatt tgaaaagtta ttggaagaca gtccaggact   1800

ttttgaagcc cttaacttgg gccaccaggc tcattttaag gagaaggttt tatcagtttt   1860

agatttttct accccctggta gaactgctgc tgctgtagca tttcttactt ttatattgga   1920

taa atg gat ccc aca aac cca ctt cag caa ggg ata cgt ctt gga ttt     1968
    Met Asp Pro Thr Asn Pro Leu Gln Gln Gly Ile Arg Leu Gly Phe
    1               5                   10                  15

cat agc agc agc ttt gtg gag aac atg gaa ggc ccg cag gct gag gat     2016
His Ser Ser Ser Phe Val Glu Asn Met Glu Gly Pro Gln Ala Glu Asp
                20                  25                  30

aat ctt aga tta ctg gcc agt gca gcc tct ggg cgt agc ggc aat cct     2064
Asn Leu Arg Leu Leu Ala Ser Ala Ala Ser Gly Arg Ser Gly Asn Pro
            35                  40                  45

gag aca ccc acc agt cat gcc agc ggt ttt gga gga gga gca gca gga     2112
Glu Thr Pro Thr Ser His Ala Ser Gly Phe Gly Gly Gly Ala Ala Gly
        50                  55                  60

gga caa ccc gag agc cgg cct gga ccc tcc ggt gga gga ggc gga gga     2160
Gly Gln Pro Glu Ser Arg Pro Gly Pro Ser Gly Gly Gly Gly Gly Gly
    65                  70                  75

gta gct gac ctg ttt cct gaa ctg cga cgg gtg ctt act agg tct acg     2208
Val Ala Asp Leu Phe Pro Glu Leu Arg Arg Val Leu Thr Arg Ser Thr
80                  85                  90                  95

tcc agt gga cag gac agg ggc att aag agg gag agg aat gct agt ggg     2256
Ser Ser Gly Gln Asp Arg Gly Ile Lys Arg Glu Arg Asn Ala Ser Gly
                100                 105                 110
```

```
cat aat tca aga act gag ttg gct tta agt tta atg agt cgc agc cgc      2304
His Asn Ser Arg Thr Glu Leu Ala Leu Ser Leu Met Ser Arg Ser Arg
            115                 120                 125

cct gaa act atc tgg tgg cat gag gtt cag agc gag ggc agg gat gaa      2352
Pro Glu Thr Ile Trp Trp His Glu Val Gln Ser Glu Gly Arg Asp Glu
        130                 135                 140

gtt tca ata ttg cag gag aaa tat tct cta gaa caa att aaa acc tgt      2400
Val Ser Ile Leu Gln Glu Lys Tyr Ser Leu Glu Gln Ile Lys Thr Cys
    145                 150                 155

tgg ttg gaa cct gag gat gat tgg gag gtg gcc att agg aat tat gct      2448
Trp Leu Glu Pro Glu Asp Asp Trp Glu Val Ala Ile Arg Asn Tyr Ala
160                 165                 170                 175

aag ata tct ctg aga cct gat aaa cag tat aga att acc aag aag att      2496
Lys Ile Ser Leu Arg Pro Asp Lys Gln Tyr Arg Ile Thr Lys Lys Ile
                180                 185                 190

aat atc aga aat gca tgc tac ata tca ggg aat ggg gca gag gtt ata      2544
Asn Ile Arg Asn Ala Cys Tyr Ile Ser Gly Asn Gly Ala Glu Val Ile
            195                 200                 205

ata gat aca cca gat aaa aca gct ttt agg tgt tgt atg atg ggt atg      2592
Ile Asp Thr Pro Asp Lys Thr Ala Phe Arg Cys Cys Met Met Gly Met
        210                 215                 220

tgg cca ggg gtg gct ggt atg gag gca gta aca ctt atg aat att agg      2640
Trp Pro Gly Val Ala Gly Met Glu Ala Val Thr Leu Met Asn Ile Arg
    225                 230                 235

ttt agg gga gat ggg tat aat ggg att gtc ttt atg gct aac act aag      2688
Phe Arg Gly Asp Gly Tyr Asn Gly Ile Val Phe Met Ala Asn Thr Lys
240                 245                 250                 255

ctg att ctg cat ggt tgt agc ttt ttt ggc ttt aat aat act tgt gtg      2736
Leu Ile Leu His Gly Cys Ser Phe Phe Gly Phe Asn Asn Thr Cys Val
                260                 265                 270

gaa gca tgg gga cag gtt agt gta aga ggc tgt agt ttc tat gca tgc      2784
Glu Ala Trp Gly Gln Val Ser Val Arg Gly Cys Ser Phe Tyr Ala Cys
            275                 280                 285

tgg att gca cta tca ggc aga acc aag agt cag ttg tct gtg aag aaa      2832
Trp Ile Ala Leu Ser Gly Arg Thr Lys Ser Gln Leu Ser Val Lys Lys
        290                 295                 300

tgc atg ttt gag aga tgt aat ctg ggc ata ctg aat gaa ggc gaa gca      2880
Cys Met Phe Glu Arg Cys Asn Leu Gly Ile Leu Asn Glu Gly Glu Ala
    305                 310                 315

agg gtc cgc cac tgt gct gct aca gaa act ggc tgc ttc att cta ata      2928
Arg Val Arg His Cys Ala Ala Thr Glu Thr Gly Cys Phe Ile Leu Ile
320                 325                 330                 335

aag gga aat gcc agt gtg aag cat aac atg atc tgt gga ccc tcg gat      2976
Lys Gly Asn Ala Ser Val Lys His Asn Met Ile Cys Gly Pro Ser Asp
                340                 345                 350

gaa agg cct tat cag atg ctg acc tgt gct gga gga cat tgc aat atg      3024
Glu Arg Pro Tyr Gln Met Leu Thr Cys Ala Gly Gly His Cys Asn Met
            355                 360                 365

ctg gct act gtg cat att gtt tct cat gca cgc aag aaa tgg cct gtt      3072
Leu Ala Thr Val His Ile Val Ser His Ala Arg Lys Lys Trp Pro Val
        370                 375                 380

ttt gaa cat aat gtg atg acc aag tgc acc atg cac gca ggt ggt cgc      3120
Phe Glu His Asn Val Met Thr Lys Cys Thr Met His Ala Gly Gly Arg
    385                 390                 395

agg gga atg ttt atg cct tac cag tgt aac atg aat cat gtg aag gtg      3168
Arg Gly Met Phe Met Pro Tyr Gln Cys Asn Met Asn His Val Lys Val
400                 405                 410                 415

atg ttg gaa cca gat gcc ttt tcc aga atg agc tta aca gga atc ttt      3216
Met Leu Glu Pro Asp Ala Phe Ser Arg Met Ser Leu Thr Gly Ile Phe
```

```
                420                 425                 430

gat atg aat gtg caa cta tgg aag att ctg aga tat gat gag acc aaa      3264
Asp Met Asn Val Gln Leu Trp Lys Ile Leu Arg Tyr Asp Glu Thr Lys
            435                 440                 445

tcg agg gtg cgc gca tgc gag tgc ggg ggc aag cat gcc agg ttc cag      3312
Ser Arg Val Arg Ala Cys Glu Cys Gly Gly Lys His Ala Arg Phe Gln
        450                 455                 460

ccg gtg tgt gtg gat gtg acg gaa gac ctg aga ccc gat cat ttg gtg      3360
Pro Val Cys Val Asp Val Thr Glu Asp Leu Arg Pro Asp His Leu Val
    465                 470                 475

ctt gcc tgc act gga gcg gag ttc ggt tct agt ggg gaa gaa act gac      3408
Leu Ala Cys Thr Gly Ala Glu Phe Gly Ser Ser Gly Glu Glu Thr Asp
480                 485                 490                 495

taaagtgagt agtggggaat gctttggagg ggattccagg cgggtaaggt gggcagattg    3468

ggtaaattct gtttgtttct gtcttgcagc tgcc atg agt gga agc gct tct ttt    3523
                                      Met Ser Gly Ser Ala Ser Phe
                                                      500

gag ggg gga gtc ttt agc cct tat ctg acg ggg cga ctc cca ccc tgg      3571
Glu Gly Gly Val Phe Ser Pro Tyr Leu Thr Gly Arg Leu Pro Pro Trp
        505                 510                 515

gca gga gtt cgt cag aat gtc atg gga tcc act gtg gat ggg aga ccc      3619
Ala Gly Val Arg Gln Asn Val Met Gly Ser Thr Val Asp Gly Arg Pro
    520                 525                 530

gtc cag ccc gcc aat tcc tca acg ctg acc tat gcc act ttg agc tct      3667
Val Gln Pro Ala Asn Ser Ser Thr Leu Thr Tyr Ala Thr Leu Ser Ser
535                 540                 545                 550

tca ccc ttg gat gca gcc gca gcc gct gcc gcc tct gct gcc gcc aac      3715
Ser Pro Leu Asp Ala Ala Ala Ala Ala Ala Ala Ser Ala Ala Ala Asn
                555                 560                 565

act gtc ctt gga atg ggc tat tat gga agc atc gtt gcc aat tcc agt      3763
Thr Val Leu Gly Met Gly Tyr Tyr Gly Ser Ile Val Ala Asn Ser Ser
            570                 575                 580

tcc tct aat aac cct tcg acc ctg gct gag gac aag cta ctt gtc ctc      3811
Ser Ser Asn Asn Pro Ser Thr Leu Ala Glu Asp Lys Leu Leu Val Leu
        585                 590                 595

ttg gct cag ctc gag gcc ttg acc cag cgc cta ggc gaa ctg tct cag      3859
Leu Ala Gln Leu Glu Ala Leu Thr Gln Arg Leu Gly Glu Leu Ser Gln
    600                 605                 610

cag gtg gcc cag ttg cgc gag caa act gag tct gct gtt gcc aca gca      3907
Gln Val Ala Gln Leu Arg Glu Gln Thr Glu Ser Ala Val Ala Thr Ala
615                 620                 625                 630

aag tct aaa taaagattcc caaatcaata aataaaggag atccttgttg              3956
Lys Ser Lys

attgtaaaac aagtgtaatg aatctttatt tgatttttcg cgcgcggtat gccctggacc    4016

accggtctcg atcattgaga actcggtgga tcttttccag gaccctgtag aggtgggatt    4076

gaatgtttag atacatgggc attaggccgt ctcgggggtg gagatagctc cattgaagag    4136

cctcatgctc cggggtagtg ttataaatca cccagtcata acaaggtcgg agtgcatggt    4196

gttgcacaat atcttttagg agcaggctaa ttgcaacggg gaggccctta gtgtaggtgt    4256

ttacaaatct gttgagctgg gacgggtgca tccggggtga aattatatgc attttggact    4316

ggatcttgag gttggcaatg ttgccgccta gatcccgtct cgggttcata ttgtgcagga    4376

ccaccaagac agtgtatccg gtgcacttgg gaaatttatc atgcagctta gagggaaaag    4436

catgaaaaaa tttggagacg cctttgtgtc cgcccagatt ctccatgcac tcatccataa    4496

tgatagcgat gggaccgtgg gcggcggcgc gggcaaacac gttccggggg tctgacacat    4556
```

```
catagttatg ctcctgagtc aggtcatcat aagccatttt aataaacttg gggcggaggg   4616

tgccagattg gggatgaaa gttccctcgg gccccggagc atagtttccc tcacatattt   4676

gcatttccca agctttcagt tcagaggggg ggatcatgtc cacctgcggg gctataaaaa   4736

ataccgtttc tggagccggg gtgattaact gggatgagag cagattcctg agcagctgag   4796

acttgccgca cccagtggga ccgtaaatga ccccgattac gggttgcaga tggtagttta   4856

gggagcggca gctgccgtcc tcccggagca ggggggccac ttcgttcatc atttccctta   4916

catggatatt ttcccgcacc aagtccgtta ggaggcgctc tccccccagg gatagaagct   4976

cctggagcga ggagaagttt ttcagcggct tcagcccgtc agccatgggc attttggaga   5036

gagtctgttg caagagctct agtcggtccc agagctcggt gatgtgttct atggcatctc   5096

gatccagcag acctcctcgt ttcgcgggtt gggacgactc ctggagtatg gtatcagacg   5156

atgggcgtcc agcgctgcca gggtccgatc tttccagggt cgcagcgtcc gagtcagggt   5216

tgtttccgtc acggtgaagg ggtgcgcgcc tggttgggcg cttgcgaggg tgcgtttcag   5276

gctcatcctg ctggtcgaga accgctgccg atcggcgccc tgcatgtcgg ccaggtagca   5336

gtttaccatg agttcgtagt tgagcgcctc ggccgcgtgg cctttggcgc ggagcttacc   5396

tttggaagtt ttctggcagg cggggcagta cagacacttg agggcataca gtttgggagc   5456

gaggaagatg gattcggggg agtatgcgtc cgcaccgcag gaggcgcaga cggtttcgca   5516

ttccacgagc caggtcagat ccggctcatc ggggtcaaaa acaagttttc ccccatgttt   5576

tttgatgcgt ttcttacctt tggtctccat gagttcgtgt ccccgctggg tgacaaagag   5636

gctgtccgtg tccccgtaga ccgattttat gggcctgtcc tcgagcggag tgcctcggtc   5696

ctcttcgtag aggaactcgg accactctga tacaaaggcg cgcgtccagg ccagcacaaa   5756

agaggccacg tgggaggggt agcggtcgtt gtcaaccagg gggtccacct tctccacggt   5816

atgtaaacac atgtccccct cctccacatc caagaatgtg attggcttgt aagtgtatgc   5876

cacgtgacca ggggtccccg ccgggggggt ataaaagggg gcgggtctct gctcgtcctc   5936

actgtcttcc ggatcgctgt ccaggagcgc cagctgttgg ggtaggtatt ccctctcgaa   5996

ggcgggcata acctctgcac tcaggttgtc agtttctagg aacgaggagg atttgatatt   6056

gacagtgcca gccgagatgc ctttcataag actctcgtcc atttggtcag aaaatacaat   6116

ctttttgttg tccagcttgg tggcaaagga tccatagagg gcattggata agagcttggc   6176

tatggagcgc atggtttggt tcttttcctt gtcagcgcgc tccttggcag caatgttgag   6236

ctggacatac tcgcgcgcca gacacttcca ttcagggaag atggttgtca gttcatctgg   6296

cacgattctg actcgccagc cctgttatg cagggtgatc agatccacac tggtggtcac   6356

ttcgcctctg aggggctcgt tggtccagca gagtcgaccc ccttttctcg aacagaaagg   6416

tgggaggggg tctagcatga gttcatcagg ggggtctgca tccatagtga agattcctgg   6476

gagcagatcc ttgtcaaaat agctgatggg tgtggggtca tccaaagcca tctgccattc   6536

tcgagctgcc agcgcgcgct catagggtt gagaggggtg ccccatggca tggggtgggt   6596

gagtgcagag gcatacatgc cacagatgtc atagacatag aggggctctt cgaggatgcc   6656

aatgtaggtg ggataacagc gcccccctct gatgcttgct cgcacatagt catagagttc   6716

atgcgagggg gcgagcagac ccgagcccaa attagtgcga ttgggttttt cagccctgta   6776

gacgatctgg cgaaagatgg catgtgaatt tgaagagatg gtgggtctct gaaagatgtt   6836

aaaatgggca tgaggtagac ctacagagtc cctgatgaag tgggcatatg actcttgcag   6896

cttggccacc agctctgcag tgacaaggac atccaaggcg cagtagtcaa gggtctcttg   6956
```

```
gatgatgtca taacctggtt ggtttttctt ttcccacagc tcgcggttga gaaggtattc   7016
ttcgcgatcc ttccagtact cttcgagggg aaacccgtct ttgtctgcac ggtaagagcc   7076
cagcatgtag aactgattaa ctgctttgta gggacagcag cccttctcca cggggagaga   7136
gtatgcttgg gctgccttgc gcagtgaggt atgagtgagg gcgaaggtgt ccctgaccat   7196
gactttgagg aactggtgct tgaagtcaat gtcatcacag gccccctgtt cccagagttg   7256
gaagtctacc cgcttcttgt aggcggggtt gggcaaagcg aaagtaacat cattaaagag   7316
aatcttgccg gccctgggca tgaaattgcg ggtgatgcgg aaaggctggg gcacctctgc   7376
ccggttattg atcacctgag cggctaggac gatctcatca aagccattga tgttgtgccc   7436
cacaatgtaa agttctatga atcgcggggt gcccctgaca tgaggcagct tcttgagttc   7496
ttcaaaagtg aggtctgtag ggtcagagag agcatagtgt tcgagggccc attcgtgcag   7556
gtgagggttt gcattgagga aggaggacca gagatccact gccagtgctg tttgtaactg   7616
gtcccgatac tggcgaaaat gctggccgac tgccatcttt tctggggtta tacagtagaa   7676
ggttttgggg tcttgctgcc agcgatccca cttgagtttc atggcgaggt cgtaggcgat   7736
attgacgagc cgctcgtccc ccgagagttt catgaccagc atgaagggga tcagctgctt   7796
gccaaaggac cccatccagg tgtaggtttc cacatcgtag gtgaggaaga gcctttctgt   7856
gcgaggatga gagccgatcg ggaagaactg gatctcctgc caccagttgg aggaatggct   7916
gttgatgtga tggaagtaga actccctgcg gcgcgccgtg cattcatgct tgtgcttgta   7976
cagacggccg cagtactcgc agcgcttcac gggatgcacc tcatgaatga gttgtacctg   8036
gcttcctttg acgagaaatt tcagtgggaa gttgaggcct ggcgcttgta cctcgcgctc   8096
tactatgtta tctgcatcgg cctggccatc ttctgtctcg atggtggtca tgctgacgag   8156
cccccgcggg aggcaagtcc agacctcggc gcgggagggg cggagctcga ggacgagagc   8216
gcgcaggccg gagctgtcca gggtcctgag tcgctgcgga gtcaggttag taggtagtgt   8276
caggagatta acttgcatga tcttttcgag ggcatgcggg aggttcagat ggtacttgat   8336
ctccacgggt ccgttggtgg tgatgtcgat ggcttgcagg gtcccatgcc ccttgggcgc   8396
caccaccgtg cccttgtttt tccttttggg cggcggtggc tctgttgctt cttgcatgtt   8456
cagaagcggt gacgagggcg cgcgccgggc ggtaggggcg gctcgggccc cggcggcatg   8516
gctggcagag gcacgtcggc gccgcgcgcg ggtaggttct ggtactgcgc cctgagaaga   8576
cttgcgtgcg cgacgacgcg gcggttgacg tcctggatct gacgcctctg ggtgaaagct   8636
accggacccg tgagcttgaa cctgaaagag agttcaacag aatcaatttc ggtatcgttg   8696
acggcggctt gcctcaggat ctcttgcacg tcgcccgagt tgtcctggta ggcgatctcg   8756
gccatgaact gctcgatttc ttcctcctga agatctccgc ggcccgctct ctcgacggtg   8816
gccgcgaggt cgttggagat gcgacccatg agttgagaga atgcattcat gcccgcctcg   8876
ttccagacgc ggctgtagac cacggccccc tcgggatctc tcgcgcgcat gaccacctgg   8936
gcgaggttga gctccacgtg gcgggtgaag accgcatagt tgcataggcg ctggaagagg   8996
tagttgagtg tggtggcgat gtgctcggtg acgaagaaat acatgatcca tcgtctcagc   9056
ggcatttcgc tgacatcgcc cagggcttcc aagcgctcca tggcctcgta gaagtccaca   9116
gcgaagttga aaaactggga gttgcgcgcg gacacggtca actcctcctc cagaagacgg   9176
atgagatcgg cgatggtggc gcgcacctcg cgctcgaagg cccccgggat ttcttcctcc   9236
tcctcttcta tctcttcttc cactaacatc tcttcttcct cttcaggcgg gggcggagga   9296
```

```
ggagggggcg cgcggcgacg ccggcggcgc acgggcagac ggtcgatgaa tctttcaatg   9356

acctctccgc ggcggcggcg catggtctcg gtgacggcgc ggccgttctc cctgggtctc   9416

agagtgaaga cgcctccgcg catctccctg aagtggtgac tggggggctc tccgttgggc   9476

agggacaggg cgctgatgat gcattttatc aattgccccg tagggactcc gcgcaaggac   9536

ctgatcgtct gaagatccac gggatctgaa aacctttcga cgaaagcgtc taaccagtcg   9596

caatcgcaag gtaggctgag cactgtttct tgcgggcggg ggtggctaga tgctcggtcg   9656

gggttctctc ttccttctcc ttcctcatca tctcgggagg gtgagacgat gctgctggtg   9716

atgaaattaa aataggcagt tctgagacgg cggatggtgg cgaggagcac caggtctttg   9776

ggtccggctt gctggatgcg caggcgatcg gccattcccc aagcattgtc ctggcatctg   9836

gccagatctt tatagtagtc ttgcatgagt cgctccacgg gcacttcttc ttcgcccgct   9896

ctgccatgca tgcgcgtgag cccgaacccg cgcatgggct ggacaagtgc caggtccgct   9956

acgacccttt cggcgaggat ggcttgctgc acctgggtga gggtggcttg gaagtcgtca  10016

aagtccacga agcgatggta ggctccggtg ttaatggtgt aggagcagtt ggccatgact  10076

gaccagttga ctgtctggtg ccccgggcgc acgagctcgg tgtacttgag gcgcgagtag  10136

gcgcgggtgt caaagatgta atcgttgcag gtgcgcacca ggtactggta gccgatgaga  10196

aagtgcggcg gtggctggcg gtagaggggc catcgctctg tagccggggc tcctggggcg  10256

aggtcttcca gcatgaggcg gtggtatccg tagatgtacc tggacatcca ggtgatcccg  10316

gaggcggtgg tggacgcccg cgggaactcg cgcactcggt tccagatgtt gcgcagcggc  10376

atgaagtagt tcatggtagg cacggtctgg ccagtgaggc gggcgcagtc attgatgctc  10436

tatagacacg gagaaaacga aagcgatgag cggctcgcct ccgtggcctg gaggaacgtg  10496

aacgggttgg gtcgcggtgt accccggttc gagacacaag ccaagcgagc acaactcggg  10556

ccggccggag ccgcggctaa cgtggtattg gcgatcccgt ctcgacccag ccgacgaata  10616

tccaggatac ggagtcgagt cgttttgctg cttgttgctt tttcctggac gggagccagt  10676

gccgcgtcaa gctttagaat gctcagttca cggggccggg agtggctcgc gcccgtagtc  10736

tggagaatca atcgccaggg ttgcgttgcg gtgtgccccg gttcgagcct tagcgtggcc  10796

cggatcggcc ggtttccgcg gcaagcgagg gtttggcagc cccgtcattt ctaagacccc  10856

gccagccgac ttctccagtt tacgggagcg agccctcttt tttttttgt ttttgtcgc   10916

ccag atg cat ccc gtg ctg cga cag atg cgc ccc cag caa cag gcc cct   10965
     Met His Pro Val Leu Arg Gln Met Arg Pro Gln Gln Gln Ala Pro
         635                 640                 645

tct cag caa cag cag cag cca caa aag gcg ctt cct gct cct gct ccc    11013
Ser Gln Gln Gln Gln Gln Pro Gln Lys Ala Leu Pro Ala Pro Ala Pro
    650                 655                 660

gca act act gca gtc gca gcc gtg tgc ggc gcg gga cag ccc gcc tat    11061
Ala Thr Thr Ala Val Ala Ala Val Cys Gly Ala Gly Gln Pro Ala Tyr
665                 670                 675                 680

gat ctg gac ttg gaa gag ggc gag gga ctg gcg cgc ctg ggt gca cca    11109
Asp Leu Asp Leu Glu Glu Gly Glu Gly Leu Ala Arg Leu Gly Ala Pro
                685                 690                 695

tcg ccc gag cgg cac ccg cgg gtg caa ctg aaa aag gac tct cgc gag    11157
Ser Pro Glu Arg His Pro Arg Val Gln Leu Lys Lys Asp Ser Arg Glu
            700                 705                 710

gcg tac gtg ccc cag cag aac ctg ttc agg gac agg agc ggc gag gag    11205
Ala Tyr Val Pro Gln Gln Asn Leu Phe Arg Asp Arg Ser Gly Glu Glu
        715                 720                 725

ccg gag gag atg cga gcc tct cgc ttt aac gcg ggt cgc gag ctg cgt    11253
```

```
Pro Glu Glu Met Arg Ala Ser Arg Phe Asn Ala Gly Arg Glu Leu Arg
    730                 735                 740

cac ggt ctg gac cga aga cgg gtg ctg cgg gac gag gat ttc gag gtc     11301
His Gly Leu Asp Arg Arg Arg Val Leu Arg Asp Glu Asp Phe Glu Val
745                 750                 755                 760

gat gaa gtg aca ggg atc agc ccc gct agg gca cat gtg gcc gcg gca     11349
Asp Glu Val Thr Gly Ile Ser Pro Ala Arg Ala His Val Ala Ala Ala
                765                 770                 775

aac ctt gtc tcg gcc tac gag cag acc gtg aag gag gag cgc aac ttc     11397
Asn Leu Val Ser Ala Tyr Glu Gln Thr Val Lys Glu Glu Arg Asn Phe
            780                 785                 790

caa aaa tca ttc aac aac cat gtg cgc acc ctg atc gcc cgt gag gaa     11445
Gln Lys Ser Phe Asn Asn His Val Arg Thr Leu Ile Ala Arg Glu Glu
        795                 800                 805

gtg acc ctg ggt ctg atg cac ctg tgg gac ctg atg gaa gct atc acc     11493
Val Thr Leu Gly Leu Met His Leu Trp Asp Leu Met Glu Ala Ile Thr
    810                 815                 820

cag aac ccc act agc aaa ccc ctg acc gct cag ctg ttt ctg gtg gtg     11541
Gln Asn Pro Thr Ser Lys Pro Leu Thr Ala Gln Leu Phe Leu Val Val
825                 830                 835                 840

caa cac agc agg gac aat gag gca ttt agg gag gcg ctg ctg aac atc     11589
Gln His Ser Arg Asp Asn Glu Ala Phe Arg Glu Ala Leu Leu Asn Ile
                845                 850                 855

acc gag ccc gag ggg aga tgg ttg tat gat ctg atc aat atc ctg cag     11637
Thr Glu Pro Glu Gly Arg Trp Leu Tyr Asp Leu Ile Asn Ile Leu Gln
            860                 865                 870

agt att ata gta cag gaa cgc agc ctg ggt ctg gcc gag aaa gtg gca     11685
Ser Ile Ile Val Gln Glu Arg Ser Leu Gly Leu Ala Glu Lys Val Ala
        875                 880                 885

gct atc aac tac tct gtc ttg agc ctg ggc aag tac tac gct cgc aag     11733
Ala Ile Asn Tyr Ser Val Leu Ser Leu Gly Lys Tyr Tyr Ala Arg Lys
    890                 895                 900

atc tac aag acc ccc tac gtg ccc ata gac aag gag gtg aag ata gat     11781
Ile Tyr Lys Thr Pro Tyr Val Pro Ile Asp Lys Glu Val Lys Ile Asp
905                 910                 915                 920

ggg ttt tac atg cgt atg act ctt aaa gtg ctg act ctc agc gac gat     11829
Gly Phe Tyr Met Arg Met Thr Leu Lys Val Leu Thr Leu Ser Asp Asp
                925                 930                 935

ctg ggg gtg tac cgc aac gac agg atg cac cgc gcg gtg agc gcc agc     11877
Leu Gly Val Tyr Arg Asn Asp Arg Met His Arg Ala Val Ser Ala Ser
            940                 945                 950

agg agg cgc gag ctg agc gac agg gaa ctt atg cac agc ttg caa aga     11925
Arg Arg Arg Glu Leu Ser Asp Arg Glu Leu Met His Ser Leu Gln Arg
        955                 960                 965

gct ctg acg ggc gca ggg acc gat ggg gag aac tac ttt gac atg ggg     11973
Ala Leu Thr Gly Ala Gly Thr Asp Gly Glu Asn Tyr Phe Asp Met Gly
    970                 975                 980

gca gac ttg caa tgg cag cct agc cgc cgg gcc ctg gac gcg gca ggg     12021
Ala Asp Leu Gln Trp Gln Pro Ser Arg Arg Ala Leu Asp Ala Ala Gly
985                 990                 995                 1000

tgt gag ctt cct tac  gta gaa gag gtg gat  gaa ggc gag gag gag      12066
Cys Glu Leu Pro Tyr  Val Glu Glu Val Asp  Glu Gly Glu Glu Glu
                1005                 1010                 1015

gag ggc gag tac ctg  gaa gac tgatggcgcg acccatattt ttgctag atg     12117
Glu Gly Glu Tyr Leu  Glu Asp                               Met
                1020

gaa cag  cag gca ccg gac ccc  gca atg cgg gcg gcg  ctg cag agc     12162
Glu Gln  Gln Ala Pro Asp Pro  Ala Met Arg Ala Ala  Leu Gln Ser
    1025                 1030                 1035
```

```
cag ccg  tcc ggc att aac tcc  tcg gac gat tgg acc  cag gcc atg      12207
Gln Pro  Ser Gly Ile Asn Ser  Ser Asp Asp Trp Thr  Gln Ala Met
    1040                 1045                 1050

caa cgc  atc atg gcg ctg acg  acc cgc aac ccc gaa  gcc ttt aga      12252
Gln Arg  Ile Met Ala Leu Thr  Thr Arg Asn Pro Glu  Ala Phe Arg
    1055                 1060                 1065

cag caa  ccc cag gcc aac cgc  ctt tcg gcc atc ctg  gag gcc gta      12297
Gln Gln  Pro Gln Ala Asn Arg  Leu Ser Ala Ile Leu  Glu Ala Val
    1070                 1075                 1080

gtt cct  tcc cgc tcc aac ccc  acc cac gag aag gtc  ctg gcc atc      12342
Val Pro  Ser Arg Ser Asn Pro  Thr His Glu Lys Val  Leu Ala Ile
    1085                 1090                 1095

gtg aac  gcg ctg gtg gag aac  aag gcc atc cgt ccc  gat gag gcc      12387
Val Asn  Ala Leu Val Glu Asn  Lys Ala Ile Arg Pro  Asp Glu Ala
    1100                 1105                 1110

ggg ctg  gta tac aat gcc ctc  ttg gag cgc gtg gcc  cgc tac aac      12432
Gly Leu  Val Tyr Asn Ala Leu  Leu Glu Arg Val Ala  Arg Tyr Asn
    1115                 1120                 1125

agc agc  aac gtg cag acc aac  ctg gac cgg atg gtg  acc gat gtg      12477
Ser Ser  Asn Val Gln Thr Asn  Leu Asp Arg Met Val  Thr Asp Val
    1130                 1135                 1140

cgc gag  gca gtg tct cag cgc  gag cgg ttc cag cgc  gat gcc aac      12522
Arg Glu  Ala Val Ser Gln Arg  Glu Arg Phe Gln Arg  Asp Ala Asn
    1145                 1150                 1155

ttg ggg  tcg ctg gtg gcg ctg  aac gcc ttc ctc agc  acc cag cct      12567
Leu Gly  Ser Leu Val Ala Leu  Asn Ala Phe Leu Ser  Thr Gln Pro
    1160                 1165                 1170

gcc aac  gtg ccc cgc ggt cag  caa gac tat aca aac  ttc cta agt      12612
Ala Asn  Val Pro Arg Gly Gln  Gln Asp Tyr Thr Asn  Phe Leu Ser
    1175                 1180                 1185

gca ctg  aga ctc atg gta acc  gaa gtc cct cag agc  gag gtg tac      12657
Ala Leu  Arg Leu Met Val Thr  Glu Val Pro Gln Ser  Glu Val Tyr
    1190                 1195                 1200

cag tcc  gga cca gac tac ttc  ttc cag acc agc aga  cag ggc ttg      12702
Gln Ser  Gly Pro Asp Tyr Phe  Phe Gln Thr Ser Arg  Gln Gly Leu
    1205                 1210                 1215

cag aca  gtg aac ctg agc cag  gct ttc aag aac ctc  aga ggc ttg      12747
Gln Thr  Val Asn Leu Ser Gln  Ala Phe Lys Asn Leu  Arg Gly Leu
    1220                 1225                 1230

tgg gga  gtg cac gct ccg gta  gga gat cgt gcg acc  gtg tct agc      12792
Trp Gly  Val His Ala Pro Val  Gly Asp Arg Ala Thr  Val Ser Ser
    1235                 1240                 1245

ttg ctg  acc ccc aac tcc cgc  cta ctg ttg ctg ctg  gta tcc ccc      12837
Leu Leu  Thr Pro Asn Ser Arg  Leu Leu Leu Leu Leu  Val Ser Pro
    1250                 1255                 1260

ttc act  gac agt ggt agc atc  gac cgc aac tcc tac  ttg ggc tac      12882
Phe Thr  Asp Ser Gly Ser Ile  Asp Arg Asn Ser Tyr  Leu Gly Tyr
    1265                 1270                 1275

ctg ctg  aac ttg tat cgc gag  gcc ata gga cag agc  cag gtg gac      12927
Leu Leu  Asn Leu Tyr Arg Glu  Ala Ile Gly Gln Ser  Gln Val Asp
    1280                 1285                 1290

gag cag  acc tat caa gaa atc  acc caa gtg agc cgt  gcc ctg ggt      12972
Glu Gln  Thr Tyr Gln Glu Ile  Thr Gln Val Ser Arg  Ala Leu Gly
    1295                 1300                 1305

cag gaa  gac acg ggt agc ttg  gaa gcc acc ttg aac  ttc ttg ctg      13017
Gln Glu  Asp Thr Gly Ser Leu  Glu Ala Thr Leu Asn  Phe Leu Leu
    1310                 1315                 1320

acc aac  cgg tcg cag aag atc  cct cct cag tat gcg  ctt acc gcg      13062
Thr Asn  Arg Ser Gln Lys Ile  Pro Pro Gln Tyr Ala  Leu Thr Ala
    1325                 1330                 1335
```

```
gag gag  gag cgg atc ttg aga  tat gtg cag cag agc  gtg gga ctg     13107
Glu Glu  Glu Arg Ile Leu Arg  Tyr Val Gln Gln Ser  Val Gly Leu
    1340                 1345                 1350

ttc ctg  atg cag gag ggg gcg  acc cct agt gcc gcg  ctg gac atg     13152
Phe Leu  Met Gln Glu Gly Ala  Thr Pro Ser Ala Ala  Leu Asp Met
    1355                 1360                 1365

aca gcg  cga aac atg gag ccc  agc atg tat gcc atg  aac cgg cct     13197
Thr Ala  Arg Asn Met Glu Pro  Ser Met Tyr Ala Met  Asn Arg Pro
    1370                 1375                 1380

ttc atc  aac aaa cta ctg gac  tac ctg cac agg gca  gcc gct atg     13242
Phe Ile  Asn Lys Leu Leu Asp  Tyr Leu His Arg Ala  Ala Ala Met
    1385                 1390                 1395

aac tct  gat tat ttc acc aat  gct atc ctt aac ccc  cac tgg ctg     13287
Asn Ser  Asp Tyr Phe Thr Asn  Ala Ile Leu Asn Pro  His Trp Leu
    1400                 1405                 1410

ccc ccg  cct gga ttt tac acg  ggc gag tac gac atg  ccc gac ccc     13332
Pro Pro  Pro Gly Phe Tyr Thr  Gly Glu Tyr Asp Met  Pro Asp Pro
    1415                 1420                 1425

aat gac  ggg ttc ctg tgg gac  gat gtg gac agc agc  ata ttc tcc     13377
Asn Asp  Gly Phe Leu Trp Asp  Asp Val Asp Ser Ser  Ile Phe Ser
    1430                 1435                 1440

ccg cct  cct ggt tat aat act  tgg aag aag gaa ggg  ggc gat aga     13422
Pro Pro  Pro Gly Tyr Asn Thr  Trp Lys Lys Glu Gly  Gly Asp Arg
    1445                 1450                 1455

aga cac  tct tcc gtg tcg ctg  tcc ggg tcg agg ggt  gct gcc gcc     13467
Arg His  Ser Ser Val Ser Leu  Ser Gly Ser Arg Gly  Ala Ala Ala
    1460                 1465                 1470

gcg gtg  ccc gag gct gca agt  cct ttc cct agc ctg  ccc ttt tct     13512
Ala Val  Pro Glu Ala Ala Ser  Pro Phe Pro Ser Leu  Pro Phe Ser
    1475                 1480                 1485

ctg aac  agt gtg cgc agc agt  gaa ctg ggg aga ata  acc cgc ccg     13557
Leu Asn  Ser Val Arg Ser Ser  Glu Leu Gly Arg Ile  Thr Arg Pro
    1490                 1495                 1500

cgc ttg  atg ggc gag gat gag  tac ttg aac gac tcc  ttg ctt aga     13602
Arg Leu  Met Gly Glu Asp Glu  Tyr Leu Asn Asp Ser  Leu Leu Arg
    1505                 1510                 1515

ccc gag  agg gaa aag aac ttc  ccc aac aat ggt ata  gag agc ctg     13647
Pro Glu  Arg Glu Lys Asn Phe  Pro Asn Asn Gly Ile  Glu Ser Leu
    1520                 1525                 1530

gtg gat  aag atg agt aga tgg  aag aca tat gca cag  gat cac aaa     13692
Val Asp  Lys Met Ser Arg Trp  Lys Thr Tyr Ala Gln  Asp His Lys
    1535                 1540                 1545

gac gag  cct agg atc ttg ggg  gct gcg agc ggg acg  acc cgt aga     13737
Asp Glu  Pro Arg Ile Leu Gly  Ala Ala Ser Gly Thr  Thr Arg Arg
    1550                 1555                 1560

cgc cag  cgc cat gac aga cag  agg ggt ctt gtg tgg  gac gat gag     13782
Arg Gln  Arg His Asp Arg Gln  Arg Gly Leu Val Trp  Asp Asp Glu
    1565                 1570                 1575

gac tcg  gcc gat gac agc agc  gtg ttg gac ttg ggt  ggg aga gga     13827
Asp Ser  Ala Asp Asp Ser Ser  Val Leu Asp Leu Gly  Gly Arg Gly
    1580                 1585                 1590

ggg ggc  aac ccg ttc gct cat  ctg cgc ccg cac ttt  ggg cgc atg     13872
Gly Gly  Asn Pro Phe Ala His  Leu Arg Pro His Phe  Gly Arg Met
    1595                 1600                 1605

ttg taaaagtgaa agtaaaataa aaaggcaact caccaaggcc atggcgacga         13925
Leu

gcgtgcgttc gttcttttct gttatctgtg tctagt atg  atg agg cga gcc gtg   13979
                                        Met  Met Arg Arg Ala Val
                                        1610                 1615
```

```
cta ggc gga gcg gtg  gtg tat ccg gag ggt  cct cct cct tcg tac      14024
Leu Gly Gly Ala Val  Val Tyr Pro Glu Gly  Pro Pro Pro Ser Tyr
                1620                 1625                 1630

gag agc gtg atg cag  cag cag gcg gcg gcg  gtg atg cag ccc tcg      14069
Glu Ser Val Met Gln  Gln Gln Ala Ala Ala  Val Met Gln Pro Ser
                1635                 1640                 1645

ctg gag gct ccc ttt  gta ccc ccg cgg tac  ctg gcg cct aca gag      14114
Leu Glu Ala Pro Phe  Val Pro Pro Arg Tyr  Leu Ala Pro Thr Glu
                1650                 1655                 1660

ggg aga aac agc att  cgt tac tcg gag ctg  gca ccc cag tac gat      14159
Gly Arg Asn Ser Ile  Arg Tyr Ser Glu Leu  Ala Pro Gln Tyr Asp
                1665                 1670                 1675

acc acc agg ttg tat  ctg gtg gac aac aag  tcg gcg gac atc gcc      14204
Thr Thr Arg Leu Tyr  Leu Val Asp Asn Lys  Ser Ala Asp Ile Ala
                1680                 1685                 1690

tca ttg aac tat cag  aac gac cac agc aac  ttc ctg acc acg gtg      14249
Ser Leu Asn Tyr Gln  Asn Asp His Ser Asn  Phe Leu Thr Thr Val
                1695                 1700                 1705

gtg cag aac aat gac  ttt acc ccc acg gag  gcc agc acc cag acc      14294
Val Gln Asn Asn Asp  Phe Thr Pro Thr Glu  Ala Ser Thr Gln Thr
                1710                 1715                 1720

atc aac ttt gac gag  cgg tcg cgg tgg ggc  ggt cag ctg aag acc      14339
Ile Asn Phe Asp Glu  Arg Ser Arg Trp Gly  Gly Gln Leu Lys Thr
                1725                 1730                 1735

atc atg cac acc aac  atg ccc aac gtg aac  gag tac atg ttc agc      14384
Ile Met His Thr Asn  Met Pro Asn Val Asn  Glu Tyr Met Phe Ser
                1740                 1745                 1750

aac aag ttc aag gcg  cgg gtg atg gtg tca  cgc aag aaa cct gaa      14429
Asn Lys Phe Lys Ala  Arg Val Met Val Ser  Arg Lys Lys Pro Glu
                1755                 1760                 1765

ggc tat aca ggg gat  aaa aat gat aca agt  cag gat att ctg gag      14474
Gly Tyr Thr Gly Asp  Lys Asn Asp Thr Ser  Gln Asp Ile Leu Glu
                1770                 1775                 1780

tat gag tgg ttt gag  ttc act tta cca gaa  ggc aac ttc tca gcc      14519
Tyr Glu Trp Phe Glu  Phe Thr Leu Pro Glu  Gly Asn Phe Ser Ala
                1785                 1790                 1795

acc atg acc atc gac  ctg atg aac aat gcc  atc att gac aac tac      14564
Thr Met Thr Ile Asp  Leu Met Asn Asn Ala  Ile Ile Asp Asn Tyr
                1800                 1805                 1810

ctg gca gtg ggc aga  cag aat gga gtg ttg  gaa agc gac atc ggt      14609
Leu Ala Val Gly Arg  Gln Asn Gly Val Leu  Glu Ser Asp Ile Gly
                1815                 1820                 1825

gtc aag ttt gat acc  agg aac ttc agg ctg  ggc tgg gac ccc ata      14654
Val Lys Phe Asp Thr  Arg Asn Phe Arg Leu  Gly Trp Asp Pro Ile
                1830                 1835                 1840

act aaa ctt gtt atg  cca gga gtc tac act  tat gaa gcc ttc cat      14699
Thr Lys Leu Val Met  Pro Gly Val Tyr Thr  Tyr Glu Ala Phe His
                1845                 1850                 1855

cct gat att gtg cta  cta cct ggc tgt ggg  gtg gac ttt act gag      14744
Pro Asp Ile Val Leu  Leu Pro Gly Cys Gly  Val Asp Phe Thr Glu
                1860                 1865                 1870

agc cgc ctt agc aac  ttg ctt ggt att agg  aag aga cac cca ttc      14789
Ser Arg Leu Ser Asn  Leu Leu Gly Ile Arg  Lys Arg His Pro Phe
                1875                 1880                 1885

cag gaa ggt ttt aaa  att atg tat gag gat  ctt gag ggg ggt aat      14834
Gln Glu Gly Phe Lys  Ile Met Tyr Glu Asp  Leu Glu Gly Gly Asn
                1890                 1895                 1900

atc ccc gcc ctt ttg  gat gta gat gcc tat  gaa aaa agc aaa aag      14879
Ile Pro Ala Leu Leu  Asp Val Asp Ala Tyr  Glu Lys Ser Lys Lys
```

```
                1905                1910                1915

gaa aac aca gac acc  acc acc act acc act  gtt act act act gaa      14924
Glu Asn Thr Asp Thr  Thr Thr Thr Thr Thr  Val Thr Thr Thr Glu
                1920                1925                1930

gta gca act gtt gca  aga cac gtt gct gaa  gta act act gaa gca      14969
Val Ala Thr Val Ala  Arg His Val Ala Glu  Val Thr Thr Glu Ala
                1935                1940                1945

gca acg gtt gtt gca  gtg gat cct att gtt  gaa gag aac aat aat      15014
Ala Thr Val Val Ala  Val Asp Pro Ile Val  Glu Glu Asn Asn Asn
                1950                1955                1960

act gtt aga gga gat  aat atc cat act gcc  aat gag atg aaa gca      15059
Thr Val Arg Gly Asp  Asn Ile His Thr Ala  Asn Glu Met Lys Ala
                1965                1970                1975

gca gct gat gat aca  aca gtt gta gtt gtg  cct ggc gct gta gtg      15104
Ala Ala Asp Asp Thr  Thr Val Val Val Val  Pro Gly Ala Val Val
                1980                1985                1990

act gaa act gaa acc  aaa acc aag aca ctc  acc att caa cct cta      15149
Thr Glu Thr Glu Thr  Lys Thr Lys Thr Leu  Thr Ile Gln Pro Leu
                1995                2000                2005

gaa aag gat acc aag  gag cgc agt tac aat  gtc atc tct ggc acc      15194
Glu Lys Asp Thr Lys  Glu Arg Ser Tyr Asn  Val Ile Ser Gly Thr
                2010                2015                2020

aat gat act gcc tat  cgt agt tgg tac cta  gca tac aac tat ggc      15239
Asn Asp Thr Ala Tyr  Arg Ser Trp Tyr Leu  Ala Tyr Asn Tyr Gly
                2025                2030                2035

gac cct gaa aaa gga  gtc cgc tcc tgg acg  ctg ctc acc act tca      15284
Asp Pro Glu Lys Gly  Val Arg Ser Trp Thr  Leu Leu Thr Thr Ser
                2040                2045                2050

gat gtc acc tgc gga  gcg gag caa gta tat  tgg tcg ctc cct gac      15329
Asp Val Thr Cys Gly  Ala Glu Gln Val Tyr  Trp Ser Leu Pro Asp
                2055                2060                2065

atg atg cag gac ccc  gtc acc ttc cga tcc  acg aga caa gtc agc      15374
Met Met Gln Asp Pro  Val Thr Phe Arg Ser  Thr Arg Gln Val Ser
                2070                2075                2080

aac tac ccc gtg gtg  ggt gca gag ctc atg  ccc gtc ttc tca aag      15419
Asn Tyr Pro Val Val  Gly Ala Glu Leu Met  Pro Val Phe Ser Lys
                2085                2090                2095

agt ttc tac aac gag  caa gcc gtg tac tcc  cag cag ctc cgc cag      15464
Ser Phe Tyr Asn Glu  Gln Ala Val Tyr Ser  Gln Gln Leu Arg Gln
                2100                2105                2110

acc acc tcg ctt acg  cac atc ttc gat cgc  ttc cct gag aat cag      15509
Thr Thr Ser Leu Thr  His Ile Phe Asp Arg  Phe Pro Glu Asn Gln
                2115                2120                2125

atc ctc atc cgc ccg  ccg gcg ccc acc att  acc acc gtt agt gaa      15554
Ile Leu Ile Arg Pro  Pro Ala Pro Thr Ile  Thr Thr Val Ser Glu
                2130                2135                2140

aac gtt cct gct ctc  aca gat cac ggg acc  ctg ccg ttg cgc agc      15599
Asn Val Pro Ala Leu  Thr Asp His Gly Thr  Leu Pro Leu Arg Ser
                2145                2150                2155

agt atc cgg gga gtc  cag cgc gtg acc gtt  act gac gcc aga cgc      15644
Ser Ile Arg Gly Val  Gln Arg Val Thr Val  Thr Asp Ala Arg Arg
                2160                2165                2170

cgc acc tgc ccc tac  gtc tac aag gcc ctg  ggc ata gtc gcg ccg      15689
Arg Thr Cys Pro Tyr  Val Tyr Lys Ala Leu  Gly Ile Val Ala Pro
                2175                2180                2185

cgc gtc ctt tca agc  cgc act ttc taaaaa atg tcc  att ctc atc tca   15737
Arg Val Leu Ser Ser  Arg Thr Phe        Met Ser  Ile Leu Ile Ser
                2190                        2195

ccc  agt aat aac acc ggt  tgg ggg ctg cgc aca  ccc acc agg atg     15782
```

-continued

```
Pro  Ser Asn Asn Thr Gly  Trp Gly Leu Arg Thr  Pro Thr Arg Met
2200                2205                2210

tac  gga ggc gct cgc aaa  cgg tct acc cag cac  cct gtg cgt gtg     15827
Tyr  Gly Gly Ala Arg Lys  Arg Ser Thr Gln His  Pro Val Arg Val
2215                2220                2225

cgc  ggg cat ttc cgc gct  ccc tgg ggc gcc ctc  aag ggc cgt act     15872
Arg  Gly His Phe Arg Ala  Pro Trp Gly Ala Leu  Lys Gly Arg Thr
2230                2235                2240

cgc  act cgg acc acc gtc  gat gat gtg atc gac  cag gtg gtt gca     15917
Arg  Thr Arg Thr Thr Val  Asp Asp Val Ile Asp  Gln Val Val Ala
2245                2250                2255

gat  gct cgt aat tat act  cct gct gca cct gca  tct act gtg gat     15962
Asp  Ala Arg Asn Tyr Thr  Pro Ala Ala Pro Ala  Ser Thr Val Asp
2260                2265                2270

gca  gtt att gac agc gtg  gtg gct gac gct cgc  gag tat gct cgc     16007
Ala  Val Ile Asp Ser Val  Val Ala Asp Ala Arg  Glu Tyr Ala Arg
2275                2280                2285

cgg  aag agc agg cga aga  cgc atc gcc agg cgc  cac cgg gct acc     16052
Arg  Lys Ser Arg Arg Arg  Arg Ile Ala Arg Arg  His Arg Ala Thr
2290                2295                2300

ccc  gct atg cga gct gca  aga gct ctg ctg cgg  aga gcc aaa cgc     16097
Pro  Ala Met Arg Ala Ala  Arg Ala Leu Leu Arg  Arg Ala Lys Arg
2305                2310                2315

gtg  ggg cga aga gcc atg  ctt aga gcg gcc aga  cgc gcg gct tca     16142
Val  Gly Arg Arg Ala Met  Leu Arg Ala Ala Arg  Arg Ala Ala Ser
2320                2325                2330

ggt  gcc agc gca ggc agg  tcc cgc agg cgc gca  gcc acg gcg gca     16187
Gly  Ala Ser Ala Gly Arg  Ser Arg Arg Arg Ala  Ala Thr Ala Ala
2335                2340                2345

gca  gcg gcc att gcc aac  atg gcc caa ccg cga  aga ggc aat gtg     16232
Ala  Ala Ala Ile Ala Asn  Met Ala Gln Pro Arg  Arg Gly Asn Val
2350                2355                2360

tac  tgg gtg cgc gat gcc  act acc ggt cag cgc  gtg ccc gtg cgc     16277
Tyr  Trp Val Arg Asp Ala  Thr Thr Gly Gln Arg  Val Pro Val Arg
2365                2370                2375

acc  cgt ccc cct cgc act  tagaagatac tgagcagtct ccgatgttgt         16325
Thr  Arg Pro Pro Arg Thr
2380                2385

gtcccagcgg cgagg atg tcc aag cgc aaa  tac aag gaa gag atg  ctc     16373
                 Met Ser Lys Arg Lys  Tyr Lys Glu Glu Met  Leu
                                2390                 2395

cag gtc atc gcg  cct gaa atc tac ggt  cca ccg gtg aag gat  gaa     16418
Gln Val Ile Ala  Pro Glu Ile Tyr Gly  Pro Pro Val Lys Asp  Glu
            2400                2405                 2410

aaa aag ccc cgc  aaa atc aag cgg gtc  aaa aag gac aaa aag  gaa     16463
Lys Lys Pro Arg  Lys Ile Lys Arg Val  Lys Lys Asp Lys Lys  Glu
            2415                2420                 2425

gaa gat ggc gat  gat ggg ctg gtg gag  ttt gtg cgc gag ttc  gct     16508
Glu Asp Gly Asp  Asp Gly Leu Val Glu  Phe Val Arg Glu Phe  Ala
            2430                2435                 2440

cca agg cgg cgc  gtg cag tgg cgc ggg  cgc agg gtg cgg ccg  gtg     16553
Pro Arg Arg Arg  Val Gln Trp Arg Gly  Arg Arg Val Arg Pro  Val
            2445                2450                 2455

ctg aga cca gga  acc acg gtg gtc ttc  acg ccc ggc gaa cgc  tcc     16598
Leu Arg Pro Gly  Thr Thr Val Val Phe  Thr Pro Gly Glu Arg  Ser
            2460                2465                 2470

agc act act ttt  aaa cgc tcc tat gat  gag gtg tac ggg gat  gat     16643
Ser Thr Thr Phe  Lys Arg Ser Tyr Asp  Glu Val Tyr Gly Asp  Asp
            2475                2480                 2485
```

```
gat att ctg gag  cag gcg gcc gac cgc  ctg ggc gag ttt gct  tat      16688
Asp Ile Leu Glu  Gln Ala Ala Asp Arg  Leu Gly Glu Phe Ala  Tyr
            2490                 2495                 2500

ggc aaa cgc agc  cgc tcc agt ccc aag  gat gaa gcg gtg tcc  atc      16733
Gly Lys Arg Ser  Arg Ser Ser Pro Lys  Asp Glu Ala Val Ser  Ile
            2505                 2510                 2515

ccc ttg gat cat  gga aat ccc acc ccg  agt ctc aaa cca gtc  acc      16778
Pro Leu Asp His  Gly Asn Pro Thr Pro  Ser Leu Lys Pro Val  Thr
            2520                 2525                 2530

ctg cag caa gtg  ctg ccc gtg cct cca  cgg aga ggc gtc aag  cga      16823
Leu Gln Gln Val  Leu Pro Val Pro Pro  Arg Arg Gly Val Lys  Arg
            2535                 2540                 2545

gag ggc gag gat  ctg tat ccc acc atg  caa ttg atg gtg ccc  aag      16868
Glu Gly Glu Asp  Leu Tyr Pro Thr Met  Gln Leu Met Val Pro  Lys
            2550                 2555                 2560

cgc cag aag ctg  gag gac gtg ctg gag  aaa atg aaa gtg gat  ccc      16913
Arg Gln Lys Leu  Glu Asp Val Leu Glu  Lys Met Lys Val Asp  Pro
            2565                 2570                 2575

gat atc cag cct  gaa gtt aaa gtc aga  ccc atc aag cag gtg  gcg      16958
Asp Ile Gln Pro  Glu Val Lys Val Arg  Pro Ile Lys Gln Val  Ala
            2580                 2585                 2590

ccc ggt ctg gga  gtg caa acc gtg gac  atc aag att ccc acc  gag      17003
Pro Gly Leu Gly  Val Gln Thr Val Asp  Ile Lys Ile Pro Thr  Glu
            2595                 2600                 2605

tcc atg gaa gtc  cag act gaa cct gca  aag cct aca gcc gcc  tcc      17048
Ser Met Glu Val  Gln Thr Glu Pro Ala  Lys Pro Thr Ala Ala  Ser
            2610                 2615                 2620

att gag gtg cag  acg gat cca tgg atg  ccc gcg ccc att gca  acc      17093
Ile Glu Val Gln  Thr Asp Pro Trp Met  Pro Ala Pro Ile Ala  Thr
            2625                 2630                 2635

gcc gcc agt acc  gtt cga aga ccc cgg  cga aag tat ggt cct  gcg      17138
Ala Ala Ser Thr  Val Arg Arg Pro Arg  Arg Lys Tyr Gly Pro  Ala
            2640                 2645                 2650

agt ctg ctg atg  ccc aac tat gct ctg  cac cca tcc att att  ccg      17183
Ser Leu Leu Met  Pro Asn Tyr Ala Leu  His Pro Ser Ile Ile  Pro
            2655                 2660                 2665

act ccg ggt tac  cga ggc act cgc tac  tac cgc agc cgg agc  acc      17228
Thr Pro Gly Tyr  Arg Gly Thr Arg Tyr  Tyr Arg Ser Arg Ser  Thr
            2670                 2675                 2680

act tcc cgc cgt  cgc aaa aca cct gca  agc cgc agt cgc cgt  cgc      17273
Thr Ser Arg Arg  Arg Lys Thr Pro Ala  Ser Arg Ser Arg Arg  Arg
            2685                 2690                 2695

cgc cgc cgc acc  gcc agc aaa ctg act  ccc gcc gct ttg gtg  cgg      17318
Arg Arg Arg Thr  Ala Ser Lys Leu Thr  Pro Ala Ala Leu Val  Arg
            2700                 2705                 2710

agg gtg tat cgc  gat ggc cgc gca gag  ccc ctg atg ctg ccg  cgc      17363
Arg Val Tyr Arg  Asp Gly Arg Ala Glu  Pro Leu Met Leu Pro  Arg
            2715                 2720                 2725

gca cgc tac cat  cca agc atc acc act  taatgactgt tgccactgcc        17410
Ala Arg Tyr His  Pro Ser Ile Thr Thr
            2730                 2735

tccttgcaga t atg gcc ctc act tgc  cgc ctt cgc gtc ccc  att act      17457
             Met Ala Leu Thr Cys  Arg Leu Arg Val Pro  Ile Thr
                             2740                 2745

ggc tac cga  gga aga aac tcg cgc  cgt aga agg atg ttg  ggt agc      17502
Gly Tyr Arg  Gly Arg Asn Ser Arg  Arg Arg Arg Met Leu  Gly Ser
        2750                 2755                 2760

ggg atg cgt  cgc cac agg cgg cgg  cgc gct atc agc aag  agg ctg      17547
Gly Met Arg  Arg His Arg Arg Arg  Arg Ala Ile Ser Lys  Arg Leu
        2765                 2770                 2775
```

```
ggg ggt ggc  ttt ctg acc gct ttg  att ccc atc atc gcc  gcg gcg     17592
Gly Gly Gly  Phe Leu Thr Ala Leu  Ile Pro Ile Ile Ala  Ala Ala
        2780                 2785                 2790

atc ggg gcg  gta cca ggc ata gct  tcc gtg gcg gtt cag  gcc tcg     17637
Ile Gly Ala  Val Pro Gly Ile Ala  Ser Val Ala Val Gln  Ala Ser
        2795                 2800                 2805

cag cgc cac  tgacattgga aaaacactta taaataaaat agaatggact          17686
Gln Arg His
        2810

ctgacgctcc tggtcctgtg actatgtttt tgtagag atg gaa gac atc aat  ttt  17741
                                        Met Glu Asp Ile Asn  Phe
                                                        2815

tca tcc ctg gct  ccg cga cac ggc acg  agg ccg tac atg ggc  acc     17786
Ser Ser Leu Ala  Pro Arg His Gly Thr  Arg Pro Tyr Met Gly  Thr
            2820                 2825                 2830

tgg agc gac atc  ggc acc agc caa ctg  aac ggg ggc gcc ttc  aat     17831
Trp Ser Asp Ile  Gly Thr Ser Gln Leu  Asn Gly Gly Ala Phe  Asn
            2835                 2840                 2845

tgg agc agt atc  tgg agc ggg ctt aaa  aat ttt ggc tct gcc  ata     17876
Trp Ser Ser Ile  Trp Ser Gly Leu Lys  Asn Phe Gly Ser Ala  Ile
            2850                 2855                 2860

aaa acc tat ggg  aac aaa gct tgg aac  agc agc aca ggg cag  gcg     17921
Lys Thr Tyr Gly  Asn Lys Ala Trp Asn  Ser Ser Thr Gly Gln  Ala
            2865                 2870                 2875

ctg agg aat aag  ctt aaa gag cag aac  ttc cag cag aag gtg  gtc     17966
Leu Arg Asn Lys  Leu Lys Glu Gln Asn  Phe Gln Gln Lys Val  Val
            2880                 2885                 2890

gat ggg atc gcc  tct ggc atc aat ggg  gtg gtg gat ctg gcc  aac     18011
Asp Gly Ile Ala  Ser Gly Ile Asn Gly  Val Val Asp Leu Ala  Asn
            2895                 2900                 2905

cag gcc gtg cag  aaa cag ata aac agc  cgc ctg gac cag ccg  ccc     18056
Gln Ala Val Gln  Lys Gln Ile Asn Ser  Arg Leu Asp Gln Pro  Pro
            2910                 2915                 2920

gca gcc cct ggc  gaa atg gaa gtg gag  gaa gag ctc cct ccc  ctg     18101
Ala Ala Pro Gly  Glu Met Glu Val Glu  Glu Glu Leu Pro Pro  Leu
            2925                 2930                 2935

gaa aag cgg gga  gac aag cgc ccg cgt  ccc gat atg gag gag  acg     18146
Glu Lys Arg Gly  Asp Lys Arg Pro Arg  Pro Asp Met Glu Glu  Thr
            2940                 2945                 2950

ctg gtg acg cgc  gga gac gag ccg cct  cca tat gag gag gca  ata     18191
Leu Val Thr Arg  Gly Asp Glu Pro Pro  Pro Tyr Glu Glu Ala  Ile
            2955                 2960                 2965

aag ctt gga atg  ccc act acc agg cct  ata gct ccc atg gcc  acc     18236
Lys Leu Gly Met  Pro Thr Thr Arg Pro  Ile Ala Pro Met Ala  Thr
            2970                 2975                 2980

ggg gta atg aaa  cct tct cag tcg cat  cga ccc gcc acc ttg  gac     18281
Gly Val Met Lys  Pro Ser Gln Ser His  Arg Pro Ala Thr Leu  Asp
            2985                 2990                 2995

ttg cct cct gcc  cct gct gct gca gcg  ccc gct cca aag cct  gtc     18326
Leu Pro Pro Ala  Pro Ala Ala Ala Ala  Pro Ala Pro Lys Pro  Val
            3000                 3005                 3010

gct acc ccg aag  ccc acc gcc gta cag  ccc gtc gcc gta gcc  aga     18371
Ala Thr Pro Lys  Pro Thr Ala Val Gln  Pro Val Ala Val Ala  Arg
            3015                 3020                 3025

ccg cgt cct ggg  ggc act ccg cgc ccg  aat gca aac tgg cag  agt     18416
Pro Arg Pro Gly  Gly Thr Pro Arg Pro  Asn Ala Asn Trp Gln  Ser
            3030                 3035                 3040

act ctg aac agc  atc gtg ggt ttg ggc  gtg cag agt gta aag  cgc     18461
Thr Leu Asn Ser  Ile Val Gly Leu Gly  Val Gln Ser Val Lys  Arg
```

```
            3045                3050                3055

cgt cgc tgc tat  taattaaata tggagtagcg cttaacttgc ttgtctgtgt      18513
Arg Arg Cys Tyr
            3060

gtatgtgtca tcaccacgcc gccacagcag cagaggagaa aggaagaggt cgcgcgccga  18573

ggctgagttg ctttcaag atg gcc acc cca tcg  atg ctg ccc cag tgg  gca  18624
                    Met Ala Thr Pro Ser  Met Leu Pro Gln Trp  Ala
                                    3065                 3070

tac atg cac atc  gcc gga cag gat gct  tcg gag tac ctg agt  ccg     18669
Tyr Met His Ile  Ala Gly Gln Asp Ala  Ser Glu Tyr Leu Ser  Pro
            3075                3080                3085

ggt ctg gtg cag  ttc gcc cgt gcc aca  gac acc tac ttc aat  ctg     18714
Gly Leu Val Gln  Phe Ala Arg Ala Thr  Asp Thr Tyr Phe Asn  Leu
            3090                3095                3100

gga aac aag ttt  agg aac ccc acc gtg  gct ccc acc cac gat  gtg     18759
Gly Asn Lys Phe  Arg Asn Pro Thr Val  Ala Pro Thr His Asp  Val
            3105                3110                3115

acc acc gac cga  agc cag cgg ctg atg  ctg cgc ttt gtg ccc  gtt     18804
Thr Thr Asp Arg  Ser Gln Arg Leu Met  Leu Arg Phe Val Pro  Val
            3120                3125                3130

gat cgg gag gac  aat act tac tct tac  aaa gtt cgc tac aca  ctg     18849
Asp Arg Glu Asp  Asn Thr Tyr Ser Tyr  Lys Val Arg Tyr Thr  Leu
            3135                3140                3145

gct gtg gga gac  aac aga gtg ctg gat  atg gcc agc acc ttc  ttt     18894
Ala Val Gly Asp  Asn Arg Val Leu Asp  Met Ala Ser Thr Phe  Phe
            3150                3155                3160

gac atc agg ggg  gtg ctt gac aga ggt  ccc agt ttc aaa ccc  tac     18939
Asp Ile Arg Gly  Val Leu Asp Arg Gly  Pro Ser Phe Lys Pro  Tyr
            3165                3170                3175

tct ggg aca gca  tac aat tcc ctg gcc  cct aag gga gct cct  aat     18984
Ser Gly Thr Ala  Tyr Asn Ser Leu Ala  Pro Lys Gly Ala Pro  Asn
            3180                3185                3190

act agt cag tgg  ata gtt aca act aat  ggg caa gat aat gca  gta     19029
Thr Ser Gln Trp  Ile Val Thr Thr Asn  Gly Gln Asp Asn Ala  Val
            3195                3200                3205

act acc act aca  aac aca ttt ggc att  gct tcc atg aaa gga  gac     19074
Thr Thr Thr Thr  Asn Thr Phe Gly Ile  Ala Ser Met Lys Gly  Asp
            3210                3215                3220

aat att act aaa  gaa ggt tta gaa att  gga aaa gat att act  gaa     19119
Asn Ile Thr Lys  Glu Gly Leu Glu Ile  Gly Lys Asp Ile Thr  Glu
            3225                3230                3235

gaa gat aaa ccc  atc tat gcc gat aaa  aca tat cag cca gaa  cct     19164
Glu Asp Lys Pro  Ile Tyr Ala Asp Lys  Thr Tyr Gln Pro Glu  Pro
            3240                3245                3250

caa gtt gga gaa  gaa tca tgg act gat  acc gat gga aca aat  gaa     19209
Gln Val Gly Glu  Glu Ser Trp Thr Asp  Thr Asp Gly Thr Asn  Glu
            3255                3260                3265

aag ttt ggc ggt  aga gcg ctt aaa ccc  gct acc aac atg aaa  cca     19254
Lys Phe Gly Gly  Arg Ala Leu Lys Pro  Ala Thr Asn Met Lys  Pro
            3270                3275                3280

tgc tat ggg tca  ttt gca aga cct aca  aac ata aaa ggt ggt  caa     19299
Cys Tyr Gly Ser  Phe Ala Arg Pro Thr  Asn Ile Lys Gly Gly  Gln
            3285                3290                3295

gct aaa aat aga  aaa gta aag ccg aca  acc gag gga ggg gtt  gaa     19344
Ala Lys Asn Arg  Lys Val Lys Pro Thr  Thr Glu Gly Gly Val  Glu
            3300                3305                3310

act gag gaa ccg  gat att gat atg gaa  ttt ttc gat ggt aga  gat     19389
Thr Glu Glu Pro  Asp Ile Asp Met Glu  Phe Phe Asp Gly Arg  Asp
            3315                3320                3325
```

```
gct gct gaa gga  gct tta tcg cct gaa  att gtg ctt tac aca  gaa     19434
Ala Ala Glu Gly  Ala Leu Ser Pro Glu  Ile Val Leu Tyr Thr  Glu
            3330                 3335                 3340

aat gta aat ttg  gaa act cca gac acc  cat gtg gta tac aaa  cca     19479
Asn Val Asn Leu  Glu Thr Pro Asp Thr  His Val Val Tyr Lys  Pro
            3345                 3350                 3355

gga act tca gat  gat aac tct cat gca  aat ttg ggt caa caa  gct     19524
Gly Thr Ser Asp  Asp Asn Ser His Ala  Asn Leu Gly Gln Gln  Ala
            3360                 3365                 3370

atg ccc aac aga  ccc aat tac att ggc  ttc aga gac aac ttt  gtt     19569
Met Pro Asn Arg  Pro Asn Tyr Ile Gly  Phe Arg Asp Asn Phe  Val
            3375                 3380                 3385

gga ctc ttg tac  tac aac agc act ggc  aac atg gga gtg ttg  gca     19614
Gly Leu Leu Tyr  Tyr Asn Ser Thr Gly  Asn Met Gly Val Leu  Ala
            3390                 3395                 3400

ggt caa gca tca  caa cta aat gca gta  gtt gac ttg cag gac  aga     19659
Gly Gln Ala Ser  Gln Leu Asn Ala Val  Val Asp Leu Gln Asp  Arg
            3405                 3410                 3415

aac act gaa ctg  tcc tat cag ctt ttg  ctt gat tct ctt ggg  gac     19704
Asn Thr Glu Leu  Ser Tyr Gln Leu Leu  Leu Asp Ser Leu Gly  Asp
            3420                 3425                 3430

aga acc aga tac  ttc agc atg tgg aat  cag gcc gtg gat agt  tat     19749
Arg Thr Arg Tyr  Phe Ser Met Trp Asn  Gln Ala Val Asp Ser  Tyr
            3435                 3440                 3445

gat cct gat gtt  cgc att att gaa aat  cat ggt atc gag gat  gaa     19794
Asp Pro Asp Val  Arg Ile Ile Glu Asn  His Gly Ile Glu Asp  Glu
            3450                 3455                 3460

cta ccc aac tac  tgt ttt cct ctg gat  ggc ata gga cca ggg  aac     19839
Leu Pro Asn Tyr  Cys Phe Pro Leu Asp  Gly Ile Gly Pro Gly  Asn
            3465                 3470                 3475

tca tat caa ggc  atc aag gct aaa aac  ggt gat aat aat gga  tgg     19884
Ser Tyr Gln Gly  Ile Lys Ala Lys Asn  Gly Asp Asn Asn Gly  Trp
            3480                 3485                 3490

gaa aaa gat act  aat gct tct act gct  aat gaa ata gcc ata  gga     19929
Glu Lys Asp Thr  Asn Ala Ser Thr Ala  Asn Glu Ile Ala Ile  Gly
            3495                 3500                 3505

aac aac ctg gct  atg gaa att aat atc  cag gct aac ctt tgg  aga     19974
Asn Asn Leu Ala  Met Glu Ile Asn Ile  Gln Ala Asn Leu Trp  Arg
            3510                 3515                 3520

agt ttt ctg tac  tcc aac gtg gct ttg  tac ctt cca gac gct  tac     20019
Ser Phe Leu Tyr  Ser Asn Val Ala Leu  Tyr Leu Pro Asp Ala  Tyr
            3525                 3530                 3535

aag tac acg cca  gcc aac att act ttg  cct gcc aat acc aac  acc     20064
Lys Tyr Thr Pro  Ala Asn Ile Thr Leu  Pro Ala Asn Thr Asn  Thr
            3540                 3545                 3550

tat gaa tac atg  aac ggg cga gtg gtg  gca cca tct ttg gtt  gat     20109
Tyr Glu Tyr Met  Asn Gly Arg Val Val  Ala Pro Ser Leu Val  Asp
            3555                 3560                 3565

tcg tac atc aac  att gga gcc agg tgg  tct ctt gac cca atg  gac     20154
Ser Tyr Ile Asn  Ile Gly Ala Arg Trp  Ser Leu Asp Pro Met  Asp
            3570                 3575                 3580

aat gtg aac ccc  ttc aat cac cac cga  aac gct ggg ctg cgt  tac     20199
Asn Val Asn Pro  Phe Asn His His Arg  Asn Ala Gly Leu Arg  Tyr
            3585                 3590                 3595

aga tcc atg ctt  ctg ggc aat ggt cgc  tat gtg cct ttc cac  atc     20244
Arg Ser Met Leu  Leu Gly Asn Gly Arg  Tyr Val Pro Phe His  Ile
            3600                 3605                 3610

caa gtg cct cag  aaa ttc ttt gct atc  aag aac ctg ctt ctc  ctc     20289
Gln Val Pro Gln  Lys Phe Phe Ala Ile  Lys Asn Leu Leu Leu  Leu
```

```
            3615                3620                3625

cca ggc tcc tat  acc tat gag tgg aac  ttc aga aag gat gtg  aac     20334
Pro Gly Ser Tyr  Thr Tyr Glu Trp Asn  Phe Arg Lys Asp Val  Asn
            3630                3635                3640

atg gtc ctg cag  agt tcc ctt ggc aat  gat ctc aga act gat  gga     20379
Met Val Leu Gln  Ser Ser Leu Gly Asn  Asp Leu Arg Thr Asp  Gly
            3645                3650                3655

gcc agc atc agt  ttt act agc atc aac  ctc tat gcc acc ttc  ttc     20424
Ala Ser Ile Ser  Phe Thr Ser Ile Asn  Leu Tyr Ala Thr Phe  Phe
            3660                3665                3670

ccc atg gct cac  aat act gct tcc acc  ctt gaa gcc atg ctg  cgc     20469
Pro Met Ala His  Asn Thr Ala Ser Thr  Leu Glu Ala Met Leu  Arg
            3675                3680                3685

aat gac aca aat  gac cag tca ttc aat  gac tac ctt tct gca  gct     20514
Asn Asp Thr Asn  Asp Gln Ser Phe Asn  Asp Tyr Leu Ser Ala  Ala
            3690                3695                3700

aac atg ctc tac  cct att cca gcc aat  gca acc aac att ccc  att     20559
Asn Met Leu Tyr  Pro Ile Pro Ala Asn  Ala Thr Asn Ile Pro  Ile
            3705                3710                3715

tcc att ccc tct  cgc aac tgg gct gcc  ttt agg ggt tgg tcc  ttc     20604
Ser Ile Pro Ser  Arg Asn Trp Ala Ala  Phe Arg Gly Trp Ser  Phe
            3720                3725                3730

acc aga ctc aaa  aca aag gaa aca ccc  tct ttg gga tca ggc  ttt     20649
Thr Arg Leu Lys  Thr Lys Glu Thr Pro  Ser Leu Gly Ser Gly  Phe
            3735                3740                3745

gat ccc tac ttt  gtt tac tct ggc tcc  att ccc tac ctg gat  ggc     20694
Asp Pro Tyr Phe  Val Tyr Ser Gly Ser  Ile Pro Tyr Leu Asp  Gly
            3750                3755                3760

acc ttc tac ctc  aac cac act ttc aag  aag gtg tcc atc atg  ttt     20739
Thr Phe Tyr Leu  Asn His Thr Phe Lys  Lys Val Ser Ile Met  Phe
            3765                3770                3775

gac tcc tca gtc  agc tgg cca ggc aat  gac aga ttg cta act  cca     20784
Asp Ser Ser Val  Ser Trp Pro Gly Asn  Asp Arg Leu Leu Thr  Pro
            3780                3785                3790

aat gag ttt gaa  atc aag cgc act gtg  gat gga gaa ggg tac  aat     20829
Asn Glu Phe Glu  Ile Lys Arg Thr Val  Asp Gly Glu Gly Tyr  Asn
            3795                3800                3805

gtg gct caa tgc  aac atg acc aag gat  tgg ttc ctg gtt cag  atg     20874
Val Ala Gln Cys  Asn Met Thr Lys Asp  Trp Phe Leu Val Gln  Met
            3810                3815                3820

ctt gcc aac tat  aac att ggc tac cag  ggc ttc tac atc cca  gag     20919
Leu Ala Asn Tyr  Asn Ile Gly Tyr Gln  Gly Phe Tyr Ile Pro  Glu
            3825                3830                3835

ggg tac aag gat  cgc atg tac tcc ttc  ttc aga aac ttc cag  ccc     20964
Gly Tyr Lys Asp  Arg Met Tyr Ser Phe  Phe Arg Asn Phe Gln  Pro
            3840                3845                3850

atg agc aga cag  gtg gtt gat gag gtg  aac tac acc gat tac  aaa     21009
Met Ser Arg Gln  Val Val Asp Glu Val  Asn Tyr Thr Asp Tyr  Lys
            3855                3860                3865

gcc gtc act cta  gca tac caa cac aac  aac tct ggc ttt gtg  ggt     21054
Ala Val Thr Leu  Ala Tyr Gln His Asn  Asn Ser Gly Phe Val  Gly
            3870                3875                3880

tac ctt gcg ccc  act atg aga cag gga  gaa cct tac ccc gct  aac     21099
Tyr Leu Ala Pro  Thr Met Arg Gln Gly  Glu Pro Tyr Pro Ala  Asn
            3885                3890                3895

tac cca tac ccc  cta atc gga acc act  gct gtt aag agt gtt  acc     21144
Tyr Pro Tyr Pro  Leu Ile Gly Thr Thr  Ala Val Lys Ser Val  Thr
            3900                3905                3910

cag aaa aag ttc  ctg tgc gac agg acc  atg tgg cgc atc ccc  ttc     21189
```

```
Gln Lys Lys Phe  Leu Cys Asp Arg Thr  Met Trp Arg Ile Pro  Phe
            3915                3920                3925

tcc agc aac ttc  atg tcc atg ggt gcc  ctt acc gac ctg gga  cag     21234
Ser Ser Asn Phe  Met Ser Met Gly Ala  Leu Thr Asp Leu Gly  Gln
            3930                3935                3940

aac atg ctt tat  gct aac tca gcc cat  gcg ctg gac atg act  ttt     21279
Asn Met Leu Tyr  Ala Asn Ser Ala His  Ala Leu Asp Met Thr  Phe
            3945                3950                3955

gag gtg gat ccc  atg gat gag ccc acc  ctg ctt tat gtt ctt  ttc     21324
Glu Val Asp Pro  Met Asp Glu Pro Thr  Leu Leu Tyr Val Leu  Phe
            3960                3965                3970

gaa gtc ttc gac  gtg gtc aga gtg cac  cag cca cac cgc ggc  gtc     21369
Glu Val Phe Asp  Val Val Arg Val His  Gln Pro His Arg Gly  Val
            3975                3980                3985

atc gag gct gtc  tac ctg cgt acc ccg  ttc tca gct ggt aac  gcc     21414
Ile Glu Ala Val  Tyr Leu Arg Thr Pro  Phe Ser Ala Gly Asn  Ala
            3990                3995                4000

acc aca taaagaagct tcttgcttct tgcaagcagc tgccatggcc tgtgggtccg     21470
Thr Thr

gcaacggatc cagcgagcaa gagctcaggg ccattgctag agacctgggc tgcggaccct  21530

atttcctggg aacctttgat aaacgcttcc cggggttcat ggcccccgac aagctcgcct  21590

gcgccattgt taacacggcc ggtcgcgaga cggggggtga gcactggctg gcttttggtt  21650

ggaatccgcg ctccaacacc tgctaccttt ttgatccctt tggcttctct gacgagcgcc  21710

tcaagcaaat ctaccagttt gagtatgagg ggcttctgcg ccgcagtgcc ctagctacca  21770

aggaccgctg tatcaccctg gaaaagtcaa cccagaccgt gcagggcccg cgctccgcag  21830

cctgtggact gttttgctgc atgttcctcc acgcttttgt gcactggcca gaccgcccca  21890

tggacggaaa ccccaccatg aagttgctga ctggggtgcc caacagcatg ctccaatcac  21950

cccaagtcca gcccaccctg cgccacaacc aggaggcgct ctaccgcttc ctaaactccc  22010

actcatctta ctttcgttct caccgcgcgc gcatcgaaaa ggccaccgcg tttaatcgaa  22070

tggatatgca ataataagtc atgtaaaccg tgttcaaata aacagcactt tattttttac  22130

atgcactgtg gctctgggtt gctcattcat tcatcattca ctcagaagtc gaaggggttc  22190

tggcgggaat cagcgtgacc cgctggcagg gatacgttgc ggaactggaa cctgttctgc  22250

cacttgaact cggggatcac cagcttggga actgggatct cggggaaggt gtcttgccac  22310

agctttctgg ttagttgcag agcaccaagc aggtcaggag cagagatctt gaaatcacag  22370

ttggggccag cattctgggc acgggagttg cggtacactg ggttgcagca ctggaacacc  22430

atcagggcgg ggtgtctcac gctcgccagc acggtcgggt cactgatggt agtcacatcc  22490

aagtcttcag cattggccat tccaaagggg gtcatcttac aggtctgcct gcccatcacg  22550

ggagcgcagc cgggcttgtg gttgcaatcg cagcgaatgg ggatcagcat catcctggcc  22610

tggtcggggg ttatccctgg atacaccgcc ttcataaagg cttcgtactg cttgaaagct  22670

tcctgagcct tacttccctc ggtgtagaac atcccacagg acttgctgga aaattgatta  22730

gtagcacagt tggcatcatt cacacagcag cgggcatcgt tgttggccag ctggaccaca  22790

ttcctgcccc agcggttctg ggtgatcttg gctcggtctg ggttctcctt catcgcgcgc  22850

tgcccgttct cgctcgccac atccatctcg atgatgtgat ccttctggat catgatagtg  22910

ccatgcaggc atttcacctt gccttcataa tcggtgcagc catgagccca cagagcgcac  22970

ccggtgcact cccaattgtt gtgggcgatc tcagaataag aatgcaccaa tccctgcatg  23030

aatcttccca tcatgctggt gagggtcttt atgctggtaa atgtcagcgg gatgccacgg  23090
```

```
tgctcctcgt tcacatactg gtggcagata cgcctgtact gctcgtgctg ctcgggcatc  23150
agcttgaaag aggttctcag gtcattatcc agcctgtacc tctccattag cacggccatt  23210
acttccatgc ccttctccca ggcagagacc aagggcaggc tcatgggatt cctaacagca  23270
atagcagcag acgcagctcc tttagccaga gggtcattct tgtcaatctt ctcaacactt  23330
ctcttgccat ccttctcagt gatgcgcact ggggggtagc tgaagcccac ggccaccagc  23390
tccgcctgtt ctctttcttc ttcgctgtcc tggctgatgt cttgcaaagg gacatgcttg  23450
gtcttcctgg gcttcttctt gggagggatc gggggagggc tgttgctccg ctccggagac  23510
agggaggacc gcgaagtttc gctcaccagt accacctggc tctcggtaga agaaccggac  23570
cccacgcggc ggtaggtgtt cctcttcggg ggcagaggtg gaggcgactg cgatggactg  23630
cggtccggcc tgggaggcgg atggctggca gagcctcttc cgcgttcggg ggtgtgctcc  23690
cggtggcggt cgcttgactg atttcctccg cggctggcca ttgtgttctc ctaggcagag  23750
aaacaacaga catggagact cagccatcgc tgccaacacc gctgcaagcg ccatcacacc  23810
tcgcccccag cagcgacgag gaggagagct taaccacccc accacccagt cccgccacca  23870
ccacctctac cctagaggat gaggaggagg tcgacgcacc ccaggagatg caggatatgg  23930
aggatgagaa agcggaagag attgaggcag atgtcgagca ggacccgggc tatgtgacac  23990
cggcggagca cgaggaggag ctgagacgct ttctagacag agaggatgac aaccgcccag  24050
agcagaaagc agatggcgat caccaggagg ctgggctcgg ggatcatgtc gccgactacc  24110
tcaccgggct tggcggggag gacgtgctcc tcaaacatct agcaaggcag tcgatcatag  24170
ttaaagacgc actgctcgac cgcaccgaag tgcccatcag tgtggaagag ctcagccgcg  24230
cctacgagct caacctgttc tcgcctcggc tgccccccaa acgtcagcca aacggcacct  24290
gtgagcccaa ccctcgcctc aacttctatc cggcctttgc tgtcccagaa gtgcttgcta  24350
cctaccacat ctttttcaag aaccaaaaga ttccagtttc ctgccgtgcc aaccgcaccc  24410
gcgccgatgc cctgctcaac ttgggtccgg gagctcgctt acctgatata gcttccttgg  24470
aagaggttcc aaagatcttc gagggtctgg gcagtgatga gactcgggcc gcaaatgctc  24530
tgcaacaggg agagaatggc atggatgaac atcacagcgc tctggtggag ttggagggag  24590
acaatgcccg gcttgcagtg ctcaagcgca gtatcgaggt cacccatttt gcataccccg  24650
ctgtcaacct gccccccaaa gtcatgagcg ctgtcatgga tcagctgctc atcaagcgcg  24710
caagccccct ttccgaagac cagaacatgc aggatccaga cgcctctgac gagggcaagc  24770
cggtggtcag tgacgagcag ctgtctcgct ggctgggcac caactccccg cgagacttgg  24830
aagagaggcg caagcttatg atggctgtag tgctagtcac tgtggagctg gagtgtctcc  24890
gccgcttttt caccgaccct gagaccctgc gcaagctcga ggagaacctg cactatactt  24950
tcagacatgg tttcgtgcgc caggcatgca agatctccaa cgtggagctc accaacctgg  25010
tctcctacat gggcattttg catgagaacc gcctggggca gagcgtgttg catacccaccc  25070
tgaaagggga ggcccgccgc gactacatcc gcgactgtgt ctacctctac ctctgccata  25130
cctggcagac tggcatgggt gtatggcagc agtgtttgga agagcagaac ctgaaagagc  25190
tggacaagct cttgcagaga tccctcaaag ccctgtggac aggttttgac gagcgcaccg  25250
tcgcctcaga cctggcagac atcatcttcc ccgagcgtct cagggttact ctgcgcaacg  25310
gcctgcctga cttcatgagc cagagcatgc ttaacaactt tcgctctttc atcctggaac  25370
gctccggtat cctgcccgcc acctgctgcg cgctgccctc cgactttgtg cctctcacct  25430
```

```
accgcgagtg ccccccgccg ctatggagcc actgctacct gttccgcctg gccaactacc  25490

tctcctacca ctcggatgtg atcgaggatg tgagcggaga cggtctgctg gagtgccact  25550

gccgctgcaa tctttgcaca ccccaccgtt ccctcgcctg caaccccag ttgctgagcg  25610

agactcagat catcggcacc ttcgagttgc agggtcccag cagtgaaggc gaggggtctt  25670

ctccggggca gagtctgaaa ctgactccgg ggctatggac ctccgcctac ctgcgcaagt  25730

tcgcccccga agactaccac ccctatgaga tcaggttcta tgaggaccaa tcacagccgc  25790

ccaaaaccga gctctcagcc tgcgtcatca ctcagggggc aattctcgcc caattgcaag  25850

ccatccaaaa atcccgccaa gaatttctgc tgaaaaaggg gaacggggtc tacctcgacc  25910

cccagaccgg tgaggagctc aacacaaggt tccctcagg atg tcc cag cgc cga    25964
                                        Met Ser Gln Arg Arg
                                            4005

gga agc aag aag ttg aag gtg cag ctg ccg ccc cca gag gat atg     26009
Gly Ser Lys Lys Leu Lys Val Gln Leu Pro Pro Pro Glu Asp Met
    4010                4015                4020

gag gaa gac tgg gac agt cag gca gag gag gag gag atg gaa gat     26054
Glu Glu Asp Trp Asp Ser Gln Ala Glu Glu Glu Glu Met Glu Asp
    4025                4030                4035

tgg gac agc cag gca gag gag gcg gac agc ctg gag gaa gac agt     26099
Trp Asp Ser Gln Ala Glu Glu Ala Asp Ser Leu Glu Glu Asp Ser
    4040                4045                4050

ttg gag gag gaa gac gag gag gca gag gag gtg gaa gaa gca gcc     26144
Leu Glu Glu Glu Asp Glu Glu Ala Glu Glu Val Glu Glu Ala Ala
    4055                4060                4065

gcc gcc aaa cag ttg tcc tcg gca gcg gag aca agc aag gcc cca     26189
Ala Ala Lys Gln Leu Ser Ser Ala Ala Glu Thr Ser Lys Ala Pro
    4070                4075                4080

gac agc agc agc agc acg gct aca atc tcc gct ccg ggt cgg ggg     26234
Asp Ser Ser Ser Ser Thr Ala Thr Ile Ser Ala Pro Gly Arg Gly
    4085                4090                4095

gcc cag cag cgt ccc aac agt aga tgg gac gag acc ggg cga ttc     26279
Ala Gln Gln Arg Pro Asn Ser Arg Trp Asp Glu Thr Gly Arg Phe
    4100                4105                4110

ccg aac ccg acc acc gct tcc aag acc ggt aag aag gag cgg cag     26324
Pro Asn Pro Thr Thr Ala Ser Lys Thr Gly Lys Lys Glu Arg Gln
    4115                4120                4125

gga tac aag tcc tgg cgg ggg cat aag aat gcc atc atc tcc tgc     26369
Gly Tyr Lys Ser Trp Arg Gly His Lys Asn Ala Ile Ile Ser Cys
    4130                4135                4140

ttg cat gaa tgc ggg ggc aac ata tcc ttc acc cgg cgc tac ctg     26414
Leu His Glu Cys Gly Gly Asn Ile Ser Phe Thr Arg Arg Tyr Leu
    4145                4150                4155

ctc ttc cac cac ggg gtg aac ttc ccc cgc aat gtc ttg cat tac     26459
Leu Phe His His Gly Val Asn Phe Pro Arg Asn Val Leu His Tyr
    4160                4165                4170

tac cgt cac ctc cac agc ccc tac tac agc cag caa gtc ccg aca     26504
Tyr Arg His Leu His Ser Pro Tyr Tyr Ser Gln Gln Val Pro Thr
    4175                4180                4185

gcc tcg gca gag aaa gac agc agc agc ggg gac ctc cag cag aaa     26549
Ala Ser Ala Glu Lys Asp Ser Ser Ser Gly Asp Leu Gln Gln Lys
    4190                4195                4200

acc agc agc agc agt tagaaaatcc agtgcagcag gaggaggact gaggatcaca   26604
Thr Ser Ser Ser Ser
    4205

gcgaacgagc cagcgcagac ccgagagctg agaaacagga tctttccaac cctctatgcc  26664

atcttccagc agagtcgggg gcaagagcag gaactgaaag taaaaaaccg atctctgcgc  26724
```

```
tcgctcaccc gaagttgttt gtatcacaag agcgaagacc aacttcagcg cactctcgag  26784

gacgccgagg ctctcttcaa caagtactgc gcgctgactc ttaaagagta gcccgcgccc  26844

gcgctcgctc gaaaaaggcg ggaattacgt cacccttggc acctgtcctt tgccctcgtc  26904

atg agt  aaa gaa att ccc acg  cct tac atg tgg agc  tat cag ccc     26949
Met Ser  Lys Glu Ile Pro Thr  Pro Tyr Met Trp Ser  Tyr Gln Pro
    4210                4215                4220

caa atg  gga ctg gca gca ggc  gcc tcc cag gac tac  tcc acc cgc     26994
Gln Met  Gly Leu Ala Ala Gly  Ala Ser Gln Asp Tyr  Ser Thr Arg
    4225                4230                4235

atg aat  tgg ctc agc gcc ggc  ccc tcg atg atc tca  cgg gtt aat     27039
Met Asn  Trp Leu Ser Ala Gly  Pro Ser Met Ile Ser  Arg Val Asn
    4240                4245                4250

gat ata  cga gct tac cga aac  cag tta ctc cta gaa  cag tca gct     27084
Asp Ile  Arg Ala Tyr Arg Asn  Gln Leu Leu Leu Glu  Gln Ser Ala
    4255                4260                4265

ctc acc  acc aca ccc cgc caa  cac ctt aat ccc cgg  aat tgg ccc     27129
Leu Thr  Thr Thr Pro Arg Gln  His Leu Asn Pro Arg  Asn Trp Pro
    4270                4275                4280

gcc gcc  ctg gtg tac cag gaa  act ccc gct ccc acc  acc gta cta     27174
Ala Ala  Leu Val Tyr Gln Glu  Thr Pro Ala Pro Thr  Thr Val Leu
    4285                4290                4295

ctt cct  cga gac gcc cag gcc  gaa gtt cag atg act  aac gca ggt     27219
Leu Pro  Arg Asp Ala Gln Ala  Glu Val Gln Met Thr  Asn Ala Gly
    4300                4305                4310

gta cag  ctg gcg ggc ggt tcc  gcc ctg tgt cgt cac  cgg cct cag     27264
Val Gln  Leu Ala Gly Gly Ser  Ala Leu Cys Arg His  Arg Pro Gln
    4315                4320                4325

cag agt  ata aaa cgc ctg gtg  atc aga ggc cga ggt  atc cag ctc     27309
Gln Ser  Ile Lys Arg Leu Val  Ile Arg Gly Arg Gly  Ile Gln Leu
    4330                4335                4340

aac gac  gag tcg gtg agc tct  tcg ctt ggt ctg cga  cca gac gga     27354
Asn Asp  Glu Ser Val Ser Ser  Ser Leu Gly Leu Arg  Pro Asp Gly
    4345                4350                4355

gtc ttc  caa atc gcc ggc tgt  ggg aga tct tcc ttc  act cct cgt     27399
Val Phe  Gln Ile Ala Gly Cys  Gly Arg Ser Ser Phe  Thr Pro Arg
    4360                4365                4370

cag gct  gtc ctg act ttg gag  agt tcg tcc tcg caa  ccc cgc tcg     27444
Gln Ala  Val Leu Thr Leu Glu  Ser Ser Ser Ser Gln  Pro Arg Ser
    4375                4380                4385

ggc ggc  atc ggg act ctc cag  ttt gtg gag gag ttt  act ccc tct     27489
Gly Gly  Ile Gly Thr Leu Gln  Phe Val Glu Glu Phe  Thr Pro Ser
    4390                4395                4400

gtc tac  ttc aac ccc ttc tcc  ggc tct cct ggc cag  tac ccg gac     27534
Val Tyr  Phe Asn Pro Phe Ser  Gly Ser Pro Gly Gln  Tyr Pro Asp
    4405                4410                4415

gag ttc  ata ccg aac ttc gac  gca atc agc gag tca  gtg gat ggc     27579
Glu Phe  Ile Pro Asn Phe Asp  Ala Ile Ser Glu Ser  Val Asp Gly
    4420                4425                4430

tat gat  tg atg tct ggt ggc gcg  gct gag tta gct cga  ctg cga cat  27626
Tyr Asp     Met Ser Gly Gly Ala  Ala Glu Leu Ala Arg  Leu Arg His
    4435                   4440                 4445

cta gac  cac tgc cgc cgc ttt  cgc tgt ttc gcc cgg  gaa ctc acc     27671
Leu Asp  His Cys Arg Arg Phe  Arg Cys Phe Ala Arg  Glu Leu Thr
    4450                4455                4460

gag ttc  atc tac ttc gaa ctc  ccc gag gag cac cct  cag gga ccg     27716
Glu Phe  Ile Tyr Phe Glu Leu  Pro Glu Glu His Pro  Gln Gly Pro
    4465                4470                4475
```

```
gcc cac  gga gtg cgg att acc  atc gaa ggg gga ata  gac tct cgc     27761
Ala His  Gly Val Arg Ile Thr  Ile Glu Gly Gly Ile  Asp Ser Arg
    4480                 4485                 4490

ctg cat  cgg atc ttc tgc cag  cga ccc gtg ctg atc  gag cgc gac     27806
Leu His  Arg Ile Phe Cys Gln  Arg Pro Val Leu Ile  Glu Arg Asp
    4495                 4500                 4505

cag gga  act aca aca gtc tcc  atc tac tgc atc tgt  aac cac ccc     27851
Gln Gly  Thr Thr Thr Val Ser  Ile Tyr Cys Ile Cys  Asn His Pro
    4510                 4515                 4520

gga ttg  cat gaa agc ctt tgc  tgt ctt att tgt gct  gag ttt aat     27896
Gly Leu  His Glu Ser Leu Cys  Cys Leu Ile Cys Ala  Glu Phe Asn
    4525                 4530                 4535

aaa aac  tgagttcaga ccctcctacg gactaccgct tcttcaaccc ggactttaca    27952
Lys Asn
    4540

acaccagcca gaagacccag acccttcctc tgatccagga ctctaattct acctccccag  28012

caccttttcc tactaacctt cccgttacta acaacctcga agctcagctg caacaccgct  28072

tctccagaag cctcctttct gccaatacta ctactcccag aaccggaggt gagctccgtg  28132

gtctccctac taacaacccc tgggtggtag cgggttttgt agcgctagga gtagttgcgg  28192

gtgggctggt gcttatactc tgctacctat acacaccttg ctgtgcttat ttagtagtat  28252

tgtgttgctg gtttaagaa atg ggg gtc gta cta  gta gcg ctt gct tta      28301
                     Met Gly Val Val Leu  Val Ala Leu Ala Leu
                                    4545                 4550

ctt tcg ctt ttg ggt  ctg ggc tct gct aat  ctc att cct ccc gat      28346
Leu Ser Leu Leu Gly  Leu Gly Ser Ala Asn  Leu Ile Pro Pro Asp
                4555                 4560                 4565

cac gat cca tgt ctg  gac ttt aat cca gag  aac tgc aca atc act      28391
His Asp Pro Cys Leu  Asp Phe Asn Pro Glu  Asn Cys Thr Ile Thr
                4570                 4575                 4580

ttt gca cct gaa aca  agt cgc ttc tgt gga  gtt gtt att agg tgc      28436
Phe Ala Pro Glu Thr  Ser Arg Phe Cys Gly  Val Val Ile Arg Cys
                4585                 4590                 4595

gga ttt gaa tgc agg  ccc att gag att aca  cac aat aac aaa act      28481
Gly Phe Glu Cys Arg  Pro Ile Glu Ile Thr  His Asn Asn Lys Thr
                4600                 4605                 4610

tgg aac aat acc tta  ttc aca ata tgg caa  cca gga gac cct cag      28526
Trp Asn Asn Thr Leu  Phe Thr Ile Trp Gln  Pro Gly Asp Pro Gln
                4615                 4620                 4625

tgg tat act gtc tct  gtc cgg ggt cct gac  ggt tcc gtc cgc atg      28571
Trp Tyr Thr Val Ser  Val Arg Gly Pro Asp  Gly Ser Val Arg Met
                4630                 4635                 4640

gct aat aac act ttt  att ttt gct gaa atg  tgc gat atg gcc atg      28616
Ala Asn Asn Thr Phe  Ile Phe Ala Glu Met  Cys Asp Met Ala Met
                4645                 4650                 4655

ttc atg agc aga cag  tat gac cta tgg cct  ccc agc aaa gag aac      28661
Phe Met Ser Arg Gln  Tyr Asp Leu Trp Pro  Pro Ser Lys Glu Asn
                4660                 4665                 4670

att gtg gca ttc tcc  att gct tat tgc ttc  tgt act tgc ctt atc      28706
Ile Val Ala Phe Ser  Ile Ala Tyr Cys Phe  Cys Thr Cys Leu Ile
                4675                 4680                 4685

act gct act ttg tgt  att tgc tta cac tta  ctt ata gca ttt cgc      28751
Thr Ala Thr Leu Cys  Ile Cys Leu His Leu  Leu Ile Ala Phe Arg
                4690                 4695                 4700

cca aaa aac agc aac  gag gaa aaa gaa aaa  gtg cct taatcttttc       28797
Pro Lys Asn Ser Asn  Glu Glu Lys Glu Lys  Val Pro
                4705                 4710

ctcacctttt ttgtttacag c atg gct tct  gtt gct gtt cta atc  ttt ata  28848
```

```
                        Met Ala Ser  Val Ala Val Leu Ile  Phe Ile
                                4715                4720

att aca tca  gtt cat aca ttt ggg  cta aaa ttt aat gat  caa ata     28893
Ile Thr Ser  Val His Thr Phe Gly  Leu Lys Phe Asn Asp  Gln Ile
        4725                4730                4735

gtc cat gta  ggt tcc aac cat aca  ctg cgt gga cca ata  ggc aat     28938
Val His Val  Gly Ser Asn His Thr  Leu Arg Gly Pro Ile  Gly Asn
        4740                4745                4750

tca gaa gta  acc tgg tac tgg tat  tat gca gat gat agc  tgg cct     28983
Ser Glu Val  Thr Trp Tyr Trp Tyr  Tyr Ala Asp Asp Ser  Trp Pro
        4755                4760                4765

gaa aaa ctt  tgt gat gac att aat  tta cat aac att ctt  aca aaa     29028
Glu Lys Leu  Cys Asp Asp Ile Asn  Leu His Asn Ile Leu  Thr Lys
        4770                4775                4780

act ctt aat  agt aag act att aaa  tat aac tgt act gat  tat gat     29073
Thr Leu Asn  Ser Lys Thr Ile Lys  Tyr Asn Cys Thr Asp  Tyr Asp
        4785                4790                4795

tta att cta  gtt aat gtc act aca  aac tat tca ggt ttt  tat tac     29118
Leu Ile Leu  Val Asn Val Thr Thr  Asn Tyr Ser Gly Phe  Tyr Tyr
        4800                4805                4810

gga act aat  ttt gaa aat gtt gca  tat tat aat att cta  gta aag     29163
Gly Thr Asn  Phe Glu Asn Val Ala  Tyr Tyr Asn Ile Leu  Val Lys
        4815                4820                4825

ttt aga cct  aca aca act aaa acg  tct agc agc agt act  ata acc     29208
Phe Arg Pro  Thr Thr Thr Lys Thr  Ser Ser Ser Ser Thr  Ile Thr
        4830                4835                4840

agc acc acg  ctt cca att aga aca  gca atg ttt caa ttg  aac aaa     29253
Ser Thr Thr  Leu Pro Ile Arg Thr  Ala Met Phe Gln Leu  Asn Lys
        4845                4850                4855

ata gaa aat  acc acc aat agc aat  tac act cta ttc aac  gat caa     29298
Ile Glu Asn  Thr Thr Asn Ser Asn  Tyr Thr Leu Phe Asn  Asp Gln
        4860                4865                4870

aat gtt caa  ggg tca tta act aca  att atc att cta cta  att gtg     29343
Asn Val Gln  Gly Ser Leu Thr Thr  Ile Ile Ile Leu Leu  Ile Val
        4875                4880                4885

ggg tta ata  att ata ata att tgc  atg ata gtc tat acc  tgc cgc     29388
Gly Leu Ile  Ile Ile Ile Ile Cys  Met Ile Val Tyr Thr  Cys Arg
        4890                4895                4900

tac aga aaa  cta cac aat aaa gta  gac ccc tat tagattccat          29431
Tyr Arg Lys  Leu His Asn Lys Val  Asp Pro Tyr
        4905                4910

acttagacat ctaacttttt ttaaaacact ttattttcag cc atg att  tct att    29485
                                               Met Ile  Ser Ile
                                                   4915

aca acc ctt  ctc tat atc act gcc  att act act gta cag  ggg ttc     29530
    Thr Thr Leu  Leu Tyr Ile Thr Ala  Ile Thr Thr Val Gln  Gly Phe
        4920                4925                4930

aca aac atc  aaa aaa aca ata cat  gtg gga tcc agt tct  aca cta     29575
Thr Asn Ile  Lys Lys Thr Ile His  Val Gly Ser Ser Ser  Thr Leu
        4935                4940                4945

gaa ggt tac  caa tcc caa tca cgt  gtt tct tgg tat tgg  tat tac     29620
Glu Gly Tyr  Gln Ser Gln Ser Arg  Val Ser Trp Tyr Trp  Tyr Tyr
        4950                4955                4960

cgt aat cag  cca gct att aca ctt  tgc aaa gga tct cag  gaa acc     29665
Arg Asn Gln  Pro Ala Ile Thr Leu  Cys Lys Gly Ser Gln  Glu Thr
        4965                4970                4975

aca ata cgc  aca atc aaa tac aaa  tgc aat aac aat aat  tta acc     29710
Thr Ile Arg  Thr Ile Lys Tyr Lys  Cys Asn Asn Asn Asn  Leu Thr
        4980                4985                4990
```

```
cta att gat  gtt aca gct caa tat  gca gga act tac tat  gga aca     29755
Leu Ile Asp  Val Thr Ala Gln Tyr  Ala Gly Thr Tyr Tyr  Gly Thr
        4995                 5000                 5005

aat ttt aac  ata gga caa gac aca  tac tat acc att aca  gta att     29800
Asn Phe Asn  Ile Gly Gln Asp Thr  Tyr Tyr Thr Ile Thr  Val Ile
        5010                 5015                 5020

aac tct act  act cct gta aca act  acc ata aaa cct aca  aaa act     29845
Asn Ser Thr  Thr Pro Val Thr Thr  Thr Ile Lys Pro Thr  Lys Thr
        5025                 5030                 5035

aaa agc aca  aaa act cac att ttc  cct agc agc aag ccc  acc tca     29890
Lys Ser Thr  Lys Thr His Ile Phe  Pro Ser Ser Lys Pro  Thr Ser
        5040                 5045                 5050

atc tat aca  act tca ctt ttg caa  cta ctt caa aag gct  aac gtt     29935
Ile Tyr Thr  Thr Ser Leu Leu Gln  Leu Leu Gln Lys Ala  Asn Val
        5055                 5060                 5065

aca gac aat  tat act att aac ccc  act ctt cct agc gaa  gag ata     29980
Thr Asp Asn  Tyr Thr Ile Asn Pro  Thr Leu Pro Ser Glu  Glu Ile
        5070                 5075                 5080

ccc aaa tca  atg ata gga att att  gct gct gtg gta gcg  gga atg     30025
Pro Lys Ser  Met Ile Gly Ile Ile  Ala Ala Val Val Ala  Gly Met
        5085                 5090                 5095

cta att ata  att cta tgt atg att  tat tat gct tgc tgc  tat aga     30070
Leu Ile Ile  Ile Leu Cys Met Ile  Tyr Tyr Ala Cys Cys  Tyr Arg
        5100                 5105                 5110

aaa tat gaa  cat gaa caa aaa ata  gac cca cta ctg agc  ttt gat     30115
Lys Tyr Glu  His Glu Gln Lys Ile  Asp Pro Leu Leu Ser  Phe Asp
        5115                 5120                 5125

att taattttttt tagagcacc atg aaa  ggt cca gtt atc cta  ttg ttt     30164
Ile                      Met Lys  Gly Pro Val Ile Leu  Leu Phe
                             5130                 5135

att tcc act  ttt tgg tgt tgt gat  act ttt tca att acc  acc aat     30209
Ile Ser Thr  Phe Trp Cys Cys Asp  Thr Phe Ser Ile Thr  Thr Asn
        5140                 5145                 5150

gtg cag act  act tta aat aac atc  atg act acc tct aac  aca caa     30254
Val Gln Thr  Thr Leu Asn Asn Ile  Met Thr Thr Ser Asn  Thr Gln
        5155                 5160                 5165

ctt tca cct  caa tct gaa gat gac  ata aaa cta caa atc  act atc     30299
Leu Ser Pro  Gln Ser Glu Asp Asp  Ile Lys Leu Gln Ile  Thr Ile
        5170                 5175                 5180

ctt att gta  att ggt tta att atc  ctt gct gtt ctc ctt  tac ttt     30344
Leu Ile Val  Ile Gly Leu Ile Ile  Leu Ala Val Leu Leu  Tyr Phe
        5185                 5190                 5195

atc ttt tgc  cgt caa ata ccc aat  gta gtt aag aaa cct  acc aga     30389
Ile Phe Cys  Arg Gln Ile Pro Asn  Val Val Lys Lys Pro  Thr Arg
        5200                 5205                 5210

cgt ccc atc  tat cga tca ata atc  agc aaa ccc cac atg  gct cta     30434
Arg Pro Ile  Tyr Arg Ser Ile Ile  Ser Lys Pro His Met  Ala Leu
        5215                 5220                 5225

aat gaa att  taatctttct cttcacagta tggtgatcaa ct atg atc cct aga   30487
Asn Glu Ile                                      Met Ile Pro Arg
        5230

aat  ttc ttc ttc acc ata  ctt atc tgc gct ttc  aat gtc tgt gct     30532
Asn  Phe Phe Phe Thr Ile  Leu Ile Cys Ala Phe  Asn Val Cys Ala
5235                 5240                 5245

aca  ttc gcc aca gtc gcc  aat gtg aca cca gat  tgt ata ggg gca     30577
Thr  Phe Ala Thr Val Ala  Asn Val Thr Pro Asp  Cys Ile Gly Ala
5250                 5255                 5260

ttt  gct tcc tac gta cta  ttt gcc ttc att acc  tgc atc tgc gtt     30622
Phe  Ala Ser Tyr Val Leu  Phe Ala Phe Ile Thr  Cys Ile Cys Val
5265                 5270                 5275
```

```
tgt  agc ata gtc tgc ctg  gtt atc aac ttc ttt  caa cta gta gac     30667
Cys  Ser Ile Val Cys Leu  Val Ile Asn Phe Phe  Gln Leu Val Asp
5280                 5285                 5290

tgg  gtt ttt gta cgc att  gcc tac cta caa cat  cac cct gaa tac     30712
Trp  Val Phe Val Arg Ile  Ala Tyr Leu Gln His  His Pro Glu Tyr
5295                 5300                 5305

cgc  aac caa aat gtt gca  gca att ctt agg ctc  att taaaaccatg      30758
Arg  Asn Gln Asn Val Ala  Ala Ile Leu Arg Leu  Ile
5310                 5315                 5320

caaactctgc tactgcttct gctagttata cacccatgtg cctcaaaccc cacaagcccc  30818

acaaaattag atctaagaaa atgtaaattt caagaaccat ggaaattcct tgattgctat  30878

catgaaacat ctgatttccc cacatactgg attacaatca ttggggttgt taatctagtc  30938

tcttgcacac tattctcttt ccttgtttac cacttatttg attttggatg gaactccctc  30998

aatgcactca cttacccaca agaaccagag gaacatatac cactacagaa catacaacca  31058

ttagcactag tagaatatga aaatgagcca cagcctccac tactccctgc cattagctac  31118

ttcaacttaa ccggtggag atg act gac cca  cac gcc gct gct gag  gaa     31167
                    Met Thr Asp Pro  His Ala Ala Ala Glu  Glu
                                5325                 5330

cta ctt gat atg  gac ggc cgt gcc tcc  gaa cag cgc ctc gct  caa     31212
Leu Leu Asp Met  Asp Gly Arg Ala Ser  Glu Gln Arg Leu Ala  Gln
            5335                 5340                 5345

cta cgc att cgc  cag cag cag gaa cgt  gcc gcc aaa gag ctc  agg     31257
Leu Arg Ile Arg  Gln Gln Gln Glu Arg  Ala Ala Lys Glu Leu  Arg
            5350                 5355                 5360

gat gct att cag  att cac cag tgc aaa  aaa ggc ata ttc tgc  ttg     31302
Asp Ala Ile Gln  Ile His Gln Cys Lys  Lys Gly Ile Phe Cys  Leu
            5365                 5370                 5375

gta aaa caa gcc  aag atc tcc tac gag  atc acc gct aac gac  cac     31347
Val Lys Gln Ala  Lys Ile Ser Tyr Glu  Ile Thr Ala Asn Asp  His
            5380                 5385                 5390

cgc ctc tca tat  gag ctt ggc ccg cag  cgt cag aaa ttc acc  tgc     31392
Arg Leu Ser Tyr  Glu Leu Gly Pro Gln  Arg Gln Lys Phe Thr  Cys
            5395                 5400                 5405

atg gtt gga atc  aac ccc ata gtc atc  acc cag caa gct gga  gat     31437
Met Val Gly Ile  Asn Pro Ile Val Ile  Thr Gln Gln Ala Gly  Asp
            5410                 5415                 5420

acc aag ggt tgc  atc cat tgt tcc tgt  gaa tcc acc gag tgc  atc     31482
Thr Lys Gly Cys  Ile His Cys Ser Cys  Glu Ser Thr Glu Cys  Ile
            5425                 5430                 5435

tac acc ctg ctg  aag acc ctt tgc ggc  ctt cga gac ctt ctg  ccc     31527
Tyr Thr Leu Leu  Lys Thr Leu Cys Gly  Leu Arg Asp Leu Leu  Pro
            5440                 5445                 5450

atg aac taatcaaccc cgcccttccc ttaccaatta caaaaagcca attaataaaa     31583
Met Asn

aatcacttac ttaaaatcag aaataaggtt tttgtctgcg ttgttttcaa gcagcacctc  31643

acttccctct tcccaacttt ggtactctaa gcctcggcgg gtggcatact tcctccacac  31703

tttgaaaggg atgtcaaatt ttagttcctc tttgcccaca atcttcattt ctttatcccc  31763

ag atg gcc  aaa cga gct cga cta  agc agc tcc ttc aat  ccg gtc tac  31810
   Met Ala  Lys Arg Ala Arg Leu  Ser Ser Ser Phe Asn  Pro Val Tyr
       5455                 5460                 5465

ccc tat  gaa gac gaa agc acc  aca cat ccc ttt ata  aac cct ggc     31855
Pro Tyr  Glu Asp Glu Ser Thr  Thr His Pro Phe Ile  Asn Pro Gly
    5470                 5475                 5480

ttc att  tca cct gat ggg ttt  gca caa agt cca gat  ggg gtt ctc     31900
```

```
Phe Ile  Ser Pro Asp Gly Phe  Ala Gln Ser Pro Asp  Gly Val Leu
    5485                 5490                 5495

aca ctt  aaa tgt ata tcc cca  ctt aat act aca ggc  gga tca tta     31945
Thr Leu  Lys Cys Ile Ser Pro  Leu Asn Thr Thr Gly  Gly Ser Leu
    5500                 5505                 5510

caa ctt  aaa gtg gga gga ggg  cta aaa gtg gac tct  aca gac gga     31990
Gln Leu  Lys Val Gly Gly Gly  Leu Lys Val Asp Ser  Thr Asp Gly
    5515                 5520                 5525

tct ctg  gaa gaa aac ata aat  aca aca gct cca ctt  act aaa act     32035
Ser Leu  Glu Glu Asn Ile Asn  Thr Thr Ala Pro Leu  Thr Lys Thr
    5530                 5535                 5540

aac cat  tct atc agt atg ttg  gta gga aat ggc tta  cat act gaa     32080
Asn His  Ser Ile Ser Met Leu  Val Gly Asn Gly Leu  His Thr Glu
    5545                 5550                 5555

gaa aac  aaa cta tgt gca aaa  ctg gga caa ggt ctt  gaa ttt aac     32125
Glu Asn  Lys Leu Cys Ala Lys  Leu Gly Gln Gly Leu  Glu Phe Asn
    5560                 5565                 5570

tca ggt  agt att tgt ata gat  cac aat aca aac aca  cta tgg aca     32170
Ser Gly  Ser Ile Cys Ile Asp  His Asn Thr Asn Thr  Leu Trp Thr
    5575                 5580                 5585

gga gtt  ccc act gag gcc aat  tgt cat atg cta gag  tac aca gat     32215
Gly Val  Pro Thr Glu Ala Asn  Cys His Met Leu Glu  Tyr Thr Asp
    5590                 5595                 5600

gac aaa  gac tgc aaa ctc aca  cta gtt ctt gtt aaa  aat gga gct     32260
Asp Lys  Asp Cys Lys Leu Thr  Leu Val Leu Val Lys  Asn Gly Ala
    5605                 5610                 5615

atg gta  aac gga tat gta tct  ctt atg ggt gcc act  gac gaa ttt     32305
Met Val  Asn Gly Tyr Val Ser  Leu Met Gly Ala Thr  Asp Glu Phe
    5620                 5625                 5630

aat gct  ata acc aca gtt aaa  att gct caa ctt act  gct gat ata     32350
Asn Ala  Ile Thr Thr Val Lys  Ile Ala Gln Leu Thr  Ala Asp Ile
    5635                 5640                 5645

tat ttt  gat aca aat gga aag  gtc ctt act gat ata  tca gcc ctt     32395
Tyr Phe  Asp Thr Asn Gly Lys  Val Leu Thr Asp Ile  Ser Ala Leu
    5650                 5655                 5660

aaa aca  gaa tta aaa tat aag  tct gga caa aat atg  gca aca ggt     32440
Lys Thr  Glu Leu Lys Tyr Lys  Ser Gly Gln Asn Met  Ala Thr Gly
    5665                 5670                 5675

gaa cca  tca aac agc aag agc  ttc atg cca agc cta  act gca tac     32485
Glu Pro  Ser Asn Ser Lys Ser  Phe Met Pro Ser Leu  Thr Ala Tyr
    5680                 5685                 5690

cca ctt  cga aat ccc act att  aaa cca gtt aga ggt  aat gag gac     32530
Pro Leu  Arg Asn Pro Thr Ile  Lys Pro Val Arg Gly  Asn Glu Asp
    5695                 5700                 5705

tac ata  tat ggc acc act tat  ttt aga tcc agc gat  gat gct ctc     32575
Tyr Ile  Tyr Gly Thr Thr Tyr  Phe Arg Ser Ser Asp  Asp Ala Leu
    5710                 5715                 5720

tta cca  cta gat aca tat gtt  atg ctt aat tac aaa  ctg tcc aat     32620
Leu Pro  Leu Asp Thr Tyr Val  Met Leu Asn Tyr Lys  Leu Ser Asn
    5725                 5730                 5735

gcc caa  tgt gca tat gca atg  cac ttt atg tgg tca  tgg aat act     32665
Ala Gln  Cys Ala Tyr Ala Met  His Phe Met Trp Ser  Trp Asn Thr
    5740                 5745                 5750

tcc att  aaa cca gaa gaa aca  gcc act acc ttt att  gct tcc ccc     32710
Ser Ile  Lys Pro Glu Glu Thr  Ala Thr Thr Phe Ile  Ala Ser Pro
    5755                 5760                 5765

ttt acc  ttt tca tac att aga  gaa gat gac tgacaacaaa aaaataaagt    32760
Phe Thr  Phe Ser Tyr Ile Arg  Glu Asp Asp
    5770                 5775
```

```
tcaacttttt tattaaacaa tcagtttaca ggattcgagt agttattttg cctcccctt  32820
cccatttcat agaatacacc aatctctccc cacgcacagc tttaaacatt tggattccat  32880
ttgaaatagt catggattta gattccacat tccacacagt ttcagagcta gataatcttg  32940
gatcagtgat agatataaat ccatcggggc agtccttcaa ggtgatttca cagtccagtt  33000
gctgtggctg cggctccgga gtctggatca gagtcatctg gaacaagaac gatgggagtc  33060
ataatccgag aacgggatcg ggcggttgtg tctcatcaaa ccccgaagca gtcgctgtct  33120
gcgccgctcc gtgcgactgc tgctgatggg atcggggtcc acagtctctc gaagcatgat  33180
tctaatagcc ctcaacatta acatcctggt gcgatgcgca cagcagcgca tcctgatctc  33240
acttagctca cagcaatagg tacaacacaa caccacaata ttgtttaaca ggccataatt  33300
aaaggcactc cagccaaaac tcatttcagg aataatttgc ccagcgtgac catcgtacca  33360
aatcctgatg taaatcagat ggcgccccct ccagaacaca ctgcccacat acatgatctc  33420
cttaggcata tgcatattca caatctctcg gtaccatgga cagcgctggt taatcatgca  33480
gccccgaata accttccgga accaaatggc cagcaatgcg cccccagcaa tacattgaag  33540
agaaccctgt cgattacagt gacaatggag aacccacttc tctcgcccat ggatcacttg  33600
ggaataaaat atatctattg tggcacaaca cagacataaa tgcatacatc ttctcatcac  33660
ccttaactct tcaggggtta aaaacatatc ccagggaata ggaagctctt gcaaaacagt  33720
aaaggtggca gaacaaggca gaccgcgaac ataacttaca ctgtgcatgg tcaaggtatt  33780
gcaatctggt aacagcggat gctcttcagt catagaagct ctggtttcac tttcctcaca  33840
gcgtggtaaa ggggccctca gttgaggttc cctggtgtaa ggatggtgtc tggcgcacga  33900
tgtcgagcgt gcacgcgacc tcgttgtaat ggagctgctt cctgacattc tcgtattttg  33960
catggcagaa cctagccttg gcacaacaca cttctcttcg ccttctatcc cgtcgcctag  34020
cacgttcagt atggtaattg aagtacagcc attcccgtag attggtcaaa agctcctcgg  34080
cttcagttgt cataaaaact ccatcatatc ttactgctct gataaaatca tttactgtag  34140
aatgggcaat gcccagccag gcaatgcaat tagcttgtgt ttcaaccaaa ggagggggag  34200
gaagacatgg aagaaccata attaattttt attccagacg atcccgcagt atttctacat  34260
ggagatcacg aagatggcac ctctcgcccc cactgtgttg atgaaaaatg acagctaggt  34320
caaacatgat gcgattttca aggtgctcaa cggtggcttc aagcaaagcc tccaaacgta  34380
catccaaaaa caaaagaaca gcaaaagcag gagcattttc taattcctca atcatcatat  34440
tacattcctg taccattccc aaataatttt catctttcca tccttgaatt attcgtgtta  34500
tttcatctgg taaatccaat ccacacatga gaaatagctc ccggagggcg ccctccaccg  34560
gcaatcttaa gcataccctc atagtgacaa aatatcgtgc tcctctgtca cctgcagcaa  34620
attgagaatg gcaatatcaa acggaatgcc actggctcta agttcttctc taagttccag  34680
ttgtaaaaac tcttgcatat catcgccaaa ctgcttagcc ataggtcctc caggaataag  34740
agcgggggac gctacagtgc agaacaagcg catgccgccc caattgcctc cagcaaaagt  34800
gaggttgcaa tatgcatact gagaacctcc agtgatatca tccagtgtac tggaaagata  34860
atcaggcaga gcttctcgta tgcaattaat aatagaaaag tctgccagat gcacatttaa  34920
agcctgtggg atgcagatgc aataagttat cgcgctgcgc tccaacattg ttagtatggt  34980
tagtctgtaa aaacaaaaaa caaaaaaaaa aaaattacat cacgctagac tggcgaacgg  35040
gtggaaaaat cactctctcc aacaccaggc aggctacagg gtctccagcg cgaccctcgt  35100
aaaacctgtc agtatgatta aaaagcatca ccgaaagggg ttgttgatgg ccagcatata  35160
```

```
ttatttgcga tgaagcatac aatccagaag tgttagtatc agttaaagaa aaaaatcggc  35220

caagatagca tctcggaacg attatgctca atctcaaatg cagcaaagcg acacctcgcg  35280

gatgcaaagt aaaatccaca ggagcataaa aaaagtaatt attcccctct tgcacaggca  35340

gcctagctcc cggcccctcc aaaatcacat ataaagcttc agcagccata gcttaccgcg  35400

caaatcaggc acagcagtca gatagagaaa aagctgtgaa ctgactgccc agcctgtgcg  35460

caatatatag agaaccctta cactgacgta attggacaaa gtctaaaaaa tcccgccaaa  35520

aaaccagcac acgcccagaa ctgtgtcacc cgctaaaaaa taattttcac ttcctcgttc  35580

cgtgaatgac gtcagttccc ctttcccacg agccgtcact tccggtcatc ttgcaacgtc  35640

acctccccgc gccggcccgc cccttttgac cgttgaaccc gctggccaat ccccttccgc  35700

cctccatttt caaaagctca tttgcatgtt ggcaccgttc catttataag gtatattatt  35760

gatgatg                                                             35767
```

<210> SEQ ID NO 35
<211> LENGTH: 495
<212> TYPE: PRT
<213> ORGANISM: Unknown
<220> FEATURE:
<223> OTHER INFORMATION: Synthetic Construct

<400> SEQUENCE: 35

```
Met Asp Pro Thr Asn Pro Leu Gln Gln Gly Ile Arg Leu Gly Phe His
1               5                   10                  15

Ser Ser Ser Phe Val Glu Asn Met Glu Gly Pro Gln Ala Glu Asp Asn
            20                  25                  30

Leu Arg Leu Leu Ala Ser Ala Ala Ser Gly Arg Ser Gly Asn Pro Glu
        35                  40                  45

Thr Pro Thr Ser His Ala Ser Gly Phe Gly Gly Gly Ala Ala Gly Gly
    50                  55                  60

Gln Pro Glu Ser Arg Pro Gly Pro Ser Gly Gly Gly Gly Gly Gly Val
65                  70                  75                  80

Ala Asp Leu Phe Pro Glu Leu Arg Arg Val Leu Thr Arg Ser Thr Ser
                85                  90                  95

Ser Gly Gln Asp Arg Gly Ile Lys Arg Glu Arg Asn Ala Ser Gly His
            100                 105                 110

Asn Ser Arg Thr Glu Leu Ala Leu Ser Leu Met Ser Arg Ser Arg Pro
        115                 120                 125

Glu Thr Ile Trp Trp His Glu Val Gln Ser Glu Gly Arg Asp Glu Val
    130                 135                 140

Ser Ile Leu Gln Glu Lys Tyr Ser Leu Glu Gln Ile Lys Thr Cys Trp
145                 150                 155                 160

Leu Glu Pro Glu Asp Asp Trp Glu Val Ala Ile Arg Asn Tyr Ala Lys
                165                 170                 175

Ile Ser Leu Arg Pro Asp Lys Gln Tyr Arg Ile Thr Lys Lys Ile Asn
            180                 185                 190

Ile Arg Asn Ala Cys Tyr Ile Ser Gly Asn Gly Ala Glu Val Ile Ile
        195                 200                 205

Asp Thr Pro Asp Lys Thr Ala Phe Arg Cys Cys Met Met Gly Met Trp
    210                 215                 220

Pro Gly Val Ala Gly Met Glu Ala Val Thr Leu Met Asn Ile Arg Phe
225                 230                 235                 240

Arg Gly Asp Gly Tyr Asn Gly Ile Val Phe Met Ala Asn Thr Lys Leu
```

```
                245                 250                 255

Ile Leu His Gly Cys Ser Phe Phe Gly Phe Asn Asn Thr Cys Val Glu
            260                 265                 270

Ala Trp Gly Gln Val Ser Val Arg Gly Cys Ser Phe Tyr Ala Cys Trp
        275                 280                 285

Ile Ala Leu Ser Gly Arg Thr Lys Ser Gln Leu Ser Val Lys Lys Cys
    290                 295                 300

Met Phe Glu Arg Cys Asn Leu Gly Ile Leu Asn Glu Gly Glu Ala Arg
305                 310                 315                 320

Val Arg His Cys Ala Ala Thr Glu Thr Gly Cys Phe Ile Leu Ile Lys
                325                 330                 335

Gly Asn Ala Ser Val Lys His Asn Met Ile Cys Gly Pro Ser Asp Glu
            340                 345                 350

Arg Pro Tyr Gln Met Leu Thr Cys Ala Gly Gly His Cys Asn Met Leu
        355                 360                 365

Ala Thr Val His Ile Val Ser His Ala Arg Lys Lys Trp Pro Val Phe
    370                 375                 380

Glu His Asn Val Met Thr Lys Cys Thr Met His Ala Gly Gly Arg Arg
385                 390                 395                 400

Gly Met Phe Met Pro Tyr Gln Cys Asn Met Asn His Val Lys Val Met
                405                 410                 415

Leu Glu Pro Asp Ala Phe Ser Arg Met Ser Leu Thr Gly Ile Phe Asp
            420                 425                 430

Met Asn Val Gln Leu Trp Lys Ile Leu Arg Tyr Asp Glu Thr Lys Ser
        435                 440                 445

Arg Val Arg Ala Cys Glu Cys Gly Gly Lys His Ala Arg Phe Gln Pro
    450                 455                 460

Val Cys Val Asp Val Thr Glu Asp Leu Arg Pro Asp His Leu Val Leu
465                 470                 475                 480

Ala Cys Thr Gly Ala Glu Phe Gly Ser Ser Gly Glu Glu Thr Asp
                485                 490                 495


<210> SEQ ID NO 36
<211> LENGTH: 138
<212> TYPE: PRT
<213> ORGANISM: Unknown
<220> FEATURE:
<223> OTHER INFORMATION: Synthetic Construct

<400> SEQUENCE: 36

Met Ser Gly Ser Ala Ser Phe Glu Gly Gly Val Phe Ser Pro Tyr Leu
1               5                   10                  15

Thr Gly Arg Leu Pro Pro Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45

Thr Tyr Ala Thr Leu Ser Ser Ser Pro Leu Asp Ala Ala Ala Ala Ala
    50                  55                  60

Ala Ala Ser Ala Ala Ala Asn Thr Val Leu Gly Met Gly Tyr Tyr Gly
65                  70                  75                  80

Ser Ile Val Ala Asn Ser Ser Ser Ser Asn Asn Pro Ser Thr Leu Ala
                85                  90                  95

Glu Asp Lys Leu Leu Val Leu Leu Ala Gln Leu Glu Ala Leu Thr Gln
            100                 105                 110

Arg Leu Gly Glu Leu Ser Gln Gln Val Ala Gln Leu Arg Glu Gln Thr
```

```
        115                 120                 125

Glu Ser Ala Val Ala Thr Ala Lys Ser Lys
    130                 135


<210> SEQ ID NO 37
<211> LENGTH: 389
<212> TYPE: PRT
<213> ORGANISM: Unknown
<220> FEATURE:
<223> OTHER INFORMATION: Synthetic Construct

<400> SEQUENCE: 37

Met His Pro Val Leu Arg Gln Met Arg Pro Gln Gln Gln Ala Pro Ser
1               5                   10                  15

Gln Gln Gln Gln Gln Pro Gln Lys Ala Leu Pro Ala Pro Ala Pro Ala
            20                  25                  30

Thr Thr Ala Val Ala Ala Val Cys Gly Ala Gly Gln Pro Ala Tyr Asp
        35                  40                  45

Leu Asp Leu Glu Glu Gly Glu Gly Leu Ala Arg Leu Gly Ala Pro Ser
    50                  55                  60

Pro Glu Arg His Pro Arg Val Gln Leu Lys Lys Asp Ser Arg Glu Ala
65                  70                  75                  80

Tyr Val Pro Gln Gln Asn Leu Phe Arg Asp Arg Ser Gly Glu Glu Pro
                85                  90                  95

Glu Glu Met Arg Ala Ser Arg Phe Asn Ala Gly Arg Glu Leu Arg His
            100                 105                 110

Gly Leu Asp Arg Arg Arg Val Leu Arg Asp Glu Asp Phe Glu Val Asp
        115                 120                 125

Glu Val Thr Gly Ile Ser Pro Ala Arg Ala His Val Ala Ala Ala Asn
    130                 135                 140

Leu Val Ser Ala Tyr Glu Gln Thr Val Lys Glu Glu Arg Asn Phe Gln
145                 150                 155                 160

Lys Ser Phe Asn Asn His Val Arg Thr Leu Ile Ala Arg Glu Glu Val
                165                 170                 175

Thr Leu Gly Leu Met His Leu Trp Asp Leu Met Glu Ala Ile Thr Gln
            180                 185                 190

Asn Pro Thr Ser Lys Pro Leu Thr Ala Gln Leu Phe Leu Val Val Gln
        195                 200                 205

His Ser Arg Asp Asn Glu Ala Phe Arg Glu Ala Leu Leu Asn Ile Thr
    210                 215                 220

Glu Pro Glu Gly Arg Trp Leu Tyr Asp Leu Ile Asn Ile Leu Gln Ser
225                 230                 235                 240

Ile Ile Val Gln Glu Arg Ser Leu Gly Leu Ala Glu Lys Val Ala Ala
                245                 250                 255

Ile Asn Tyr Ser Val Leu Ser Leu Gly Lys Tyr Tyr Ala Arg Lys Ile
            260                 265                 270

Tyr Lys Thr Pro Tyr Val Pro Ile Asp Lys Glu Val Lys Ile Asp Gly
        275                 280                 285

Phe Tyr Met Arg Met Thr Leu Lys Val Leu Thr Leu Ser Asp Asp Leu
    290                 295                 300

Gly Val Tyr Arg Asn Asp Arg Met His Arg Ala Val Ser Ala Ser Arg
305                 310                 315                 320

Arg Arg Glu Leu Ser Asp Arg Glu Leu Met His Ser Leu Gln Arg Ala
                325                 330                 335

Leu Thr Gly Ala Gly Thr Asp Gly Glu Asn Tyr Phe Asp Met Gly Ala
```

```
            340                 345                 350

Asp Leu Gln Trp Gln Pro Ser Arg Arg Ala Leu Asp Ala Ala Gly Cys
        355                 360                 365

Glu Leu Pro Tyr Val Glu Glu Val Asp Glu Gly Glu Glu Glu Glu Gly
    370                 375                 380

Glu Tyr Leu Glu Asp
385


<210> SEQ ID NO 38
<211> LENGTH: 587
<212> TYPE: PRT
<213> ORGANISM: Unknown
<220> FEATURE:
<223> OTHER INFORMATION: Synthetic Construct

<400> SEQUENCE: 38

Met Glu Gln Gln Ala Pro Asp Pro Ala Met Arg Ala Ala Leu Gln Ser
1               5                   10                  15

Gln Pro Ser Gly Ile Asn Ser Ser Asp Asp Trp Thr Gln Ala Met Gln
            20                  25                  30

Arg Ile Met Ala Leu Thr Thr Arg Asn Pro Glu Ala Phe Arg Gln Gln
        35                  40                  45

Pro Gln Ala Asn Arg Leu Ser Ala Ile Leu Glu Ala Val Val Pro Ser
    50                  55                  60

Arg Ser Asn Pro Thr His Glu Lys Val Leu Ala Ile Val Asn Ala Leu
65                  70                  75                  80

Val Glu Asn Lys Ala Ile Arg Pro Asp Glu Ala Gly Leu Val Tyr Asn
                85                  90                  95

Ala Leu Leu Glu Arg Val Ala Arg Tyr Asn Ser Ser Asn Val Gln Thr
            100                 105                 110

Asn Leu Asp Arg Met Val Thr Asp Val Arg Glu Ala Val Ser Gln Arg
        115                 120                 125

Glu Arg Phe Gln Arg Asp Ala Asn Leu Gly Ser Leu Val Ala Leu Asn
    130                 135                 140

Ala Phe Leu Ser Thr Gln Pro Ala Asn Val Pro Arg Gly Gln Gln Asp
145                 150                 155                 160

Tyr Thr Asn Phe Leu Ser Ala Leu Arg Leu Met Val Thr Glu Val Pro
                165                 170                 175

Gln Ser Glu Val Tyr Gln Ser Gly Pro Asp Tyr Phe Phe Gln Thr Ser
            180                 185                 190

Arg Gln Gly Leu Gln Thr Val Asn Leu Ser Gln Ala Phe Lys Asn Leu
        195                 200                 205

Arg Gly Leu Trp Gly Val His Ala Pro Val Gly Asp Arg Ala Thr Val
    210                 215                 220

Ser Ser Leu Leu Thr Pro Asn Ser Arg Leu Leu Leu Leu Leu Val Ser
225                 230                 235                 240

Pro Phe Thr Asp Ser Gly Ser Ile Asp Arg Asn Ser Tyr Leu Gly Tyr
                245                 250                 255

Leu Leu Asn Leu Tyr Arg Glu Ala Ile Gly Gln Ser Gln Val Asp Glu
            260                 265                 270

Gln Thr Tyr Gln Glu Ile Thr Gln Val Ser Arg Ala Leu Gly Gln Glu
        275                 280                 285

Asp Thr Gly Ser Leu Glu Ala Thr Leu Asn Phe Leu Leu Thr Asn Arg
    290                 295                 300

Ser Gln Lys Ile Pro Pro Gln Tyr Ala Leu Thr Ala Glu Glu Glu Arg
```

```
305                 310                 315                 320

Ile Leu Arg Tyr Val Gln Gln Ser Val Gly Leu Phe Leu Met Gln Glu
                325                 330                 335

Gly Ala Thr Pro Ser Ala Ala Leu Asp Met Thr Ala Arg Asn Met Glu
            340                 345                 350

Pro Ser Met Tyr Ala Met Asn Arg Pro Phe Ile Asn Lys Leu Leu Asp
        355                 360                 365

Tyr Leu His Arg Ala Ala Ala Met Asn Ser Asp Tyr Phe Thr Asn Ala
    370                 375                 380

Ile Leu Asn Pro His Trp Leu Pro Pro Pro Gly Phe Tyr Thr Gly Glu
385                 390                 395                 400

Tyr Asp Met Pro Asp Pro Asn Asp Gly Phe Leu Trp Asp Asp Val Asp
                405                 410                 415

Ser Ser Ile Phe Ser Pro Pro Pro Gly Tyr Asn Thr Trp Lys Lys Glu
            420                 425                 430

Gly Gly Asp Arg Arg His Ser Ser Val Ser Leu Ser Gly Ser Arg Gly
        435                 440                 445

Ala Ala Ala Ala Val Pro Glu Ala Ala Ser Pro Phe Pro Ser Leu Pro
    450                 455                 460

Phe Ser Leu Asn Ser Val Arg Ser Ser Glu Leu Gly Arg Ile Thr Arg
465                 470                 475                 480

Pro Arg Leu Met Gly Glu Asp Glu Tyr Leu Asn Asp Ser Leu Leu Arg
                485                 490                 495

Pro Glu Arg Glu Lys Asn Phe Pro Asn Asn Gly Ile Glu Ser Leu Val
            500                 505                 510

Asp Lys Met Ser Arg Trp Lys Thr Tyr Ala Gln Asp His Lys Asp Glu
        515                 520                 525

Pro Arg Ile Leu Gly Ala Ala Ser Gly Thr Thr Arg Arg Arg Gln Arg
    530                 535                 540

His Asp Arg Gln Arg Gly Leu Val Trp Asp Asp Glu Asp Ser Ala Asp
545                 550                 555                 560

Asp Ser Ser Val Leu Asp Leu Gly Gly Arg Gly Gly Gly Asn Pro Phe
                565                 570                 575

Ala His Leu Arg Pro His Phe Gly Arg Met Leu
            580                 585


<210> SEQ ID NO 39
<211> LENGTH: 584
<212> TYPE: PRT
<213> ORGANISM: Unknown
<220> FEATURE:
<223> OTHER INFORMATION: Synthetic Construct

<400> SEQUENCE: 39

Met Met Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Ala Val
            20                  25                  30

Met Gln Pro Ser Leu Glu Ala Pro Phe Val Pro Pro Arg Tyr Leu Ala
        35                  40                  45

Pro Thr Glu Gly Arg Asn Ser Ile Arg Tyr Ser Glu Leu Ala Pro Gln
    50                  55                  60

Tyr Asp Thr Thr Arg Leu Tyr Leu Val Asp Asn Lys Ser Ala Asp Ile
65                  70                  75                  80

Ala Ser Leu Asn Tyr Gln Asn Asp His Ser Asn Phe Leu Thr Thr Val
```

```
                85                  90                  95

Val Gln Asn Asn Asp Phe Thr Pro Thr Glu Ala Ser Thr Gln Thr Ile
            100                 105                 110

Asn Phe Asp Glu Arg Ser Arg Trp Gly Gly Gln Leu Lys Thr Ile Met
        115                 120                 125

His Thr Asn Met Pro Asn Val Asn Glu Tyr Met Phe Ser Asn Lys Phe
    130                 135                 140

Lys Ala Arg Val Met Val Ser Arg Lys Lys Pro Glu Gly Tyr Thr Gly
145                 150                 155                 160

Asp Lys Asn Asp Thr Ser Gln Asp Ile Leu Glu Tyr Glu Trp Phe Glu
                165                 170                 175

Phe Thr Leu Pro Glu Gly Asn Phe Ser Ala Thr Met Thr Ile Asp Leu
            180                 185                 190

Met Asn Asn Ala Ile Ile Asp Asn Tyr Leu Ala Val Gly Arg Gln Asn
        195                 200                 205

Gly Val Leu Glu Ser Asp Ile Gly Val Lys Phe Asp Thr Arg Asn Phe
    210                 215                 220

Arg Leu Gly Trp Asp Pro Ile Thr Lys Leu Val Met Pro Gly Val Tyr
225                 230                 235                 240

Thr Tyr Glu Ala Phe His Pro Asp Ile Val Leu Leu Pro Gly Cys Gly
                245                 250                 255

Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
        275                 280                 285

Gly Gly Asn Ile Pro Ala Leu Leu Asp Val Asp Ala Tyr Glu Lys Ser
    290                 295                 300

Lys Lys Glu Asn Thr Asp Thr Thr Thr Thr Thr Thr Val Thr Thr Thr
305                 310                 315                 320

Glu Val Ala Thr Val Ala Arg His Val Ala Glu Val Thr Thr Glu Ala
                325                 330                 335

Ala Thr Val Val Ala Val Asp Pro Ile Val Glu Glu Asn Asn Asn Thr
            340                 345                 350

Val Arg Gly Asp Asn Ile His Thr Ala Asn Glu Met Lys Ala Ala Ala
        355                 360                 365

Asp Asp Thr Thr Val Val Val Val Pro Gly Ala Val Val Thr Glu Thr
    370                 375                 380

Glu Thr Lys Thr Lys Thr Leu Thr Ile Gln Pro Leu Glu Lys Asp Thr
385                 390                 395                 400

Lys Glu Arg Ser Tyr Asn Val Ile Ser Gly Thr Asn Asp Thr Ala Tyr
                405                 410                 415

Arg Ser Trp Tyr Leu Ala Tyr Asn Tyr Gly Asp Pro Glu Lys Gly Val
            420                 425                 430

Arg Ser Trp Thr Leu Leu Thr Thr Ser Asp Val Thr Cys Gly Ala Glu
        435                 440                 445

Gln Val Tyr Trp Ser Leu Pro Asp Met Met Gln Asp Pro Val Thr Phe
    450                 455                 460

Arg Ser Thr Arg Gln Val Ser Asn Tyr Pro Val Val Gly Ala Glu Leu
465                 470                 475                 480

Met Pro Val Phe Ser Lys Ser Phe Tyr Asn Glu Gln Ala Val Tyr Ser
                485                 490                 495

Gln Gln Leu Arg Gln Thr Thr Ser Leu Thr His Ile Phe Asp Arg Phe
            500                 505                 510
```

```
Pro Glu Asn Gln Ile Leu Ile Arg Pro Pro Ala Pro Thr Ile Thr Thr
        515                 520                 525

Val Ser Glu Asn Val Pro Ala Leu Thr Asp His Gly Thr Leu Pro Leu
    530                 535                 540

Arg Ser Ser Ile Arg Gly Val Gln Arg Val Thr Val Thr Asp Ala Arg
545                 550                 555                 560

Arg Arg Thr Cys Pro Tyr Val Tyr Lys Ala Leu Gly Ile Val Ala Pro
                565                 570                 575

Arg Val Leu Ser Ser Arg Thr Phe
            580


<210> SEQ ID NO 40
<211> LENGTH: 192
<212> TYPE: PRT
<213> ORGANISM: Unknown
<220> FEATURE:
<223> OTHER INFORMATION: Synthetic Construct

<400> SEQUENCE: 40

Met Ser Ile Leu Ile Ser Pro Ser Asn Asn Thr Gly Trp Gly Leu Arg
1               5                   10                  15

Thr Pro Thr Arg Met Tyr Gly Gly Ala Arg Lys Arg Ser Thr Gln His
            20                  25                  30

Pro Val Arg Val Arg Gly His Phe Arg Ala Pro Trp Gly Ala Leu Lys
        35                  40                  45

Gly Arg Thr Arg Thr Arg Thr Thr Val Asp Asp Val Ile Asp Gln Val
    50                  55                  60

Val Ala Asp Ala Arg Asn Tyr Thr Pro Ala Ala Pro Ala Ser Thr Val
65                  70                  75                  80

Asp Ala Val Ile Asp Ser Val Val Ala Asp Ala Arg Glu Tyr Ala Arg
                85                  90                  95

Arg Lys Ser Arg Arg Arg Arg Ile Ala Arg Arg His Arg Ala Thr Pro
            100                 105                 110

Ala Met Arg Ala Ala Arg Ala Leu Leu Arg Arg Ala Lys Arg Val Gly
        115                 120                 125

Arg Arg Ala Met Leu Arg Ala Ala Arg Arg Ala Ala Ser Gly Ala Ser
    130                 135                 140

Ala Gly Arg Ser Arg Arg Arg Ala Ala Thr Ala Ala Ala Ala Ala Ile
145                 150                 155                 160

Ala Asn Met Ala Gln Pro Arg Arg Gly Asn Val Tyr Trp Val Arg Asp
                165                 170                 175

Ala Thr Thr Gly Gln Arg Val Pro Val Arg Thr Arg Pro Pro Arg Thr
            180                 185                 190


<210> SEQ ID NO 41
<211> LENGTH: 350
<212> TYPE: PRT
<213> ORGANISM: Unknown
<220> FEATURE:
<223> OTHER INFORMATION: Synthetic Construct

<400> SEQUENCE: 41

Met Ser Lys Arg Lys Tyr Lys Glu Glu Met Leu Gln Val Ile Ala Pro
1               5                   10                  15

Glu Ile Tyr Gly Pro Pro Val Lys Asp Glu Lys Lys Pro Arg Lys Ile
            20                  25                  30

Lys Arg Val Lys Lys Asp Lys Lys Glu Glu Asp Gly Asp Asp Gly Leu
```

```
        35                  40                  45

Val Glu Phe Val Arg Glu Phe Ala Pro Arg Arg Arg Val Gln Trp Arg
    50                  55                  60

Gly Arg Arg Val Arg Pro Val Leu Arg Pro Gly Thr Thr Val Val Phe
65                  70                  75                  80

Thr Pro Gly Glu Arg Ser Ser Thr Thr Phe Lys Arg Ser Tyr Asp Glu
                85                  90                  95

Val Tyr Gly Asp Asp Asp Ile Leu Glu Gln Ala Ala Asp Arg Leu Gly
            100                 105                 110

Glu Phe Ala Tyr Gly Lys Arg Ser Arg Ser Ser Pro Lys Asp Glu Ala
        115                 120                 125

Val Ser Ile Pro Leu Asp His Gly Asn Pro Thr Pro Ser Leu Lys Pro
    130                 135                 140

Val Thr Leu Gln Gln Val Leu Pro Val Pro Pro Arg Arg Gly Val Lys
145                 150                 155                 160

Arg Glu Gly Glu Asp Leu Tyr Pro Thr Met Gln Leu Met Val Pro Lys
                165                 170                 175

Arg Gln Lys Leu Glu Asp Val Leu Glu Lys Met Lys Val Asp Pro Asp
            180                 185                 190

Ile Gln Pro Glu Val Lys Val Arg Pro Ile Lys Gln Val Ala Pro Gly
        195                 200                 205

Leu Gly Val Gln Thr Val Asp Ile Lys Ile Pro Thr Glu Ser Met Glu
    210                 215                 220

Val Gln Thr Glu Pro Ala Lys Pro Thr Ala Ala Ser Ile Glu Val Gln
225                 230                 235                 240

Thr Asp Pro Trp Met Pro Ala Pro Ile Ala Thr Ala Ala Ser Thr Val
                245                 250                 255

Arg Arg Pro Arg Arg Lys Tyr Gly Pro Ala Ser Leu Leu Met Pro Asn
            260                 265                 270

Tyr Ala Leu His Pro Ser Ile Ile Pro Thr Pro Gly Tyr Arg Gly Thr
        275                 280                 285

Arg Tyr Tyr Arg Ser Arg Ser Thr Thr Ser Arg Arg Arg Lys Thr Pro
    290                 295                 300

Ala Ser Arg Ser Arg Arg Arg Arg Arg Arg Thr Ala Ser Lys Leu Thr
305                 310                 315                 320

Pro Ala Ala Leu Val Arg Arg Val Tyr Arg Asp Gly Arg Ala Glu Pro
                325                 330                 335

Leu Met Leu Pro Arg Ala Arg Tyr His Pro Ser Ile Thr Thr
            340                 345                 350


<210> SEQ ID NO 42
<211> LENGTH: 75
<212> TYPE: PRT
<213> ORGANISM: Unknown
<220> FEATURE:
<223> OTHER INFORMATION: Synthetic Construct

<400> SEQUENCE: 42

Met Ala Leu Thr Cys Arg Leu Arg Val Pro Ile Thr Gly Tyr Arg Gly
1               5                   10                  15

Arg Asn Ser Arg Arg Arg Arg Met Leu Gly Ser Gly Met Arg Arg His
            20                  25                  30

Arg Arg Arg Arg Ala Ile Ser Lys Arg Leu Gly Gly Gly Phe Leu Thr
        35                  40                  45

Ala Leu Ile Pro Ile Ile Ala Ala Ala Ile Gly Ala Val Pro Gly Ile
```

```
    50                  55                  60

Ala Ser Val Ala Val Gln Ala Ser Gln Arg His
65                  70                  75


<210> SEQ ID NO 43
<211> LENGTH: 250
<212> TYPE: PRT
<213> ORGANISM: Unknown
<220> FEATURE:
<223> OTHER INFORMATION: Synthetic Construct

<400> SEQUENCE: 43

Met Glu Asp Ile Asn Phe Ser Ser Leu Ala Pro Arg His Gly Thr Arg
1               5                   10                  15

Pro Tyr Met Gly Thr Trp Ser Asp Ile Gly Thr Ser Gln Leu Asn Gly
            20                  25                  30

Gly Ala Phe Asn Trp Ser Ser Ile Trp Ser Gly Leu Lys Asn Phe Gly
        35                  40                  45

Ser Ala Ile Lys Thr Tyr Gly Asn Lys Ala Trp Asn Ser Ser Thr Gly
    50                  55                  60

Gln Ala Leu Arg Asn Lys Leu Lys Glu Gln Asn Phe Gln Gln Lys Val
65                  70                  75                  80

Val Asp Gly Ile Ala Ser Gly Ile Asn Gly Val Val Asp Leu Ala Asn
                85                  90                  95

Gln Ala Val Gln Lys Gln Ile Asn Ser Arg Leu Asp Gln Pro Pro Ala
            100                 105                 110

Ala Pro Gly Glu Met Glu Val Glu Glu Glu Leu Pro Pro Leu Glu Lys
        115                 120                 125

Arg Gly Asp Lys Arg Pro Arg Pro Asp Met Glu Glu Thr Leu Val Thr
    130                 135                 140

Arg Gly Asp Glu Pro Pro Pro Tyr Glu Glu Ala Ile Lys Leu Gly Met
145                 150                 155                 160

Pro Thr Thr Arg Pro Ile Ala Pro Met Ala Thr Gly Val Met Lys Pro
                165                 170                 175

Ser Gln Ser His Arg Pro Ala Thr Leu Asp Leu Pro Pro Ala Pro Ala
            180                 185                 190

Ala Ala Ala Pro Ala Pro Lys Pro Val Ala Thr Pro Lys Pro Thr Ala
        195                 200                 205

Val Gln Pro Val Ala Val Ala Arg Pro Arg Pro Gly Gly Thr Pro Arg
    210                 215                 220

Pro Asn Ala Asn Trp Gln Ser Thr Leu Asn Ser Ile Val Gly Leu Gly
225                 230                 235                 240

Val Gln Ser Val Lys Arg Arg Arg Cys Tyr
                245                 250


<210> SEQ ID NO 44
<211> LENGTH: 943
<212> TYPE: PRT
<213> ORGANISM: Unknown
<220> FEATURE:
<223> OTHER INFORMATION: Synthetic Construct

<400> SEQUENCE: 44

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30
```

```
Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Gln Asp Asn
    130                 135                 140

Ala Val Thr Thr Thr Thr Asn Thr Phe Gly Ile Ala Ser Met Lys Gly
145                 150                 155                 160

Asp Asn Ile Thr Lys Glu Gly Leu Glu Ile Gly Lys Asp Ile Thr Glu
                165                 170                 175

Glu Asp Lys Pro Ile Tyr Ala Asp Lys Thr Tyr Gln Pro Glu Pro Gln
            180                 185                 190

Val Gly Glu Glu Ser Trp Thr Asp Thr Asp Gly Thr Asn Glu Lys Phe
        195                 200                 205

Gly Gly Arg Ala Leu Lys Pro Ala Thr Asn Met Lys Pro Cys Tyr Gly
    210                 215                 220

Ser Phe Ala Arg Pro Thr Asn Ile Lys Gly Gly Gln Ala Lys Asn Arg
225                 230                 235                 240

Lys Val Lys Pro Thr Thr Glu Gly Gly Val Glu Thr Glu Glu Pro Asp
                245                 250                 255

Ile Asp Met Glu Phe Phe Asp Gly Arg Asp Ala Ala Glu Gly Ala Leu
            260                 265                 270

Ser Pro Glu Ile Val Leu Tyr Thr Glu Asn Val Asn Leu Glu Thr Pro
        275                 280                 285

Asp Thr His Val Val Tyr Lys Pro Gly Thr Ser Asp Asp Asn Ser His
    290                 295                 300

Ala Asn Leu Gly Gln Gln Ala Met Pro Asn Arg Pro Asn Tyr Ile Gly
305                 310                 315                 320

Phe Arg Asp Asn Phe Val Gly Leu Leu Tyr Tyr Asn Ser Thr Gly Asn
                325                 330                 335

Met Gly Val Leu Ala Gly Gln Ala Ser Gln Leu Asn Ala Val Val Asp
            340                 345                 350

Leu Gln Asp Arg Asn Thr Glu Leu Ser Tyr Gln Leu Leu Leu Asp Ser
        355                 360                 365

Leu Gly Asp Arg Thr Arg Tyr Phe Ser Met Trp Asn Gln Ala Val Asp
    370                 375                 380

Ser Tyr Asp Pro Asp Val Arg Ile Ile Glu Asn His Gly Ile Glu Asp
385                 390                 395                 400

Glu Leu Pro Asn Tyr Cys Phe Pro Leu Asp Gly Ile Gly Pro Gly Asn
                405                 410                 415

Ser Tyr Gln Gly Ile Lys Ala Lys Asn Gly Asp Asn Asn Gly Trp Glu
            420                 425                 430

Lys Asp Thr Asn Ala Ser Thr Ala Asn Glu Ile Ala Ile Gly Asn Asn
        435                 440                 445

Leu Ala Met Glu Ile Asn Ile Gln Ala Asn Leu Trp Arg Ser Phe Leu
```

```
    450                 455                 460

Tyr Ser Asn Val Ala Leu Tyr Leu Pro Asp Ala Tyr Lys Tyr Thr Pro
465                 470                 475                 480

Ala Asn Ile Thr Leu Pro Ala Asn Thr Asn Thr Tyr Glu Tyr Met Asn
                485                 490                 495

Gly Arg Val Val Ala Pro Ser Leu Val Asp Ser Tyr Ile Asn Ile Gly
            500                 505                 510

Ala Arg Trp Ser Leu Asp Pro Met Asp Asn Val Asn Pro Phe Asn His
        515                 520                 525

His Arg Asn Ala Gly Leu Arg Tyr Arg Ser Met Leu Leu Gly Asn Gly
    530                 535                 540

Arg Tyr Val Pro Phe His Ile Gln Val Pro Gln Lys Phe Phe Ala Ile
545                 550                 555                 560

Lys Asn Leu Leu Leu Leu Pro Gly Ser Tyr Thr Tyr Glu Trp Asn Phe
                565                 570                 575

Arg Lys Asp Val Asn Met Val Leu Gln Ser Ser Leu Gly Asn Asp Leu
            580                 585                 590

Arg Thr Asp Gly Ala Ser Ile Ser Phe Thr Ser Ile Asn Leu Tyr Ala
        595                 600                 605

Thr Phe Phe Pro Met Ala His Asn Thr Ala Ser Thr Leu Glu Ala Met
    610                 615                 620

Leu Arg Asn Asp Thr Asn Asp Gln Ser Phe Asn Asp Tyr Leu Ser Ala
625                 630                 635                 640

Ala Asn Met Leu Tyr Pro Ile Pro Ala Asn Ala Thr Asn Ile Pro Ile
                645                 650                 655

Ser Ile Pro Ser Arg Asn Trp Ala Ala Phe Arg Gly Trp Ser Phe Thr
            660                 665                 670

Arg Leu Lys Thr Lys Glu Thr Pro Ser Leu Gly Ser Gly Phe Asp Pro
        675                 680                 685

Tyr Phe Val Tyr Ser Gly Ser Ile Pro Tyr Leu Asp Gly Thr Phe Tyr
    690                 695                 700

Leu Asn His Thr Phe Lys Lys Val Ser Ile Met Phe Asp Ser Ser Val
705                 710                 715                 720

Ser Trp Pro Gly Asn Asp Arg Leu Leu Thr Pro Asn Glu Phe Glu Ile
                725                 730                 735

Lys Arg Thr Val Asp Gly Glu Gly Tyr Asn Val Ala Gln Cys Asn Met
            740                 745                 750

Thr Lys Asp Trp Phe Leu Val Gln Met Leu Ala Asn Tyr Asn Ile Gly
        755                 760                 765

Tyr Gln Gly Phe Tyr Ile Pro Glu Gly Tyr Lys Asp Arg Met Tyr Ser
    770                 775                 780

Phe Phe Arg Asn Phe Gln Pro Met Ser Arg Gln Val Val Asp Glu Val
785                 790                 795                 800

Asn Tyr Thr Asp Tyr Lys Ala Val Thr Leu Ala Tyr Gln His Asn Asn
                805                 810                 815

Ser Gly Phe Val Gly Tyr Leu Ala Pro Thr Met Arg Gln Gly Glu Pro
            820                 825                 830

Tyr Pro Ala Asn Tyr Pro Tyr Pro Leu Ile Gly Thr Thr Ala Val Lys
        835                 840                 845

Ser Val Thr Gln Lys Lys Phe Leu Cys Asp Arg Thr Met Trp Arg Ile
    850                 855                 860

Pro Phe Ser Ser Asn Phe Met Ser Met Gly Ala Leu Thr Asp Leu Gly
865                 870                 875                 880
```

```
Gln Asn Met Leu Tyr Ala Asn Ser Ala His Ala Leu Asp Met Thr Phe
                885                 890                 895

Glu Val Asp Pro Met Asp Glu Pro Thr Leu Leu Tyr Val Leu Phe Glu
            900                 905                 910

Val Phe Asp Val Val Arg Val His Gln Pro His Arg Gly Val Ile Glu
        915                 920                 925

Ala Val Tyr Leu Arg Thr Pro Phe Ser Ala Gly Asn Ala Thr Thr
    930                 935                 940


<210> SEQ ID NO 45
<211> LENGTH: 205
<212> TYPE: PRT
<213> ORGANISM: Unknown
<220> FEATURE:
<223> OTHER INFORMATION: Synthetic Construct

<400> SEQUENCE: 45

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
            20                  25                  30

Met Glu Asp Trp Asp Ser Gln Ala Glu Glu Ala Asp Ser Leu Glu Glu
        35                  40                  45

Asp Ser Leu Glu Glu Glu Asp Glu Glu Ala Glu Glu Val Glu Glu Ala
    50                  55                  60

Ala Ala Ala Lys Gln Leu Ser Ser Ala Ala Glu Thr Ser Lys Ala Pro
65                  70                  75                  80

Asp Ser Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
            100                 105                 110

Pro Thr Thr Ala Ser Lys Thr Gly Lys Lys Glu Arg Gln Gly Tyr Lys
        115                 120                 125

Ser Trp Arg Gly His Lys Asn Ala Ile Ile Ser Cys Leu His Glu Cys
    130                 135                 140

Gly Gly Asn Ile Ser Phe Thr Arg Arg Tyr Leu Leu Phe His His Gly
145                 150                 155                 160

Val Asn Phe Pro Arg Asn Val Leu His Tyr Tyr Arg His Leu His Ser
                165                 170                 175

Pro Tyr Tyr Ser Gln Gln Val Pro Thr Ala Ser Ala Glu Lys Asp Ser
            180                 185                 190

Ser Ser Gly Asp Leu Gln Gln Lys Thr Ser Ser Ser Ser
        195                 200                 205


<210> SEQ ID NO 46
<211> LENGTH: 227
<212> TYPE: PRT
<213> ORGANISM: Unknown
<220> FEATURE:
<223> OTHER INFORMATION: Synthetic Construct

<400> SEQUENCE: 46

Met Ser Lys Glu Ile Pro Thr Pro Tyr Met Trp Ser Tyr Gln Pro Gln
1               5                   10                  15

Met Gly Leu Ala Ala Gly Ala Ser Gln Asp Tyr Ser Thr Arg Met Asn
            20                  25                  30

Trp Leu Ser Ala Gly Pro Ser Met Ile Ser Arg Val Asn Asp Ile Arg
```

```
        35                  40                  45

Ala Tyr Arg Asn Gln Leu Leu Leu Glu Gln Ser Ala Leu Thr Thr Thr
    50                  55                  60

Pro Arg Gln His Leu Asn Pro Arg Asn Trp Pro Ala Ala Leu Val Tyr
65                  70                  75                  80

Gln Glu Thr Pro Ala Pro Thr Thr Val Leu Leu Pro Arg Asp Ala Gln
                85                  90                  95

Ala Glu Val Gln Met Thr Asn Ala Gly Val Gln Leu Ala Gly Gly Ser
            100                 105                 110

Ala Leu Cys Arg His Arg Pro Gln Gln Ser Ile Lys Arg Leu Val Ile
        115                 120                 125

Arg Gly Arg Gly Ile Gln Leu Asn Asp Glu Ser Val Ser Ser Ser Leu
    130                 135                 140

Gly Leu Arg Pro Asp Gly Val Phe Gln Ile Ala Gly Cys Gly Arg Ser
145                 150                 155                 160

Ser Phe Thr Pro Arg Gln Ala Val Leu Thr Leu Glu Ser Ser Ser Ser
                165                 170                 175

Gln Pro Arg Ser Gly Gly Ile Gly Thr Leu Gln Phe Val Glu Glu Phe
            180                 185                 190

Thr Pro Ser Val Tyr Phe Asn Pro Phe Ser Gly Ser Pro Gly Gln Tyr
        195                 200                 205

Pro Asp Glu Phe Ile Pro Asn Phe Asp Ala Ile Ser Glu Ser Val Asp
    210                 215                 220

Gly Tyr Asp
225


<210> SEQ ID NO 47
<211> LENGTH: 105
<212> TYPE: PRT
<213> ORGANISM: Unknown
<220> FEATURE:
<223> OTHER INFORMATION: Synthetic Construct

<400> SEQUENCE: 47

Met Ser Gly Gly Ala Ala Glu Leu Ala Arg Leu Arg His Leu Asp His
1               5                   10                  15

Cys Arg Arg Phe Arg Cys Phe Ala Arg Glu Leu Thr Glu Phe Ile Tyr
            20                  25                  30

Phe Glu Leu Pro Glu Glu His Pro Gln Gly Pro Ala His Gly Val Arg
        35                  40                  45

Ile Thr Ile Glu Gly Gly Ile Asp Ser Arg Leu His Arg Ile Phe Cys
    50                  55                  60

Gln Arg Pro Val Leu Ile Glu Arg Asp Gln Gly Thr Thr Thr Val Ser
65                  70                  75                  80

Ile Tyr Cys Ile Cys Asn His Pro Gly Leu His Glu Ser Leu Cys Cys
                85                  90                  95

Leu Ile Cys Ala Glu Phe Asn Lys Asn
            100                 105


<210> SEQ ID NO 48
<211> LENGTH: 172
<212> TYPE: PRT
<213> ORGANISM: Unknown
<220> FEATURE:
<223> OTHER INFORMATION: Synthetic Construct

<400> SEQUENCE: 48
```

```
Met Gly Val Val Leu Val Ala Leu Ala Leu Leu Ser Leu Leu Gly Leu
1               5                   10                  15

Gly Ser Ala Asn Leu Ile Pro Pro Asp His Asp Pro Cys Leu Asp Phe
            20                  25                  30

Asn Pro Glu Asn Cys Thr Ile Thr Phe Ala Pro Glu Thr Ser Arg Phe
        35                  40                  45

Cys Gly Val Val Ile Arg Cys Gly Phe Glu Cys Arg Pro Ile Glu Ile
    50                  55                  60

Thr His Asn Asn Lys Thr Trp Asn Asn Thr Leu Phe Thr Ile Trp Gln
65                  70                  75                  80

Pro Gly Asp Pro Gln Trp Tyr Thr Val Ser Val Arg Gly Pro Asp Gly
                85                  90                  95

Ser Val Arg Met Ala Asn Asn Thr Phe Ile Phe Ala Glu Met Cys Asp
            100                 105                 110

Met Ala Met Phe Met Ser Arg Gln Tyr Asp Leu Trp Pro Pro Ser Lys
        115                 120                 125

Glu Asn Ile Val Ala Phe Ser Ile Ala Tyr Cys Phe Cys Thr Cys Leu
    130                 135                 140

Ile Thr Ala Thr Leu Cys Ile Cys Leu His Leu Leu Ile Ala Phe Arg
145                 150                 155                 160

Pro Lys Asn Ser Asn Glu Glu Lys Glu Lys Val Pro
                165                 170


<210> SEQ ID NO 49
<211> LENGTH: 201
<212> TYPE: PRT
<213> ORGANISM: Unknown
<220> FEATURE:
<223> OTHER INFORMATION: Synthetic Construct

<400> SEQUENCE: 49

Met Ala Ser Val Ala Val Leu Ile Phe Ile Ile Thr Ser Val His Thr
1               5                   10                  15

Phe Gly Leu Lys Phe Asn Asp Gln Ile Val His Val Gly Ser Asn His
            20                  25                  30

Thr Leu Arg Gly Pro Ile Gly Asn Ser Glu Val Thr Trp Tyr Trp Tyr
        35                  40                  45

Tyr Ala Asp Asp Ser Trp Pro Glu Lys Leu Cys Asp Asp Ile Asn Leu
    50                  55                  60

His Asn Ile Leu Thr Lys Thr Leu Asn Ser Lys Thr Ile Lys Tyr Asn
65                  70                  75                  80

Cys Thr Asp Tyr Asp Leu Ile Leu Val Asn Val Thr Thr Asn Tyr Ser
                85                  90                  95

Gly Phe Tyr Tyr Gly Thr Asn Phe Glu Asn Val Ala Tyr Tyr Asn Ile
            100                 105                 110

Leu Val Lys Phe Arg Pro Thr Thr Thr Lys Thr Ser Ser Ser Ser Thr
        115                 120                 125

Ile Thr Ser Thr Thr Leu Pro Ile Arg Thr Ala Met Phe Gln Leu Asn
    130                 135                 140

Lys Ile Glu Asn Thr Thr Asn Ser Asn Tyr Thr Leu Phe Asn Asp Gln
145                 150                 155                 160

Asn Val Gln Gly Ser Leu Thr Thr Ile Ile Ile Leu Leu Ile Val Gly
                165                 170                 175

Leu Ile Ile Ile Ile Ile Cys Met Ile Val Tyr Thr Cys Arg Tyr Arg
            180                 185                 190
```

Lys Leu His Asn Lys Val Asp Pro Tyr
195 200

<210> SEQ ID NO 50
<211> LENGTH: 215
<212> TYPE: PRT
<213> ORGANISM: Unknown
<220> FEATURE:
<223> OTHER INFORMATION: Synthetic Construct

<400> SEQUENCE: 50

Met Ile Ser Ile Thr Thr Leu Leu Tyr Ile Thr Ala Ile Thr Thr Val
1 5 10 15

Gln Gly Phe Thr Asn Ile Lys Lys Thr Ile His Val Gly Ser Ser Ser
20 25 30

Thr Leu Glu Gly Tyr Gln Ser Gln Ser Arg Val Ser Trp Tyr Trp Tyr
35 40 45

Tyr Arg Asn Gln Pro Ala Ile Thr Leu Cys Lys Gly Ser Gln Glu Thr
50 55 60

Thr Ile Arg Thr Ile Lys Tyr Lys Cys Asn Asn Asn Asn Leu Thr Leu
65 70 75 80

Ile Asp Val Thr Ala Gln Tyr Ala Gly Thr Tyr Tyr Gly Thr Asn Phe
85 90 95

Asn Ile Gly Gln Asp Thr Tyr Tyr Thr Ile Thr Val Ile Asn Ser Thr
100 105 110

Thr Pro Val Thr Thr Thr Ile Lys Pro Thr Lys Thr Lys Ser Thr Lys
115 120 125

Thr His Ile Phe Pro Ser Ser Lys Pro Thr Ser Ile Tyr Thr Thr Ser
130 135 140

Leu Leu Gln Leu Leu Gln Lys Ala Asn Val Thr Asp Asn Tyr Thr Ile
145 150 155 160

Asn Pro Thr Leu Pro Ser Glu Glu Ile Pro Lys Ser Met Ile Gly Ile
165 170 175

Ile Ala Ala Val Val Ala Gly Met Leu Ile Ile Ile Leu Cys Met Ile
180 185 190

Tyr Tyr Ala Cys Cys Tyr Arg Lys Tyr Glu His Glu Gln Lys Ile Asp
195 200 205

Pro Leu Leu Ser Phe Asp Ile
210 215

<210> SEQ ID NO 51
<211> LENGTH: 102
<212> TYPE: PRT
<213> ORGANISM: Unknown
<220> FEATURE:
<223> OTHER INFORMATION: Synthetic Construct

<400> SEQUENCE: 51

Met Lys Gly Pro Val Ile Leu Leu Phe Ile Ser Thr Phe Trp Cys Cys
1 5 10 15

Asp Thr Phe Ser Ile Thr Thr Asn Val Gln Thr Thr Leu Asn Asn Ile
20 25 30

Met Thr Thr Ser Asn Thr Gln Leu Ser Pro Gln Ser Glu Asp Asp Ile
35 40 45

Lys Leu Gln Ile Thr Ile Leu Ile Val Ile Gly Leu Ile Ile Leu Ala
50 55 60

Val Leu Leu Tyr Phe Ile Phe Cys Arg Gln Ile Pro Asn Val Val Lys
65 70 75 80

```
Lys Pro Thr Arg Arg Pro Ile Tyr Arg Ser Ile Ile Ser Lys Pro His
                85                  90                  95

Met Ala Leu Asn Glu Ile
            100


<210> SEQ ID NO 52
<211> LENGTH: 91
<212> TYPE: PRT
<213> ORGANISM: Unknown
<220> FEATURE:
<223> OTHER INFORMATION: Synthetic Construct

<400> SEQUENCE: 52

Met Ile Pro Arg Asn Phe Phe Phe Thr Ile Leu Ile Cys Ala Phe Asn
1               5                   10                  15

Val Cys Ala Thr Phe Ala Thr Val Ala Asn Val Thr Pro Asp Cys Ile
            20                  25                  30

Gly Ala Phe Ala Ser Tyr Val Leu Phe Ala Phe Ile Thr Cys Ile Cys
        35                  40                  45

Val Cys Ser Ile Val Cys Leu Val Ile Asn Phe Phe Gln Leu Val Asp
    50                  55                  60

Trp Val Phe Val Arg Ile Ala Tyr Leu Gln His His Pro Glu Tyr Arg
65                  70                  75                  80

Asn Gln Asn Val Ala Ala Ile Leu Arg Leu Ile
                85                  90


<210> SEQ ID NO 53
<211> LENGTH: 132
<212> TYPE: PRT
<213> ORGANISM: Unknown
<220> FEATURE:
<223> OTHER INFORMATION: Synthetic Construct

<400> SEQUENCE: 53

Met Thr Asp Pro His Ala Ala Ala Glu Glu Leu Leu Asp Met Asp Gly
1               5                   10                  15

Arg Ala Ser Glu Gln Arg Leu Ala Gln Leu Arg Ile Arg Gln Gln Gln
            20                  25                  30

Glu Arg Ala Ala Lys Glu Leu Arg Asp Ala Ile Gln Ile His Gln Cys
        35                  40                  45

Lys Lys Gly Ile Phe Cys Leu Val Lys Gln Ala Lys Ile Ser Tyr Glu
    50                  55                  60

Ile Thr Ala Asn Asp His Arg Leu Ser Tyr Glu Leu Gly Pro Gln Arg
65                  70                  75                  80

Gln Lys Phe Thr Cys Met Val Gly Ile Asn Pro Ile Val Ile Thr Gln
                85                  90                  95

Gln Ala Gly Asp Thr Lys Gly Cys Ile His Cys Ser Cys Glu Ser Thr
            100                 105                 110

Glu Cys Ile Tyr Thr Leu Leu Lys Thr Leu Cys Gly Leu Arg Asp Leu
        115                 120                 125

Leu Pro Met Asn
    130


<210> SEQ ID NO 54
<211> LENGTH: 325
<212> TYPE: PRT
<213> ORGANISM: Unknown
<220> FEATURE:
<223> OTHER INFORMATION: Synthetic Construct
```

<400> SEQUENCE: 54

```
Met Ala Lys Arg Ala Arg Leu Ser Ser Ser Phe Asn Pro Val Tyr Pro
1               5                   10                  15

Tyr Glu Asp Glu Ser Thr Thr His Pro Phe Ile Asn Pro Gly Phe Ile
            20                  25                  30

Ser Pro Asp Gly Phe Ala Gln Ser Pro Asp Gly Val Leu Thr Leu Lys
        35                  40                  45

Cys Ile Ser Pro Leu Asn Thr Thr Gly Gly Ser Leu Gln Leu Lys Val
    50                  55                  60

Gly Gly Gly Leu Lys Val Asp Ser Thr Asp Gly Ser Leu Glu Glu Asn
65                  70                  75                  80

Ile Asn Thr Thr Ala Pro Leu Thr Lys Thr Asn His Ser Ile Ser Met
                85                  90                  95

Leu Val Gly Asn Gly Leu His Thr Glu Glu Asn Lys Leu Cys Ala Lys
            100                 105                 110

Leu Gly Gln Gly Leu Glu Phe Asn Ser Gly Ser Ile Cys Ile Asp His
        115                 120                 125

Asn Thr Asn Thr Leu Trp Thr Gly Val Pro Thr Glu Ala Asn Cys His
    130                 135                 140

Met Leu Glu Tyr Thr Asp Asp Lys Asp Cys Lys Leu Thr Leu Val Leu
145                 150                 155                 160

Val Lys Asn Gly Ala Met Val Asn Gly Tyr Val Ser Leu Met Gly Ala
                165                 170                 175

Thr Asp Glu Phe Asn Ala Ile Thr Thr Val Lys Ile Ala Gln Leu Thr
            180                 185                 190

Ala Asp Ile Tyr Phe Asp Thr Asn Gly Lys Val Leu Thr Asp Ile Ser
        195                 200                 205

Ala Leu Lys Thr Glu Leu Lys Tyr Lys Ser Gly Gln Asn Met Ala Thr
    210                 215                 220

Gly Glu Pro Ser Asn Ser Lys Ser Phe Met Pro Ser Leu Thr Ala Tyr
225                 230                 235                 240

Pro Leu Arg Asn Pro Thr Ile Lys Pro Val Arg Gly Asn Glu Asp Tyr
                245                 250                 255

Ile Tyr Gly Thr Thr Tyr Phe Arg Ser Ser Asp Asp Ala Leu Leu Pro
            260                 265                 270

Leu Asp Thr Tyr Val Met Leu Asn Tyr Lys Leu Ser Asn Ala Gln Cys
        275                 280                 285

Ala Tyr Ala Met His Phe Met Trp Ser Trp Asn Thr Ser Ile Lys Pro
    290                 295                 300

Glu Glu Thr Ala Thr Thr Phe Ile Ala Ser Pro Phe Thr Phe Ser Tyr
305                 310                 315                 320

Ile Arg Glu Asp Asp
                325
```

<210> SEQ ID NO 55
<211> LENGTH: 560
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (9)..(551)
<223> OTHER INFORMATION: E1b[1]9K

<400> SEQUENCE: 55

```
tgccatcc atg gag gtt tgg gct atc ttg gaa gat ctc aga cag act agg      50
         Met Glu Val Trp Ala Ile Leu Glu Asp Leu Arg Gln Thr Arg
         1               5                   10

caa ctg cta gaa aac gcc tcg gac gga gtc tct agt ctt tgg aga ttc       98
Gln Leu Leu Glu Asn Ala Ser Asp Gly Val Ser Ser Leu Trp Arg Phe
15                  20                  25                  30

tgg ttc ggt ggt gat cta gct agg cta gtc ttt agg gta aaa cgg gag      146
Trp Phe Gly Gly Asp Leu Ala Arg Leu Val Phe Arg Val Lys Arg Glu
                35                  40                  45

tat agt gaa gaa ttt gaa aag tta ttg gaa gac agt cca gga ctt ttt      194
Tyr Ser Glu Glu Phe Glu Lys Leu Leu Glu Asp Ser Pro Gly Leu Phe
            50                  55                  60

gaa gcc ctt aac ttg ggc cac cag gct cat ttt aag gag aag gtt tta      242
Glu Ala Leu Asn Leu Gly His Gln Ala His Phe Lys Glu Lys Val Leu
        65                  70                  75

tca gtt tta gat ttt tct acc cct ggt aga act gct gct gct gta gca      290
Ser Val Leu Asp Phe Ser Thr Pro Gly Arg Thr Ala Ala Ala Val Ala
    80                  85                  90

ttt ctt act ttt ata ttg gat aaa tgg atc cca caa acc cac ttc agc      338
Phe Leu Thr Phe Ile Leu Asp Lys Trp Ile Pro Gln Thr His Phe Ser
95                  100                 105                 110

aag gga tac gtc ttg gat ttc ata gca gca gct ttg tgg aga aca tgg      386
Lys Gly Tyr Val Leu Asp Phe Ile Ala Ala Ala Leu Trp Arg Thr Trp
                115                 120                 125

aag gcc cgc agg ctg agg ata atc tta gat tac tgg cca gtg cag cct      434
Lys Ala Arg Arg Leu Arg Ile Ile Leu Asp Tyr Trp Pro Val Gln Pro
            130                 135                 140

ctg ggc gta gcg gca atc ctg aga cac cca cca gtc atg cca gcg gtt      482
Leu Gly Val Ala Ala Ile Leu Arg His Pro Pro Val Met Pro Ala Val
        145                 150                 155

ttg gag gag gag cag cag gag gac aac ccg aga gcc ggc ctg gac cct      530
Leu Glu Glu Glu Gln Gln Glu Asp Asn Pro Arg Ala Gly Leu Asp Pro
    160                 165                 170

ccg gtg gag gag gcg gag gag tagctgacc                                560
Pro Val Glu Glu Ala Glu Glu
175                 180
```

<210> SEQ ID NO 56
<211> LENGTH: 181
<212> TYPE: PRT
<213> ORGANISM: Unknown
<220> FEATURE:
<223> OTHER INFORMATION: Synthetic Construct

<400> SEQUENCE: 56

```
Met Glu Val Trp Ala Ile Leu Glu Asp Leu Arg Gln Thr Arg Gln Leu
1               5                   10                  15

Leu Glu Asn Ala Ser Asp Gly Val Ser Ser Leu Trp Arg Phe Trp Phe
            20                  25                  30

Gly Gly Asp Leu Ala Arg Leu Val Phe Arg Val Lys Arg Glu Tyr Ser
        35                  40                  45

Glu Glu Phe Glu Lys Leu Leu Glu Asp Ser Pro Gly Leu Phe Glu Ala
    50                  55                  60

Leu Asn Leu Gly His Gln Ala His Phe Lys Glu Lys Val Leu Ser Val
65                  70                  75                  80

Leu Asp Phe Ser Thr Pro Gly Arg Thr Ala Ala Ala Val Ala Phe Leu
                85                  90                  95

Thr Phe Ile Leu Asp Lys Trp Ile Pro Gln Thr His Phe Ser Lys Gly
            100                 105                 110
```

```
Tyr Val Leu Asp Phe Ile Ala Ala Ala Leu Trp Arg Thr Trp Lys Ala
        115                 120                 125

Arg Arg Leu Arg Ile Ile Leu Asp Tyr Trp Pro Val Gln Pro Leu Gly
    130                 135                 140

Val Ala Ala Ile Leu Arg His Pro Pro Val Met Pro Ala Val Leu Glu
145                 150                 155                 160

Glu Glu Gln Gln Glu Asp Asn Pro Arg Ala Gly Leu Asp Pro Pro Val
                165                 170                 175

Glu Glu Ala Glu Glu
            180


<210> SEQ ID NO 57
<211> LENGTH: 9860
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (6)..(791)
<223> OTHER INFORMATION: protease
<220> FEATURE:
<221> NAME/KEY: CDS
<222> LOCATION: (2472)..(4964)
<223> OTHER INFORMATION: 100K
<220> FEATURE:
<221> NAME/KEY: CDS
<222> LOCATION: (6569)..(6994)
<223> OTHER INFORMATION: E3©R1ålpha
<220> FEATURE:
<221> NAME/KEY: CDS
<222> LOCATION: (9433)..(9852)
<223> OTHER INFORMATION: E3®IDeta

<400> SEQUENCE: 57

catgg atg agc cca ccc tgc ttt atg ttc ttt tcg aag tct tcg acg tgg      50
      Met Ser Pro Pro Cys Phe Met Phe Phe Ser Lys Ser Ser Thr Trp
      1               5                   10                  15

tca gag tgc acc agc cac acc gcg gcg tca tcg agg ctg tct acc tgc       98
Ser Glu Cys Thr Ser His Thr Ala Ala Ser Ser Arg Leu Ser Thr Cys
                20                  25                  30

gta ccc cgt tct cag ctg gta acg cca cca cat aaa gaa gct tct tgc      146
Val Pro Arg Ser Gln Leu Val Thr Pro Pro His Lys Glu Ala Ser Cys
            35                  40                  45

ttc ttg caa gca gct gcc atg gcc tgt ggg tcc ggc aac gga tcc agc      194
Phe Leu Gln Ala Ala Ala Met Ala Cys Gly Ser Gly Asn Gly Ser Ser
        50                  55                  60

gag caa gag ctc agg gcc att gct aga gac ctg ggc tgc gga ccc tat      242
Glu Gln Glu Leu Arg Ala Ile Ala Arg Asp Leu Gly Cys Gly Pro Tyr
    65                  70                  75

ttc ctg gga acc ttt gat aaa cgc ttc ccg ggg ttc atg gcc ccc gac      290
Phe Leu Gly Thr Phe Asp Lys Arg Phe Pro Gly Phe Met Ala Pro Asp
80                  85                  90                  95

aag ctc gcc tgc gcc att gtt aac acg gcc ggt cgc gag acg ggg ggt      338
Lys Leu Ala Cys Ala Ile Val Asn Thr Ala Gly Arg Glu Thr Gly Gly
                100                 105                 110

gag cac tgg ctg gct ttt ggt tgg aat ccg cgc tcc aac acc tgc tac      386
Glu His Trp Leu Ala Phe Gly Trp Asn Pro Arg Ser Asn Thr Cys Tyr
            115                 120                 125

ctt ttt gat ccc ttt ggc ttc tct gac gag cgc ctc aag caa atc tac      434
Leu Phe Asp Pro Phe Gly Phe Ser Asp Glu Arg Leu Lys Gln Ile Tyr
        130                 135                 140

cag ttt gag tat gag ggg ctt ctg cgc cgc agt gcc cta gct acc aag      482
```

```
Gln Phe Glu Tyr Glu Gly Leu Leu Arg Arg Ser Ala Leu Ala Thr Lys
    145                 150                 155

gac cgc tgt atc acc ctg gaa aag tca acc cag acc gtg cag ggc ccg      530
Asp Arg Cys Ile Thr Leu Glu Lys Ser Thr Gln Thr Val Gln Gly Pro
160                 165                 170                 175

cgc tcc gca gcc tgt gga ctg ttt tgc tgc atg ttc ctc cac gct ttt      578
Arg Ser Ala Ala Cys Gly Leu Phe Cys Cys Met Phe Leu His Ala Phe
                180                 185                 190

gtg cac tgg cca gac cgc ccc atg gac gga aac ccc acc atg aag ttg      626
Val His Trp Pro Asp Arg Pro Met Asp Gly Asn Pro Thr Met Lys Leu
            195                 200                 205

ctg act ggg gtg ccc aac agc atg ctc caa tca ccc caa gtc cag ccc      674
Leu Thr Gly Val Pro Asn Ser Met Leu Gln Ser Pro Gln Val Gln Pro
        210                 215                 220

acc ctg cgc cac aac cag gag gcg ctc tac cgc ttc cta aac tcc cac      722
Thr Leu Arg His Asn Gln Glu Ala Leu Tyr Arg Phe Leu Asn Ser His
    225                 230                 235

tca tct tac ttt cgt tct cac cgc gcg cgc atc gaa aag gcc acc gcg      770
Ser Ser Tyr Phe Arg Ser His Arg Ala Arg Ile Glu Lys Ala Thr Ala
240                 245                 250                 255

ttt aat cga atg gat atg caa taataagtca tgtaaaccgt gttcaaataa         821
Phe Asn Arg Met Asp Met Gln
                260

acagcacttt atttttaca tgcactgtgg ctctgggttg ctcattcatt catcattcac      881

tcagaagtcg aaggggttct ggcgggaatc agcgtgaccc gctggcaggg atacgttgcg     941

gaactggaac ctgttctgcc acttgaactc ggggatcacc agcttgggaa ctgggatctc    1001

ggggaaggtg tcttgccaca gctttctggt tagttgcaga gcaccaagca ggtcaggagc    1061

agagatcttg aaatcacagt tggggccagc attctgggca cgggagttgc ggtacactgg    1121

gttgcagcac tggaacacca tcagggcggg gtgtctcacg ctcgccagca cggtcgggtc    1181

actgatggta gtcacatcca agtcttcagc attggccatt ccaaaggggg tcatcttaca    1241

ggtctgcctg cccatcacgg gagcgcagcc gggcttgtgg ttgcaatcgc agcgaatggg    1301

gatcagcatc atcctggcct ggtcgggggt tatccctgga tacaccgcct tcataaaggc    1361

ttcgtactgc ttgaaagctt cctgagcctt acttccctcg gtgtagaaca tcccacagga    1421

cttgctggaa aattgattag tagcacagtt ggcatcattc acacagcagc gggcatcgtt    1481

gttggccagc tggaccacat tcctgcccca gcggttctgg gtgatcttgg ctcggtctgg    1541

gttctccttc atcgcgcgct gcccgttctc gctcgccaca tccatctcga tgatgtgatc    1601

cttctggatc atgatagtgc catgcaggca tttcaccttg ccttcataat cggtgcagcc    1661

atgagcccac agagcgcacc cggtgcactc ccaattgttg tgggcgatct cagaataaga    1721

atgcaccaat ccctgcatga atcttcccat catgctggtg agggtcttta tgctggtaaa    1781

tgtcagcggg atgccacggt gctcctcgtt cacatactgg tggcagatac gcctgtactg    1841

ctcgtgctgc tcgggcatca gcttgaaaga ggttctcagg tcattatcca gcctgtacct    1901

ctccattagc acggccatta cttccatgcc cttctcccag gcagagacca agggcaggct    1961

catgggattc ctaacagcaa tagcagcaga cgcagctcct ttagccagag ggtcattctt    2021

gtcaatcttc tcaacacttc tcttgccatc cttctcagtg atgcgcactg gggggtagct    2081

gaagcccacg gccaccagct ccgcctgttc tctttcttct tcgctgtcct ggctgatgtc    2141

ttgcaaaggg acatgcttgg tcttcctggg cttcttcttg ggagggatcg ggggagggct    2201

gttgctccgc tccggagaca gggaggaccg cgaagtttcg ctcaccagta ccacctggct    2261
```

```
ctcggtagaa gaaccggacc ccacgcggcg gtaggtgttc ctcttcgggg gcagaggtgg   2321

aggcgactgc gatggactgc ggtccggcct gggaggcgga tggctggcag agcctcttcc   2381

gcgttcgggg gtgtgctccc ggtggcggtc gcttgactga tttcctccgc ggctggccat   2441

tgtgttctcc taggcagaga aacaacagac atg gag act cag cca tcg ctg cca   2495
                                 Met Glu Thr Gln Pro Ser Leu Pro
                                         265                 270

aca ccg ctg caa gcg cca tca cac ctc gcc ccc agc agc gac gag gag      2543
Thr Pro Leu Gln Ala Pro Ser His Leu Ala Pro Ser Ser Asp Glu Glu
                275                 280                 285

gag agc tta acc acc cca cca ccc agt ccc gcc acc acc acc tct acc      2591
Glu Ser Leu Thr Thr Pro Pro Pro Ser Pro Ala Thr Thr Thr Ser Thr
            290                 295                 300

cta gag gat gag gag gag gtc gac gca ccc cag gag atg cag gat atg      2639
Leu Glu Asp Glu Glu Glu Val Asp Ala Pro Gln Glu Met Gln Asp Met
        305                 310                 315

gag gat gag aaa gcg gaa gag att gag gca gat gtc gag cag gac ccg      2687
Glu Asp Glu Lys Ala Glu Glu Ile Glu Ala Asp Val Glu Gln Asp Pro
    320                 325                 330

ggc tat gtg aca ccg gcg gag cac gag gag gag ctg aga cgc ttt cta      2735
Gly Tyr Val Thr Pro Ala Glu His Glu Glu Glu Leu Arg Arg Phe Leu
335                 340                 345                 350

gac aga gag gat gac aac cgc cca gag cag aaa gca gat ggc gat cac      2783
Asp Arg Glu Asp Asp Asn Arg Pro Glu Gln Lys Ala Asp Gly Asp His
                355                 360                 365

cag gag gct ggg ctc ggg gat cat gtc gcc gac tac ctc acc ggg ctt      2831
Gln Glu Ala Gly Leu Gly Asp His Val Ala Asp Tyr Leu Thr Gly Leu
            370                 375                 380

ggc ggg gag gac gtg ctc ctc aaa cat cta gca agg cag tcg atc ata      2879
Gly Gly Glu Asp Val Leu Leu Lys His Leu Ala Arg Gln Ser Ile Ile
        385                 390                 395

gtt aaa gac gca ctg ctc gac cgc acc gaa gtg ccc atc agt gtg gaa      2927
Val Lys Asp Ala Leu Leu Asp Arg Thr Glu Val Pro Ile Ser Val Glu
    400                 405                 410

gag ctc agc cgc gcc tac gag ctc aac ctg ttc tcg cct cgg ctg ccc      2975
Glu Leu Ser Arg Ala Tyr Glu Leu Asn Leu Phe Ser Pro Arg Leu Pro
415                 420                 425                 430

ccc aaa cgt cag cca aac ggc acc tgt gag ccc aac cct cgc ctc aac      3023
Pro Lys Arg Gln Pro Asn Gly Thr Cys Glu Pro Asn Pro Arg Leu Asn
                435                 440                 445

ttc tat ccg gcc ttt gct gtc cca gaa gtg ctt gct acc tac cac atc      3071
Phe Tyr Pro Ala Phe Ala Val Pro Glu Val Leu Ala Thr Tyr His Ile
            450                 455                 460

ttt ttc aag aac caa aag att cca gtt tcc tgc cgt gcc aac cgc acc      3119
Phe Phe Lys Asn Gln Lys Ile Pro Val Ser Cys Arg Ala Asn Arg Thr
        465                 470                 475

cgc gcc gat gcc ctg ctc aac ttg ggt ccg gga gct cgc tta cct gat      3167
Arg Ala Asp Ala Leu Leu Asn Leu Gly Pro Gly Ala Arg Leu Pro Asp
    480                 485                 490

ata gct tcc ttg gaa gag gtt cca aag atc ttc gag ggt ctg ggc agt      3215
Ile Ala Ser Leu Glu Glu Val Pro Lys Ile Phe Glu Gly Leu Gly Ser
495                 500                 505                 510

gat gag act cgg gcc gca aat gct ctg caa cag gga gag aat ggc atg      3263
Asp Glu Thr Arg Ala Ala Asn Ala Leu Gln Gln Gly Glu Asn Gly Met
                515                 520                 525

gat gaa cat cac agc gct ctg gtg gag ttg gag gga gac aat gcc cgg      3311
Asp Glu His His Ser Ala Leu Val Glu Leu Glu Gly Asp Asn Ala Arg
            530                 535                 540

ctt gca gtg ctc aag cgc agt atc gag gtc acc cat ttt gca tac ccc      3359
```

```
Leu Ala Val Leu Lys Arg Ser Ile Glu Val Thr His Phe Ala Tyr Pro
        545                 550                 555

gct gtc aac ctg ccc ccc aaa gtc atg agc gct gtc atg gat cag ctg      3407
Ala Val Asn Leu Pro Pro Lys Val Met Ser Ala Val Met Asp Gln Leu
    560                 565                 570

ctc atc aag cgc gca agc ccc ctt tcc gaa gac cag aac atg cag gat      3455
Leu Ile Lys Arg Ala Ser Pro Leu Ser Glu Asp Gln Asn Met Gln Asp
575                 580                 585                 590

cca gac gcc tct gac gag ggc aag ccg gtg gtc agt gac gag cag ctg      3503
Pro Asp Ala Ser Asp Glu Gly Lys Pro Val Val Ser Asp Glu Gln Leu
                595                 600                 605

tct cgc tgg ctg ggc acc aac tcc ccg cga gac ttg gaa gag agg cgc      3551
Ser Arg Trp Leu Gly Thr Asn Ser Pro Arg Asp Leu Glu Glu Arg Arg
            610                 615                 620

aag ctt atg atg gct gta gtg cta gtc act gtg gag ctg gag tgt ctc      3599
Lys Leu Met Met Ala Val Val Leu Val Thr Val Glu Leu Glu Cys Leu
        625                 630                 635

cgc cgc ttt ttc acc gac cct gag acc ctg cgc aag ctc gag gag aac      3647
Arg Arg Phe Phe Thr Asp Pro Glu Thr Leu Arg Lys Leu Glu Glu Asn
    640                 645                 650

ctg cac tat act ttc aga cat ggt ttc gtg cgc cag gca tgc aag atc      3695
Leu His Tyr Thr Phe Arg His Gly Phe Val Arg Gln Ala Cys Lys Ile
655                 660                 665                 670

tcc aac gtg gag ctc acc aac ctg gtc tcc tac atg ggc att ttg cat      3743
Ser Asn Val Glu Leu Thr Asn Leu Val Ser Tyr Met Gly Ile Leu His
                675                 680                 685

gag aac cgc ctg ggg cag agc gtg ttg cat acc acc ctg aaa ggg gag      3791
Glu Asn Arg Leu Gly Gln Ser Val Leu His Thr Thr Leu Lys Gly Glu
            690                 695                 700

gcc cgc cgc gac tac atc cgc gac tgt gtc tac ctc tac ctc tgc cat      3839
Ala Arg Arg Asp Tyr Ile Arg Asp Cys Val Tyr Leu Tyr Leu Cys His
        705                 710                 715

acc tgg cag act ggc atg ggt gta tgg cag cag tgt ttg gaa gag cag      3887
Thr Trp Gln Thr Gly Met Gly Val Trp Gln Gln Cys Leu Glu Glu Gln
    720                 725                 730

aac ctg aaa gag ctg gac aag ctc ttg cag aga tcc ctc aaa gcc ctg      3935
Asn Leu Lys Glu Leu Asp Lys Leu Leu Gln Arg Ser Leu Lys Ala Leu
735                 740                 745                 750

tgg aca ggt ttt gac gag cgc acc gtc gcc tca gac ctg gca gac atc      3983
Trp Thr Gly Phe Asp Glu Arg Thr Val Ala Ser Asp Leu Ala Asp Ile
                755                 760                 765

atc ttc ccc gag cgt ctc agg gtt act ctg cgc aac ggc ctg cct gac      4031
Ile Phe Pro Glu Arg Leu Arg Val Thr Leu Arg Asn Gly Leu Pro Asp
            770                 775                 780

ttc atg agc cag agc atg ctt aac aac ttt cgc tct ttc atc ctg gaa      4079
Phe Met Ser Gln Ser Met Leu Asn Asn Phe Arg Ser Phe Ile Leu Glu
        785                 790                 795

cgc tcc ggt atc ctg ccc gcc acc tgc tgc gcg ctg ccc tcc gac ttt      4127
Arg Ser Gly Ile Leu Pro Ala Thr Cys Cys Ala Leu Pro Ser Asp Phe
    800                 805                 810

gtg cct ctc acc tac cgc gag tgc ccc ccg ccg cta tgg agc cac tgc      4175
Val Pro Leu Thr Tyr Arg Glu Cys Pro Pro Pro Leu Trp Ser His Cys
815                 820                 825                 830

tac ctg ttc cgc ctg gcc aac tac ctc tcc tac cac tcg gat gtg atc      4223
Tyr Leu Phe Arg Leu Ala Asn Tyr Leu Ser Tyr His Ser Asp Val Ile
                835                 840                 845

gag gat gtg agc gga gac ggt ctg ctg gag tgc cac tgc cgc tgc aat      4271
Glu Asp Val Ser Gly Asp Gly Leu Leu Glu Cys His Cys Arg Cys Asn
            850                 855                 860
```

```
ctt tgc aca ccc cac cgt tcc ctc gcc tgc aac ccc cag ttg ctg agc     4319
Leu Cys Thr Pro His Arg Ser Leu Ala Cys Asn Pro Gln Leu Leu Ser
        865                 870                 875

gag act cag atc atc ggc acc ttc gag ttg cag ggt ccc agc agt gaa     4367
Glu Thr Gln Ile Ile Gly Thr Phe Glu Leu Gln Gly Pro Ser Ser Glu
    880                 885                 890

ggc gag ggg tct tct ccg ggg cag agt ctg aaa ctg act ccg ggg cta     4415
Gly Glu Gly Ser Ser Pro Gly Gln Ser Leu Lys Leu Thr Pro Gly Leu
895                 900                 905                 910

tgg acc tcc gcc tac ctg cgc aag ttc gcc ccc gaa gac tac cac ccc     4463
Trp Thr Ser Ala Tyr Leu Arg Lys Phe Ala Pro Glu Asp Tyr His Pro
                915                 920                 925

tat gag atc agg ttc tat gag gac caa tca cag ccg ccc aaa acc gag     4511
Tyr Glu Ile Arg Phe Tyr Glu Asp Gln Ser Gln Pro Pro Lys Thr Glu
            930                 935                 940

ctc tca gcc tgc gtc atc act cag ggg gca att ctc gcc caa ttg caa     4559
Leu Ser Ala Cys Val Ile Thr Gln Gly Ala Ile Leu Ala Gln Leu Gln
        945                 950                 955

gcc atc caa aaa tcc cgc caa gaa ttt ctg ctg aaa aag ggg aac ggg     4607
Ala Ile Gln Lys Ser Arg Gln Glu Phe Leu Leu Lys Lys Gly Asn Gly
    960                 965                 970

gtc tac ctc gac ccc cag acc ggt gag gag ctc aac aca agg ttc cct     4655
Val Tyr Leu Asp Pro Gln Thr Gly Glu Glu Leu Asn Thr Arg Phe Pro
975                 980                 985                 990

cag gat gtc cca gcg ccg agg aag caa gaa  gtt gaa ggt gca gct  gcc   4703
Gln Asp Val Pro Ala Pro Arg Lys Gln Glu  Val Glu Gly Ala Ala  Ala
                995                 1000                1005

gcc ccc aga gga  tat gga gga aga ctg  gga cag tca ggc aga  gga      4748
Ala Pro Arg Gly  Tyr Gly Gly Arg Leu  Gly Gln Ser Gly Arg  Gly
            1010                1015                1020

gga gga gat gga  aga ttg gga cag cca  ggc aga gga ggc gga  cag      4793
Gly Gly Asp Gly  Arg Leu Gly Gln Pro  Gly Arg Gly Gly Gly  Gln
            1025                1030                1035

cct gga gga aga  cag ttt gga gga gga  aga cga gga ggc aga  gga      4838
Pro Gly Gly Arg  Gln Phe Gly Gly Gly  Arg Arg Gly Gly Arg  Gly
            1040                1045                1050

ggt gga aga agc  agc cgc cgc caa aca  gtt gtc ctc ggc agc  gga      4883
Gly Gly Arg Ser  Ser Arg Arg Gln Thr  Val Val Leu Gly Ser  Gly
            1055                1060                1065

gac aag caa ggc  ccc aga cag cag cag  cag cac ggc tac aat  ctc      4928
Asp Lys Gln Gly  Pro Arg Gln Gln Gln  Gln His Gly Tyr Asn  Leu
            1070                1075                1080

cgc tcc ggg tcg  ggg ggc cca gca gcg  tcc caa cag tagatgggac        4974
Arg Ser Gly Ser  Gly Gly Pro Ala Ala  Ser Gln Gln
            1085                1090

gagaccgggc gattcccgaa cccgaccacc gcttccaaga ccggtaagaa ggagcggcag   5034

ggatacaagt cctggcgggg gcataagaat gccatcatct cctgcttgca tgaatgcggg   5094

ggcaacatat ccttcacccg gcgctacctg ctcttccacc acggggtgaa cttcccccgc   5154

aatgtcttgc attactaccg tcacctccac agcccctact acagccagca agtcccgaca   5214

gcctcggcag agaaagacag cagcagcggg gacctccagc agaaaaccag cagcagcagt   5274

tagaaaatcc agtgcagcag gaggaggact gaggatcaca gcgaacgagc cagcgcagac   5334

ccgagagctg agaaacagga tctttccaac cctctatgcc atcttccagc agagtcgggg   5394

gcaagagcag gaactgaaag taaaaaaccg atctctgcgc tcgctcaccc gaagttgttt   5454

gtatcacaag agcgaagacc aacttcagcg cactctcgag gacgccgagg ctctcttcaa   5514

caagtactgc gcgctgactc ttaaagagta gcccgcgccc gcgctcgctc gaaaaaggcg   5574
```

```
ggaattacgt caccettggc acctgtcctt tgccctcgtc atgagtaaag aaattcccac   5634

gccttacatg tggagctatc agccccaaat gggactggca gcaggcgcct cccaggacta   5694

ctccacccgc atgaattggc tcagcgccgg cccctcgatg atctcacggg ttaatgatat   5754

acgagcttac cgaaaccagt tactcctaga acagtcagct ctcaccacca caccccgcca   5814

acaccttaat ccccggaatt ggcccgccgc cctggtgtac caggaaactc ccgctcccac   5874

caccgtacta cttcctcgag acgcccaggc cgaagttcag atgactaacg caggtgtaca   5934

gctggcgggc ggttccgccc tgtgtcgtca ccggcctcag cagagtataa aacgcctggt   5994

gatcagaggc cgaggtatcc agctcaacga cgagtcggtg agctcttcgc ttggtctgcg   6054

accagacgga gtcttccaaa tcgccggctg tgggagatct tccttcactc ctcgtcaggc   6114

tgtcctgact ttggagagtt cgtcctcgca accccgctcg ggcggcatcg ggactctcca   6174

gtttgtggag gagtttactc cctctgtcta cttcaacccc ttctccggct ctcctggcca   6234

gtacccggac gagttcatac cgaacttcga cgcaatcagc gagtcagtgg atggctatga   6294

ttgatgtctg gtggcgcggc tgagttagct cgactgcgac atctagacca ctgccgccgc   6354

tttcgctgtt tcgcccggga actcaccgag ttcatctact tcgaactccc cgaggagcac   6414

cctcagggac cggcccacgg agtgcggatt accatcgaag gggaatagaa ctctcgcctg   6474

catcggatct tctgccagcg acccgtgctg atcgagcgcg accagggaac tacaacagtc   6534

tccatctact gcatctgtaa ccaccccgga ttgc atg aaa gcc ttt gct gtc      6586
                                      Met Lys Ala Phe Ala Val
                                          1095

tta tt gtg ctg agt tta ata aaa act gag ttc aga ccc tcc tac         6631
Leu Phe Val Leu Ser Leu Ile Lys Thr Glu Phe Arg Pro Ser Tyr
1100                1105                1110

gga cta ccg ctt ctt caa ccc gga ctt tac aac acc agc cag aag        6676
Gly Leu Pro Leu Leu Gln Pro Gly Leu Tyr Asn Thr Ser Gln Lys
1115                1120                1125

acc cag acc ctt cct ctg atc cag gac tct aat tct acc tcc cca        6721
Thr Gln Thr Leu Pro Leu Ile Gln Asp Ser Asn Ser Thr Ser Pro
1130                1135                1140

gca cct ttt cct act aac ctt ccc gtt act aac aac ctc gaa gct        6766
Ala Pro Phe Pro Thr Asn Leu Pro Val Thr Asn Asn Leu Glu Ala
1145                1150                1155

cag ctg caa cac cgc ttc tcc aga agc ctc ctt tct gcc aat act        6811
Gln Leu Gln His Arg Phe Ser Arg Ser Leu Leu Ser Ala Asn Thr
1160                1165                1170

act act ccc aga acc gga ggt gag ctc cgt ggt ctc cct act aac        6856
Thr Thr Pro Arg Thr Gly Gly Glu Leu Arg Gly Leu Pro Thr Asn
1175                1180                1185

aac ccc tgg gtg gta gcg ggt ttt gta gcg cta gga gta gtt gcg        6901
Asn Pro Trp Val Val Ala Gly Phe Val Ala Leu Gly Val Val Ala
1190                1195                1200

ggt ggg ctg gtg ctt ata ctc tgc tac cta tac aca cct tgc tgt        6946
Gly Gly Leu Val Leu Ile Leu Cys Tyr Leu Tyr Thr Pro Cys Cys
1205                1210                1215

gct tat tta gta gta ttg tgt tgc tgg ttt aag aaa tgg ggg tcg        6991
Ala Tyr Leu Val Val Leu Cys Cys Trp Phe Lys Lys Trp Gly Ser
1220                1225                1230

tac tagtagcgct tgctttactt tcgcttttgg gtctgggctc tgctaatctc         7044
Tyr
1235

attcctcccg atcacgatcc atgtctggac tttaatccag agaactgcac aatcactttt   7104
```

```
gcacctgaaa caagtcgctt ctgtggagtt gttattaggt gcggatttga atgcaggccc   7164
attgagatta cacacaataa caaaacttgg aacaatacct tattcacaat atggcaacca   7224
ggagaccctc agtggtatac tgtctctgtc cggggtcctg acggttccgt ccgcatggct   7284
aataacactt ttatttttgc tgaaatgtgc gatatggcca tgttcatgag cagacagtat   7344
gacctatggc ctcccagcaa agagaacatt gtggcattct ccattgctta ttgcttctgt   7404
acttgcctta tcactgctac tttgtgtatt tgcttacact tacttatagc atttcgccca   7464
aaaaacagca acgaggaaaa agaaaaagtg ccttaatctt ttcctcacct tttttgttta   7524
cagcatggct tctgttgctg ttctaatctt tataattaca tcagttcata catttgggct   7584
aaaatttaat gatcaaatag tccatgtagg ttccaaccat acactgcgtg gaccaatagg   7644
caattcagaa gtaacctggt actggtatta tgcagatgat agctggcctg aaaaactttg   7704
tgatgacatt aatttacata acattcttac aaaaactctt aatagtaaga ctattaaata   7764
taactgtact gattatgatt taattctagt taatgtcact acaaactatt caggttttta   7824
ttacggaact aattttgaaa atgttgcata ttataatatt ctagtaaagt ttagacctac   7884
aacaactaaa acgtctagca gcagtactat aaccagcacc acgcttccaa ttagaacagc   7944
aatgtttcaa ttgaacaaaa tagaaaatac caccaatagc aattacactc tattcaacga   8004
tcaaaatgtt caagggtcat taactacaat tatcattcta ctaattgtgg ggttaataat   8064
tataataatt tgcatgatag tctatacctg ccgctacaga aaactacaca ataaagtaga   8124
cccctattag attccatact tagacatcta actttttta aaacacttta ttttcagcca   8184
tgatttctat tacaaccctt ctctatatca ctgccattac tactgtacag gggttcacaa   8244
acatcaaaaa aacaatacat gtgggatcca gttctacact agaaggttac caatcccaat   8304
cacgtgtttc ttggtattgg tattaccgta atcagccagc tattacactt tgcaaaggat   8364
ctcaggaaac cacaatacgc acaatcaaat acaaatgcaa taacaataat ttaaccctaa   8424
ttgatgttac agctcaatat gcaggaactt actatggaac aaattttaac ataggacaag   8484
acacatacta taccattaca gtaattaact ctactactcc tgtaacaact accataaaac   8544
ctacaaaaac taaaagcaca aaaactcaca ttttccctag cagcaagccc acctcaatct   8604
atacaacttc acttttgcaa ctacttcaaa aggctaacgt tacagacaat tatactatta   8664
accccactct tcctagcgaa gagataccca aatcaatgat aggaattatt gctgctgtgg   8724
tagcgggaat gctaattata attctatgta tgatttatta tgcttgctgc tatagaaaat   8784
atgaacatga acaaaaaata gacccactac tgagctttga tatttaattt tttttagagc   8844
accatgaaag gtccagttat cctattgttt atttccactt tttggtgttg tgatactttt   8904
tcaattacca ccaatgtgca gactacttta aataacatca tgactacctc taacacacaa   8964
ctttcacctc aatctgaaga tgacataaaa ctacaaatca ctatccttat tgtaattggt   9024
ttaattatcc ttgctgttct cctttacttt atcttttgcc gtcaaatacc caatgtagtt   9084
aagaaaccta ccagacgtcc catctatcga tcaataatca gcaaaccccca catggctcta   9144
aatgaaattt aatctttctc ttcacagtat ggtgatcaac tatgatccct agaaatttct   9204
tcttcaccat acttatctgc gctttcaatg tctgtgctac attcgccaca gtcgccaatg   9264
tgacaccaga ttgtataggg gcatttgctt cctacgtact atttgccttc attacctgca   9324
tctgcgtttg tagcatagtc tgcctggtta tcaacttctt tcaactagta gactgggttt   9384
ttgtacgcat tgcctaccta caacatcacc ctgaataccg caaccaaa atg ttg cag   9441
                                                    Met Leu Gln
```

```
caa ttc  tta ggc tca ttt aaa  acc atg caa act ctg  cta ctg ctt      9486
Gln Phe  Leu Gly Ser Phe Lys  Thr Met Gln Thr Leu  Leu Leu Leu
    1240                 1245                 1250

ctg cta  gtt ata cac cca tgt  gcc tca aac ccc aca  agc ccc aca      9531
Leu Leu  Val Ile His Pro Cys  Ala Ser Asn Pro Thr  Ser Pro Thr
    1255                 1260                 1265

aaa tta  gat cta aga aaa tgt  aaa ttt caa gaa cca  tgg aaa ttc      9576
Lys Leu  Asp Leu Arg Lys Cys  Lys Phe Gln Glu Pro  Trp Lys Phe
    1270                 1275                 1280

ctt gat  tgc tat cat gaa aca  tct gat ttc ccc aca  tac tgg att      9621
Leu Asp  Cys Tyr His Glu Thr  Ser Asp Phe Pro Thr  Tyr Trp Ile
    1285                 1290                 1295

aca atc  att ggg gtt gtt aat  cta gtc tct tgc aca  cta ttc tct      9666
Thr Ile  Ile Gly Val Val Asn  Leu Val Ser Cys Thr  Leu Phe Ser
    1300                 1305                 1310

ttc ctt  gtt tac cac tta ttt  gat ttt gga tgg aac  tcc ctc aat      9711
Phe Leu  Val Tyr His Leu Phe  Asp Phe Gly Trp Asn  Ser Leu Asn
    1315                 1320                 1325

gca ctc  act tac cca caa gaa  cca gag gaa cat ata  cca cta cag      9756
Ala Leu  Thr Tyr Pro Gln Glu  Pro Glu Glu His Ile  Pro Leu Gln
    1330                 1335                 1340

aac ata  caa cca tta gca cta  gta gaa tat gaa aat  gag cca cag      9801
Asn Ile  Gln Pro Leu Ala Leu  Val Glu Tyr Glu Asn  Glu Pro Gln
    1345                 1350                 1355

cct cca  cta ctc cct gcc att  agc tac ttc aac tta  acc ggt gga      9846
Pro Pro  Leu Leu Pro Ala Ile  Ser Tyr Phe Asn Leu  Thr Gly Gly
    1360                 1365                 1370

gat gac  tgacccac                                                  9860
Asp Asp
    1375
```

<210> SEQ ID NO 58
<211> LENGTH: 262
<212> TYPE: PRT
<213> ORGANISM: Unknown
<220> FEATURE:
<223> OTHER INFORMATION: Synthetic Construct

<400> SEQUENCE: 58

```
Met Ser Pro Pro Cys Phe Met Phe Phe Ser Lys Ser Ser Thr Trp Ser
1               5                   10                  15

Glu Cys Thr Ser His Thr Ala Ala Ser Ser Arg Leu Ser Thr Cys Val
            20                  25                  30

Pro Arg Ser Gln Leu Val Thr Pro Pro His Lys Glu Ala Ser Cys Phe
        35                  40                  45

Leu Gln Ala Ala Ala Met Ala Cys Gly Ser Gly Asn Gly Ser Ser Glu
    50                  55                  60

Gln Glu Leu Arg Ala Ile Ala Arg Asp Leu Gly Cys Gly Pro Tyr Phe
65                  70                  75                  80

Leu Gly Thr Phe Asp Lys Arg Phe Pro Gly Phe Met Ala Pro Asp Lys
                85                  90                  95

Leu Ala Cys Ala Ile Val Asn Thr Ala Gly Arg Glu Thr Gly Gly Glu
            100                 105                 110

His Trp Leu Ala Phe Gly Trp Asn Pro Arg Ser Asn Thr Cys Tyr Leu
        115                 120                 125

Phe Asp Pro Phe Gly Phe Ser Asp Glu Arg Leu Lys Gln Ile Tyr Gln
    130                 135                 140

Phe Glu Tyr Glu Gly Leu Leu Arg Arg Ser Ala Leu Ala Thr Lys Asp
145                 150                 155                 160
```

```
Arg Cys Ile Thr Leu Glu Lys Ser Thr Gln Thr Val Gln Gly Pro Arg
                165                 170                 175

Ser Ala Ala Cys Gly Leu Phe Cys Cys Met Phe Leu His Ala Phe Val
            180                 185                 190

His Trp Pro Asp Arg Pro Met Asp Gly Asn Pro Thr Met Lys Leu Leu
        195                 200                 205

Thr Gly Val Pro Asn Ser Met Leu Gln Ser Pro Gln Val Gln Pro Thr
    210                 215                 220

Leu Arg His Asn Gln Glu Ala Leu Tyr Arg Phe Leu Asn Ser His Ser
225                 230                 235                 240

Ser Tyr Phe Arg Ser His Arg Ala Arg Ile Glu Lys Ala Thr Ala Phe
                245                 250                 255

Asn Arg Met Asp Met Gln
            260


<210> SEQ ID NO 59
<211> LENGTH: 831
<212> TYPE: PRT
<213> ORGANISM: Unknown
<220> FEATURE:
<223> OTHER INFORMATION: Synthetic Construct

<400> SEQUENCE: 59

Met Glu Thr Gln Pro Ser Leu Pro Thr Pro Leu Gln Ala Pro Ser His
1               5                   10                  15

Leu Ala Pro Ser Ser Asp Glu Glu Glu Ser Leu Thr Thr Pro Pro Pro
            20                  25                  30

Ser Pro Ala Thr Thr Thr Ser Thr Leu Glu Asp Glu Glu Glu Val Asp
        35                  40                  45

Ala Pro Gln Glu Met Gln Asp Met Glu Asp Glu Lys Ala Glu Glu Ile
    50                  55                  60

Glu Ala Asp Val Glu Gln Asp Pro Gly Tyr Val Thr Pro Ala Glu His
65                  70                  75                  80

Glu Glu Glu Leu Arg Arg Phe Leu Asp Arg Glu Asp Asp Asn Arg Pro
                85                  90                  95

Glu Gln Lys Ala Asp Gly Asp His Gln Glu Ala Gly Leu Gly Asp His
            100                 105                 110

Val Ala Asp Tyr Leu Thr Gly Leu Gly Gly Glu Asp Val Leu Leu Lys
        115                 120                 125

His Leu Ala Arg Gln Ser Ile Ile Val Lys Asp Ala Leu Leu Asp Arg
    130                 135                 140

Thr Glu Val Pro Ile Ser Val Glu Glu Leu Ser Arg Ala Tyr Glu Leu
145                 150                 155                 160

Asn Leu Phe Ser Pro Arg Leu Pro Pro Lys Arg Gln Pro Asn Gly Thr
                165                 170                 175

Cys Glu Pro Asn Pro Arg Leu Asn Phe Tyr Pro Ala Phe Ala Val Pro
            180                 185                 190

Glu Val Leu Ala Thr Tyr His Ile Phe Phe Lys Asn Gln Lys Ile Pro
        195                 200                 205

Val Ser Cys Arg Ala Asn Arg Thr Arg Ala Asp Ala Leu Leu Asn Leu
    210                 215                 220

Gly Pro Gly Ala Arg Leu Pro Asp Ile Ala Ser Leu Glu Glu Val Pro
225                 230                 235                 240

Lys Ile Phe Glu Gly Leu Gly Ser Asp Glu Thr Arg Ala Ala Asn Ala
                245                 250                 255
```

```
Leu Gln Gln Gly Glu Asn Gly Met Asp Glu His His Ser Ala Leu Val
            260                 265                 270

Glu Leu Glu Gly Asp Asn Ala Arg Leu Ala Val Leu Lys Arg Ser Ile
        275                 280                 285

Glu Val Thr His Phe Ala Tyr Pro Ala Val Asn Leu Pro Pro Lys Val
    290                 295                 300

Met Ser Ala Val Met Asp Gln Leu Leu Ile Lys Arg Ala Ser Pro Leu
305                 310                 315                 320

Ser Glu Asp Gln Asn Met Gln Asp Pro Asp Ala Ser Asp Glu Gly Lys
                325                 330                 335

Pro Val Val Ser Asp Glu Gln Leu Ser Arg Trp Leu Gly Thr Asn Ser
            340                 345                 350

Pro Arg Asp Leu Glu Glu Arg Arg Lys Leu Met Met Ala Val Val Leu
        355                 360                 365

Val Thr Val Glu Leu Glu Cys Leu Arg Arg Phe Phe Thr Asp Pro Glu
    370                 375                 380

Thr Leu Arg Lys Leu Glu Glu Asn Leu His Tyr Thr Phe Arg His Gly
385                 390                 395                 400

Phe Val Arg Gln Ala Cys Lys Ile Ser Asn Val Glu Leu Thr Asn Leu
                405                 410                 415

Val Ser Tyr Met Gly Ile Leu His Glu Asn Arg Leu Gly Gln Ser Val
            420                 425                 430

Leu His Thr Thr Leu Lys Gly Glu Ala Arg Arg Asp Tyr Ile Arg Asp
        435                 440                 445

Cys Val Tyr Leu Tyr Leu Cys His Thr Trp Gln Thr Gly Met Gly Val
    450                 455                 460

Trp Gln Gln Cys Leu Glu Glu Gln Asn Leu Lys Glu Leu Asp Lys Leu
465                 470                 475                 480

Leu Gln Arg Ser Leu Lys Ala Leu Trp Thr Gly Phe Asp Glu Arg Thr
                485                 490                 495

Val Ala Ser Asp Leu Ala Asp Ile Ile Phe Pro Glu Arg Leu Arg Val
            500                 505                 510

Thr Leu Arg Asn Gly Leu Pro Asp Phe Met Ser Gln Ser Met Leu Asn
        515                 520                 525

Asn Phe Arg Ser Phe Ile Leu Glu Arg Ser Gly Ile Leu Pro Ala Thr
    530                 535                 540

Cys Cys Ala Leu Pro Ser Asp Phe Val Pro Leu Thr Tyr Arg Glu Cys
545                 550                 555                 560

Pro Pro Pro Leu Trp Ser His Cys Tyr Leu Phe Arg Leu Ala Asn Tyr
                565                 570                 575

Leu Ser Tyr His Ser Asp Val Ile Glu Asp Val Ser Gly Asp Gly Leu
            580                 585                 590

Leu Glu Cys His Cys Arg Cys Asn Leu Cys Thr Pro His Arg Ser Leu
        595                 600                 605

Ala Cys Asn Pro Gln Leu Leu Ser Glu Thr Gln Ile Ile Gly Thr Phe
    610                 615                 620

Glu Leu Gln Gly Pro Ser Ser Glu Gly Glu Gly Ser Ser Pro Gly Gln
625                 630                 635                 640

Ser Leu Lys Leu Thr Pro Gly Leu Trp Thr Ser Ala Tyr Leu Arg Lys
                645                 650                 655

Phe Ala Pro Glu Asp Tyr His Pro Tyr Glu Ile Arg Phe Tyr Glu Asp
            660                 665                 670
```

```
Gln Ser Gln Pro Pro Lys Thr Glu Leu Ser Ala Cys Val Ile Thr Gln
        675                 680                 685

Gly Ala Ile Leu Ala Gln Leu Gln Ala Ile Gln Lys Ser Arg Gln Glu
    690                 695                 700

Phe Leu Leu Lys Lys Gly Asn Gly Val Tyr Leu Asp Pro Gln Thr Gly
705                 710                 715                 720

Glu Glu Leu Asn Thr Arg Phe Pro Gln Asp Val Pro Ala Pro Arg Lys
                725                 730                 735

Gln Glu Val Glu Gly Ala Ala Ala Ala Pro Arg Gly Tyr Gly Gly Arg
            740                 745                 750

Leu Gly Gln Ser Gly Arg Gly Gly Gly Asp Gly Arg Leu Gly Gln Pro
        755                 760                 765

Gly Arg Gly Gly Gly Gln Pro Gly Gly Arg Gln Phe Gly Gly Gly Arg
    770                 775                 780

Arg Gly Gly Arg Gly Gly Gly Arg Ser Ser Arg Arg Gln Thr Val Val
785                 790                 795                 800

Leu Gly Ser Gly Asp Lys Gln Gly Pro Arg Gln Gln Gln Gln His Gly
                805                 810                 815

Tyr Asn Leu Arg Ser Gly Ser Gly Gly Pro Ala Ala Ser Gln Gln
            820                 825                 830


<210> SEQ ID NO 60
<211> LENGTH: 142
<212> TYPE: PRT
<213> ORGANISM: Unknown
<220> FEATURE:
<223> OTHER INFORMATION: Synthetic Construct

<400> SEQUENCE: 60

Met Lys Ala Phe Ala Val Leu Phe Val Leu Ser Leu Ile Lys Thr Glu
1               5                   10                  15

Phe Arg Pro Ser Tyr Gly Leu Pro Leu Leu Gln Pro Gly Leu Tyr Asn
            20                  25                  30

Thr Ser Gln Lys Thr Gln Thr Leu Pro Leu Ile Gln Asp Ser Asn Ser
        35                  40                  45

Thr Ser Pro Ala Pro Phe Pro Thr Asn Leu Pro Val Thr Asn Asn Leu
    50                  55                  60

Glu Ala Gln Leu Gln His Arg Phe Ser Arg Ser Leu Leu Ser Ala Asn
65                  70                  75                  80

Thr Thr Thr Pro Arg Thr Gly Gly Glu Leu Arg Gly Leu Pro Thr Asn
                85                  90                  95

Asn Pro Trp Val Val Ala Gly Phe Val Ala Leu Gly Val Val Ala Gly
            100                 105                 110

Gly Leu Val Leu Ile Leu Cys Tyr Leu Tyr Thr Pro Cys Cys Ala Tyr
        115                 120                 125

Leu Val Val Leu Cys Cys Trp Phe Lys Lys Trp Gly Ser Tyr
    130                 135                 140


<210> SEQ ID NO 61
<211> LENGTH: 140
<212> TYPE: PRT
<213> ORGANISM: Unknown
<220> FEATURE:
<223> OTHER INFORMATION: Synthetic Construct

<400> SEQUENCE: 61

Met Leu Gln Gln Phe Leu Gly Ser Phe Lys Thr Met Gln Thr Leu Leu
1               5                   10                  15
```

```
Leu Leu Leu Leu Val Ile His Pro Cys Ala Ser Asn Pro Thr Ser Pro
            20                  25                  30

Thr Lys Leu Asp Leu Arg Lys Cys Lys Phe Gln Glu Pro Trp Lys Phe
        35                  40                  45

Leu Asp Cys Tyr His Glu Thr Ser Asp Phe Pro Thr Tyr Trp Ile Thr
    50                  55                  60

Ile Ile Gly Val Val Asn Leu Val Ser Cys Thr Leu Phe Ser Phe Leu
65                  70                  75                  80

Val Tyr His Leu Phe Asp Phe Gly Trp Asn Ser Leu Asn Ala Leu Thr
                85                  90                  95

Tyr Pro Gln Glu Pro Glu Glu His Ile Pro Leu Gln Asn Ile Gln Pro
            100                 105                 110

Leu Ala Leu Val Glu Tyr Glu Asn Glu Pro Gln Pro Pro Leu Leu Pro
        115                 120                 125

Ala Ile Ser Tyr Phe Asn Leu Thr Gly Gly Asp Asp
    130                 135                 140


<210> SEQ ID NO 62
<211> LENGTH: 1500
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (573)..(1149)
<223> OTHER INFORMATION: E1a
<220> FEATURE:
<221> NAME/KEY: CDS
<222> LOCATION: (1243)..(1448)
<223> OTHER INFORMATION: E1a

<400> SEQUENCE: 62

catcatcaat aatatacctt ataaatggaa cggtgccaac atgcaaatga gcttttgaaa      60

atggagggcg gaaggggatt ggccagcggg ttcaacggtc aaaaggggcg ggccggcgcg     120

gggaggtgac gtggttagtg tgggaggagt tatgttgcaa gttctcgcgg taaatgtgac     180

gtaaaacgag gtgtggtttg aacacggaag tacacagttt tcccgcgctg actgacagga     240

tatgaggtag ttttgggcgg atgcaagtga aaattctcca ttttcgcgcg aaaactgaat     300

gaggaagtga atttctgagt aatttcgagt ttatgacagg gcggagtatt taccgagggc     360

cgagtagact ttgaccgatt acgtggaggt ttcgattacc gtgtttttca cctaaatttc     420

cgcgtacggt gtcaaagtcc tgtgttttta cgtaggcgtc agctgatcgc tagggtattt     480

aaacctgacg agttccgtca agaggccact cttgagtgcc agcgagaaga gatttctcct     540

ccgcgccgcg agtcagatct ccactttgaa aa atg aga cac ctg cga ttc ctg       593
                                    Met Arg His Leu Arg Phe Leu
                                    1               5

cct cag gaa atc tcc att gcg acc ggg aat gaa ata ctg cag ttt gtg       641
Pro Gln Glu Ile Ser Ile Ala Thr Gly Asn Glu Ile Leu Gln Phe Val
        10                  15                  20

gta gat gcc ctg atg gga gac gat ccg gag ccg cct gcg cag cct ttc       689
Val Asp Ala Leu Met Gly Asp Asp Pro Glu Pro Pro Ala Gln Pro Phe
    25                  30                  35

gat cct cct acg ctt cat gaa ctg tat gat tta gag gta gac ggg ccg       737
Asp Pro Pro Thr Leu His Glu Leu Tyr Asp Leu Glu Val Asp Gly Pro
40                  45                  50                  55

gag gat cct aac gag gaa gct gtg aat ggt ttt ttc agc gat tct atg       785
Glu Asp Pro Asn Glu Glu Ala Val Asn Gly Phe Phe Ser Asp Ser Met
```

```
                60                  65                  70

cta tta gct gct agt gaa gga gtg gac tta gac cca cct tct gag acc      833
Leu Leu Ala Ala Ser Glu Gly Val Asp Leu Asp Pro Pro Ser Glu Thr
            75                  80                  85

ctt gat acc cca ggg gtg gtg gtg gaa agc ggc aga ggt ggg aaa aaa      881
Leu Asp Thr Pro Gly Val Val Val Glu Ser Gly Arg Gly Gly Lys Lys
        90                  95                  100

ttg cct gaa ctt ggt gct gct gaa atg gat ttg cac tgt tat gaa gag      929
Leu Pro Glu Leu Gly Ala Ala Glu Met Asp Leu His Cys Tyr Glu Glu
    105                 110                 115

ggc ttt cct ccg agt gat gat gaa gat gag gaa aat gtg cag tcg atc      977
Gly Phe Pro Pro Ser Asp Asp Glu Asp Glu Glu Asn Val Gln Ser Ile
120                 125                 130                 135

cag acc gca gct ggt gag gga atg aaa gct gcc aat gat ggt ttt aag     1025
Gln Thr Ala Ala Gly Glu Gly Met Lys Ala Ala Asn Asp Gly Phe Lys
                140                 145                 150

ttg gac tac ccg gag ctg cct gga cat ggc tgt aag tct tgt gaa ttt     1073
Leu Asp Tyr Pro Glu Leu Pro Gly His Gly Cys Lys Ser Cys Glu Phe
            155                 160                 165

cac agg aat agt act gga cta aaa gaa ctg ttg tgc tcg ctt tgc tat     1121
His Arg Asn Ser Thr Gly Leu Lys Glu Leu Leu Cys Ser Leu Cys Tyr
        170                 175                 180

atg aga acg cac tgc cat ttt att tac a gtaagtgtgt ttaagttaaa         1169
Met Arg Thr His Cys His Phe Ile Tyr
    185                 190

tttaaaggga cagtgtagca gtgttaataa ctgtgaatgt gggatttatg tttttgctt   1229

gtgattttta tag gt  cct gtg tct gat gct gat gaa tcg cct tct cct      1277
               Ser Pro Val Ser Asp Ala Asp Glu Ser Pro Ser Pro
                       195                 200

gat tca act acc tca cct cct gaa att cag gcg cca gtc cct gca aac     1325
Asp Ser Thr Thr Ser Pro Pro Glu Ile Gln Ala Pro Val Pro Ala Asn
205                 210                 215                 220

gta tgc aag ccc att cct gtg aag gct aag cct ggg aaa cgc cct gct     1373
Val Cys Lys Pro Ile Pro Val Lys Ala Lys Pro Gly Lys Arg Pro Ala
                225                 230                 235

gtg gat aag ctg gag gac ttg ctt gag ggt ggg gat gga cct ttg gac     1421
Val Asp Lys Leu Glu Asp Leu Leu Glu Gly Gly Asp Gly Pro Leu Asp
            240                 245                 250

ttg agt acc cgg aaa ctg cca agg caa tgagtaccct gcacctgtgt           1468
Leu Ser Thr Arg Lys Leu Pro Arg Gln
        255                 260

ttatttaatg tgacgtcagt atttatgtga ga                                 1500
```

<210> SEQ ID NO 63
<211> LENGTH: 261
<212> TYPE: PRT
<213> ORGANISM: Unknown
<220> FEATURE:
<223> OTHER INFORMATION: Synthetic Construct

<400> SEQUENCE: 63

```
Met Arg His Leu Arg Phe Leu Pro Gln Glu Ile Ser Ile Ala Thr Gly
1               5                   10                  15

Asn Glu Ile Leu Gln Phe Val Val Asp Ala Leu Met Gly Asp Asp Pro
            20                  25                  30

Glu Pro Pro Ala Gln Pro Phe Asp Pro Pro Thr Leu His Glu Leu Tyr
        35                  40                  45

Asp Leu Glu Val Asp Gly Pro Glu Asp Pro Asn Glu Glu Ala Val Asn
    50                  55                  60
```

```
Gly Phe Phe Ser Asp Ser Met Leu Leu Ala Ala Ser Glu Gly Val Asp
65                  70                  75                  80

Leu Asp Pro Pro Ser Glu Thr Leu Asp Thr Pro Gly Val Val Val Glu
                85                  90                  95

Ser Gly Arg Gly Gly Lys Lys Leu Pro Glu Leu Gly Ala Ala Glu Met
            100                 105                 110

Asp Leu His Cys Tyr Glu Glu Gly Phe Pro Pro Ser Asp Asp Glu Asp
        115                 120                 125

Glu Glu Asn Val Gln Ser Ile Gln Thr Ala Ala Gly Glu Gly Met Lys
    130                 135                 140

Ala Ala Asn Asp Gly Phe Lys Leu Asp Tyr Pro Glu Leu Pro Gly His
145                 150                 155                 160

Gly Cys Lys Ser Cys Glu Phe His Arg Asn Ser Thr Gly Leu Lys Glu
                165                 170                 175

Leu Leu Cys Ser Leu Cys Tyr Met Arg Thr His Cys His Phe Ile Tyr
            180                 185                 190

Ser Pro Val Ser Asp Ala Asp Glu Ser Pro Ser Pro Asp Ser Thr Thr
        195                 200                 205

Ser Pro Pro Glu Ile Gln Ala Pro Val Pro Ala Asn Val Cys Lys Pro
    210                 215                 220

Ile Pro Val Lys Ala Lys Pro Gly Lys Arg Pro Ala Val Asp Lys Leu
225                 230                 235                 240

Glu Asp Leu Leu Glu Gly Gly Asp Gly Pro Leu Asp Leu Ser Thr Arg
                245                 250                 255

Lys Leu Pro Arg Gln
            260


<210> SEQ ID NO 64
<211> LENGTH: 900
<212> TYPE: DNA
<213> ORGANISM: Unknown
<220> FEATURE:
<223> OTHER INFORMATION: Simian adenovirus 41.2
<220> FEATURE:
<221> NAME/KEY: CDS
<222> LOCATION: (10)..(367)
<223> OTHER INFORMATION: 33K
<220> FEATURE:
<221> NAME/KEY: CDS
<222> LOCATION: (537)..(892)
<223> OTHER INFORMATION: 33K

<400> SEQUENCE: 64

tccctcagg atg tcc cag cgc cga gga agc aag aag ttg aag gtg cag ctg      51
          Met Ser Gln Arg Arg Gly Ser Lys Lys Leu Lys Val Gln Leu
          1               5                   10

ccg ccc cca gag gat atg gag gaa gac tgg gac agt cag gca gag gag       99
Pro Pro Pro Glu Asp Met Glu Glu Asp Trp Asp Ser Gln Ala Glu Glu
15                  20                  25                  30

gag gag atg gaa gat tgg gac agc cag gca gag gag gcg gac agc ctg      147
Glu Glu Met Glu Asp Trp Asp Ser Gln Ala Glu Glu Ala Asp Ser Leu
      35                  40                  45

gag gaa gac agt ttg gag gag gaa gac gag gag gca gag gag gtg gaa      195
Glu Glu Asp Ser Leu Glu Glu Glu Asp Glu Glu Ala Glu Glu Val Glu
  50                  55                  60

gaa gca gcc gcc gcc aaa cag ttg tcc tcg gca gcg gag aca agc aag      243
Glu Ala Ala Ala Ala Lys Gln Leu Ser Ser Ala Ala Glu Thr Ser Lys
65                  70                  75

gcc cca gac agc agc agc agc acg gct aca atc tcc gct ccg ggt cgg      291
```

```
Ala Pro Asp Ser Ser Ser Ser Thr Ala Thr Ile Ser Ala Pro Gly Arg
80                  85                  90

ggg gcc cag cag cgt ccc aac agt aga tgg gac gag acc ggg cga ttc      339
Gly Ala Gln Gln Arg Pro Asn Ser Arg Trp Asp Glu Thr Gly Arg Phe
95                  100                 105                 110

ccg aac ccg acc acc gct tcc aag acc g gtaagaagga gcggcaggga          387
Pro Asn Pro Thr Thr Ala Ser Lys Thr
        115

tacaagtcct ggcgggggca taagaatgcc atcatctcct gcttgcatga atgcgggggc    447

aacatatcct tcacccggcg ctacctgctc ttccaccacg ggtgaactt cccccgcaat     507

gtcttgcatt actaccgtca cctccacag cc  cct act aca gcc agc aag tcc      559
                                Ala Pro Thr Thr Ala Ser Lys Ser
                                120                 125

cga cag cct cgg cag aga aag aca gca gca gcg ggg acc tcc agc aga      607
Arg Gln Pro Arg Gln Arg Lys Thr Ala Ala Ala Gly Thr Ser Ser Arg
        130                 135                 140

aaa cca gca gca gca gtt aga aaa tcc agt gca gca gga gga gga ctg      655
Lys Pro Ala Ala Ala Val Arg Lys Ser Ser Ala Ala Gly Gly Gly Leu
    145                 150                 155

agg atc aca gcg aac gag cca gcg cag acc cga gag ctg aga aac agg      703
Arg Ile Thr Ala Asn Glu Pro Ala Gln Thr Arg Glu Leu Arg Asn Arg
160                 165                 170                 175

atc ttt cca acc ctc tat gcc atc ttc cag cag agt cgg ggg caa gag      751
Ile Phe Pro Thr Leu Tyr Ala Ile Phe Gln Gln Ser Arg Gly Gln Glu
                180                 185                 190

cag gaa ctg aaa gta aaa aac cga tct ctg cgc tcg ctc acc cga agt      799
Gln Glu Leu Lys Val Lys Asn Arg Ser Leu Arg Ser Leu Thr Arg Ser
            195                 200                 205

tgt ttg tat cac aag agc gaa gac caa ctt cag cgc act ctc gag gac      847
Cys Leu Tyr His Lys Ser Glu Asp Gln Leu Gln Arg Thr Leu Glu Asp
        210                 215                 220

gcc gag gct ctc ttc aac aag tac tgc gcg ctg act ctt aaa gag          892
Ala Glu Ala Leu Phe Asn Lys Tyr Cys Ala Leu Thr Leu Lys Glu
    225                 230                 235

tagcccgc                                                             900


<210> SEQ ID NO 65
<211> LENGTH: 238
<212> TYPE: PRT
<213> ORGANISM: Unknown
<220> FEATURE:
<223> OTHER INFORMATION: Synthetic Construct

<400> SEQUENCE: 65

Met Ser Gln Arg Arg Gly Ser Lys Lys Leu Lys Val Gln Leu Pro Pro
1               5                   10                  15

Pro Glu Asp Met Glu Glu Asp Trp Asp Ser Gln Ala Glu Glu Glu Glu
            20                  25                  30

Met Glu Asp Trp Asp Ser Gln Ala Glu Glu Ala Asp Ser Leu Glu Glu
        35                  40                  45

Asp Ser Leu Glu Glu Glu Asp Glu Glu Ala Glu Glu Val Glu Glu Ala
    50                  55                  60

Ala Ala Ala Lys Gln Leu Ser Ser Ala Ala Glu Thr Ser Lys Ala Pro
65                  70                  75                  80

Asp Ser Ser Ser Ser Thr Ala Thr Ile Ser Ala Pro Gly Arg Gly Ala
                85                  90                  95

Gln Gln Arg Pro Asn Ser Arg Trp Asp Glu Thr Gly Arg Phe Pro Asn
            100                 105                 110
```

```
Pro Thr Thr Ala Ser Lys Thr Ala Pro Thr Thr Ala Ser Lys Ser Arg
        115                 120                 125

Gln Pro Arg Gln Arg Lys Thr Ala Ala Ala Gly Thr Ser Ser Arg Lys
    130                 135                 140

Pro Ala Ala Ala Val Arg Lys Ser Ser Ala Ala Gly Gly Gly Leu Arg
145                 150                 155                 160

Ile Thr Ala Asn Glu Pro Ala Gln Thr Arg Glu Leu Arg Asn Arg Ile
                165                 170                 175

Phe Pro Thr Leu Tyr Ala Ile Phe Gln Gln Ser Arg Gly Gln Glu Gln
            180                 185                 190

Glu Leu Lys Val Lys Asn Arg Ser Leu Arg Ser Leu Thr Arg Ser Cys
        195                 200                 205

Leu Tyr His Lys Ser Glu Asp Gln Leu Gln Arg Thr Leu Glu Asp Ala
    210                 215                 220

Glu Ala Leu Phe Asn Lys Tyr Cys Ala Leu Thr Leu Lys Glu
225                 230                 235


<210> SEQ ID NO 66
<211> LENGTH: 48
<212> TYPE: DNA
<213> ORGANISM: Unknown
<220> FEATURE:
<223> OTHER INFORMATION: based on Simian adenovirus 41.2

<400> SEQUENCE: 66

gatcggcgcg ccacgcgtgc ggccgcttac aggattcgag cagttatt                48


<210> SEQ ID NO 67
<211> LENGTH: 20
<212> TYPE: DNA
<213> ORGANISM: Unknown
<220> FEATURE:
<223> OTHER INFORMATION: Simian adenovirus 41.2

<400> SEQUENCE: 67

ctggccctgt ggttccgcag                                               20


<210> SEQ ID NO 68
<211> LENGTH: 30
<212> TYPE: DNA
<213> ORGANISM: Unknown
<220> FEATURE:
<223> OTHER INFORMATION: Simian adenovirus 41.2

<400> SEQUENCE: 68

gatcacgcgt taacgcaggt gtacagctgg                                    30


<210> SEQ ID NO 69
<211> LENGTH: 50
<212> TYPE: DNA
<213> ORGANISM: Unknown
<220> FEATURE:
<223> OTHER INFORMATION: Simian adenovirus 41.2

<400> SEQUENCE: 69

catgacgcgt actgattttt caataaaaag ttaaatttat ttttgttgtc              50
```

SIMIAN ADENOVIRUS 41 AND USES THEREOF

CROSS-REFERENCE TO RELATED APPLICATIONS

This application is a continuation of U.S. patent application Ser. No. 13/321,985, filed Nov. 22, 2011, now U.S. Pat. No. 8,846,031, issued Sep. 30, 2014, which is national stage of International Patent Application No. PCT/US2010/036332, filed May 27, 2010 (now expired), which claims the benefit under 35 USC 119(e) of U.S. Patent Application No. 61/182,290, filed on May 29, 2009, and 61/219,917, filed Jun. 24, 2009, all of which are incorporated by reference herein.

STATEMENT REGARDING FEDERALLY SPONSORED RESEARCH OR DEVELOPMENT

This invention was made with government support under grant number P30-DK47757 awarded by the National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. These file is labeled "UPN_U4710C1_ST25.txt".

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.,* 81:2573-2604 (November 2000)]. The virus genome is a linear, double-stranded DNA with a terminal protein attached covalently to the 5' terminus, which have inverted terminal repeats (ITRs). The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

A classification scheme has been developed for the Mastadenovirus family, which includes human, simian, bovine, equine, porcine, ovine, canine and opossum adenoviruses. This classification scheme was developed based on the differing abilities of the adenovirus sequences in the family to agglutinate red blood cells. The result was six subgroups, now referred to as subgroups A, B, C, D, E and F. See, T. Shenk et al., *Adenoviridae: The Viruses and their Replication*", Ch. 67, in FIELD'S VIROLOGY, 6th Ed., edited by B. N Fields et al, (Lippincott Raven Publishers, Philadelphia, 1996), p. 111-2112.

Recombinant adenoviruses have been described for delivery of heterologous molecules to host cells. See, U.S. Pat. No. 6,083,716, which describes the genome of two chimpanzee adenoviruses. Simian adenoviruses, C5, C6 and C7, have been described in U.S. Pat. No. 7,247,472 as being useful as vaccine vectors. Other chimpanzee adenoviruses are described in WO 2005/1071093 as being useful for making adenovirus vaccine carriers.

Additional adenovirus isolates useful in preparing vectors useful for therapy and/or immunogenic applications are needed.

SUMMARY OF THE INVENTION

Isolated nucleic acid sequences and amino acid sequences of simian adenovirus 41 (SAdV-41) and vectors containing these sequences are provided herein. Also provided are a number of methods for using the vectors and cells of the invention.

The methods described herein involve delivering one or more selected heterologous gene(s) to a mammalian patient by administering a vector of the invention. Use of the compositions described herein for vaccination permits presentation of a selected antigen for the elicitation of protective immune responses. The vectors based on simian adenovirus 41 may also be used for producing heterologous gene products in vitro. Such gene products are themselves useful in a variety for a variety of purposes such as are described herein.

These and other embodiments and advantages of the invention are described in more detail below.

DETAILED DESCRIPTION OF THE INVENTION

Novel nucleic acid and amino acid sequences from simian adenovirus 41, which was isolated from chimpanzee feces, are provided. Also provided are novel adenovirus vectors and packaging cell lines to produce those vectors for use in the in vitro production of recombinant proteins or fragments or other reagents. Further provided are compositions for use in delivering a heterologous molecule for therapeutic or vaccine purposes. Such therapeutic or vaccine compositions contain the adenoviral vectors carrying an inserted heterologous molecule. In addition, the novel SAdV-41 sequences are useful in providing the essential helper functions required for production of recombinant adeno-associated viral (AAV) vectors. Thus, helper constructs, methods and cell lines which use these sequences in such production methods, are provided.

The SAdV-41 sequence has been determined by the inventors to be within the same subgroup as human subgroup B adenoviruses. Human species B adenoviruses have previously been subclassified into B:1 and B:2 subclades based on restriction enzyme digestion patterns and are seen to cluster separately. SAdV-41 clusters with the human B:1 isolates.

In one embodiment, the invention provides a novel adenovirus isolate which is termed SAdV41.1. In another embodiment, the invention provides a novel adenovirus isolate termed SAdV41.2. These two isolates have hexon proteins which are 100% identical at the amino acid level (i.e., SEQ ID NO: 11 and SEQ ID NO:44 are identical). Except where otherwise specified, the constructs described herein and the uses for the adenoviral sequences and constructs are applicable to both SAdV41 isolates described herein.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95, 96, 97, 98, 98.5, 99, or 99.5% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95, 96, 97, 98, 98.5, 99, or 99.5% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein. In one embodiment, there is amino acid identity in at least about 95, 96, 97, 98, 98.5, 99 or 99.5% of the aligned sequences.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI® utilities [InVitrogen] are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

"Recombinant", as applied to a polynucleotide, means that the polynucleotide is the product of various combinations of cloning, restriction or ligation steps, and other procedures that result in a construct that is distinct from a polynucleotide found in nature. A recombinant virus is a viral particle having packaged therein a heterologous polynucleotide (e.g., an expression cassette). In certain embodiments, a viral particle may be generated which does not contain an expression cassette or other heterologous polynucleotide. Such a construct is termed herein an "empty capsid" and may be used, e.g., as described in International Patent Publication No. WO 2008/010864, published 24 Jan. 2008.

The terms respectively include replicates of the original polynucleotide construct and progeny of the original virus construct.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. A site-specific recombination site that has been cloned into a genome of a virus or viral vector, wherein the genome of the virus does not naturally contain it, is a heterologous recombination site. When a polynucleotide with an encoding sequence for a recombinase is used to genetically alter a cell that does not normally express the recombinase, both the polynucleotide and the recombinase are heterologous to the cell.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

I. The Simian Adenovirus Sequences

The invention provides nucleic acid sequences and amino acid sequences of simian adenovirus 41 (SAdV-41), which is isolated from the other material with which they are associated in nature.

A. Nucleic Acid Sequences

The SAdV-41.1 nucleic acid sequences provided herein include nucleotides 1 to 35100 of SEQ ID NO:1. See, Sequence Listing, which is incorporated by reference herein. The nucleic acid sequences of SAdV41.2, 1 to 35776, are provided in SEQ ID NO: 34. In one embodiment, the nucleic acid sequences of the invention further encompass the strand which is complementary to the sequences of SEQ ID NO: 1 or SEQ ID NO: 34, as well as the RNA and cDNA sequences corresponding to the sequences of the following sequences and their complementary strands. In another embodiment, the nucleic acid sequences further encompass sequences which are greater than 98.5% identical, and preferably, greater than about 99% identical, to the Sequence Listing. Also included in one embodiment, are natural variants and engineered modifications of the sequences provided in SEQ ID NO: 1 or SEQ ID NO: 34, and its complementary strand. Such modifications include, for example, labels that are known in the art, methylation, and substitution of one or more of the naturally occurring nucleotides with a degenerate nucleotide.

TABLE 1

| | Regions | SAdV-41.1 ORF SEQ ID NO: 1 | SAdV-41.2 ORF SEQ ID NO: 34 |
|---|---|---|---|
| ITR | | 1 . . . 112 | 1 . . . 132 |
| E1a | 13S | Complement | Complement |
| | 12S | (564 . . . 1140, | (573 . . . 1149, |
| | 9S | 1229 . . . 1434) | 1243 . . . 1448) |
| E1b | Small T/19K | 1605 . . . 2147 | 1619 . . . 2161 |
| | Large T/55K | 1910 . . . 3394 | 1924 . . . 3408 |
| | IX | 3491 . . . 3904 | 3503 . . . 3916 |
| E2b | pTP | Complement | Complement |
| | | (8447 . . . 10402, | (8459 . . . 10435, |
| | | 13871 . . . 13879) | 13909 . . . 13917) |
| | Polymerase | Complement | Complement |
| | | (5076 . . . 8645, | (5088 . . . 8657, |
| | | 13871 . . . 13879) | 13909 . . . 13917) |
| | IVa2 | Complement | Complement |
| | | (3973 . . . 5303, | (3985 . . . 5315, |
| | | 5582 . . . 5594) | 5594 . . . 5606) |
| L1 | 52/55D | 10883 . . . 12049 | 10921 . . . 12087 |
| | IIIa | 12077 . . . 13837 | 12115 . . . 13875 |
| L2 | Penton | 13924 . . . 15675 | 13962 . . . 15713 |
| | VII | 15683 . . . 16258 | 15720 . . . 16295 |
| | V | 16304 . . . 17353 | 16341 . . . 17390 |
| | pX | 17385 . . . 17609 | 17422 . . . 17646 |
| L3 | VI | 17686 . . . 18435 | 17724 . . . 18473 |
| | Hexon | 18550 . . . 21378 | 18592 . . . 21420 |
| | Endo-protease | 21412 . . . 22038 | 21296 . . . 22081 |
| E2a | DBP | Complement | Complement |
| | | (22133 . . . 23689) | (22175 . . . 23731) |
| L4 | 100 kD | 23720 . . . 26212 | 23762 . . . 26254 |
| | 33 kD | Complement | Complement |
| | homolog | (25908 . . . 26265, | (25950 . . . 26307, |
| | | 26434 . . . 26793) | 26477 . . . 26832) |
| | 22 kD | 25908 . . . 26525 | 25950 . . . 26564 |
| | VIII | 26866 . . . 27546 | 26905 . . . 27585 |
| E3 | 12.5K | 27549 . . . 27863 | 27588 . . . 27902 |
| | CR1-alpha | 27820 . . . 28263 | 27859 . . . 28284 |
| | gp19K | 28251 . . . 28787 | 28272 . . . 28787 |
| | CR1-beta | 28820 . . . 29428 | 28819 . . . 29421 |
| | CR1-delta | | 30138 . . . 30443 |
| | CR1-gamma | 29442 . . . 29780 | 29474 . . . 30118 |
| | RID-alpha | 29822 . . . 30094 | 30476 . . . 30748 |
| | RID-beta | 30066 . . . 30491 | 30723 . . . 31142 |
| | 14.7K | 30487 . . . 30891 | 31138 . . . 31533 |
| L5 | Fiber | 31118 . . . 32080 | 31766 . . . 32740 |
| E4 | Orf 6/7 | Complement | Complement |
| | | (32126 . . . 32374, | (32789 . . . 33037, |
| | | 33097 . . . 33300) | 33760 . . . 33963) |
| | Orf 6 | Complement | Complement |
| | | (32374 . . . 33300) | (33037 . . . 33963) |
| | Orf 4 | Complement | Complement |
| | | (33176 . . . 33556) | (33839 . . . 34219) |
| | Orf 3 | Complement | Complement |
| | | (33569 . . . 33919) | (34232 . . . 34582) |
| | Orf 2 | Complement | Complement |
| | | (33919 . . . 34305) | (34582 . . . 34968) |
| | Orf1 | Complement | Complement |
| | | (34350 . . . 34721) | (35018 . . . 35389) |
| ITR | | Complement | Complement |
| | | (34989 . . . 35100) | (35636 . . . 35767) |

In one embodiment, fragments of the sequences of SAdV-41, and their complementary strand, cDNA and RNA complementary thereto are provided. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables herein. The tables provide the transcript regions and open reading frames in the SAdV-41 sequences. For certain genes, the transcripts and open reading frames (ORFs) are located on the strand complementary to that presented in SEQ ID NO: 1 and SEQ ID NO: 34. See, e.g., E2b, E4 and E2a. The calculated molecular weights of the encoded proteins are also shown. Note that the E1a open reading frame of SAdV-41 and the E2b open reading frame contain internal splice sites. These splice sites are noted in the table above.

The SAdV-41 adenoviral nucleic acid sequences are useful as therapeutic agents and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The SAdV-41 sequences are also useful as antisense delivery vectors, gene therapy vectors, or vaccine vectors. Thus, further provided are nucleic acid molecules, gene delivery vectors, and host cells which contain the SAdV-41 sequences.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4ORF6 region.

In addition, the adenoviral gene sequences and fragments thereof are useful for providing the helper functions necessary for production of helper-dependent viruses (e.g., adenoviral vectors deleted of essential functions, or adeno-associated viruses (AAV)). For such production methods, the SAdV-41 sequences can be utilized in such a method in a manner similar to those described for the human Ad. However, due to the differences in sequences between the SAdV-41 sequences and those of human Ad, the use of the SAdV-41 sequences greatly minimize or eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258,595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The SAdV-41 sequences which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the SAdV-41 sequences may be utilized in these rAAV production methods.

Alternatively, recombinant SAdV-41 vectors may be utilized in these methods. Such recombinant adenoviral simian vectors may include, e.g., a hybrid chimp Ad/AAV in which chimp Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or SAdV-41 gene sequences will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an SAdV-41 E1a protein may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the SAdV-41 sequences can be readily adapted for use for a variety of viral and non-viral vector systems for in vitro, ex vivo or in vivo delivery of therapeutic and immunogenic molecules. For example, the SAdV-41 simian Ad sequences can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of naked DNA, a plasmid, a virus or any other genetic element.

B. SAdV-41 Adenoviral Proteins

Gene products of the SAdV-41 adenovirus, such as proteins, enzymes, and fragments thereof, which are encoded by the adenoviral nucleic acids described herein are provided. Further encompassed are SAdV-41 proteins, enzymes, and fragments thereof, having the amino acid sequences encoded by these nucleic acid sequences which are generated by other methods. Such proteins include those encoded by the open reading frames identified in the table above, the proteins in the Table below (also shown in the Sequence Listing) and fragments thereof of the proteins and polypeptides.

TABLE 2

| Simian Ad 41 PROTEIN SEQUENCES | | | |
|---|---|---|---|
| | Regions | SAdV41.1 SEQ ID NO: | SAdV41.2 SEQ ID NO: |
| E1a | 13S | 29 | 63 |
| | 12S | | |
| | 9S | | |
| E1b | Small T/19K | 23 | 56 |
| | Large T/55K | 2 | 35 |
| | IX | 3 | 36 |
| L1 | 52/55D | 4 | 37 |
| | IIIa | 5 | 38 |
| L2 | Penton | 6 | 39 |
| | VII | 7 | 40 |
| | V | 8 | 41 |
| | pX | 9 | 42 |
| L3 | VI | 10 | 43 |
| | Hexon | 11 | 44 |
| | Endoprotease | 12 | 58 |
| L4 | 100 kD | 13 | 59 |
| | 33 kD homolog | 31 | 65 |
| | 22 kD | 25 | 45 |
| | VIII | 14 | 46 |
| E3 | E3/12.5k | 15 | 47 |
| | CR1-alpha | 26 | 60 |
| | gp19K | 16 | 48 |
| | CR1-beta | 17 | 49 |
| | CR1-gamma | 18 | 50 |
| | CR1-delta | | 51 |
| | RID-alpha | 19 | 52 |
| | RID-beta | 27 | 61 |
| | E3/14.7K | 20 | 53 |
| L5 | Fiber | 21 | 54 |

Thus, in one aspect, unique simian adenoviral 41 proteins which are substantially pure, i.e., are free of other viral and proteinaceous proteins are provided. Preferably, these proteins are at least 10% homogeneous, more preferably 60% homogeneous, and most preferably 95% homogeneous.

In one embodiment, unique simian-derived capsid proteins are provided. As used herein, a simian-derived capsid protein includes any adenoviral capsid protein that contains a SAdV-41 capsid protein or a fragment thereof, as defined above, including, without limitation, chimeric capsid proteins, fusion proteins, artificial capsid proteins, synthetic capsid proteins, and recombinant capsid proteins, without limitation to means of generating these proteins.

Suitably, these simian-derived capsid proteins contain one or more SAdV-41 regions or fragments thereof (e.g., a hexon, penton, fiber, or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotype which may be of human or non-human origin. Such Ad may be obtained from a variety of sources including the ATCC, commercial and academic sources, or the sequences of the Ad may be obtained from GenBank or other suitable sources.

The SAdV-41.1 penton protein is provided in SEQ ID NO:6 and the SAdV41.2 penton protein is provided in SEQ ID NO: 39. Suitably, this penton protein, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above and in SEQ ID NO:6 and/or 39. Other suitable fragments include shorter internal, C-terminal, or N-terminal fragments. Further, the penton protein may be modified for a variety of purposes known to those of skill in the art.

Also provided are the amino acid sequences of the hexon protein of SAdV-41.1 [SEQ ID NO:11] and SAdV41.2 [SEQ ID NO: 44] (these two virus have hexons that are 100% identical at the amino acid level). Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 11 or 44. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of the simian hexon proteins, with reference to SEQ ID NO: 11 or SEQ ID NO: 44. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one embodiment, an adenovirus having an altered hexon protein utilizing the sequences of a SAdV-41 hexon protein may be generated. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of SAdV-41. In one embodiment, a loop region of the SAdV-41 hexon protein is replaced by a loop region from another adenovirus serotype. In another embodiment, the loop region of the SAdV-41 hexon is used to replace a loop region from another adenovirus serotype. Suitable adenovirus serotypes may be readily selected from among human and non-human serotypes, as described herein. The selection of a suitable serotype is not a limitation of the present invention. Still other uses for the SAdV-41 hexon protein sequences will be readily apparent to those of skill in the art.

The fiber protein of SAdV-41.1 has the amino acid sequence of SEQ ID NO:21 and the fiber protein of SAdV-41.2 has the amino acid sequence of SEQ ID NO: 54. Suitably, this fiber protein, or unique fragments thereof, may be utilized for a variety of purposes. One suitable fragment is the fiber knob, located within SEQ ID NO: 21 or SEQ ID NO: 54. Examples of other suitable fragments include the fiber having N-terminal and/or C-terminal truncations of about 50, 100, 150, or 200 amino acids, based upon the amino acid numbering provided in SEQ ID NO: 21 or SEQ ID NO: 54. Still other suitable fragments include internal fragments. Further, the fiber protein may be modified using a variety of techniques known to those of skill in the art.

Unique fragments of the proteins of the SAdV-41 are at least 8 amino acids in length. However, fragments of other desired lengths can be readily utilized. In addition, modifications as may be introduced to enhance yield and/or expression of a SAdV41 gene product, e.g., construction of a fusion molecule in which all or a fragment of the SAdV41 gene product is fused (either directly or via a linker) with a fusion partner to enhance are provided herein. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. Further encompassed are proteins having at least about 99% identity to the SAdV41 proteins provided herein.

As described herein, vectors of the invention containing the adenoviral capsid proteins of SAdV-41 are particularly well suited for use in applications in which the neutralizing antibodies diminish the effectiveness of other Ad serotype based vectors, as well as other viral vectors. The rAd vectors are particularly advantageous in readministration for repeat gene therapy or for boosting immune response (vaccine titers).

Under certain circumstances, it may be desirable to use one or more of the SAdV41 gene products (e.g., a capsid protein or a fragment thereof) to generate an antibody. The term "an antibody," as used herein, refers to an immunoglobulin molecule which is able to specifically bind to an epitope. The antibodies may exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g., Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science,* 233:747-753; Queen et al., 1989 *Proc. Nat'l. Acad. Sci. USA,* 86:10029-10033; PCT Patent Application No. PCT/WO9007861; and Riechmann et al., *Nature,* 332:323-327 (1988); Huse et al, 1988a *Science,* 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol*., Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a SAdV41 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP), alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods described herein are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of SAdV-41 may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the SAdV-41 sequences can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10): 795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other SAdV-41 adenoviral proteins may be used as alone, or in combination with other adenoviral protein, for a variety of purposes which will be readily apparent to one of skill in the art. In addition, still other uses for the SAdV-41 adenoviral proteins will be readily apparent to one of skill in the art.

II. Recombinant Adenoviral Vectors

The compositions described herein include vectors that deliver a heterologous molecule to cells, either for therapeutic or vaccine purposes. As used herein, a vector may include any genetic element including, without limitation, naked DNA, a phage, transposon, cosmid, episome, plasmid, or a virus. Such vectors contain simian adenovirus DNA of SAdV41 and a minigene. By "minigene" is meant the combination of a selected heterologous gene and the other regulatory elements necessary to drive translation, transcription and/or expression of the gene product in a host cell.

Typically, a SAdV-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences. A SAdV-41 based adenoviral vector may also contain additional adenoviral sequences.

Suitably, these SAdV-41 based adenoviral vectors contain one or more adenoviral elements derived from the adenoviral genome of the invention. In one embodiment, the vectors contain adenoviral ITRs from SAdV41 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid protein of the adenovirus is from a different adenovirus than the adenovirus which provides the ITRs.

Further, chimeric or hybrid adenoviruses may be constructed using the adenoviruses described herein using techniques known to those of skill in the art. See, e.g., U.S. Pat. No. 7,291,498.

The selection of the adenoviral source of the ITRs and the source of any other adenoviral sequences present in vector is not a limitation of the present embodiment. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other simian or from human adenoviruses are described in the published literature [see, for example, U.S. Pat. No. 5,240,846]. The DNA sequences of a number of adenovirus types are available from GenBank, including type Ad5 [GenBank Accession No. M73260]. The adenovirus sequences may be obtained from any known adenovirus serotype, such as serotypes 2, 3, 4, 7, 12 and 40, and further including any of the presently identified human types. Similarly adenoviruses known to infect non-human animals (e.g., simians) may also be employed in the vector constructs of this invention. See, e.g., U.S. Pat. No. 6,083,716.

The viral sequences, helper viruses (if needed), and recombinant viral particles, and other vector components and sequences employed in the construction of the vectors described herein are obtained as described above. The DNA sequences of the SAdV41 simian adenovirus sequences of the invention are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this embodiment.

A. The "Minigene"

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

In one embodiment, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.,* 78(Pt 1):13-21 (January 1997); Furler, S., et al, *Gene Ther.,* 8(11):864-873 (June 2001); Klump H., et al., *Gene Ther.,* 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this embodiment.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product.

A great number of expression control sequences, including promoters which are native, constitutive, inducible and/or tissue-specific, are known in the art and may be utilized. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)]. Other systems include the FK506 dimer, VP16 or p65 using castradiol, diphenol murislerone, the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al., *Nat. Biotech.,* 17:241-245 (1999)). Examples of promoters that are tissue-specific are known for liver (albumin, Miyatake et al., *J. Virol.,* 71:5124-32 (1997); hepatitis B virus core promoter, Sandig et al., *Gene Ther.,* 3:1002-9 (1996); alpha-fetoprotein (AFP), Arbuthnot et al., *Hum. Gene Ther.,* 7:1503-14 (1996)), bone osteocalcin (Stein et al., *Mol. Biol. Rep.,* 24:185-96 (1997)); bone sialoprotein (Chen et al., *J. Bone Miner. Res.,* 11:654-64 (1996)), lymphocytes (CD2, Hansal et al., *J. Immunol.,* 161:1063-8 (1998); immunoglobulin heavy chain; T cell receptor chain), neuronal such as neuron-specific enolase (NSE) promoter (Andersen et al., *Cell. Mol. Neurobiol.,* 13:503-15 (1993)), neurofilament light-chain gene (Piccioli et al., *Proc. Natl. Acad. Sci. USA,* 88:5611-5 (1991)), and the neuron-specific vgf gene (Piccioli et al., *Neuron,* 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Viral Vector

In one embodiment, the simian adenoviral plasmids (or other vectors) are used to produce adenoviral vectors. In one embodiment, the adenoviral vectors are adenoviral particles which are replication—defective. In one embodiment, the adenoviral particles are rendered replication-defective by deletions in the E1a and/or E1b genes. Alternatively, the adenoviruses are rendered replication-defective by another means, optionally while retaining the E1a and/or E1b genes. The adenoviral vectors can also contain other mutations to the adenoviral genome, e.g., temperature-sensitive mutations or deletions in other genes. In other embodiments, it is desirable to retain an intact E1a and/or E1b region in the adenoviral vectors. Such an intact E1 region may be located in its native location in the adenoviral genome or placed in the site of a deletion in the native adenoviral genome (e.g., in the E3 region).

In the construction of useful simian adenovirus vectors for delivery of a gene to the human (or other mammalian) cell, a range of adenovirus nucleic acid sequences can be employed in the vectors. For example, all or a portion of the adenovirus delayed early gene E3 may be eliminated from the simian adenovirus sequence which forms a part of the recombinant virus. The function of simian E3 is believed to be irrelevant to the function and production of the recombinant virus particle. Simian adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and $IVa_2$ may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the simian adenovirus gene content of the viral vectors employed to carry the minigene, a helper adenovirus or non-replicating virus fragment may be necessary to provide sufficient simian adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264: 16985-16987 (1989); K. J. Fisher and J. M. Wilson, *Biochem.* 1, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant simian adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from SAdV41 under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired SAdV41 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant simian adenovirus E1 deleted vectors. Additionally, or alternatively, cell lines that express one or more simian adenoviral gene products, e.g., E1a, E1b, E2a, and/or E4 ORF6, can be constructed using essentially the same procedures are used in the generation of recombinant simian viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther,* 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant simian adenoviruses are useful in transferring a selected transgene to a selected cell. In in vivo experiments with the recombinant virus grown in the packaging cell lines, the E1-deleted recombinant simian adenoviral vectors of the invention demonstrate utility in transferring a transgene to a non-simian, preferably a human, cell.

IV. Use of the Recombinant Adenovirus Vectors

The recombinant simian adenovirus—41 based vectors are useful for gene transfer to a human or non-simian veterinary patient in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A SAdV41-derived recombinant simian adenoviral vector provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the SAdV41 recombinant adenoviral vectors will be utilized for delivery of therapeutic or immunogenic molecules, as described below. It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first simian capsid, delivery with a rAd with a second simian capsid, and delivery with a third simian capsid. A variety of other regimens which use the Ad capsids of the invention alone, in combination with one another, or in combination with other adenoviruses (which are preferably immunologically non-crossreactive) will be apparent to those of skill in the art. Optionally, such a regimen may involve administration of rAd with capsids of other non-human primate adenoviruses, human adenoviruses, or artificial sequences such as are described herein. Each phase of the regimen may involve administration of a series of injections (or other delivery routes) with a single Ad capsid followed by a series with another capsid from a different Ad source. Alternatively, the SAdV-41 vectors may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described recombinant vectors are administered to humans according to published methods for gene therapy. A simian viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The simian adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, intracochlear delivery (to the ear), direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 μL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus. Dosages will range depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be delivered. In another example, a suitable human or veterinary dosage may be in the range of about $1\times10^{11}$ to about $1\times10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{in}$ cells and CTLs to reduce the occurrence of CTL elimination of the vector. A variety of useful immune modulators and dosages for use of same are disclosed, for example, in Yang et al., *J. Virol.,* 70(9) (September, 1996); International Patent Application No. WO96/12406, published May 2, 1996; and International Patent Application No. PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The simian adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a SAdV41 simian adenoviral vector, followed by re-administration with a vector from the same serotype adenovirus. Particularly desirable regimens involve administration of a SAdV41 simian adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a SAdV41 vector and repeat administration with one or more adenoviral vectors of the same or different serotypes. In another example, a therapeutic regimen involves administration of an adenoviral vector followed by repeat administration with a SAdV41 vector which has a capsid which differs from the source of the capsid in the first delivered adenoviral vector, and optionally further administration with another vector which is the same or, preferably, differs from the source of the adenoviral capsid of the vector in the prior administration steps. These regimens are not limited to delivery of adenoviral vectors constructed using the SAdV41 simian sequences. Rather, these regimens can readily utilize vectors other adenoviral sequences, including, without limitation, other simian adenoviral sequences, (e.g., Pan9 or C68, C1, etc), other non-human primate adenoviral sequences, or human adenoviral sequences, in combination with one or more of the SAdV41 vectors. Examples of such simian, other non-human primate and human adenoviral serotypes are discussed elsewhere in this document. Further, these therapeutic regimens may involve either simultaneous or sequential delivery of SAdV41 adenoviral vectors in combination with non-adenoviral vectors, non-viral vectors, and/or a variety of other therapeutically useful compounds or molecules. The invention is not limited to these therapeutic regimens, a variety of which will be readily apparent to one of skill in the art.

B. Ad-Mediated Delivery of Immunogenic Transgenes

The recombinant SAdV-41 vectors may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. A recombinant simian Ad can contain in any of its adenovirus sequence deletions a gene encoding a desired immunogen. The simian adenovirus is likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g., adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant SAdV-41 vectors are expected to be highly efficacious at inducing cytolytic T cells and antibodies to the inserted heterologous antigenic protein expressed by the vector.

For example, immunogens may be selected from a variety of viral families. Example of viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including *Rubella* virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies).

Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, J. Virol., 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhabinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Immunogens which are useful to immunize a human or non-human animal against other pathogens include, e.g., bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella; *Franisella tularensis* (which causes tularemia); yersinia (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the SAdV-41 vectors to deliver immunogens against the variable region of the T cells are anticipated to elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant simian adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the recombinant SAdV-41 vectors may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant SAdV-41 vector to boost the immune response to a vector (either viral or DNA-based) carrying an antigen, or a protein. In still another alternative, an immunization regimen involves administration of a protein followed by booster with a vector encoding the antigen.

In one embodiment, a method of priming and boosting an immune response to a selected antigen by delivering a plasmid DNA vector carrying said antigen, followed by boosting with a recombinant SAdV-41 vector is described. In one embodiment, the prime-boost regimen involves the expression of multiproteins from the prime and/or the boost vehicle. See, e.g., R. R. Amara, *Science,* 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant SAdV-41 adenovirus construct. Still other regimens are described in WO 99/16884 and WO 01/54719.

However, the prime-boost regimens are not limited to immunization for HIV or to delivery of these antigens. For example, priming may involve delivering with a first SAdV-41 vector followed by boosting with a second Ad vector, or with a composition containing the antigen itself in protein form. In one example, the prime-boost regimen can provide a protective immune response to the virus, bacteria or other organism from which the antigen is derived. In another embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The amount or situs of injection(s) or to pharmaceutical carrier is not a limitation. Rather, the regimen may involve a priming and/or boosting step, each of which may include a single dose or dosage that is administered hourly, daily, weekly or monthly, or yearly. As an example, the mammals may receive one or two doses containing between about 10 μg to about 50 μg of plasmid in carrier. A desirable amount of a DNA composition ranges between about 1 μg to about 10,000 μg of the DNA vector. Dosages may vary from about 1 μg to 1000 μg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions described herein may be administered to a mammal according to the routes described above, in a sustained release formulation using a biodegradable biocompatible polymer, or by on-site delivery using micelles, gels and liposomes. Optionally, the priming step also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a crossreactive antigen, as that encoded by the priming composition.

In another embodiment, the SAdV-41 vectors are also well suited for use in a variety of other immunization and therapeutic regimens. Such regimens may involve delivery of SAdV-41 vectors simultaneously or sequentially with Ad vectors of different serotype capsids, regimens in which SAdV-41 vectors are delivered simultaneously or sequentially with non-Ad vectors, regimens in which the SAdV-41 vectors are delivered simultaneously or sequentially with proteins, peptides, and/or other biologically useful therapeutic or immunogenic compounds. Such uses will be readily apparent to one of skill in the art.

The following examples illustrate the cloning of SAdV-41 and the construction of exemplary recombinant SAdV-41 vectors. These examples are illustrative only, and do not limit the scope of the present invention.

Example 1

Isolation of Simian Adenovirus 41 and PCR Analysis

Stool samples from a variety of great apes were obtained from 9 different zoos in the United States. SAdV-41.1 was isolated from a gorilla housed in Buffalo.

Stool samples were recovered from the floors of the facilities that houses the animals and were frozen and sent to University of Pennsylvania. They were thawed and suspended in Hanks' Balanced Salt solution, the particulates pelleted by centrifugation, and sterile filtered through 0.2 micron syringe filters. 100 ml of each filtered sample was inoculated into A549 cells grown in Ham's F12 with 10% FBS, 1% Penn-Strep and 50 mg/ml gentamicin. After about 1 to 2 weeks in culture, visual cytopathic effect (CPE) was obvious in cell cultures with several of the inocula. The presence of adenoviruses in the cultures was confirmed by PCR amplification of an internal 1.9 kb of the hexon—the region encompassing the hypervariable (HVR) regions and that is predominantly responsible for conferring serotype specificity. The primer pair that was utilized for PCR was CAGGATGCTTCGGAGTACCTGAG [SEQ ID NO: 32] and TTGGCNGGDATDGGGTAVAGCATGTT [SEQ ID NO: 33]. The sequence obtained from this region was used to make an initial determination of adenoviral species and novelty of the serotype. The sequence was determined to be a member of species B.

Adenoviral isolates that were determined to be novel were plaque purified on A549 cells, propagated to high titer and purified on cesium chloride gradients using standard procedures. Viral DNAs obtained from purified virus preparations were completely sequenced (Qiagen Genomics Services, Hilden, Germany).

The resulting simian adenovirus 41.1 genomic sequence was subsequently deposited with GenBank under Accession Number FJ025913 pursuant to confidentiality provisions until following the filing of this application.

Using similar methods, simian adenovirus 41.2, complete genome, was isolated from a gorilla housed in Atlanta. This sequence was deposited with GenBank under Accession Number FJ025927, pursuant to confidentiality provisions until following the filing of this application.

Example 2

Vector Construction Using SAdV41.1

An E1 deleted vector using the SAdV-41 can be prepared. Because both published reports and the inventors experience with AdC1 have indicated that E1 deletions in subgroup B adenoviruses are not complemented by the Ad5 E1 genes in HEK 293 cells, a hybrid adenovirus based on the strategy using AdC1 [Roy et al., *J Virol. Methods*. (2007) 141, 14-21; Roy et al., *J Gen Virol*. (2006) 87, 2477-2485], where the left and right ends of a chimeric construct are derived from the chimpanzee adenovirus Pan 5 (a.k.a. Simian adenovirus 22) can be utilized.

The species E adenovirus that was used was SAdV-36, which is described in International Patent Application No. PCT/US09/01344, filed Mar. 3, 2009, which is incorporated by referenced herein. The starting plasmid was a molecular clone of E1-deleted SAdV36-pC36 IP.

A. Construction of Plasmid(p) C36Asc-Not for the Creation of Hybrid Adenovirus Vectors.

C36 fwd-SEQ ID NO: 66] gatcGGCGCGCCACGCGT-GCGGCCGCttacaggattcgagcagttatt and C36rev-CTGGC-CCTGTGGTTCCGCAG [SEQ ID NO: 67] were used to generate a 763 bp fragment using pC36 IP as template. The PCR fragment harbors the end of E4 orf 6/7 along with a 5' extension encoding the restriction sites for AscI MluI and NotI.

The PCR fragment was digested with AscI and Acc65I and ligated into pC36 IP cut with the same enzymes, to generate pC36Asc-Not. Mini-preps were checked with SmaI to confirm the presence of the expected fragments. The mini-prep was further diagnosed to confirm the presence of the AscI, MluI and NotI sites.

B. Construction of an E1-Deleted Adenovirus Vector Based on SAdV-41.

The primers: C41 fwd-gatcACGCGTtaacgcaggtgtaca-gctgg [SEQ ID NO: 68] and C41 rev-[SEQ ID NO: 69]: CATGacgcgtACTGATTTTTCAATAAAAGTTAAATTT-ATTTTTGTTGTC (Phusion polymerase, 55° annealing, 2 minute extension, 30 cycles) were used to generate a 4972 bp fragment using SAdV41.1 (clone DP957) as template. The PCR primers contain MluI sites for insertion into the MluI site of pAsc-Not.

The AscI (7936)-BsrGI fragment of SAdV-41.1 was inserted into pC36 Asc-Not, which was prepared as described in part A above. The plasmid pC36/41 IP harbors a chimeric adenovirus genome (chimeric between SAdV-36 and SAdV-41.1) flanked by PacI restriction sites. The left end, extending from the ITR to the AscI site (at by #6047), is derived from SAdV-36. The E1 gene of SAdV-36 has been deleted and in its place, restriction sites for the enzymes I-CeuI and PI-SceI have been inserted for the insertion of transgene cassettes. The right end-extending from the NotI site to the ITR is also derived from SAdV-36. This harbors the E4 genes. The SAdV-41.1 genome is present between the AscI and the NotI sites. The fusion at the AscI site between SAdV-36 and SAdV-41.1 generates a chimeric open reading frame (encoding DNA polymerase).

A transgene cassette designed to express FluA NP was ligated between the I-CeuI and PI-SceI sites of pC36/41 IP. The nucleotide sequence encoding the H1N1 influenza A virus nucleoprotein (NP) (A/Puerto Rico/8/34/Mount Sinai, GenBank accession number AF389119.1) was codon optimized and completely synthesized (Celtek Genes, Nashville, Tenn.). An expression cassette (approximately 2.5 kb) composed of the human cytomegalovirus early promoter, an artificial intron derived from the Promega (Madison, Wis.) plasmid pCI, the codon optimized influenza A NP coding sequence and the bovine growth hormone polyadenylation signal was constructed in a shuttle plasmid.

The resulting plasmid was transfected into HEK293 cells and cytopathic effect was observed indicating the successful rescue of recombinant SAdV-41.1 based adenovirus vector designed to transduce cell to express the FluA antigen. Adenovirus may be was purified by cesium chloride density gradient centrifugation and the particle titer determined by measuring absorbance at 260 and 280 nm.

The protocols contained in Roy, et al. ["Partial protection against H5N1 influenza in mice with a single dose of a chimpanzee adenovirus vector expressing nucleoprotein", *Vaccine* 25:6845-6851 (Aug. 6, 2007)], which is herein incorporated by reference, may be utilized to assess T cell induction by the resulting recombinant adenovirus virus.

All documents recited above, the Sequence Listing, and the entirety of US Provisional Patent Application Nos. 61/182,290 (filed May 29, 2009) and 61/219,917 (filed Jun. 24, 2009), are incorporated herein by reference. Numerous modifications and variations are included in the scope of the above-identified specification and are expected to be obvious to one of skill in the art. Such modifications and alterations to the compositions and processes, such as selections of different minigenes or selection or dosage of the vectors or immune modulators are believed to be within the scope of the claims appended hereto.

TABLE 3

(Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 113-122 | CCGGCGCGGG | ---------- |
| 134 | G | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 138 | G | C |
| 213 | C | G |
| 768 | T | G |
| 954 | A | C |
| 990 | T | G |
| 1034 | A | G |
| 1161 | T | C |
| 1165 | G | C |
| 1191 | G | - |
| 1199-1200 | GT | AA |
| 1223 | T | C |
| 1227-1231 | TGCTT | ----- |
| 1384 | G | A |
| 1456 | A | G |
| 1566 | G | A |
| 1653 | A | G |
| 1662 | G | A |
| 1902 | A | T |
| 1905 | T | C |
| 2058 | G | A |
| 2079 | A | G |
| 2081 | T | C |
| 2372 | G | A |
| 2465 | A | G |
| 2482 | G | A |
| 2492 | G | A |
| 2523 | T | G |
| 2537 | A | C |
| 2582 | T | C |
| 2612 | T | C |
| 2624 | A | G |
| 2627 | A | C |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 2639 | T | A |
| 2720 | C | G |
| 2742 | G | T |
| 2744 | A | T |
| 2753 | G | A |
| 2756 | T | C |
| 2760 | G | A |
| 2762 | A | C |
| 2765 | A | G |
| 2768 | C | T |
| 2843 | T | C |
| 2855 | T | C |
| 2876 | C | T |
| 2974 | C | T |
| 2981 | A | G |
| 3245 | T | C |
| 3434 | T | G |
| 3443 | A | G |
| 3487 | G | C |
| 3620 | A | G |
| 3689 | C | T |
| 3773 | T | A |
| 4151 | C | T |
| 4292 | C | T |
| 4454 | G | C |
| 4514 | A | G |
| 4691 | A | G |
| 4757 | C | G |
| 4783 | G | A |
| 5060 | T | G |
| 5063 | T | C |
| 5134 | A | G |
| 5137 | A | G |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 5209 | C | T |
| 5365 | C | T |
| 6547 | T | C |
| 6652 | G | A |
| 6655 | G | A |
| 7120 | G | T |
| 7225 | G | A |
| 7228 | A | G |
| 7267 | T | C |
| 7315 | A | G |
| 7417 | A | G |
| 7438 | C | T |
| 7624 | C | T |
| 7627 | A | G |
| 7669 | T | G |
| 7720 | C | G |
| 7741 | A | G |
| 7765 | G | A |
| 7786 | G | T |
| 7959 | T | A |
| 7978 | G | A |
| 8341 | C | T |
| 8361 | T | A |
| 8472 | A | G |
| 8505 | G | T |
| 8526 | C | T |
| 9066 | T | C |
| 9422 | G | A |
| 9448 | C | T |
| 9624 | T | C |
| 9644-9664 | GGCTAGATGCTCGGT CGGGGT | --------------- ------ |
| 9703 | G | A |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 9903 | G | A |
| 9953 | G | A |
| 10044 | T | C |
| 10115 | G | T |
| 10131 | G | T |
| 10254 | T | G |
| 10338 | C | T |
| 10536-10537 | AC | CA |
| 10574 | C | T |
| 10665 | C | - |
| 10680-10681 | TG | CA |
| 10700 | T | C |
| 10716 | C | T |
| 10796 | T | C |
| 10906 | T | G |
| 10909-10912 | GTTT | ---- |
| 10999 | G | T |
| 11053 | A | T |
| 11098 | G | A |
| 11212 | G | C |
| 11230 | T | C |
| 11257 | T | C |
| 11312 | G | A |
| 11353 | A | C |
| 11359 | T | C |
| 11398 | C | T |
| 11506 | C | A |
| 11572 | T | C |
| 11587 | G | A |
| 11605 | G | A |
| 11623 | T | C |
| 11653 | A | G |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 11662 | C | T |
| 11666 | C | T |
| 11678 | C | G |
| 11692 | T | C |
| 11704 | T | G |
| 11800 | T | C |
| 11809 | T | C |
| 11812 | A | G |
| 11815 | G | T |
| 11827 | C | T |
| 11839 | G | A |
| 11851 | C | T |
| 11941 | C | G |
| 11950 | C | A |
| 11995 | G | A |
| 12106 | A | G |
| 12475 | C | A |
| 12490 | A | C |
| 12589 | T | C |
| 12610 | C | T |
| 12682 | C | T |
| 12736 | G | A |
| 12749 | T | C |
| 12766 | T | C |
| 12769 | G | A |
| 12781 | T | C |
| 12805 | C | T |
| 12824 | T | C |
| 12853 | T | C |
| 12916 | A | G |
| 12922 | C | T |
| 12943 | T | C |
| 12967 | C | T |
| 12991 | T | C |
| 13007 | T | C |
| 13082 | T | C |
| 13084 | G | C |
| 13123 | G | A |
| 13162 | G | C |
| 13216 | A | G |
| 13237 | A | G |
| 13243 | T | C |
| 13273 | C | T |
| 13276 | T | C |
| 13387 | T | C |
| 13399 | T | C |
| 13525 | T | C |
| 13657 | T | C |
| 14953 | G | T |
| 15357 | C | T |
| 16036 | C | T |
| 16135 | A | G |
| 16165 | G | A |
| 16180 | A | G |
| 16264 | T | C |
| 16528 | G | A |
| 16545-16546 | GG | AA |
| 16597 | A | G |
| 16699 | A | G |
| 16726 | A | G |
| 16738 | C | A |
| 16765 | G | A |
| 16771 | C | A |
| 16798 | G | A |
| 16819 | C | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 16859 | T | C |
| 17041-17042 | TA | CG |
| 17048 | G | A |
| 17053 | C | T |
| 17074 | A | T |
| 17080 | G | A |
| 17090 | A | G |
| 17099 | G | A |
| 17112-17113 | TT | CC |
| 17153 | A | T |
| 17188 | G | A |
| 17288 | A | G |
| 17410 | A | G |
| 17585 | C | T |
| 17665 | A | - |
| 17926 | G | A |
| 17929 | G | A |
| 18001 | G | A |
| 18054 | A | C |
| 18163 | C | G |
| 18172 | G | A |
| 18193 | A | G |
| 18350 | G | T |
| 18482-18485 | TTAA | ---- |
| 18542 | A | G |
| 18704 | C | T |
| 21080 | A | G |
| 21254 | T | C |
| 21401 | G | A |
| 21429 | A | - |
| 21543 | G | T |
| 21583 | G | A |
| 21606 | T | C |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 21633 | T | A |
| 21660 | T | C |
| 21693 | C | T |
| 21705 | T | G |
| 21954 | A | G |
| 22069 | A | G |
| 22071 | T | C |
| 22074 | A | T |
| 22391 | C | T |
| 22478 | A | G |
| 22682 | A | C |
| 22688 | A | G |
| 24112 | C | A |
| 24259 | G | A |
| 24263 | C | A |
| 24266 | C | G |
| 24298 | T | C |
| 24442 | T | A |
| 24448 | A | T |
| 24577 | T | G |
| 24595 | A | C |
| 24616 | G | A |
| 24619 | C | G |
| 24649 | A | C |
| 24661 | C | T |
| 24697 | T | C |
| 24715 | C | A |
| 24813 | G | C |
| 24844 | G | A |
| 24934 | C | T |
| 24967 | T | C |
| 25057 | G | A |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 25060 | C | T |
| 25064 | T | C |
| 25069 | T | C |
| 25081 | A | G |
| 25093 | C | T |
| 25285 | C | T |
| 25540 | T | C |
| 25549 | G | T |
| 25591 | C | T |
| 25621 | T | C |
| 25702 | T | C |
| 25744 | C | T |
| 25802 | A | G |
| 25988 | G | A |
| 26012 | T | C |
| 26148 | G | A |
| 26162 | G | A |
| 26191 | C | T |
| 26411 | G | A |
| 26486 | C | T |
| 26517 | G | A |
| 26520 | G | A |
| 27372 | A | G |
| 27444 | A | G |
| 27528 | T | C |
| 27918 | C | A |
| 27923 | C | T |
| 27925 | T | A |
| 27929-27930 | AC | TT |
| 28000 | A | G |
| 28044 | T | A |
| 28046-28047 | TT | CC |
| 28064-28065 | TT | AA |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 28079 | A | G |
| 28094 | A | C |
| 28171 | A | G |
| 28236 | A | C |
| 28284 | T | C |
| 28317 | G | T |
| 28320 | C | T |
| 28357-28358 | AT | CG |
| 28361 | C | A |
| 28376 | C | G |
| 28392 | C | G |
| 28394 | C | T |
| 28416 | A | G |
| 28434 | A | C |
| 28500 | C | T |
| 28568 | C | T |
| 28612 | T | C |
| 28634 | T | C |
| 28739 | C | A |
| 28749 | C | A |
| 28753 | T | C |
| 28762-28764 | CTT | TCA |
| 28766 | G | A |
| 28770 | A | G |
| 28772 | T | G |
| 28776 | T | A |
| 28784 | A | G |
| 28787 | T | C |
| 28794-28795 | TT | AC |
| 28800 | C | T |
| 28802 | A | C |
| 28814 | C | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 28826 | A | G |
| 28830 | G | A |
| 28837 | A | G |
| 28839 | T | C |
| 28845-28847 | CCT | TTC |
| 28849 | A | T |
| 28851 | C | G |
| 28856 | T | C |
| 28861 | T | C |
| 28871-28872 | GC | AT |
| 28875 | C | T |
| 28877 | G | A |
| 28880 | G | A |
| 28882-28883 | TG | -A |
| 28885 | T | C |
| 28887-28888 | TA | -- |
| 28897-28898 | AA | TG |
| 28900 | T | - |
| 28901 | A | - |
| 28904 | T | G |
| 28907 | G | T |
| 28912 | T | - |
| 28915-28916 | AT | TA |
| 28920-28921 | GG | CA |
| 28923-28931 | TAAAATTTA | --------- |
| 28935-28936 | AT | GA |
| 28940-28941 | AT | CA |
| 28943 | G | A |
| 28945-28946 | CC | AA |
| 28950 | T | C |
| 28954-28956 | TTC | CGA |
| 28960-28963 | CCAT | TTTC |
| 28967 | C | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 28969-28971 | GCG | AGT |
| 28975 | A | G |
| 28978 | A | T |
| 28980 | T | A |
| 28982-28984 | GGC | --- |
| 28987-28988 | TT | AC |
| 28992-28993 | AA | TT |
| 28996-28997 | AA | CT |
| 29004 | A | T |
| 29009 | T | - |
| 29011 | T | C |
| 29014-29015 | TG | AA |
| 29017-29019 | AGA | C-- |
| 29024-29026 | AGC | CCA |
| 29030 | C | G |
| 29033-29034 | GA | -- |
| 29041-29043 | TTG | GAT |
| 29045-29046 | GA | AC |
| 29049-29051 | ACA | GGT |
| 29054 | A | C |
| 29056 | T | C |
| 29059-29061 | ACA | -TG |
| 29063 | A | G |
| 29065-29067 | CAT | TGG |
| 29069 | C | G |
| 29071-29076 | TACAAA | ------ |
| 29078-29079 | AC | TT |
| 29083-29084 | TA | GT |
| 29088-29092 | GTAAG | AATCT |
| 29094-29096 | CTA | ACC |
| 29100 | A | C |
| 29103-29104 | AT | TC |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29107 | C | T |
| 29110 | T | C |
| 29112 | C | A |
| 29114 | G | A |
| 29117 | T | C |
| 29119-29120 | TG | AA |
| 29122-29123 | TT | CC |
| 29127-29128 | TT | CA |
| 29132 | G | A |
| 29134 | T | C |
| 19140 | C | T |
| 29145 | C | A |
| 29147 | A | G |
| 29149-29160 | CTATTCAGGTTT | ------------ |
| 29165 | T | G |
| 29167 | C | A |
| 29173-29174 | TA | AT |
| 29176 | T | C |
| 29178 | T | A |
| 29181 | A | G |
| 29183 | A | G |
| 29187-29188 | TT | -- |
| 29190 | C | A |
| 29193 | A | C |
| 29199-29214 | ATATTCTAGTAAAGT T | --------------- - |
| 29119-29220 | CC | AT |
| 29223 | C | G |
| 29225-29226 | AC | GT |
| 29229-29231 | CTA | TAG |
| 29233 | A | C |
| 29236-29237 | GT | TC |
| 29241-29242 | GC | AG |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29245-29271 | GAGTACTATAACCAG CACCACGCTTCC | --------------- ------------ |
| 29273 | A | T |
| 29275 | T | C |
| 29277 | G | A |
| 29280 | C | G |
| 29284-29310 | AATGTTTCAATTGAA CAAAATAGAAAA | --------------- ------------ |
| 29314 | C | A |
| 29317 | C | T |
| 29320-29323 | TAGC | |
| 29325 | A | G |
| 29331-29336 | CTCTAT | ----GA |
| 29339 | A | C |
| 29342 | G | A |
| 29344 | T | C |
| 29350-29352 | TGT | ATC |
| 29355 | A | T |
| 29358-29359 | GG | CA |
| 29363 | T | C |
| 29366-29373 | ACTACAAT | -------C |
| 29378-29379 | AT | -- |
| 29381 | C | T |
| 29388-29397 | TTGTGGGGTT | C |
| 29399 | A | G |
| 29402-29403 | AT | CA |
| 29408-29409 | AT | CC |
| 29415 | G | A |
| 29418-29468 | TGATAGTCTATACCT GCCGCTACAGAAAAC TACACAATAAAGTAG ACCCCT | --------------- --------------- --------------- ------ |
| 29472 | A | G |
| 29474 | A | C |
| 29477-29478 | CC | -- |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29481-29482 | AC | GT |
| 29484 | T | A |
| 29486-29487 | GA | CT |
| 29492 | T | A |
| 29495-29530 | CTTTTTTTAAAACAC TTTATTTTCAGCCAT GATTTC | --------------- --------------- ------ |
| 29539 | C | T |
| 29543 | T | G |
| 29545 | T | - |
| 29549 | T | C |
| 29551 | T | C |
| 29554-29585 | CTGCCATTACTACTG TACAGGGGTTCACAA AC | --------------- --------------- -- |
| 29591-29592 | AA | TG |
| 29595-29596 | AC | GA |
| 29600-29614 | ACATGTGGGATCCAG | --------------- |
| 29616 | T | C |
| 29620-29640 | CACTAGAAGGTTACC AATCCC | --------------- ------ |
| 29646-29647 | CG | -A |
| 29650-29658 | TTTCTTGGT | --------- |
| 29664 | T | G |
| 29667 | T | C |
| 29669-29670 | CC | TT |
| 29673-29681 | GATCAGCCA | A-------- |
| 29684-29685 | TA | GG |
| 29687-29688 | TA | GG |
| 29691 | C | G |
| 29693-29694 | TT | -- |
| 29696-29697 | CA | GG |
| 29700 | G | T |
| 29705-29706 | TC | AT |
| 29708-29711 | GGAA | ---- |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29713 | C | T |
| 29716 | C | T |
| 29721 | C | T |
| 29723 | C | T |
| 29725-29726 | CA | TG |
| 29731-29732 | AA | CC |
| 29735-29760 | CAAATGCAATAACAA TAATTTAACCC | --------------- ----------- |
| 29762-29763 | AA | GC |
| 29767 | A | C |
| 29770 | T | C |
| 29776-29785 | CTCAATATGC | ---------- |
| 29787-29791 | GGAAC | AAGTT |
| 29795 | C | T |
| 29800 | G | A |
| 29802-29803 | AC | GA |
| 29807-29820 | TTTTAACATAGGAC | -------------- |
| 29822 | A | G |
| 29825 | C | G |
| 29828-29830 | ATA | CCC |
| 29834-29837 | TACC | CTAA |
| 29841-29845 | ACAGT | TTGAC |
| 29847 | A | T |
| 29852 | C | T |
| 29854 | C | T |
| 29856-29863 | ACTACTCC | -------T |
| 29865 | G | A |
| 29868-29876 | ACAACTACC | G-------- |
| 29879 | A | G |
| 29884-29890 | CTACAAA | ------- |
| 29896-29912 | AAAGCACAAAAACTC AC | GG------------- -T |
| 29915 | T | C |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29918-29962 | CCCTAGCAGCAAGCC CACCTCAATCTATAC AACTTCACTTTTGCA | --------------- --------------- --------------G |
| 29964 | C | T |
| 29967 | C | T |
| 29970-29991 | CAAAAGGCTAACGTT ACAGACA | --------------- ------- |
| 29993 | T | C |
| 29995-29996 | AT | GC |
| 29998-29999 | CT | GC |
| 30005 | C | T |
| 30007-30009 | CCA | TTT |
| 30013-30021 | TTCCTAGCG | --------- |
| 30024-30026 | GAG | TTA |
| 3028 | T | C |
| 30032 | C | A |
| 30034 | A | C |
| 30036 | T | C |
| 30040-30060 | TGATAGGAATTATTG CTGCTG | C-------------- ------ |
| 30062 | G | A |
| 30066 | G | A |
| 30068-30088 | GGGAATGCTAATTAT AATTCT | A-------------- ------ |
| 30093-30098 | ATGATT | GCAGAC |
| 30101 | T | C |
| 30103 | A | T |
| 30105 | G | A |
| 30107-30108 | TT | CA |
| 30110-30112 | CTG | TCA |
| 30114 | T | C |
| 30118-30132 | GAAAATATGAACATG | --------------- |
| 30140-30163 | AATAGACCCACTACT GAGCTTTGA | C-------------- --------- |
| 30166-30167 | TT | CC |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30169 | A | C |
| 30171 | T | G |
| 30177 | T | C |
| 30180 | G | A |
| 30182-30233 | GCACCATGAAAGGTC CAGTTATCCTATTGT TTATTTCCACTTTTT GGTGTTG | --------------- --------------- --------------- ------- |
| 30235 | G | A |
| 30240-30262 | TTTTTCAATTACCAC CAATGTGC | --------------- -------- |
| 30268-30280 | ACTTTAAATAACA | ------------- |
| 30282 | C | T |
| 30284-30285 | TG | AT |
| 30290 | C | A |
| 30294 | T | C |
| 30298-30315 | ACACAACTTTCACCT CAA | --------------- --- |
| 30319 | G | A |
| 30325-30328 | GACA | TTTC |
| 30330-30331 | AA | TC |
| 30336 | A | T |
| 30346-30348 | ATC | GCT |
| 30355 | G | A |
| 30363 | T | A |
| 30369 | T | A |
| 30372 | C | T |
| 30375 | T | A |
| 30378-30379 | TG | AA |
| 30381 | T | C |
| 30384 | C | T |
| 30387 | T | A |
| 30394 | A | G |
| 30405-30406 | TC | CA |
| 30411 | C | A |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30420-30423 | AGTT | TCAC |
| 30426-30431 | GAAACC | ACCCAT |
| 30343-30435 | CC | AA |
| 30437-30438 | GA | AG |
| 30444 | C | T |
| 30447 | C | T |
| 30450-30454 | TCGAT | CAACC |
| 30456 | A | C |
| 30459-30460 | AA | CT |
| 30462 | C | A |
| 30466 | A | G |
| 30468 | A | G |
| 30473 | C | A |
| 30476 | A | T |
| 30478 | G | A |
| 30480-30481 | CT | AC |
| 30484-30486 | CTA | TGG |
| 30488-30489 | AT | GG |
| 30495 | T | C |
| 30508 | T | C |
| 30510 | C | T |
| 30512-30513 | CT | TC |
| 30515-30516 | CA | TT |
| 30531 | A | T |
| 30536 | T | C |
| 30554 | C | T |
| 30569 | T | C |
| 30576-30577 | GC | CT |
| 30579 | T | C |
| 30585 | G | A |
| 30590 | T | C |
| 30596-30597 | AT | CC |
| 30599 | C | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30602-30603 | CA | TG |
| 30605 | A | G |
| 30609 | G | A |
| 30611 | C | T |
| 30613-30614 | AT | GC |
| 30617-30618 | GA | CT |
| 30626 | T | C |
| 30629 | T | C |
| 30635-30636 | GG | AG |
| 30644-30645 | TT | CA |
| 30651 | G | T |
| 30653 | A | G |
| 30656 | A | T |
| 30662 | C | A |
| 30665 | C | G |
| 30668 | T | C |
| 30674 | C | T |
| 30680 | C | T |
| 30683-30684 | TT | GA |
| 30691 | T | C |
| 30698 | C | T |
| 29705-29706 | TC | AT |
| 29708-29711 | GGAA | ---- |
| 29703 | C | T |
| 29706 | C | T |
| 29721 | C | T |
| 29723 | C | T |
| 29725-29726 | CA | TG |
| 29731-29732 | AA | CC |
| 29735-29760 | CAAATGCAATAACAA TAATTTAACCC | --------------- ----------- |
| 29762-29763 | AA | GC |
| 29767 | A | C |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 29770 | T | C |
| 29776-29785 | CTCAATATGC | ---------- |
| 29787-29792 | GGAAC | AAGTT |
| 29795 | C | T |
| 29880 | G | A |
| 29802-29803 | AC | GA |
| 29807-29820 | TTTTAACATAGGAC | -------------- |
| 29822 | A | G |
| 29825 | C | G |
| 29828-29830 | ATA | CCC |
| 29834-29837 | TACC | CTAA |
| 29841-29845 | ACAGT | TTGAC |
| 29847 | A | T |
| 29852 | C | T |
| 29854 | C | T |
| 29856-29863 | ACTACTCC | -------T |
| 29865 | G | A |
| 29868-29876 | ACAACTACC | G-------- |
| 29879 | A | G |
| 29884-29890 | CTACAAA | ------- |
| 29896-29912 | AAAGCACAAAAACTC AC | GG------------- -T |
| 29915 | T | C |
| 29918-29962 | CCCTAGCAGCAAGCC CACCTCAATCTATAC AACTTCACTTTTGCA | --------------- --------------- --------------G |
| 29964 | C | T |
| 29967 | C | T |
| 29970-29991 | CAAAAGGCTAACGTT ACAGACA | --------------- ------- |
| 29993 | T | C |
| 22995-29996 | AT | GC |
| 29998-30000 | CT | GC |
| 30005 | C | T |
| 30007-30009 | CCA | TTT |
| 30013-30021 | TTCCTAGCG | --------- |
| 30024-30026 | GAG | TTA |
| 30028 | T | C |
| 30032 | C | A |
| 30034 | A | C |
| 30036 | T | C |
| 30040-30060 | TGATAGGAATTATTG CTGCTG | C-------------- ------ |
| 30062 | G | A |
| 30066 | G | A |
| 30068-30088 | GGGAATGCTAATTAT AATTCT | A-------------- ------ |
| 30093-30098 | ATGATT | GCAGAC |
| 30101 | T | C |
| 30103 | A | T |
| 30105 | G | A |
| 30107-30108 | TT | CA |
| 30110-30112 | CTG | TCA |
| 30114 | T | C |
| 30118-30132 | GAAAATATGAACATG | --------------- |
| 30140-30163 | AATAGACCCACTACT GAGCTTTGA | C-------------- --------- |
| 30166-30167 | TT | CC |
| 30169 | A | C |
| 30171 | T | G |
| 30177 | T | C |
| 30180 | G | A |
| 30182-30233 | GCACCATGAAAGGTC CAGTTATCCTATTGT TTATTTCCACTTTTT GGTGTTG | --------------- --------------- --------------- ------- |
| 30235 | G | A |
| 30240-30262 | TTTTTCAATTACCAC CAATGTGC | --------------- -------- |
| 30268-30280 | ACTTTAAATAACA | ------------- |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30282 | C | T |
| 30284-30285 | TG | AT |
| 30290 | C | A |
| 30294 | T | C |
| 30298-30315 | ACACAACTTTCACCT CAA | --------------- --- |
| 30319 | G | A |
| 30325-30328 | GACA | TTTC |
| 30330-30331 | AA | TC |
| 30336 | A | T |
| 30346-30348 | ATC | GCT |
| 30355 | G | A |
| 30363 | T | A |
| 30369 | T | A |
| 30372 | C | T |
| 30375 | T | A |
| 30378-30379 | TG | AA |
| 30381 | T | C |
| 30384 | C | T |
| 30387 | T | A |
| 30394 | A | G |
| 30405-30406 | TC | CA |
| 30408 | A | C |
| 30411 | A | C |
| 30420-30423 | AGTT | TCAC |
| 30426-30431 | GAAACC | ACCCAT |
| 30434-30435 | CC | AA |
| 30437-30438 | GA | AG |
| 30444 | C | T |
| 30447 | C | T |
| 30450-30454 | C | T |
| 30456 | TCGAT | CAACC |
| 30459-30460 | AA | CT |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30462 | C | A |
| 30466 | A | G |
| 30468 | A | G |
| 30473 | C | A |
| 30476 | A | T |
| 30478 | G | A |
| 30480-30486 | CT--CTA | ACGGTGG |
| 30488-30489 | AT | GG |
| 30495 | T | C |
| 30500-30505 | ------ | ACATCT |
| 30508 | T | C |
| 30510 | C | T |
| 30512-30513 | CT | TC |
| 30515-30516 | CA | TT |
| 30531 | A | T |
| 30533-30536 | ---T | AAAC |
| 30554 | C | T |
| 30569 | T | C |
| 30576-30577 | GC | CT |
| 30579 | T | C |
| 30585 | G | A |
| 30590 | T | C |
| 30596-30597 | AT | CC |
| 30599 | C | T |
| 30602-30603 | CA | TG |
| 30605 | A | G |
| 30609 | G | A |
| 30611 | C | T |
| 30613-30614 | AT | GC |
| 30617-30618 | GA | CT |
| 30626 | A | T |
| 30629 | T | C |
| 30635-30636 | GG | AC |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30644-30645 | TT | CA |
| 30651 | G | T |
| 30653 | A | G |
| 60656 | A | T |
| 30662 | C | A |
| 30665 | C | G |
| 30674 | T | C |
| 30680 | C | T |
| 30683-30684 | TT | GA |
| 30691 | T | C |
| 30698 | C | T |
| 30707 | C | T |
| 30710 | C | T |
| 30713 | C | T |
| 30716 | T | C |
| 30722-30723 | AG | TA |
| 30732 | G | A |
| 30740 | A | G |
| 30755-30757 | ACA | GAG |
| 30761 | T | C |
| 30764 | C | T |
| 30767 | T | A |
| 30782-30783 | AA | TG |
| 30786 | G | A |
| 30791 | A | G |
| 30795 | A | C |
| 30797 | T | A |
| 30800 | C | T |
| 30803 | G | A |
| 30806-30807 | CA | TC |
| 30819 | G | A |
| 30822-30823 | AA | GG |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30826 | C | T |
| 30833-30834 | TG | CA |
| 30837 | T | G |
| 30840-30841 | GC | AT |
| 30843-30844 | AG | GC |
| 30846-30847 | TA | GC |
| 30851-30852 | AC | TG |
| 30855 | A | C |
| 30860 | C | A |
| 30862 | T | A |
| 30868-30869 | AA | GC |
| 30871 | C | A |
| 30877-30880 | AGCC | CCTA |
| 30883-30884 | AC | CT |
| 30888-30890 | ATT | CCC |
| 30892 | G | A |
| 30897 | A | T |
| 30912 | T | C |
| 30918 | A | G |
| 30927 | A | T |
| 30933-30934 | TG | CA |
| 30936 | T | A |
| 30939 | C | T |
| 30943 | C | A |
| 30952-30953 | TC | AT |
| 30960 | C | T |
| 30963-30964 | CA | AC |
| 30966 | A | C |
| 30969 | C | T |
| 30975 | T | A |
| 30987-30988 | GG | AA |
| 30990-30991 | TG | CC |
| 30997 | C | G |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 30999 | A | G |
| 31002 | C | A |
| 31004-31005 | CT | GC |
| 31011-31012 | AC | CA |
| 31017-31018 | CT | TG |
| 31020 | T | A |
| 31029 | T | A |
| 31032 | C | T |
| 31034 | A | C |
| 31036 | T | A |
| 31038 | A | G |
| 31050 | A | G |
| 31056-31058 | CTC | TGT |
| 31061 | T | C |
| 31075 | T | C |
| 31090 | G | C |
| 31101 | A | C |
| 31110 | G | A |
| 31116 | A | G |
| 31123 | T | C |
| 31132 | G | A |
| 31189 | T | C |
| 31198 | G | A |
| 31215 | A | T |
| 31234 | T | C |
| 31276 | C | A |
| 31282 | T | C |
| 31321 | A | G |
| 31340 | C | G |
| 31375 | G | A |
| 31387 | C | T |
| 31405 | C | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 31441 | C | G |
| 31462 | C | T |
| 31471 | T | G |
| 31477 | C | T |
| 31576 | T | C |
| 31592 | C | A |
| 31594 | T | C |
| 31597 | G | A |
| 31615-31618 | CCCG | AAAC |
| 31620-31623 | CCTT | ATAC |
| 31626-31627 | CT | TC |
| 31629 | A | T |
| 31632 | A | C |
| 31637-31639 | CAA | --- |
| 31643 | G | T |
| 31657-31658 | AA | T- |
| 31680 | T | C |
| 31683 | G | A |
| 31693-31695 | TGC | CAA |
| 31707 | G | T |
| 31735 | T | C |
| 31758 | T | C |
| 31798 | T | C |
| 31804 | C | T |
| 31810 | G | T |
| 31829 | T | C |
| 31831-31833 | ATC | --T |
| 31856 | A | T |
| 31874 | T | C |
| 31895 | C | T |
| 31900 | G | A |
| 31903 | C | G |
| 31905 | A | T |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 31913 | T | C |
| 31928 | T | C |
| 31930 | C | T |
| 31940 | A | C |
| 31943-31944 | TG | CA |
| 31953 | G | A |
| 31960 | G | A |
| 31962 | C | T |
| 31970 | G | A |
| 31976-31977 | CA | AG |
| 31979 | A | T |
| 31988-31990 | TAT | CGC |
| 31992 | T | G |
| 31994 | C | T |
| 32002-32003 | AT | CC |
| 32006 | T | C |
| 32012 | C | T |
| 32015 | A | T |
| 32018-32019 | AT | TC |
| 32021 | A | T |
| 32024 | A | G |
| 32036-32037 | AG | TA |
| 32039 | A | G |
| 32045 | A | T |
| 32047 | A | C |
| 32049 | G | A |
| 32051 | G | T |
| 32055 | T | A |
| 32060 | A | T |
| 32066-32067 | AT | GA |
| 32069-32070 | TC | AT |
| 32072 | G | A |
| 32078-32079 | AA | GG |
| 32087 | T | C |
| 32089-32092 | CAAC | TCTT |
| 32096 | T | A |
| 32105 | T | A |
| 32112-32113 | AA | GC |
| 32117 | T | C |
| 32120 | T | C |
| 32123-32124 | CA | AG |
| 32127 | A | T |
| 32129 | G | A |
| 32131-32133 | TGG | CAT |
| 32135 | A | G |
| 32144 | C | G |
| 32148 | C | G |
| 32150-32154 | TACTG | ATTAA |
| 32159 | A | C |
| 32161 | A | G |
| 32170 | G | A |
| 32173-32174 | CA | TT |
| 32180 | G | A |
| 32184 | C | G |
| 32186 | A | T |
| 32192-32193 | TG | AA |
| 32205-32207 | GGT | AAC |
| 32210 | T | C |
| 32213 | T | A |
| 32217 | A | T |
| 32222 | T | C |
| 32225-32226 | CA | TG |
| 32228 | T | C |
| 32230-32232 | CA | TT |
| 32237-32238 | AC | TT |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 32246 | A | C |
| 32250 | G | A |
| 32252-32256 | TCCCA | GAATC |
| 32258-32264 | TGAGGCC | GTCCATT |
| 32267 | T | C |
| 32271 | C | A |
| 32273 | T | C |
| 32276-32277 | GC | TA |
| 32279-32280 | AG | GC |
| 32282-32283 | GT | AC |
| 32285-32287 | CAC | --- |
| 32297 | A | T |
| 32301 | T | A |
| 32306 | A | G |
| 32309 | C | A |
| 32312 | A | T |
| 32318-32319 | TC | CT |
| 32321-32323 | TGT | AAC |
| 32335-32336 | CT | GA |
| 32345 | C | T |
| 32347 | G | C |
| 32357-32358 | TC | AT |
| 32360-32361 | TA | GG |
| 32363 | G | A |
| 32366 | T | G |
| 32369-32370 | CA | AT |
| 32375-32379 | CGAAT | TATTG |
| 32381 | T | A |
| 32384-32385 | TG | CT |
| 32387-32388 | TA | AC |
| 32391-32393 | ACC | TTT |
| 32395 | C | A |
| 32397-32402 | GTTAAA | CGGGCC |
| 32404 | T | C |
| 32408-32409 | TC | AA |
| 32411-32412 | AC | TA |
| 32414 | T | C |
| 32417-32424 | TGCTGATA | AATAAGGC |
| 32427-32429 | TAT | AGC |
| 32436 | A | G |
| 32438-32440 | AAA | CTC |
| 32444 | A | C |
| 32447-32448 | GG | TT |
| 32450 | C | A |
| 32453 | T | A |
| 32456-32460 | TGATA | AAGCC |
| 32467 | C | A |
| 32471 | T | A |
| 32477-32479 | AGA | CCC |
| 32481 | T | C |
| 32483 | A | G |
| 32486-32487 | AT | TC |
| 32489 | T | C |
| 32491-32492 | AG | GA |
| 32494 | C | A |
| 32498-32499 | AC | CA |
| 32501-32502 | AA | TG |
| 32504 | T | C |
| 32509-32510 | CA | AC |
| 32513 | A | T |
| 32515-32518 | GTGA | ACAC |
| 32520-32521 | CC | TT |
| 32523 | T | A |
| 32525 | A | T |
| 32528-32529 | CA | TG |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 32537 | C | T |
| 32540 | C | T |
| 32546 | A | C |
| 32550-32552 | CTA | ACT |
| 32555 | T | A |
| 32558 | A | C |
| 32561 | C | T |
| 32564-32565 | AC | CT |
| 32568-32570 | CGA | --- |
| 32574-32575 | CC | GA |
| 32581-32582 | TT | CA |
| 32584-32592 | AACCAGTTA | --------- |
| 32594 | A | G |
| 32596 | G | A |
| 32600 | T | A |
| 32603-32604 | GG | AA |
| 32622-62623 | AC | TG |
| 32629 | T | A |
| 32632 | G | A |
| 32636 | C | A |
| 32638-32639 | GC | CT |
| 32642 | T | A |
| 32645 | T | C |
| 32648-32649 | TC | AT |
| 32651 | C | G |
| 32653-32654 | TA | AC |
| 32657 | A | G |
| 32663-32699 | TACATAT | AGTTGCC |
| 32672 | T | C |
| 32674-32675 | TG | CA |
| 32681-32688 | TTACAAAC | CAGACGGA |
| 32691-32692 | TC | AG |
| 32695 | A | G |
| 32699-32704 | CCAATG | TGCGT |
| 32706 | G | T |
| 32708 | A | T |
| 32714 | A | T |
| 32718-32721 | CACT | ACTA |
| 32724-32726 | ATG | GCT |
| 32730 | T | A |
| 32732 | A | T |
| 32734-32735 | GG | TA |
| 32737 | A | G |
| 32739 | A | G |
| 32741-32743 | TTC | AAA |
| 32746-32750 | TTAAA | CACCC |
| 32753 | A | T |
| 32757-32759 | GAA | ACT |
| 32762-32766 | AGCCA | CATAG |
| 32768 | T | A |
| 32772 | T | C |
| 32775 | A | G |
| 32778 | G | A |
| 32780 | T | C |
| 32789 | T | C |
| 32792 | C | T |
| 32798 | A | C |
| 32801 | C | T |
| 32811 | G | A |
| 32829-32830 | AA | -- |
| 32835 | G | T |
| 32838 | C | T |
| 32847 | T | - |
| 32851 | A | G |
| 32854 | C | A |

TABLE 3-continued (Comparison of nucleotide sequences of SAdV-41.2 vs. SAdV-41.1)
The table provides an alignment of nucleotide sequences in SEQ ID NOs: 1 (SAdV-41.1) and 34 (SAdV-41.2). Nucleotide(s) alignment position 1 corresponds to nucleotide 1 of SEQ ID NOs: 1 and 34. Where one isolate contains no sequences and the other has an insertion, a dash (-) is used. Where the sequences are identical, no information is provided in the Table.

| Nucleotide(s) Alignment Position | SAdV-41.2 | SAdV-41.1 |
|---|---|---|
| 32908-32909 | GA | CG |
| 32961 | A | G |
| 33952 | A | C |
| 34040 | G | A |
| 34052 | C | T |
| 34062 | A | G |
| 34068 | T | G |
| 34071 | T | C |
| 34073 | T | G |
| 34080 | T | C |
| 34083 | A | G |
| 34089 | T | C |
| 34107 | A | G |
| 34116-34117 | GA | AT |
| 34149 | C | A |
| 34152 | C | T |
| 34155 | G | A |
| 34158 | T | C |
| 34209 | T | C |
| 34219 | T | A |
| 34221 | G | T |
| 34260 | A | G |
| 34309 | T | G |
| 34334 | C | T |
| 34404 | G | A |
| 34416 | A | C |
| 34644 | T | C |
| 34988 | C | A |
| 35086-35090 | AAAAA | ----- |
| 35196 | A | G |
| 35451 | A | T |
| 35572 | A | G |
| 35600 | C | A |
| 35614 | G | A |
| 35617 | C | G |
| 35622 | T | A |
| 35626 | C | T |
| 35640 | A | T |
| 35661-35662 | GA | AT |
| 35672 | G | A |
| 35677 | C | G |
| 35689-35690 | GC | AT |
| 35703 | T | C |
| 35761 | G | A |

TABLE 4

(Sequence Listing Free Text)
The following information is provided for sequences containing free text under numeric identifier <223>.

| SEQ ID NO: (containing free text) | Free text under <223> |
|---|---|
| 1 | Simian adenovirus 41.1 |
| 2 | Synthetic Construct |
| 3 | Synthetic Construct |
| 4 | Synthetic Construct |
| 5 | Synthetic Construct |
| 6 | Synthetic Construct |
| 7 | Synthetic Construct |
| 8 | Synthetic Construct |
| 9 | Synthetic Construct |
| 10 | Synthetic Construct |
| 11 | Synthetic Construct |
| 12 | Synthetic Construct |
| 13 | Synthetic Construct |
| 14 | Synthetic Construct |
| 15 | Synthetic Construct |
| 16 | Synthetic Construct |
| 17 | Synthetic Construct |
| 18 | Synthetic Construct |
| 19 | Synthetic Construct |
| 20 | Synthetic Construct |
| 21 | Synthetic Construct |
| 22 | Simian adenovirus 41.1 |
| 23 | Synthetic Construct |
| 24 | Simian adenovirus 41.1 |
| 25 | Synthetic Construct |
| 26 | Synthetic Construct |
| 27 | Synthetic Construct |
| 28 | Simian adenovirus 41.1 |
| 29 | Synthetic Construct |

TABLE 4-continued (Sequence Listing Free Text)
The following information is provided for sequences containing free text under numeric identifier <223>.

| SEQ ID NO: (containing free text) | Free text under <223> |
|---|---|
| 30 | Simian adenovirus 41.1 |
| 31 | Synthetic Construct |
| 32 | based on Simian adenovirus 41.1 |
| 33 | based on Simian adenovirus 41.1 |
| 34 | Simian adenovirus 41.2 |
| 35 | Synthetic Construct |
| 36 | Synthetic Construct |
| 37 | Synthetic Construct |
| 38 | Synthetic Construct |
| 39 | Synthetic Construct |
| 40 | Synthetic Construct |
| 41 | Synthetic Construct |
| 42 | Synthetic Construct |
| 43 | Synthetic Construct |
| 44 | Synthetic Construct |
| 45 | Synthetic Construct |
| 46 | Synthetic Construct |
| 47 | Synthetic Construct |
| 48 | Synthetic Construct |
| 49 | Synthetic Construct |
| 50 | Synthetic Construct |
| 51 | Synthetic Construct |
| 52 | Synthetic Construct |
| 53 | Synthetic Construct |
| 54 | Synthetic Construct |
| 55 | Simian adenovirus 41.2 |
| 56 | Synthetic Construct |
| 57 | Simian adenovirus 41.2 |
| 58 | Synthetic Construct |
| 59 | Synthetic Construct |
| 60 | Synthetic Construct |
| 61 | Synthetic Construct |
| 62 | Simian adenovirus 41.2 |
| 63 | Synthetic Construct |
| 64 | Simian adenovirus 41.2 |
| 65 | Synthetic Construct |
| 66 | based on Simian adenovirus 41.2 |
| 67 | Simian adenovirus 41.2 |
| 68 | Simian adenovirus 41.2 |
| 69 | Simian adenovirus 41.2 |

The invention claimed is:

1. A vector comprising a nucleic acid sequence encoding a simian adenovirus 41 (SAdV-41) hexon protein with the amino acids 1 to 943 of SEQ ID NO: 11 or the amino acids 1 to 943 of SEQ ID NO: 44; said vector further comprising a heterologous gene operably linked to expression control sequences.

2. A composition comprising the vector according to claim 1 and a pharmaceutically acceptable carrier.

3. The vector according to claim 1, comprising a nucleic acid sequence encoding a SAdV-41.1 penton protein with the amino acids 1 to 584 of SEQ ID NO: 6 or a SAdV-41.2 penton protein with the amino acids 1 to 584 of SEQ ID NO: 39.

4. The vector according to claim 1, comprising a nucleic acid sequence encoding a SAdV-41.1 fiber protein with the amino acids 1 to 321 of SEQ ID NO: 21 or a SAdV-41.2 fiber protein with the amino acids 1 to 325 of SEQ ID NO: 54.

5. The vector according to claim 1, comprising at least one nucleic acid sequence encoding:

a SAdV-41.1 penton protein with the amino acids 1 to 584 of SEQ ID NO: 6 or a SAdV-41.2 penton protein with the amino acids 1 to 584 of SEQ ID NO: 39; and a SAdV-41.1 fiber protein with the amino acids 1 to 321 of SEQ ID NO: 21 or a SAdV-41.2 fiber protein with the amino acids 1 to 325 of SEQ ID NO: 54.

6. The vector according to claim 5, comprising at least one nucleic acid sequence encoding the SAdV-41 hexon protein with the amino acids 1 to 943 of SEQ ID NO: 11 or the amino acids 1 to 943 of SEQ ID NO: 44;

the SAdV-41.1 penton protein with the amino acids 1 to 584 of SEQ ID NO: 6; and the SAdV-41.1 fiber protein with the amino acids 1 to 321 of SEQ ID NO: 21.

7. The vector according to claim 5, comprising at least one nucleic acid sequence encoding the SAdV-41 hexon protein with the amino acids 1 to 943 of SEQ ID NO: 11 or amino acids 1 to 943 of SEQ ID NO: 44;

the SAdV-41.2 penton protein with the amino acids 1 to 584 of SEQ ID NO: 39; and the SAdV-41.2 fiber protein with the amino acids 1 to 325 of SEQ ID NO: 54.

8. The vector according to claim 1, comprising at least one nucleic acid sequence encoding one or more simian adenovirus proteins selected from E1a having the amino acid sequence of SEQ ID NO: 29 or SEQ ID NO: 63;

E1b, small T/19K having the amino acid sequence of SEQ ID NO: 23 or SEQ ID NO: 56;

E1b, large T/55K having the amino acid sequence of SEQ ID NO: 2 or SEQ ID NO: 35;

IX, having the amino acid sequence of SEQ ID NO: 3 or SEQ ID NO: 36;

52/55D, having the amino acid sequence of SEQ ID NO: 4 or SEQ ID NO: 37;

IIIa, having the amino acid sequence of SEQ ID NO: 5 or SEQ ID NO: 38;

Penton, having the amino acid sequence of SEQ ID NO: 6 or SEQ ID NO: 39;

VII, having the amino acid sequence of SEQ ID NO: 7 or SEQ ID NO: 40;

V, having the amino acid sequence of SEQ ID NO: 8 or SEQ ID NO: 41;

pX, having the amino acid sequence of SEQ ID NO:9 or SEQ ID NO: 36;

VI, having the amino acid sequence of SEQ ID NO: 10 or SEQ ID NO: 43;

Endoprotease, having the amino acid sequence of SEQ ID NO: 12 or SEQ ID NO: 58;

100 kD, having the amino acid sequence of SEQ ID NO: 13 or SEQ ID NO: 59;

33 kD homolog, having the amino acid sequence of SEQ ID NO: 31 or SEQ ID NO: 65;

22 kD, having the amino acid sequence of SEQ ID NO: 25 or SEQ ID NO: 45;

VIII, having the amino acid sequence of SEQ ID NO: 14 or SEQ ID NO: 46;

E3/12.5 K, having the amino acid sequence of SEQ ID NO: 15 or SEQ ID NO: 47;

CR1-alpha, having the amino acid sequence of SEQ ID NO: 26 or SEQ ID NO: 60;

gp19K, having the amino acid sequence of SEQ ID NO: 16 or SEQ ID NO: 48;

CR1-beta, having the amino acid sequence of SEQ ID NO: 17 or SEQ ID NO: 49;

CR1-gamma, having the amino acid sequence of SEQ ID NO: 18 or SEQ ID NO: 50;

RID-alpha, having the amino acid sequence of SEQ ID NO: 19 or SEQ ID NO: 52;

RID-beta, having the amino acid sequence of SEQ ID NO: 27 or SEQ ID NO: 61;

E3/14.7K, having the amino acid sequence of SEQ ID NO: 20 or SEQ ID NO: 53; and

Fiber, having the amino acid sequence of SEQ ID NO: 21 or SEQ ID NO: 54.

* * * * *

UNITED STATES PATENT AND TRADEMARK OFFICE
CERTIFICATE OF CORRECTION

PATENT NO. : 9,617,561 B2
APPLICATION NO. : 14/462986
DATED : April 11, 2017
INVENTOR(S) : Soumitra Roy, James M. Wilson and Luc H. Vandenberghe Page 1 of 1

It is certified that error appears in the above-identified patent and that said Letters Patent is hereby corrected as shown below:

In the Specification

Column 1, Lines 14-16, the paragraph immediately following the heading "STATEMENT REGARDING FEDERALLY SPONSORED RESEARCH OR DEVELOPMENT" is replaced with the following paragraph:
-- This invention was made with government support under DK047757 awarded by the National Institutes of Health. The government has certain rights in the invention. --

Signed and Sealed this
First Day of October, 2019

Andrei Iancu
*Director of the United States Patent and Trademark Office*